(12) United States Patent
Claussnitzer et al.

(10) Patent No.: US 11,987,790 B2
(45) Date of Patent: May 21, 2024

(54) METHODS FOR HIGH-RESOLUTION GENOME-WIDE FUNCTIONAL DISSECTION OF TRANSCRIPTIONAL REGULATORY REGIONS

(71) Applicants: MASSACHUSETTS INSTITUTE OF TECHNOLOGY, Cambridge, MA (US); BETH ISRAEL DEACONESS MEDICAL CENTER, Boston, MA (US)

(72) Inventors: Melina Claussnitzer, Boston, MA (US); Liang He, Cambridge, MA (US); Manolis Kellis, Cambridge, MA (US); Xinchen Wang, Cambridge, MA (US)

(73) Assignees: Massachusetts Institute of Technology, Cambridge, MA (US); Beth Israel Deaconess Medical Center, Boston, MA (US)

( * ) Notice: Subject to any disclaimer, the term of this patent is extended or adjusted under 35 U.S.C. 154(b) by 816 days.

(21) Appl. No.: 16/757,296

(22) PCT Filed: Oct. 17, 2018

(86) PCT No.: PCT/US2018/056371
§ 371 (c)(1),
(2) Date: Apr. 17, 2020

(87) PCT Pub. No.: WO2019/079514
PCT Pub. Date: Apr. 25, 2019

(65) Prior Publication Data
US 2020/0407710 A1  Dec. 31, 2020

Related U.S. Application Data

(60) Provisional application No. 62/573,506, filed on Oct. 17, 2017.

(51) Int. Cl.
| | | |
|---|---|---|
| *C12N 15/10* | (2006.01) | |
| *C12N 15/67* | (2006.01) | |
| *C12N 15/86* | (2006.01) | |
| *C40B 40/02* | (2006.01) | |

(52) U.S. Cl.
CPC ......... *C12N 15/1051* (2013.01); *C12N 15/67* (2013.01); *C12N 15/86* (2013.01); *C40B 40/02* (2013.01); *C12N 2310/20* (2017.05)

(58) Field of Classification Search
None
See application file for complete search history.

(56) References Cited

FOREIGN PATENT DOCUMENTS

| WO | 2016089920 A1 | 6/2016 |
|---|---|---|
| WO | 2019079514 A1 | 4/2019 |

OTHER PUBLICATIONS

"International Preliminary Report on Patentability issued in International Application No. PCT/US2018/056371", dated Apr. 30, 2020, 10 pages.
"International Search Report and Written Opinion issued in International Application No. PCT/US2018/056371", dated Feb. 15, 2019, 14 pages.
Arnold, et al., "Genome-Wide Quantitative Enhancer Activity Maps Identified by Starr-Seq", Science, vol. 339, No. 6123, Mar. 1, 2013, 1074-1077.
Barakat, et al., "Functional Dissection of the Enhancer Repertoire in Human Embryonic Stem Cells", Cell Stem Cell, vol. 23, No. 2, Aug. 2, 2018, 22 pages.
Buenrostro, et al., "Transposition of Native Chromatin for Fast and Sensitive Epigenomic Profiling of Open Chromatin, DNA-Binding Proteins and Nucleosome Position", Nature Methods, vol. 10, No. 12, Dec. 2013, 15 pages.
Dao, et al., "Genome-Wide Characterization of Mammalian Promoters with Distal Enhancer Functions", Nature Genetics, vol. 49, Jun. 5, 2017, 12 pages.
Ernst, et al., "Discovery and Characterization of Chromatin States for Systematic Annotation of the Human Genome", Nature Biotechnology, vol. 28, No. 8, Aug. 2010, 25 pages.
Ernst, et al., "Genome-Scale High-Resolution Mapping of Activating and Repressive Nucleotides in Regulatory Regions", Nature Biotechnology, vol. 34, No. 11, Nov. 2016, 35 pages.
Ernst, et al., "Mapping and Analysis of Chromatin State Dynamics in Nine Human Cell Types", Nature, vol. 473, No. 7345, May 5, 2011, 9 pages.
Farh, et al., "Genetic and Epigenetic Fine Mapping of Causal Autoimmune Disease Variants", Nature, vol. 518, No. 7539, Feb. 19, 2015, 41 pages.
Gusev, et al., "Partitioning Heritability of Regulatory and Cell-Type-Specific Variants across 11 Common Diseases", American Journal of Human Genetics, vol. 95, No. 5, Nov. 6, 2014, 535-552.
Hitomi, et al., "Identification of the Functional Variant Driving ORMDL3 and GSDMB Expression in Human Chromosome 17Q12-21 in Primary Biliary Cholangitis", Scientific Reports, vol. 7, No. 2904, Jun. 6, 2017, 10 pages.
Huang, et al., "cis-Regulatory Circuits Regulating NEK6 Kinase Overexpression in Transformed B Cells Are Super-Enhancer Independent", Cell Reports, vol. 18, No. 12, Mar. 21, 2017, 27 pages.
Inoue, et al., "A Systematic Comparison Reveals Substantial Differences in Chromosomal Versus Episomal Encoding of Enhancer Activity", Genome Research, vol. 27, No. 1, Jan. 2017, 38-52.
Jostins, et al., "Host-Microbe Interactions have Shaped the Genetic Architecture of Inflammatory Bowel Disease", Nature, vol. 491, No. 7422, Nov. 1, 2012, 18 pages.

(Continued)

*Primary Examiner* — Nancy J Leith
(74) *Attorney, Agent, or Firm* — F. Brent Nix, Esq.; Johnson, Marcou. Isaacs & Nix, LLC; Drew P. Harding

(57) ABSTRACT

Embodiments disclosed herein provide a general, scalable, high-throughput, and high-resolution approach for experimental dissection of regulatory regions and driver nucleotides in the context of human biology and disease. Applicants present HiDRA, a novel high-resolution global screen for transcriptional regulatory activity in accessible chromatin regions, enabling high-efficiency, high-throughput, and high-resolution inference of regulatory activity.

20 Claims, 72 Drawing Sheets
Specification includes a Sequence Listing.

(56) References Cited

OTHER PUBLICATIONS

Kalita, et al., "QUASAR-MPRA: Accurate Allele-specific Analysis for Massively Parallel Reporter Assays", Bioinformatics, vol. 34, No. 5, Mar. 1, 2018, 787-794.

Kheradpour, et al., "Systematic Discovery and Characterization of Regulatory Motifs in Encode TF Binding Experiments", Nucleic Acids Research, vol. 42, No. 5, Mar. 2014, 12 pages.

Liu, et al., "Functional Assessment of Human Enhancer Activities using Whole-Genome Starr-Sequencing", Genome Biology, vol. 18, No. 219, Nov. 20, 2017, 13 pages.

Long, et al., "Ever-Changing Landscapes: Transcriptional Enhancers in Development and Evolution", Cell, vol. 167, No. 5, Nov. 17, 2016, 33 pages.

Love, et al., "Moderated Estimation of Fold Change and Dispersion for RNA-seq Data with DESeq2", Genome Biology, vol. 15, No. 12, 2014, 21 pages.

Maurano, et al., "Systematic Localization of Common Disease-Associated Variation in Regulatory DNA", Science, vol. 337, No. 6099, Sep. 7, 2012, 15 pages.

Melnikov, et al., "Rapid Systematic Dissection and Optimization of Inducible Enhancers in Human Cells using a Massively Parallel Reporter Assay", Nature Biotechnology, vol. 30, No. 3, Feb. 26, 2012, 20 pages.

Mifsud, et al., "Mapping Long-Range Promoter Contacts in Human Cells with High-Resolution Capture Hi-c", Nature Genetics, vol. 47, No. 6, Jun. 2015, 12 pages.

Montefiori, et al., "Reducing Mitochondrial reads in ATAC-Seq using CRISPR/Cas9", Scientific Reports, vol. 7, No. 1, May 26, 2017, 9 pages.

Muerdter, et al., "Resolving Systematic Errors in Widely used Enhancer Activity Assays in Human Cells", Nature Methods, vol. 15, No. 2, Feb. 2018, 28 pages.

Murtha, et al., "FIREWACH: High-Throughput Functional Detection of Transcriptional Regulatory Modules in Mammalian Cells", Nature Methods, vol. 11, No. 5, May 2014, 24 pages.

Nord, et al., "Rapid and Pervasive Changes in Genome-wide Enhancer Usage during Mammalian Development", Cell, vol. 155, No. 7, Dec. 19, 2013, 1521-1531.

Patwardhan, et al., "Massively Parallel Functional Dissection of Mammalian Enhancers in Vivo", Nature Biotechnology, vol. 30, No. 3, Feb. 26, 2012, 22 pages.

Pradeepa, et al., "Histone H3 Globular Domain Acetylation Identifies a New Class of Enhancers", Nature Genetics, vol. 48, No. 6, Jun. 2016, 20 pages.

Rada-Iglesias, et al., "A Unique Chromatin Signature Uncovers Early Developmental Enhancers in Humans", Nature, vol. 470, No. 7333, Feb. 10, 2011, 7 pages.

Roadmap Epigenomics Consortium, et al., "Integrative Analysis of 111 Reference Human Epigenomes", Nature, vol. 518, No. 7539, Feb. 19, 2015, 32 pages.

Stange, et al., "Uncertainty Quantification for the Family-Wise Error Rate in Multivariate Copula Models", AStA Advances in Statistical Analysis, vol. 99, Nov. 30, 2014, 30 pages.

Taiwo, et al., "Methylome Analysis using Medip-Seq with Low DNA Concentrations", Nature Protocols, vol. 7, No. 4, Mar. 8, 2012, 20 pages.

Tewhey, et al., "Direct Identification of Hundreds of Expression-Modulating Variants using a Multiplexed Reporter Assay", Cell, vol. 165, No. 6, Jun. 2, 2016, 1519-1529.

Vanhille, et al., "High-Throughput and Quantitative Assessment of Enhancer Activity in Mammals by Capstarr-Seq", Nature Communications, vol. 6, No. 6905, Apr. 15, 2015, 10 pages.

Vockley, et al., "Direct GR Binding Sites Potentiate Clusters of TF Binding across the Human Genome", Cell, vol. 166, No. 5, Aug. 25, 2016, 36 pages.

Wang, et al., "Discovery and Validation of Sub-Threshold Genome-Wide Association Study Loci using Epigenomic Signatures", Elife, vol. 5, No. 10557, May 10, 2016, 24 pages.

Wang, et al., "High-Resolution Genome-Wide Functional Dissection of Transcriptional Regulatory Regions in Human", Nature Communications, vol. 9, No. 1, 52 pages, 2018.

Wang, et al., "High-Resolution Genome-Wide Functional Dissection of Transcriptional Regulatory Regions in Human", Nature Communications, vol. 9, No. 1, Sep. 27, 2017, 23 pages.

Young, "Invitation to Pay Additional Fees for International Application No. PCT/US2018/056371 filed Oct. 17, 2018", dated Dec. 26, 2018.

Zabidi, et al., "Enhancer-Core-Promoter Specificity Separates Developmental and Housekeeping Gene Regulation", Nature, vol. 518, No. 7540, Feb. 26, 2015, 32 pages.

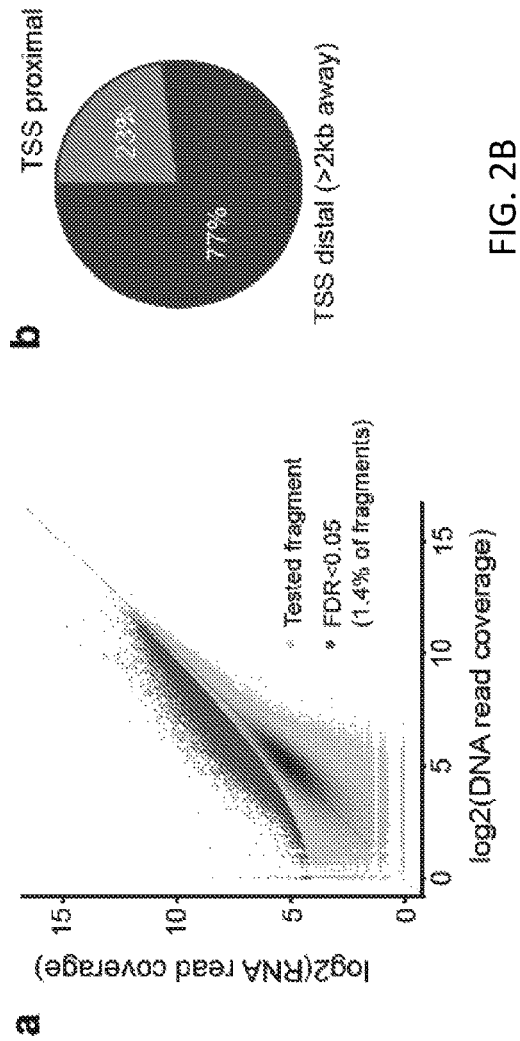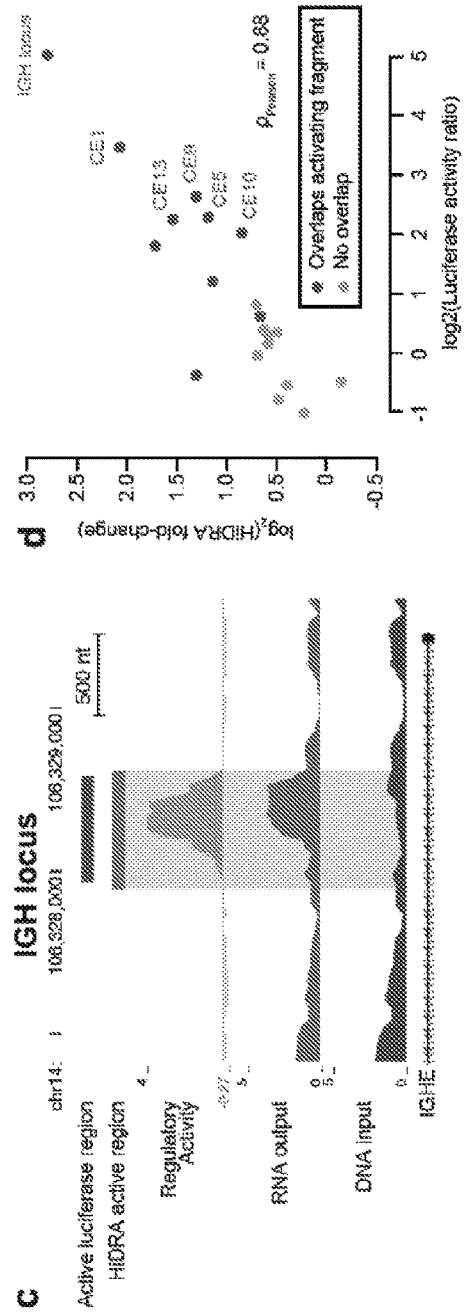
FIG. 2A
FIG. 2B
FIG. 2C
FIG. 2D

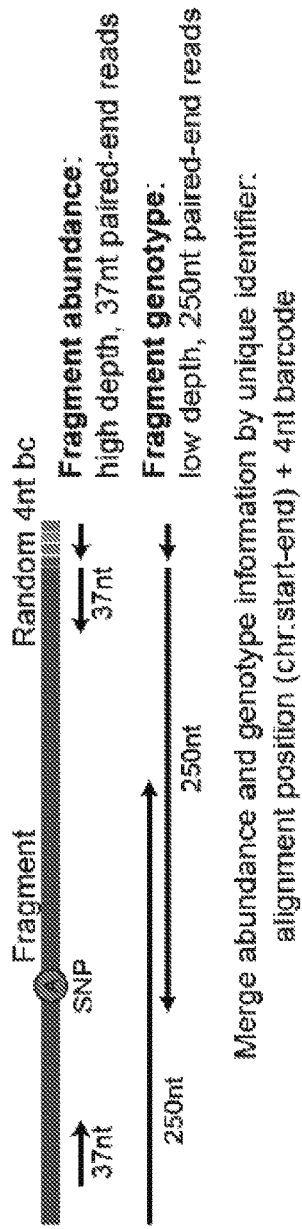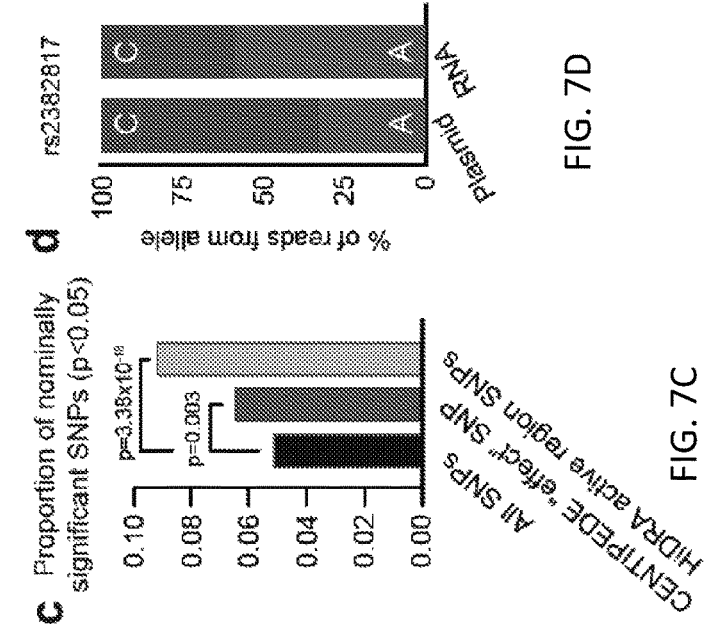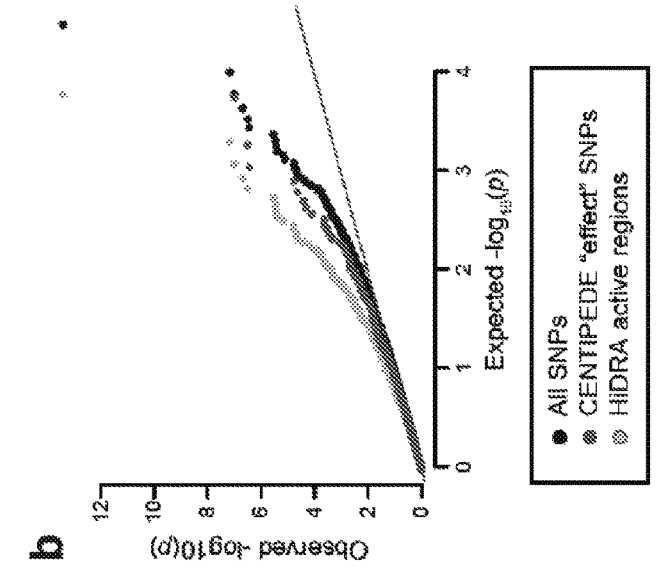
FIG. 7A
FIG. 7B
FIG. 7C
FIG. 7D

METHODS FOR HIGH-RESOLUTION GENOME-WIDE FUNCTIONAL DISSECTION OF TRANSCRIPTIONAL REGULATORY REGIONS

CROSS-REFERENCE TO RELATED APPLICATIONS

This application is a national stage application of International Patent Application No. PCT/US2018/056371 filed Oct. 17, 2018, and claims the benefit of U.S. Provisional Application No. 62/573,506, filed Oct. 17, 2017. The entire contents of the above-identified applications are hereby fully incorporated herein by reference.

STATEMENT REGARDING FEDERALLY SPONSORED RESEARCH

This invention was made with government support under Grant No. HG008155 awarded by the National Institutes of Health. The government has certain rights in the invention.

REFERENCE TO AN ELECTRONIC SEQUENCE LISTING

The contents of the electronic sequence listing (BROD-2330US_ST25.txt," 1,661 bytes and created on Jul. 16, 2020) is herein incorporated by reference in its entirety.

TECHNICAL FIELD

The subject matter disclosed herein is generally directed to genome-wide methods of detecting regulatory regions, in particular enhancer regions.

BACKGROUND

Precise spatiotemporal control of gene expression is achieved by the interplay between non-coding regulatory elements, including distal enhancers and proximal promoters, and the transcriptional regulators they help recruit or repel, thus modulating the expression of nearby genes. Unlike protein-coding genes, which can be readily identified by their sequence properties and evolutionary signatures, gene-regulatory elements lack highly-predictive sequence patterns and show only modest evolutionary conservation at the nucleotide level. Thus, systematic recognition of gene-regulatory elements has relied on mapping of their epigenomic signatures, including DNA accessibility, histone modifications, and DNA methylation. For example, both enhancers and promoters have high DNA accessibility and low H3K27me3, but distal enhancers show relatively higher H3K27ac and H3K4me1 while promoters show relatively higher H3K9ac and H3K4me3. However, many regions showing such epigenomic marks do not experimentally drive reporter gene expression, and some regions driving gene expression lack endogenous signatures. Moreover, epigenomic signatures are often low-resolution, with important driver regulatory nucleotides comprising only a small subset of the larger regions showing epigenomic signatures.

Experimental dissection of enhancer and promoter regions has been traditionally expensive, laborious, low throughput, and low-resolution, lacking the resolution to pinpoint individual regulatory driver nucleotides without recourse to extensive mutagenesis. Several high-throughput reporter assays for enhancer function have recently been developed, enabling the testing of tens of thousands of distinct DNA sequences simultaneously, including MPRA and CRE-Seq. These assays entail microarray-based oligonucleotide synthesis technology to generate the tested elements and their barcodes, cloning the oligonucleotides into a common episomal reporter vector, and using high-throughput sequencing to quantify expression. Technical limitations of oligonucleotide synthesis currently restrict the maximum tested DNA fragment length to ~230 nucleotides, and the maximum number of tested constructs to ~240,000 sequences per array. Although still limited in the number of target regions, Sharpr-MPRA enabled higher-resolution inferences by densely tiling target regions with multiple overlapping constructs, and exploiting subtle differences between the measured activity of neighboring constructs to achieve offset resolution (~5 bp) instead of construct resolution (~230 bp). STARR-Seq integrated random genomic fragments downstream of the transcription start site of episomal reporter genes, thus foregoing the oligo synthesis step and the need for barcodes as the tested elements were transcribed and serve as their own activity reporters. However, STARR-seq fragments are selected by random genomic fragmentation. As random genomic fragmentation does not densely cover regulatory elements, STARR-seq has limited efficiency and resolution at regulatory regions.

Thus, there is a need for improved genome wide methods for identifying regulatory elements.

SUMMARY

Genome-wide epigenomic maps revealed millions of regions showing signatures of enhancers, promoters, and other gene-regulatory elements. However, high-throughput experimental validation of their function and high-resolution dissection of their driver nucleotides remain limited in their scale and length of regions tested. It is an objective of the present invention to provide a general, scalable, high-throughput, and high-resolution approach for experimental dissection of regulatory regions and driver nucleotides in the context of human biology and disease.

Here, Applicants present a new method, HiDRA (High-resolution Dissection of Regulatory Activity, also known as High-Definition Reporter Assay), that overcomes prior limitations by combining components of Sharpr-MPRA and STARR-Seq with genome-wide selection of accessible regions from ATAC-Seq (e.g. "ATAC-STARR-seq"). Applicants used HiDRA to test ~7 million DNA fragments preferentially selected from accessible chromatin in the GM12878 lymphoblastoid cell line. By design, accessibility selected fragments were highly overlapping (up to 370 per region), enabling the pinpointing of driver regulatory nucleotides by exploiting subtle differences in reporter activity between partially-overlapping fragments, using a new machine learning model SHARPR2 (also known as SHARPR-RE (SHARPR-Random Endpoints)). The resulting maps included ~65,000 regions showing significant enhancer function and were enriched for endogenous active hi stone marks (including H3K9ac, H3K27ac), regulatory sequence motifs, and regions bound by immune regulators. Within them, Applicants discovered 13,000 high-resolution driver elements enriched for regulatory motifs and evolutionarily-conserved nucleotides. Additionally, the maps could predict causal genetic variants underlying disease from genome-wide association studies (GWAS).

In one aspect, the present invention provides for a method of identifying genomic enhancer regulatory elements comprising: fragmenting genomic DNA at accessible chromatin in a population of cells thereby generating genomic DNA fragments, wherein said fragmenting comprises transposition; amplifying the genomic DNA fragments; enriching the amplified genomic DNA fragments by size; integrating the enriched fragments into a vector to obtain a vector library, wherein the vector encodes a reporter gene and the enriched fragments are integrated into an untranslated region (UTR) of the reporter gene, whereby transcription of the reporter gene results in a transcript comprising the integrated fragment sequence; transfecting or transducing a cell line with the vector library, wherein the transcript comprising the integrated fragment sequences is expressed in the cell line; and sequencing the transcript expressed in the cell line, whereby integrated fragments comprising enhancer activity are identified. The amplified genomic DNA fragments may be selected for a size between about 150-500 nucleotides long. The amplified genomic DNA fragments may be selected for a size between about 230-500 nucleotides long. The enriched fragments may be integrated in a UTR downstream of the reporter gene.

In one embodiment, the method may further comprise removing mitochondrial DNA from the genomic DNA fragments. The mitochondrial DNA may be removed by treating the genomic DNA fragments with a CRISPR system comprising guide sequences targeting mitochondrial DNA sequences, wherein mitochondrial DNA is cleaved. The mitochondrial DNA may be removed after enriching amplified fragmented genomic DNA by size and before integration of the enriched fragments.

In one embodiment, the vector may be a plasmid. The vector may be a viral vector. The viral vector may be a lentiviral vector. The viral vector may be an integrating or non-integrating lentiviral vector.

In one embodiment, identifying enhancer regulatory elements may comprise measuring the ratio of the number of RNA sequencing reads comprising a fragment to the representation of the fragment in the non-transfected vector library.

In one embodiment, identifying enhancer regulatory elements comprises comparing a sequenced genomic fragment to the chromatin state of the genomic locus of the fragment in the cell line, wherein fragments present in an enhancer chromatin state are selected. The enhancer chromatin state may comprise H3K27ac (histone H3 lysine 27 acetylation) and H3K4me1 (histone H3 lysine 4 mono-methylation).

In one embodiment, identifying enhancer regulatory elements comprises comparing a sequenced genomic fragment to Long-Terminal-Repeat (LTR) retrotransposon sequences, wherein LTR sequences are not selected.

In one embodiment, the method according to any embodiment herein, may further comprise detecting expression of the reporter gene in the cell line and sorting the cells based on the reporter levels. Not being bound by a theory, a detectable reporter (e.g., GFP, YFP, RFP) may be used to sort cells based on expression. Not being bound by a theory, only sequencing cells that express the detectable marker may decrease sequencing cost.

In one embodiment, the population of cells may be obtained from a tissue sample. In one embodiment, the population of cells may be a tissue specific cell line. In one embodiment, the population of cells is obtained by pooling cells or tissues from more than one individual. The individuals may be chosen to maximize genetic diversity at informative disease variants. The cells may comprise immune cells. The cells may comprise cancer cells. In one embodiment, the population of cells may be derived from the same cell line used for transfecting or transducing, whereby enhancer regulatory elements active in the cell line may be identified. In other words, fragments are obtained from a cell line to obtain a vector library and the vector library is assayed in the same cell line. Not being bound by a theory, different cell lines express different activators and repressors and have different chromatin states. Therefore, fragmenting accessible chromatin in a cell line may provide fragments that function optimally in the same cell line. Not being bound by a theory, different regulatory elements may be identified by assaying a vector library in different cell types.

In certain embodiments, nuclei are isolated from the population of cells before fragmenting genomic DNA. In certain embodiments, the present invention applies ATAC-seq to obtain fragments of genomic DNA present in accessible chromatin in a cell. The ATAC-seq protocol described herein utilizes a buffer that results in a crude nuclei preparation. In certain embodiments, tissue samples to be analyzed are frozen. As described herein, components of Div-seq can be used for single-nucleus isolation and RNA-Seq. Div-seq is compatible with frozen or fixed tissue. In certain embodiments, nuclei are isolated from frozen tissue and genomic fragments obtained from the isolated nuclei following the steps described herein.

In certain embodiments, the genomic fragments are amplified by error-prone PCR. In certain embodiments, the fragments are amplified in an amplification reaction comprising a mutagen. Not being bound by a theory, mutations affecting regulatory activity of a fragment may be determined by introducing mutations during PCR amplification.

In certain embodiments, the method may further comprise high-resolution mapping of driver elements of enhancer activity within identified enhancer regulatory elements by a method comprising comparing the fragment enrichment enhancer activity of a set of overlapping fragments represented in the vector library, whereby driver elements of enhancer activity are identified for enhancer regulatory elements. The driver element may comprise a minimum of 18 driver nucleotides. Not being bound by a theory the resolution of driver elements increases with increasing overlapping fragments, however after about 40 overlapping fragments the resolution does not extend past 18 driver nucleotides. In certain embodiments, comparing may comprise uploading the overlapping fragment sequences into a computing system and applying an algorithm, wherein the algorithm compares the fragment enrichment enhancer activity of the overlapping fragments. The algorithm may estimate regulatory scores for nucleotides in the identified set of overlapping fragments. The set of overlapping fragments may comprise at least 10 unique overlapping fragments. The method may further comprise identifying driver element variants. The driver element variants may comprise genome wide association (GWAS) variants. GWAS variants are available on public data bases and are well known in the art. Not being bound by a theory, GWAS variants with unknown function may be linked to a regulatory element or driver element using the present invention. The GWAS variants may be genetic variants associated with a disease. In certain embodiments, identifying driver element variants may comprise resequencing the input vector library using reads sufficiently long to identify sequence variants. Not being bound by a theory, RNA-seq may not provide reads long enough to identify sequence variants. The method may further comprise correlating driver element variants with a disease. Not being bound by a theory, new variants previously not associated with a disease may be identified.

In another aspect, the present invention provides for a method of identifying genomic enhancer regulatory elements comprising: fragmenting genomic DNA in a population of cells, wherein the fragmented genomic DNA is fragmented to create fragments comprising overhanging ends; filling in the overhanging ends with at least one labeled nucleotide, wherein the labeled nucleotide is used to isolate the nucleic acids; joining the filled in ends of the fragmented genomic DNA, wherein the joined fragments comprise contact domains; isolating the joined genomic DNA fragments using the labeled nucleotide; amplifying the isolated joined genomic DNA fragments; integrating the amplified fragments into a vector to obtain an input vector library, wherein the vector encodes a reporter gene and the fragments are integrated into an untranslated region (UTR) of the reporter gene, whereby transcription of the reporter gene results in a transcript comprising the integrated fragment sequence; transfecting or transducing a cell line with the vector library; and sequencing the transcripts expressed in the cell line, whereby integrated fragments comprising enhancer activity may be identified. Not being bound by a theory, a regulatory sequence may depend upon a chromatin loop to be formed to bring two sequences together at a contact domain. The present invention may allow for identifying previously unknown regulatory sequences that function at contact domains. The genomic DNA fragments may be held in a fixed position relative to one another. The nucleic acids may be fixed in position relative to one another by crosslinking. The crosslinking may comprise treatment with a chemical crosslinker. The chemical crosslinker may comprise an aldehyde. The aldehyde may comprise formaldehyde. The method may further comprise reversing the crosslinking. Reversing the crosslinking may comprise contacting the sample with Proteinase K.

In another aspect, the present invention provides for identifying repressor regulatory elements. In one embodiment, the reporter gene is constitutively expressed and integrated fragments having repressor activity are identified by measuring depletion of fragments in relation to their representation in the input vector library.

In another aspect, the present invention provides for a system for identifying enhancer regulatory elements comprising a computing element configured for applying an algorithm as described herein to sequenced transcripts as described herein.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

(FIG. 1A) The Tn5 transposase preferentially fragments genomic DNA at regions of open chromatin. Fragments are then size-selected on an agarose gel and mtDNA contamination is removed by selective CRISPR-Cas9 degradation. The fragment library is amplified by PCR and cloned into a enhancer reporter vector. (FIG. 1B) Size distribution of HiDRA library fragments. Bimodal shape is due to Tn5 preference to cut adjacent to nucleosomes (FIG. 1C) Number of predicted enhancer, active TSS and ATAC-seq peaks covered by multiple unique HiDRA fragments. (FIG. 1D) HiDRA plasmid library recapitulates genomic coverage of a conventional ATAC-seq experiment.

FIG. 2A-2E—HiDRA identifies transcriptional regulatory elements. (FIG. 2A) Scatterplot of abundances for HiDRA fragments in input (plasmid DNA) and output (RNA) samples. Abundances calculated after merging all five replicates. Active HiDRA fragments called by DESeq2 highlighted with red dots, blue color intensity corresponds to greater density of points. (FIG. 2B) The majority of HiDRA active regions are distal to annotated TSSs (>2 kb). (FIG. 2C) HiDRA identifies enhancer activity within an intron in the immunoglobulin heavy chain locus. Red bar, DNA segment active in luciferase assay performed by Huang et al. (2017). Orange bar and highlight, region identified by HiDRA as having transcriptional regulatory activity. (FIG. 2D) Quantitative comparison of luciferase assay activity levels to HiDRA for 21 predicted enhancer elements. HiDRA signal corresponds to maximum activity within the region tested by luciferase, and luciferase value corresponds to median normalized activity over biological replicates. Pearson correlation calculated after log 2 transformation. FIG. 2E Luciferase experiments are colored in red or grey depending on whether DNA fragments drive luciferase activity in GM12878 cells as determined by Huang et al. (2017).

(FIG. 3A) Overlap of active HiDRA fragments with different endogenous chromatin states. Heights correspond to proportion of nucleotides within active HiDRA fragments in each chromatin state. Inset: histone modification enrichments in each of 18 ChromHMM chromatin states (FIG. 3B) HiDRA fragment regulatory activity (fold-change increase in RNA levels) across different chromatin states. Numbers correspond to chromatin state numbers in 18-state ChromHMIM model.

(FIG. 4A) The majority of ChromHMM-predicted TssFlnkUp regions are not near annotated TSSs, but share a similar genomic distribution pattern to predicted active enhancers. (FIG. 4B, FIG. 4C) Endogenously inactive genomic regions have low levels of TF binding (FIG. 4B) but comparable TF motif composition (FIG. 4C) to predicted active regions. (FIG. 4D, FIG. 4E) Endogenously inactive chromatin states overlapping active HiDRA fragments are more likely to be active in other human tissues (FIG. 4D) and are enriched for LTR retrotransposons (FIG. 4E) compared to endogenously active regions. Colored bars, regions from each chromatin state overlapping active HiDRA regions. Grey bars, regions from each chromatin state overlapping all HiDRA fragments tested.

(FIG. 5A) Example region used in high-resolution mapping. Fragment activity shown on log 2 scale with two fragments with highest and lowest activity removed for color scale to avoid outliers. The transparent red bar indicates the driver element identified at the regional FWER<0.05. (FIG. 5B) Size distribution of driver elements. (FIG. 5C) Enrichment of immune-related TF motifs in driver elements compared to shuffled driver elements within tiled regions. (FIG. 5D) TF motifs enriched in driver elements cluster into groups of co-occurring motifs, suggesting diversity of TF motifs involved in transcriptional regulatory activity (FIG. 5E) Significantly more driver elements are evolutionary conserved compared to shuffled driver elements within tiled regions. Evolutionary conservation cut-off chosen as conservation score for top 5% of shuffled regions.

(FIG. 6A) Driver elements overlap more GWAS fine-mapped SNPs associated with 21 human immune-related complex traits than randomly shuffled regions. (FIG. 6B) Example locus at rs12946510 that overlaps a high-resolution driver element. Highlighted segment indicates the driver element identified at the regional FWER<0.05. Red bar at top corresponds to region with luciferase activity as demonstrated by Hitomi et al. (2017).

FIG. 7A-7F—Identification of human genetic variants that alter HiDRA activity. (FIG. 7A) Overview of genotyping approach for HiDRA fragments. HiDRA fragments were originally quantified at high-depth using 37nt paired-end reads. At this read length the allele composition of fragments is mostly unobserved. As every HiDRA fragment has a unique identifier (genomic alignment position and random 4nt barcode), long-read re-sequencing of the HiDRA library can assign SNP genotypes to fragments that were previously quantified for activity using short reads. (FIG. 7B) q-q plot for allelic imbalance at SNPs covered by HiDRA fragments. CENTIPEDE "effect" SNPs were identified by Moyer-brailean et al. (2016). (FIG. 7C) "Effect" SNPs and SNPs within HiDRA active regions are more likely to be nominally significant for allelic imbalance. (FIG. 7D) The A allele of rs2382817, a SNP associated with inflammatory bowel disease, is more active in the HiDRA assay than the C allele. (FIG. 7E) Alelle-specific HiDRA activity signal tracks for rs2382817. (FIG. 7F) rs2382817 alleles are correlated with differences in expression of the nearby TMBIM1 gene in EBV-transformed lymphocytes.

(FIG. 10A) HiDRA fragments within active enhancer state regions have greater regulatory activity than those within active TSS state regions. (FIG. 10B) Motif enrichment is calculated separately for active TSS state regions (left) and active enhancer state regions (right) that overlap active HiDRA fragments. Only top 16 motifs are shown for each group after filtering to keep only motifs corresponding to expressed TFs in GM12878 (RPKM>5). Numbers within bars correspond to false discovery rate.

(FIG. 14A) The majority of driver elements discovered by HiDRA are distal to annotated transcription start sites (FIG. 14B) Genomic distribution of driver elements reveals that majority of driver elements are found in TSS, TSS-flanking and predicted enhancer regions.

FIG. 16B shows the Q-Q plot suggests that this is a heavy-tailed distribution.

FIG. 17A): the distribution of ln(#RNA/#DNA) after normalization with respect to fragment length. In the plot, the fragment length is categorized into five groups. FIG. 17B): the distribution of fragment length with respect to the size of the tiled region in which the fragment is located. The size of tiled regions is defined by the number of fragments in the tiled region. The plots are based on the library described in the main text in which the fragments are ranged between 100-600nt (with 99% between 168-473nt).

The red bars are the empirical power for the predicted 20 bp core driver element. The blue bars are the empirical power for the identified drivers with a significant regulatory score based on a regional FWER=5%.

Figure 20A:
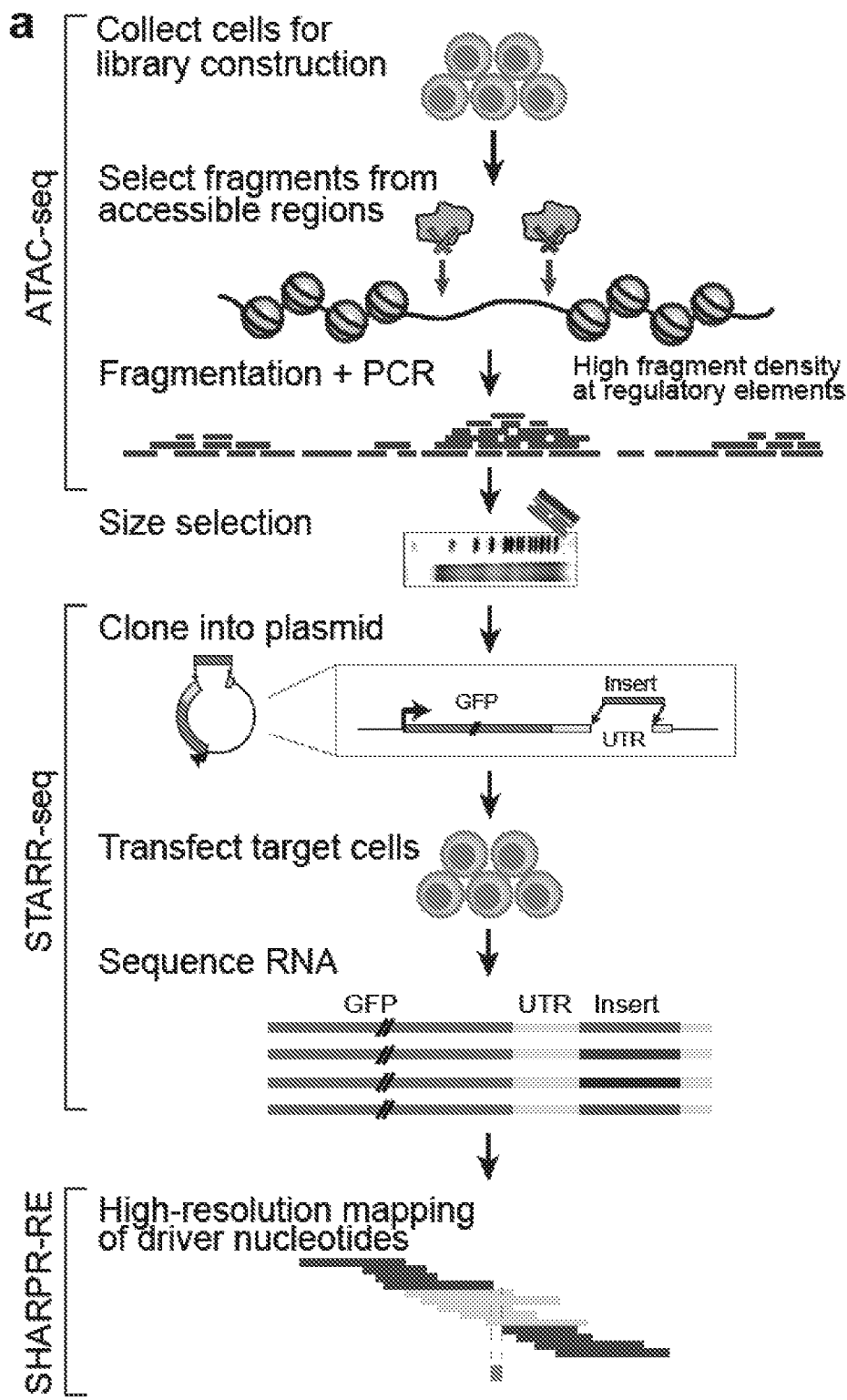
Figure 20B:
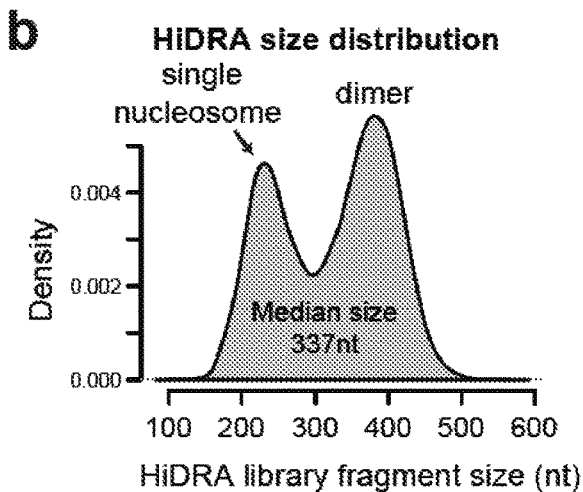

FIG. 20A-20D Overview of HiDRA. FIG. 20A: Cells with desired genotype and open chromatin patterns are selected for library construction. Tn5 transposase is used to preferentially fragment genomic DNA at regions of open chromatin. Fragments are then size-selected on an agarose gel and mtDNA contamination is removed by selective CRISPR-Cas9 degradation. The fragment library is amplified by PCR and cloned into a enhancer reporter vector. Gel image adapted from Buenrostro et al. (2013). Fragments are cloned into the STARR-seq vector backbone, introduced into target cells (which can differ from cells used to construct library), and RNA is collected and sequenced. After data processing, the activity of partially-overlapping fragments is compared to identify driver nucleotides using the SHARPR-RE algorithm. FIG. 20B: Size distribution of HiDRA library fragments. Bimodal shape is due to Tn5 preference to cut adjacent to nucleosomes (FIG. 20C) Number of ChromHMM-predicted active enhancer, active TSS and ATAC-seq peaks covered by multiple unique HiDRA fragments. (FIG. 20D) HiDRA plasmid library recapitulates genomic coverage of a conventional ATAC-seq experiment.

Figures 21A, 21B:
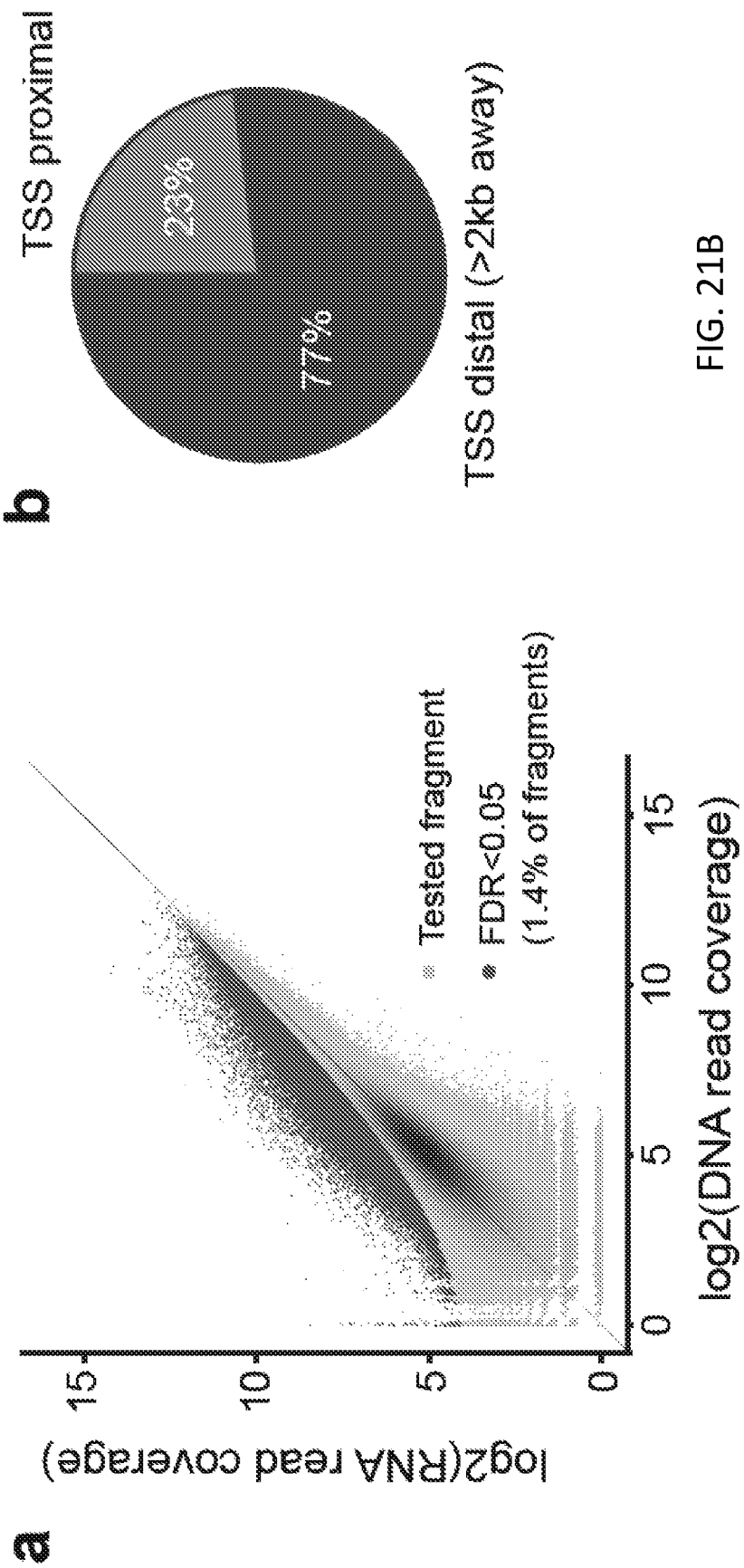
Figure 21C:
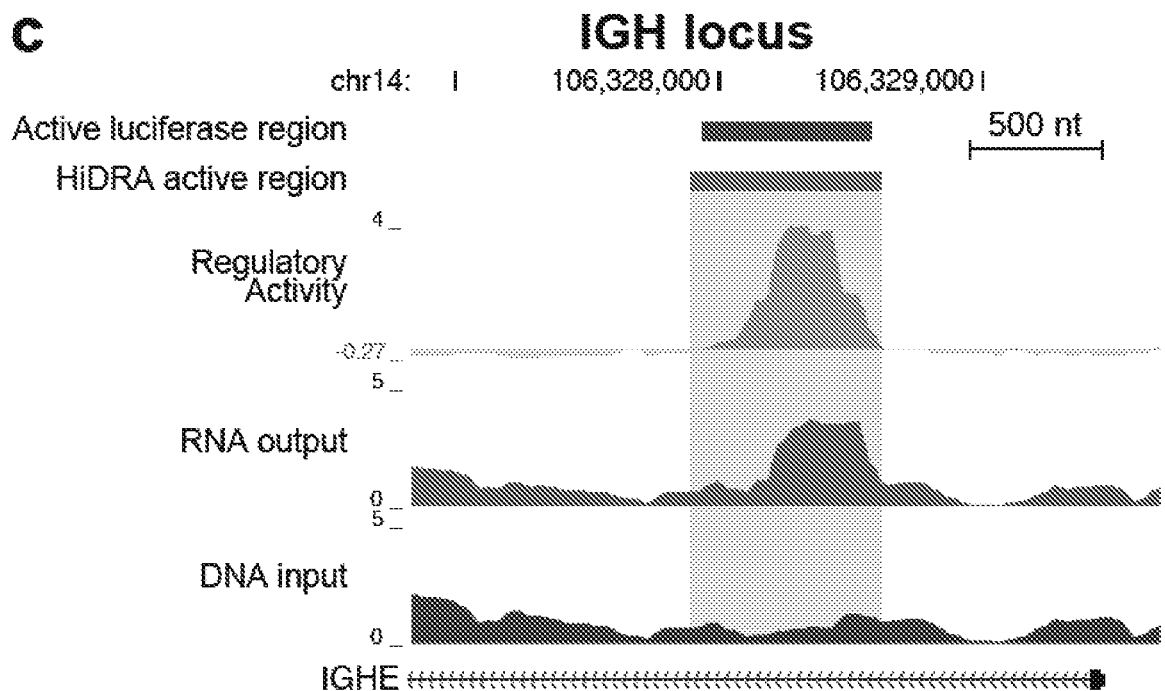
Figure 21D:
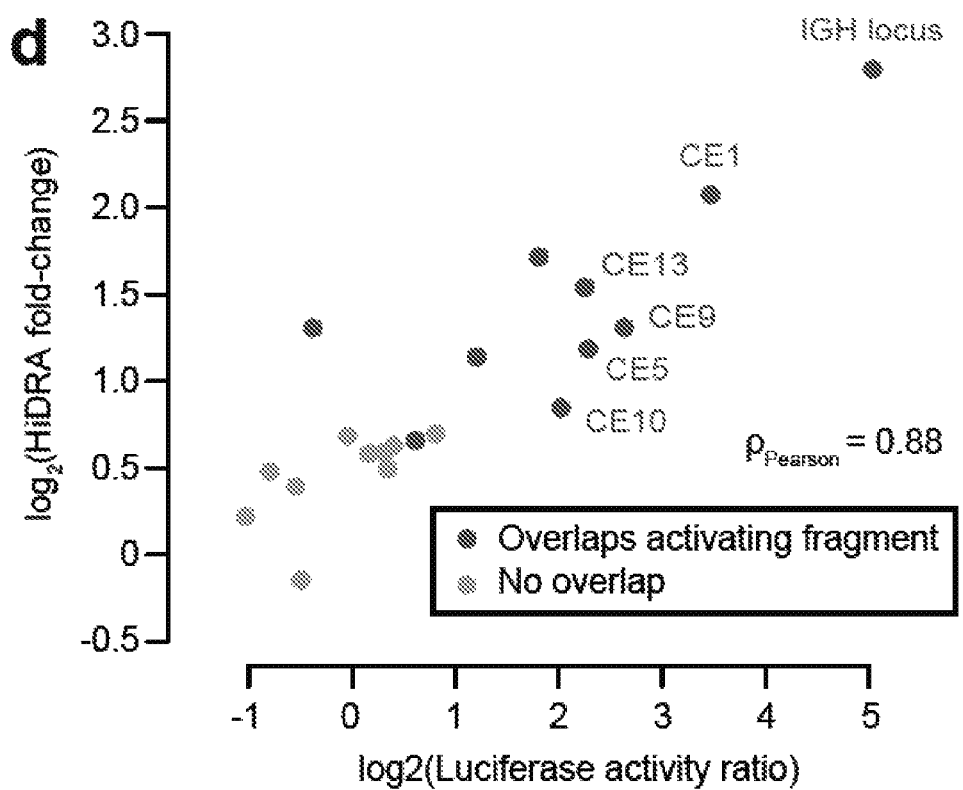
Figure 21E:
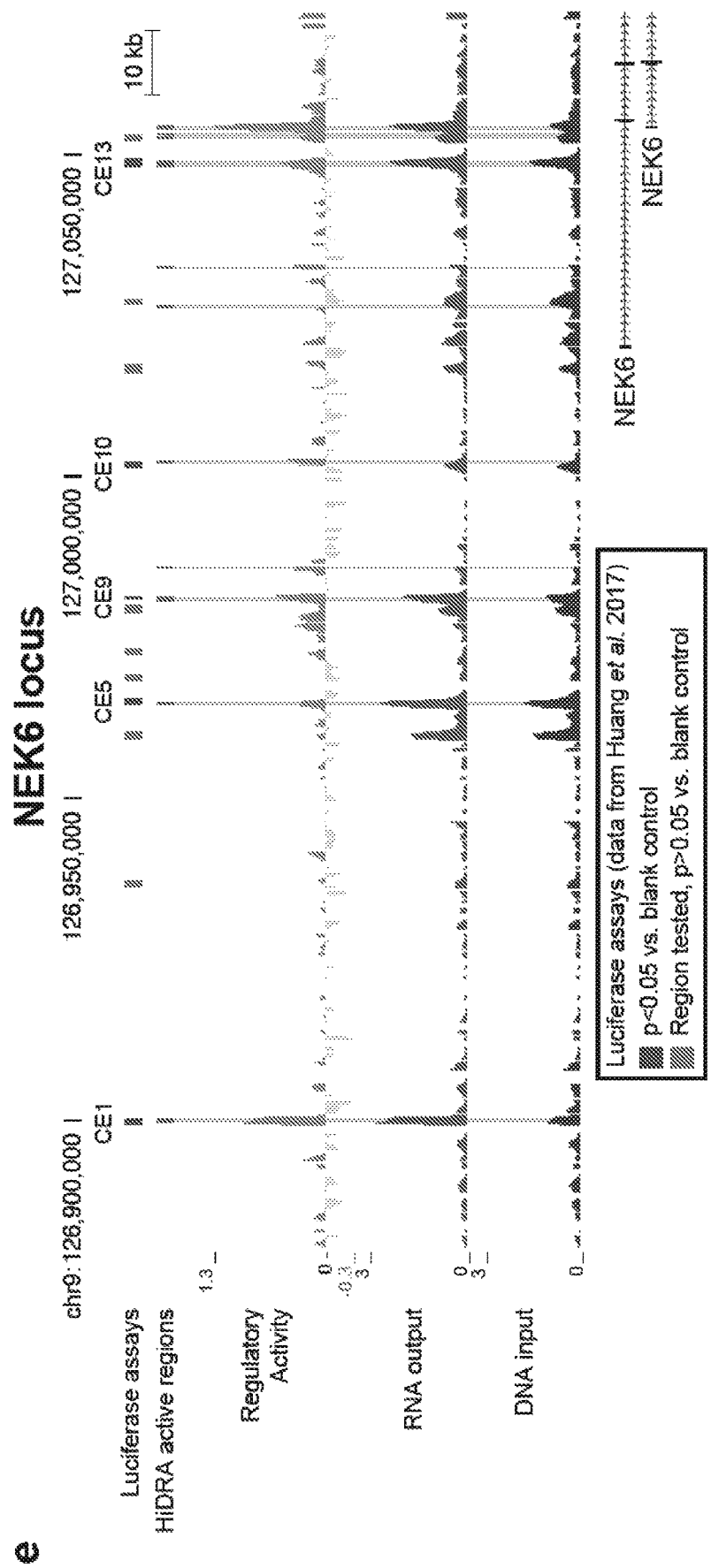

FIG. 21A-21E—HiDRA identifies transcriptional regulatory elements. HiDRA identifies transcriptional regulatory elements. FIG. 21A: Scatterplot of abundances for HiDRA fragments in input (plasmid DNA) and output (RNA) samples. Abundances calculated after merging all five replicates. Active HiDRA fragments called by DESeq2 highlighted with red dots (FDR<0.05), blue color intensity corresponds to greater density of points. FIG. 21B: The majority of HiDRA active regions are distal to annotated TSSs (>2 kb). FIG. 21C: HiDRA identifies enhancer activity within an intron in the immunoglobulin heavy chain locus. Red bar, DNA segment active in luciferase assay performed by Huang et al. (2017). Orange bar and highlight, region identified by HiDRA as having transcriptional regulatory activity. FIG. 21D: Quantitative comparison of luciferase assay activity levels to HiDRA for 21 predicted enhancer elements. HiDRA signal corresponds to maximum activity within the region tested by luciferase, and luciferase value corresponds to median normalized activity over biological replicates. Pearson correlation calculated after log2 transformation. FIG. 21E: Comparison of HiDRA-called active regions with luciferase assay results for 13 enhancers at the NEK6 locus. Luciferase experiments are colored in red or grey depending on whether DNA fragments drive luciferase activity in GM12878 cells as determined by Huang et al. (2017).

Figure 22A:
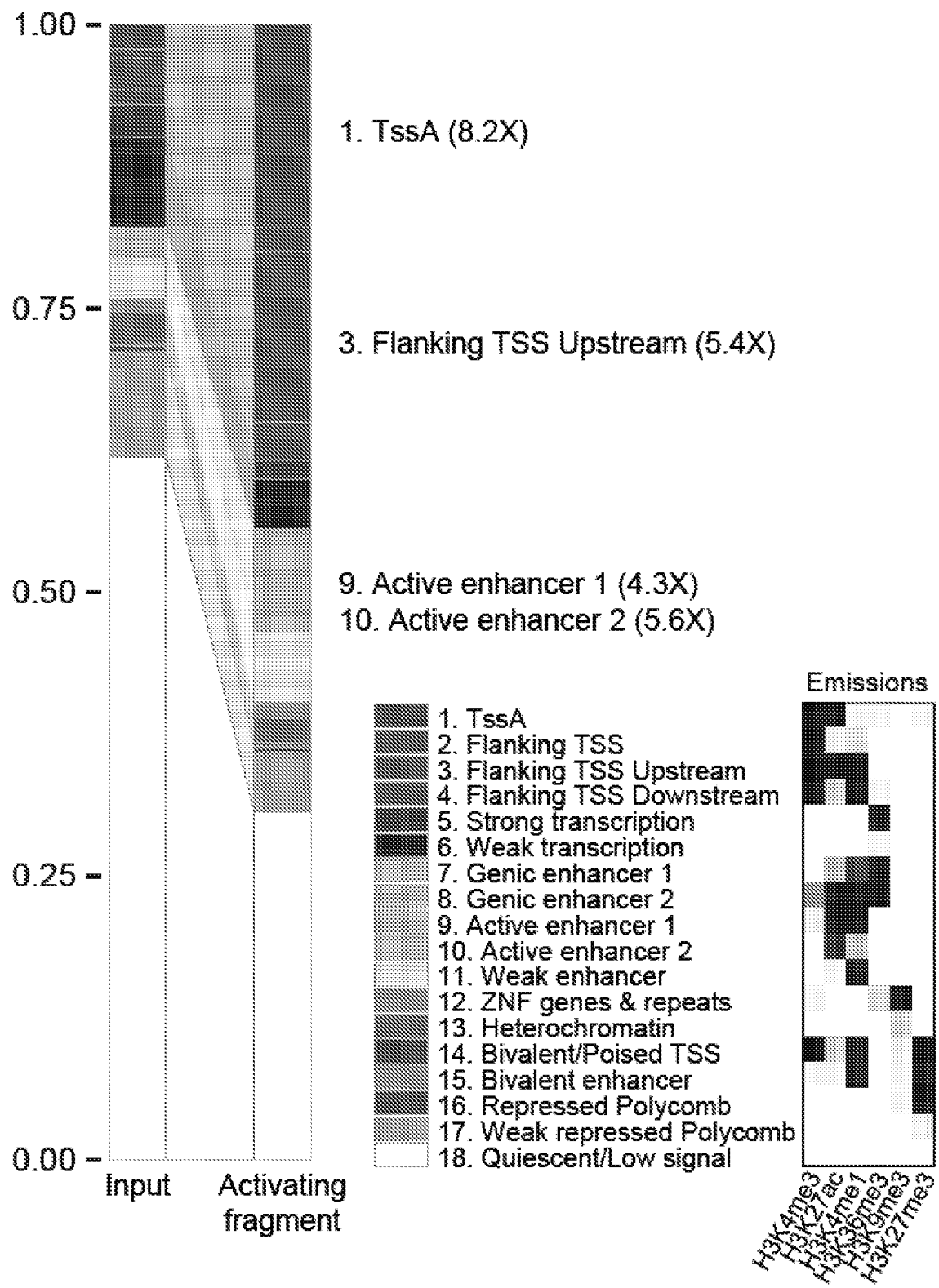
Figure 22B:
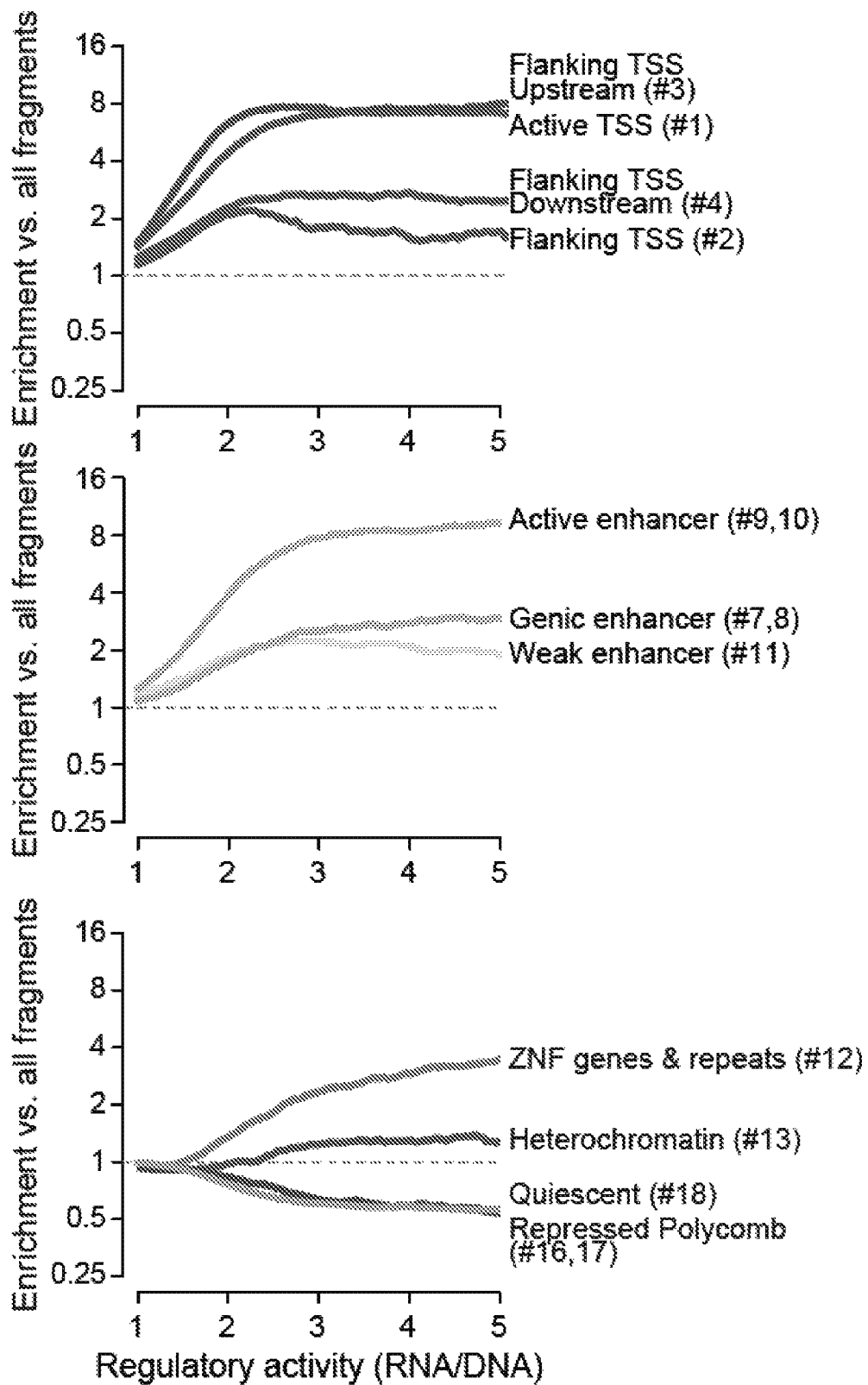
Figures 22C, 22D:
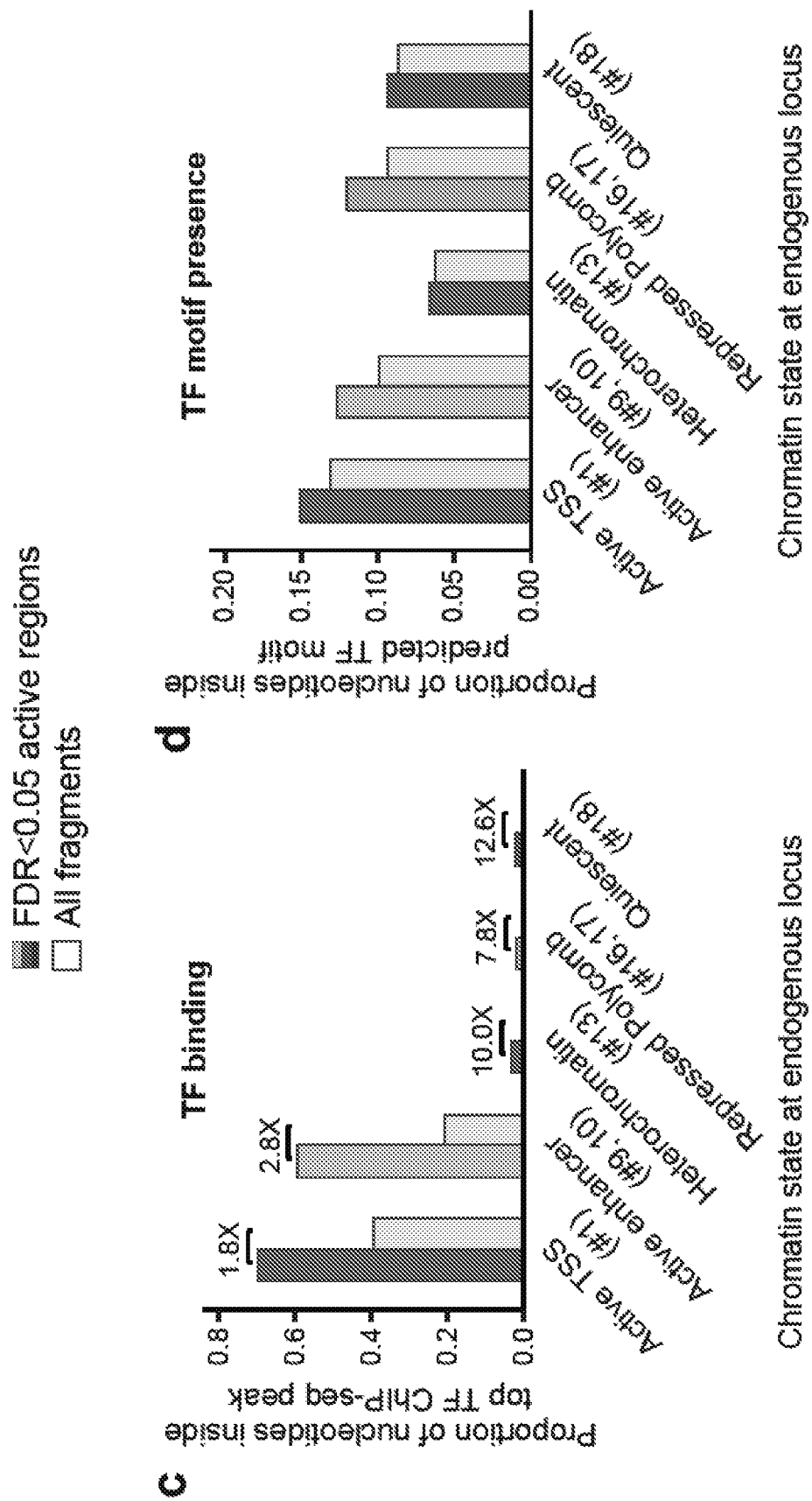

FIG. 22A-22D—Active HiDRA fragments are enriched in endogenously active regulatory regions. FIG. 22A: Overlap of active HiDRA fragments with different endogenous chromatin states. Heights correspond to proportion of nucleotides within active HiDRA fragments in each chromatin state. Inset: histone modification enrichments in each of 18 ChromHMM chromatin states. FIG. 22B: HiDRA fragment regulatory activity (fold-change increase in RNA levels) across different chromatin states. Numbers correspond to chromatin state numbers in 18-state ChromHMM model. FIG. 22C, FIG. 22D—Endogenously inactive genomic regions have low levels of TF binding (FIG. 22C) but comparable TF motif composition (FIG. 22D) to predicted active regions. Colored bars, regions from each chromatin state overlapping active HiDRA regions. Grey bars, regions from each chromatin state overlapping all fragments tested.

Figure 23A:
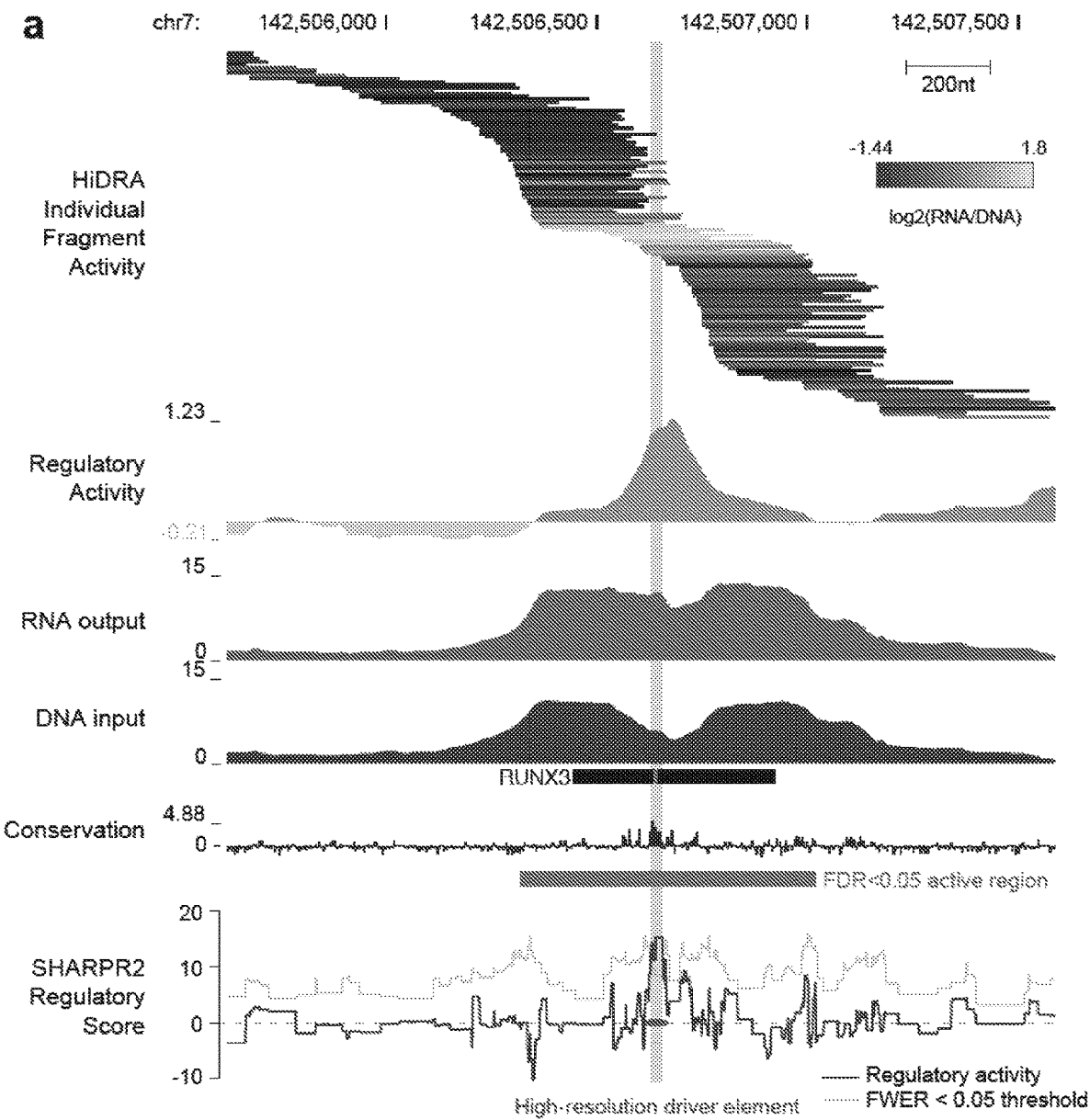
Figure 23B:
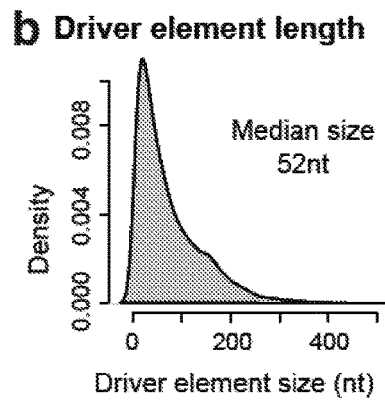
Figure 23C:
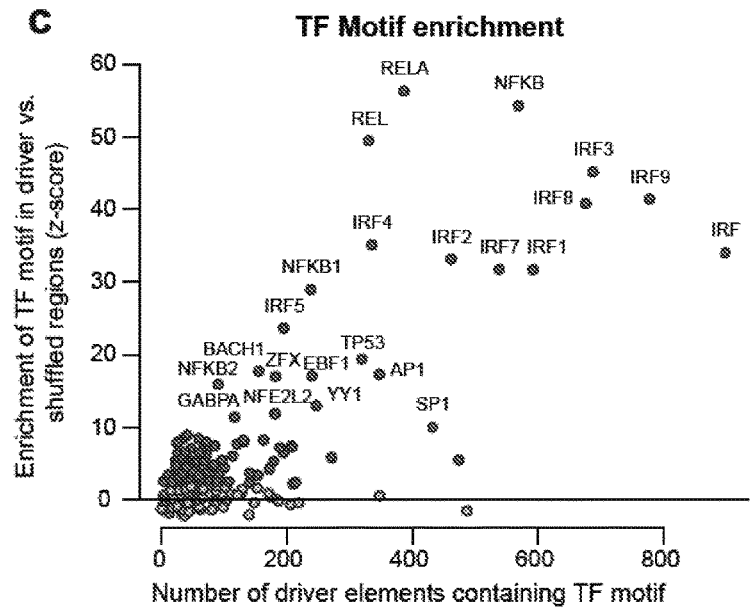

FIG. 23A-23F—High-resolution mapping of transcriptional regulatory elements with SHARPR-RE. FIG. 23A—Example region used in high-resolution mapping. Fragment activity shown on log2 scale with two fragments with highest and lowest activity removed for color scale to avoid outliers. The transparent red bar indicates the driver element identified at the regional FWER<0.05. FIG. 23B: Size distribution of driver elements. FIG. 23C: Enrichment of immune-related TF motifs in driver elements compared to shuffled driver elements within tiled regions.

Figure 23D:
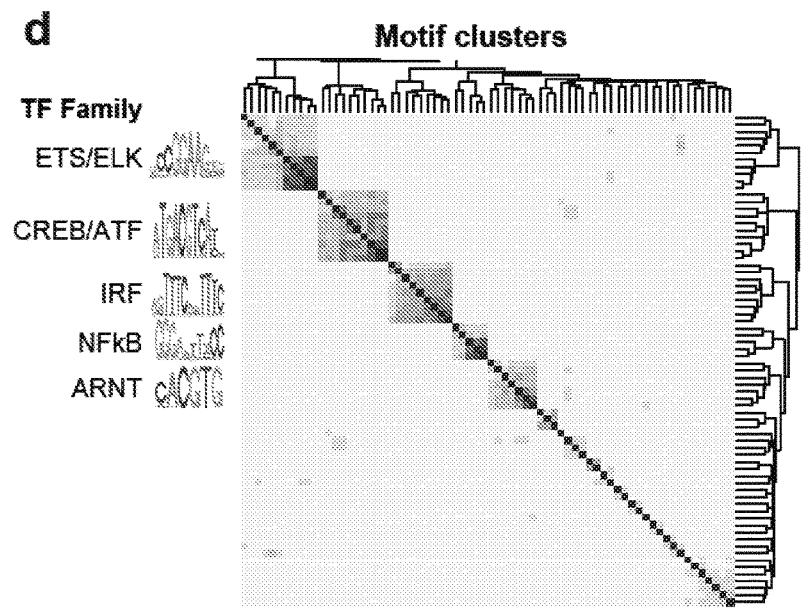
Figure 23E:
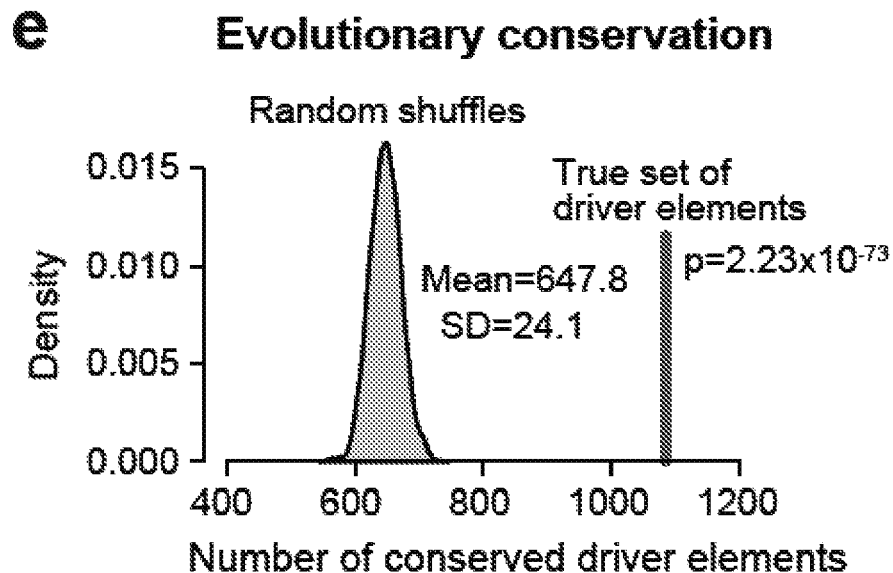
Figure 23F:
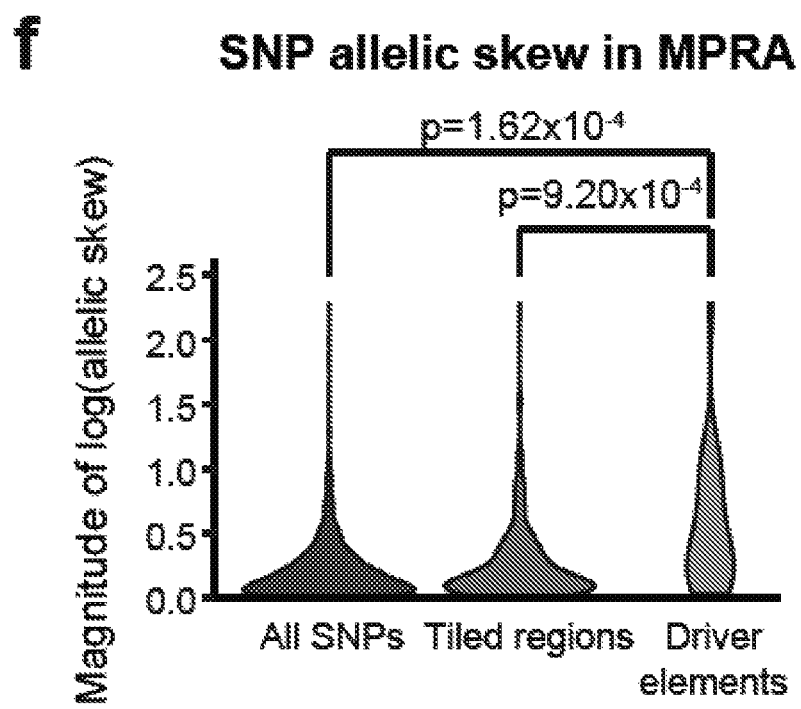

FIG. 23D: TF motifs enriched in driver elements cluster into groups of co-occurring motifs, suggesting diversity of TF motifs involved in transcriptional regulatory activity. FIG. 23E: Significantly more driver elements are evolutionary conserved compared to shuffled driver elements within tiled regions. Evolutionary conservation cut-off chosen as conservation score for top 5% of shuffled regions. FIG. 23F: SNPs within driver elements have significantly greater allelic skew by MPRA (Tewhey et al. Cell, 2016) compared to those within tiled regions or across the genome.

Figure 24A:
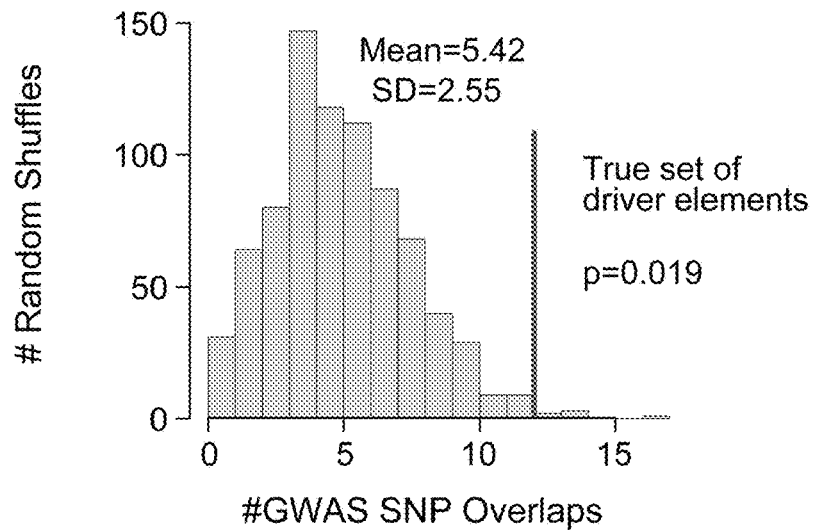
Figure 24B:
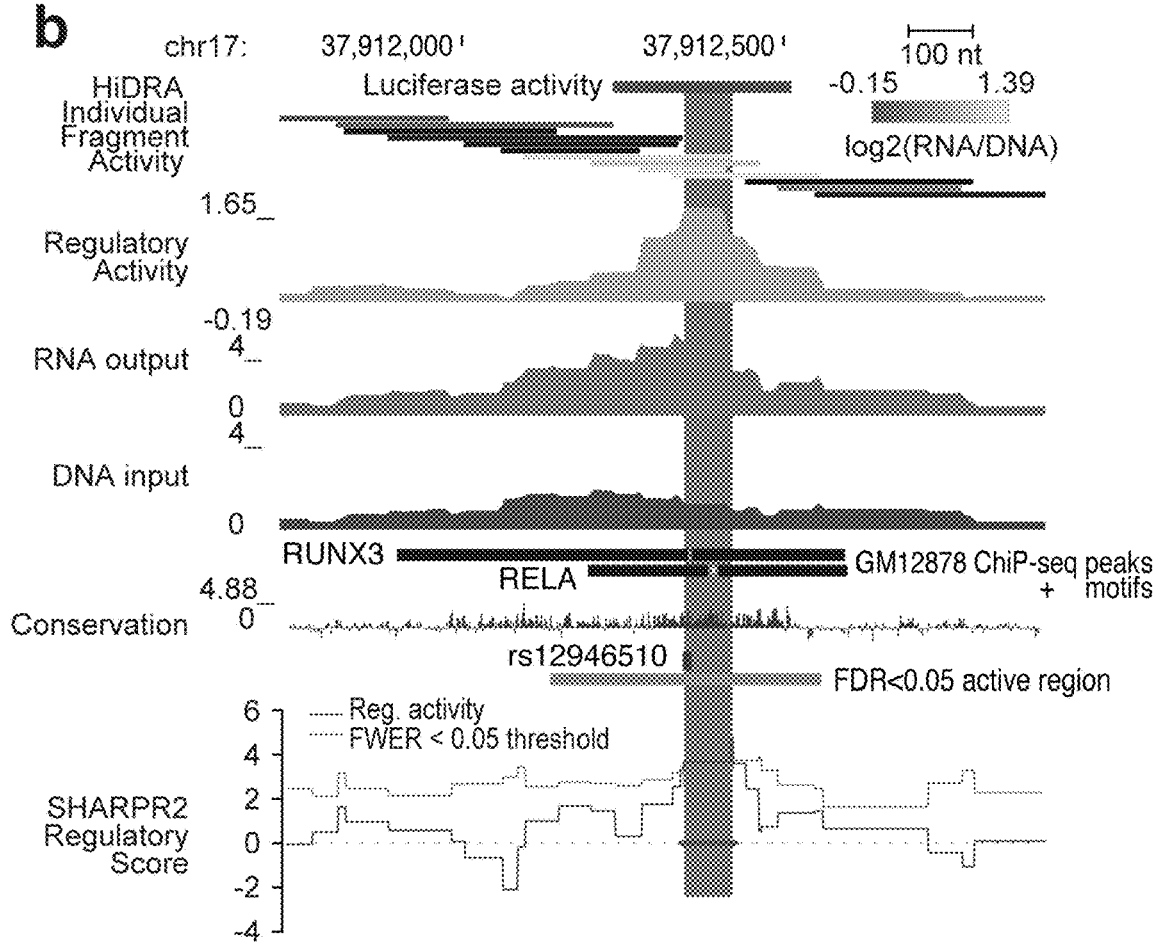

FIG. 24A-24B—High-resolution driver elements are enriched for fine-mapped GWAS SNPs. FIG. 24A: Driver elements overlap more GWAS fine-mapped SNPs associated with 21 human immune-related complex traits than randomly shuffled regions. p-value calculated empirically by random shuffling of driver element positions within tiled regions. FIG. 24B: Example locus at rs12946510 that overlaps a high-resolution driver element. Highlighted segment indicates the driver element identified at the regional FWER<0.05. Red bar at top corresponds to region with luciferase activity as demonstrated by Hitomi et al. (2017).

Figure 25A:
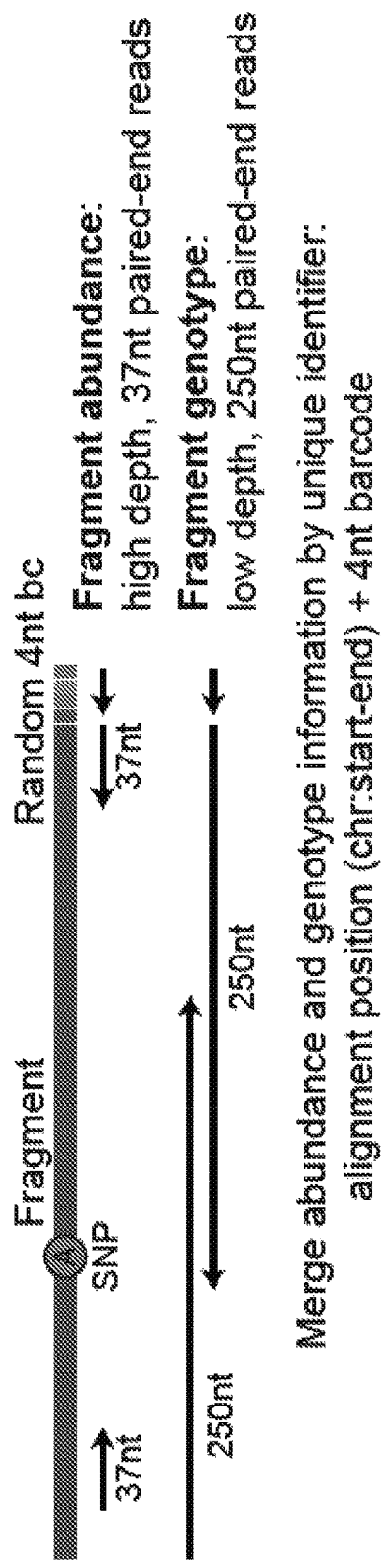
Figures 25B, 25C, 25D:
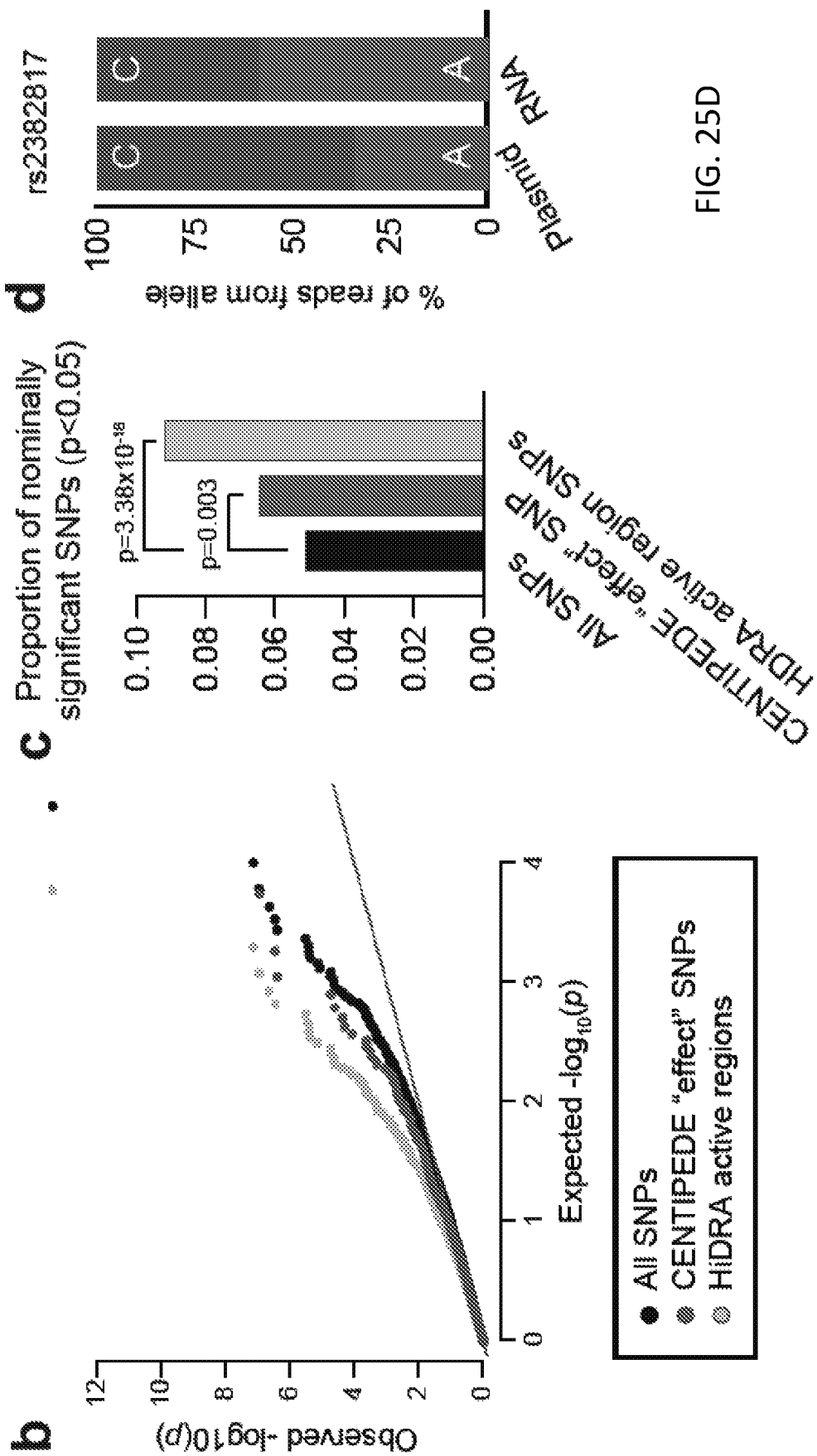

FIG. 25A-25E—Identification of human genetic variants that alter HiDRA activity. FIG. 25A: Overview of genotyping approach for HiDRA fragments. HiDRA fragments were originally quantified at high-depth using 37nt paired-end reads. At this read length the allele composition of fragments is mostly unobserved. As every HiDRA fragment has a unique identifier (genomic alignment position and random 4nt barcode), long-read re-sequencing of the HiDRA library can assign SNP genotypes to fragments that were previously quantified for activity using short reads. FIG. 25B: q-q plot for allelic imbalance at SNPs covered by HiDRA fragments. CENTIPEDE "effect" SNPs were identified by Moyer-brailean et al. (2016). FIG. 25C: "Effect" SNPs and SNPs within HiDRA active regions are more likely to be nominally significant for allelic imbalance. p-values from Fisher's exact test. FIG. 25D: The A allele of rs2382817, a SNP associated with inflammatory bowel disease, is more active in the HiDRA assay than the C allele.

Figure 25E:
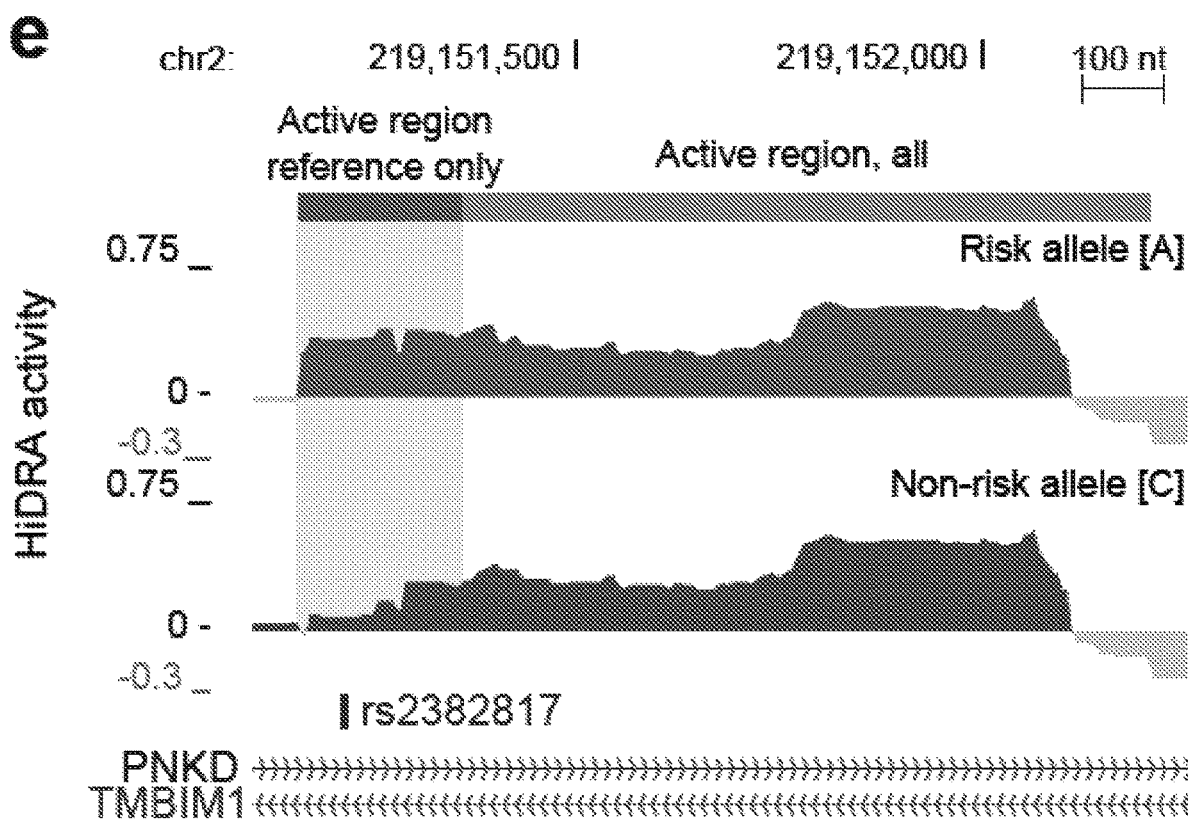

FIG. 25E: Alelle-specific HiDRA activity signal tracks for rs2382817.

Figure 26A:
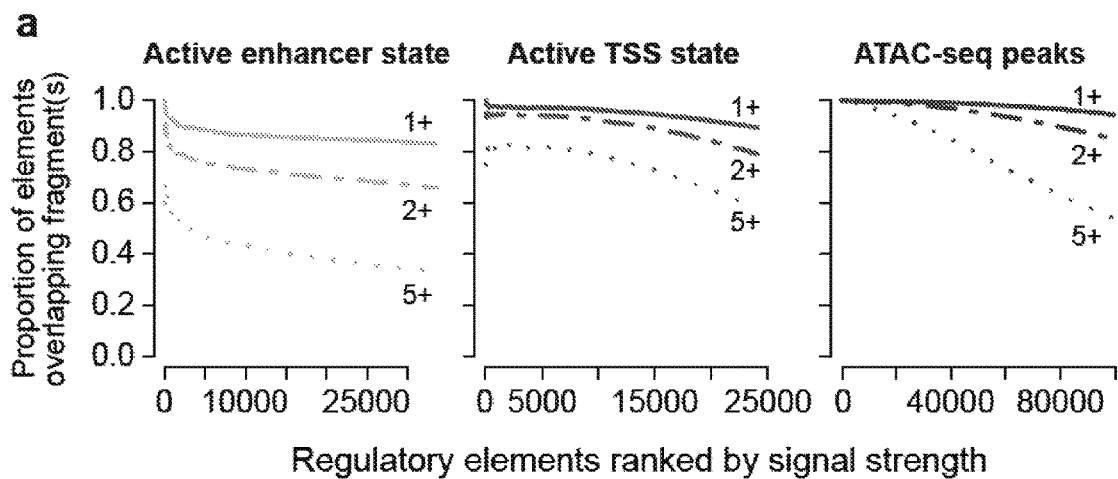
Figure 26B:
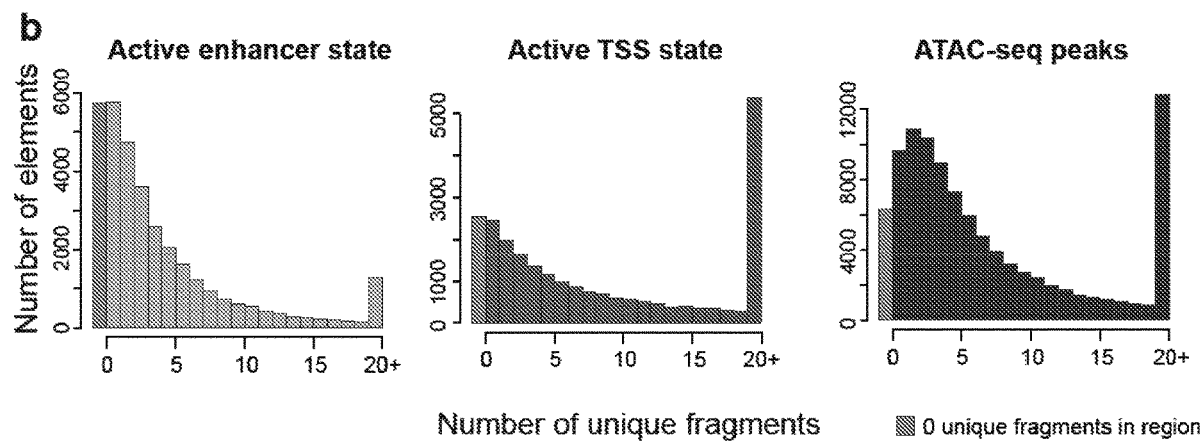
Figure 26C:
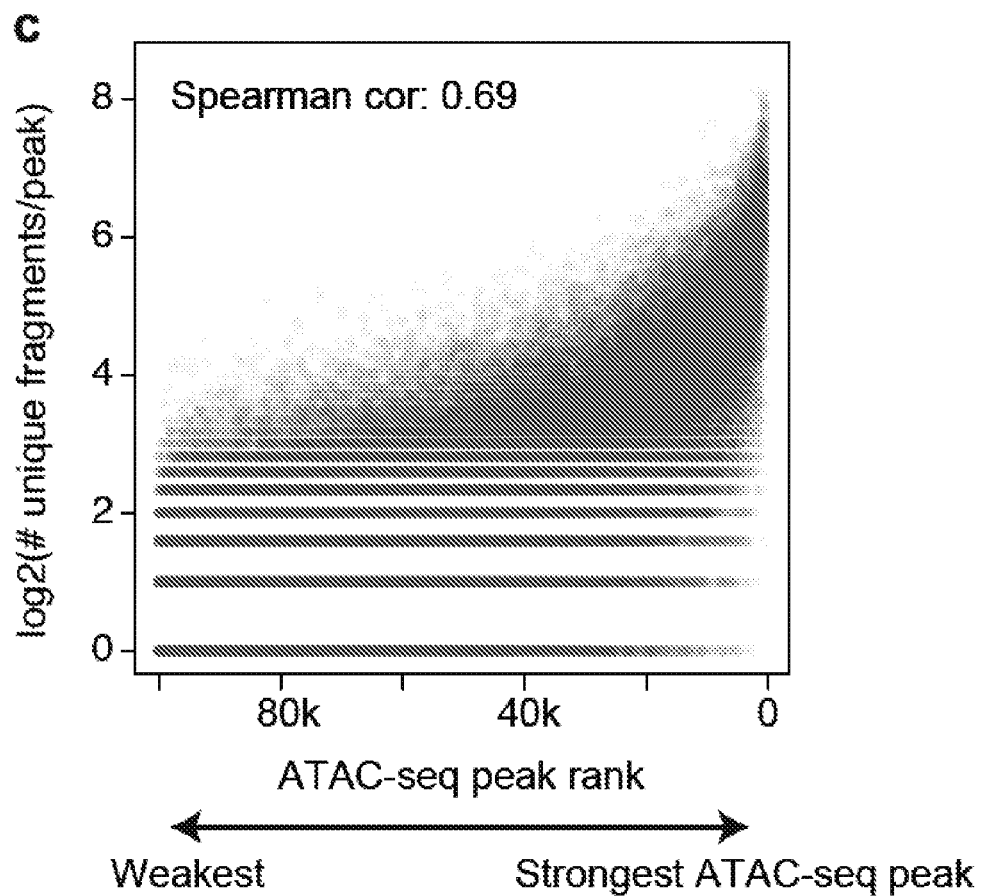
Figure 27A:
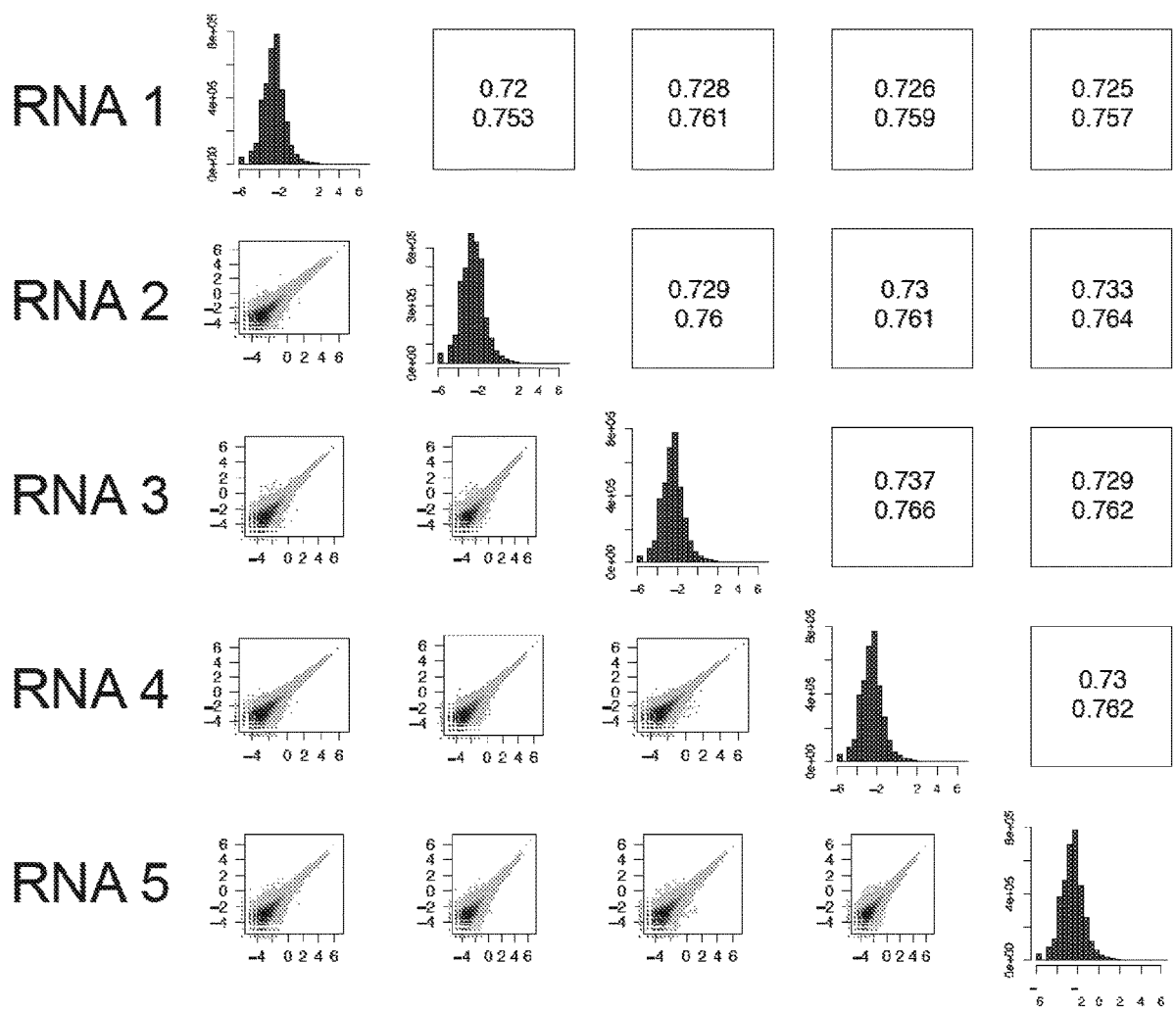
Figure 27B:
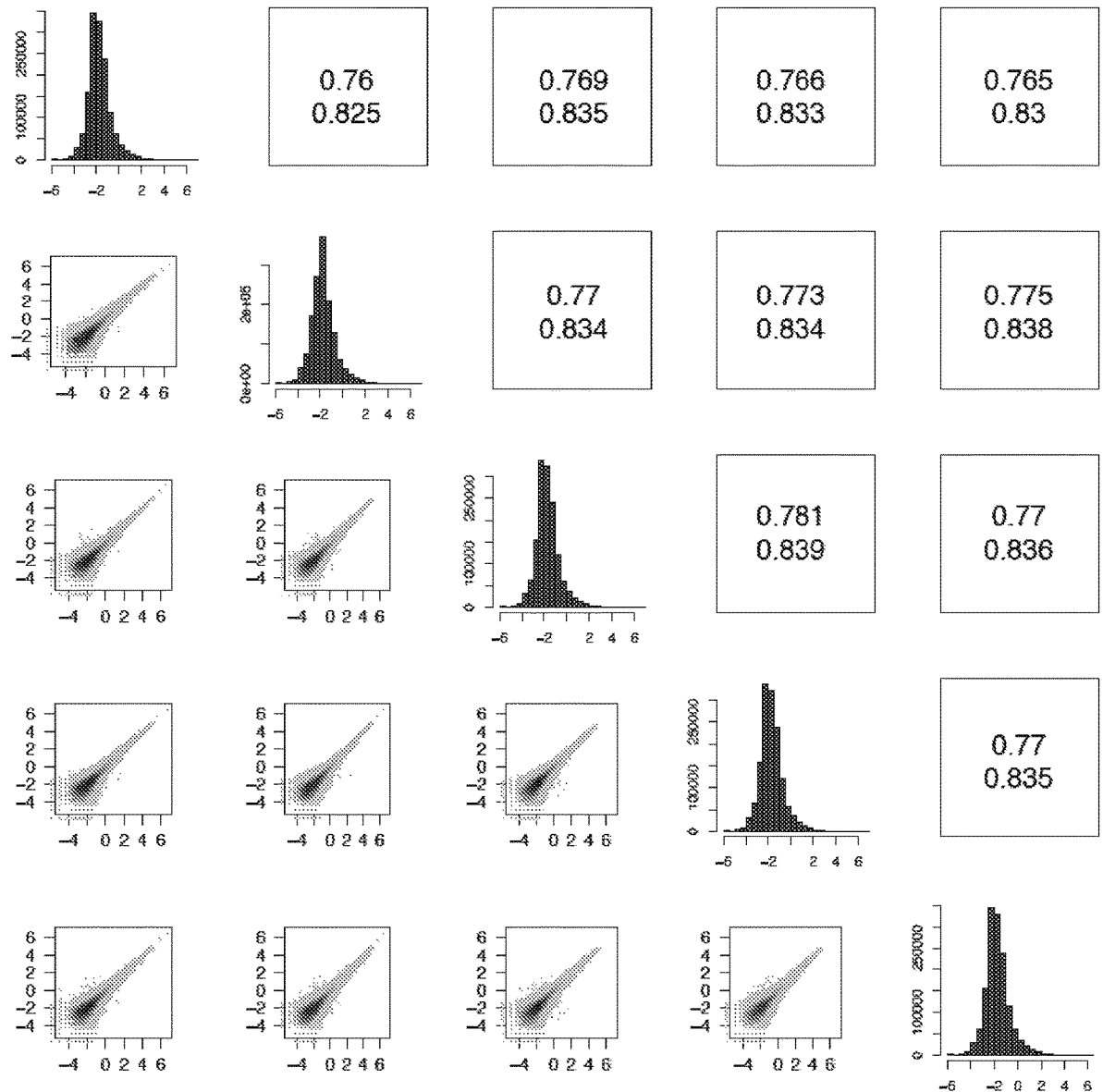
Figure 27C:
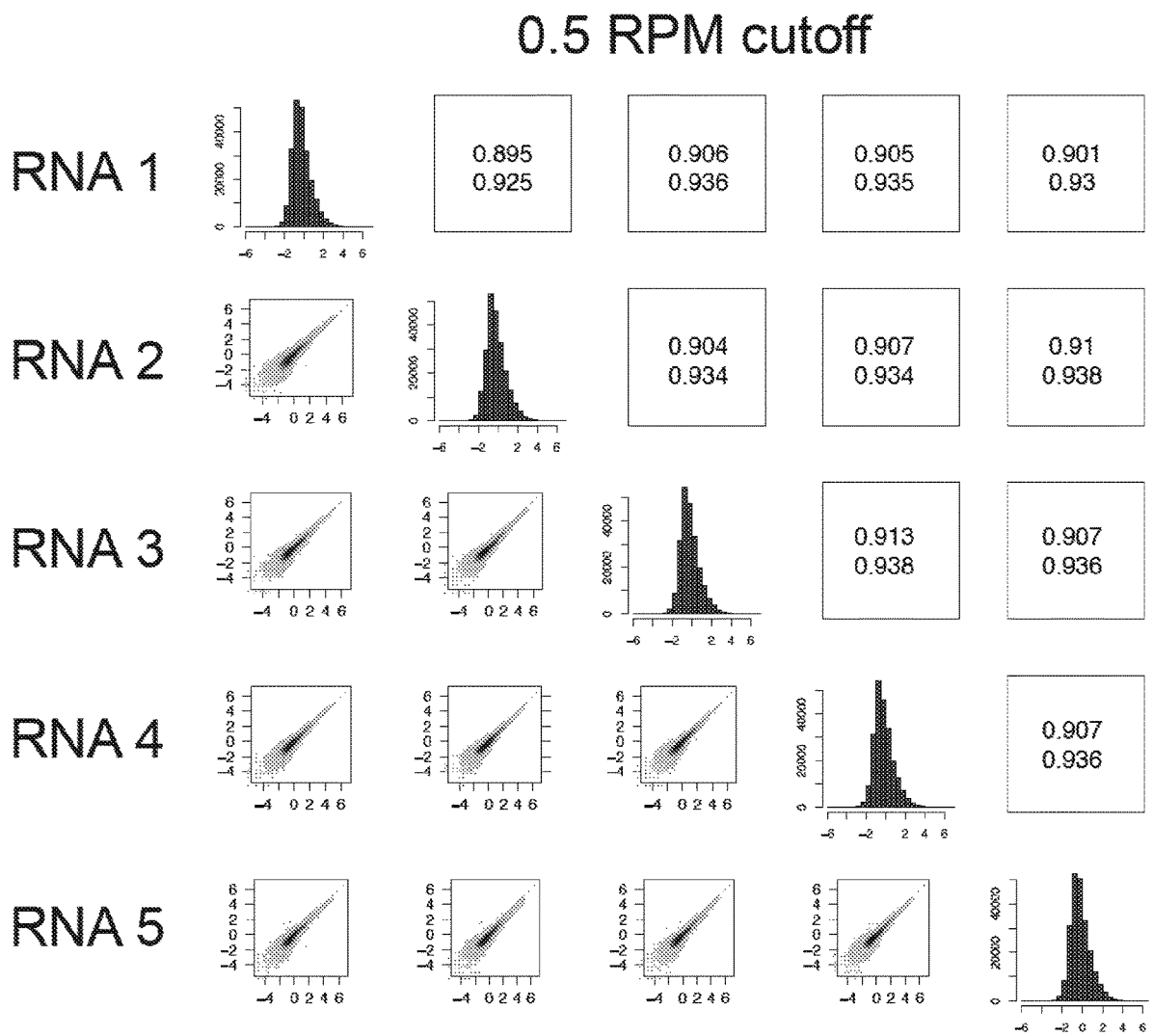
Figure 27D:
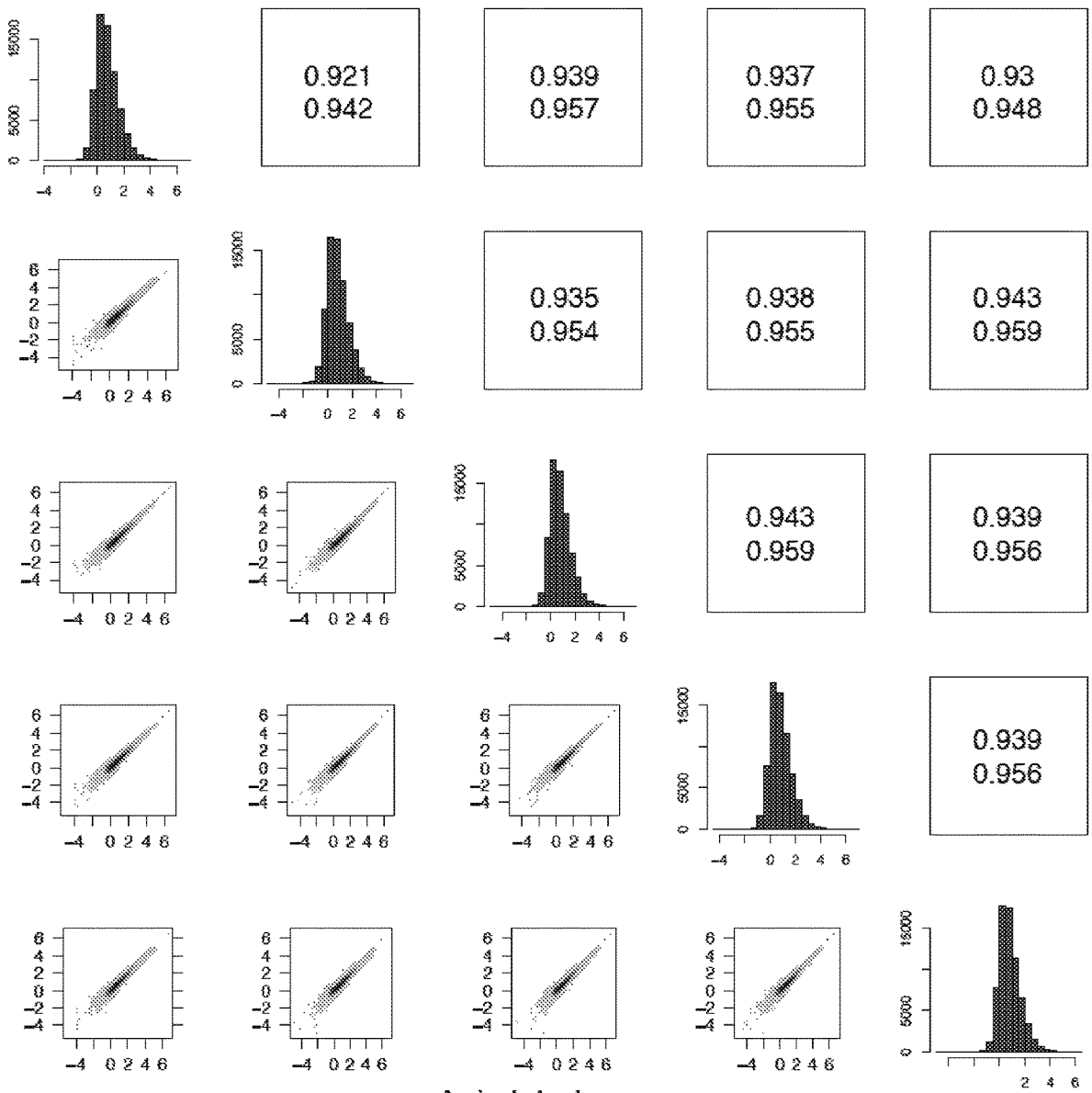

FIG. 26A-26C—HiDRA coverage is greater for highly active regulatory elements. (FIG. 26A) ChromHMM-defined active enhancer and active TSS chromatin states were ranked by H3K27ac signal strength, and ATAC-seq peaks were ranked by density of ATAC-seq reads from Buenrostro et al. (2013). Solid, dashed and dotted lines correspond to coverage with at least 1, 2 and 5 unique HiDRA fragments. (FIG. 26B) Number of unique HiDRA fragments in ChromHMM-defined active enhancer and active TSS elements, and ATAC-seq peaks. (FIG. 26C) Positive relationship between ATAC-seq peak strength and number of unique HiDRA fragments. Discrete bands at bottom of scatterplot represent peaks with 1-6 unique fragments.

FIG. 27A-27D—Correlation between RNA samples from HiDRA. Correlation is shown at four different RPM cut-offs (FIG. 27A for 0.1 RPM cutoff, FIG. 27B for 0.2 PRM cutoff, FIG. 27C for 0.5 RPM cutoff, and FIG. 27D for 1.0 RPM cutoff). Only fragments passing the minimum RPM cut-off in plasmid samples are shown. Unlike gene expression analysis where read counts from many unique fragments are collapsed into one gene expression value, in HiDRA we consider each fragment on its own. Given the high number of unique features in HiDRA, Poisson "shot noise" will decrease correlations between replicates for low RPM cutoffs.

Figure 28:
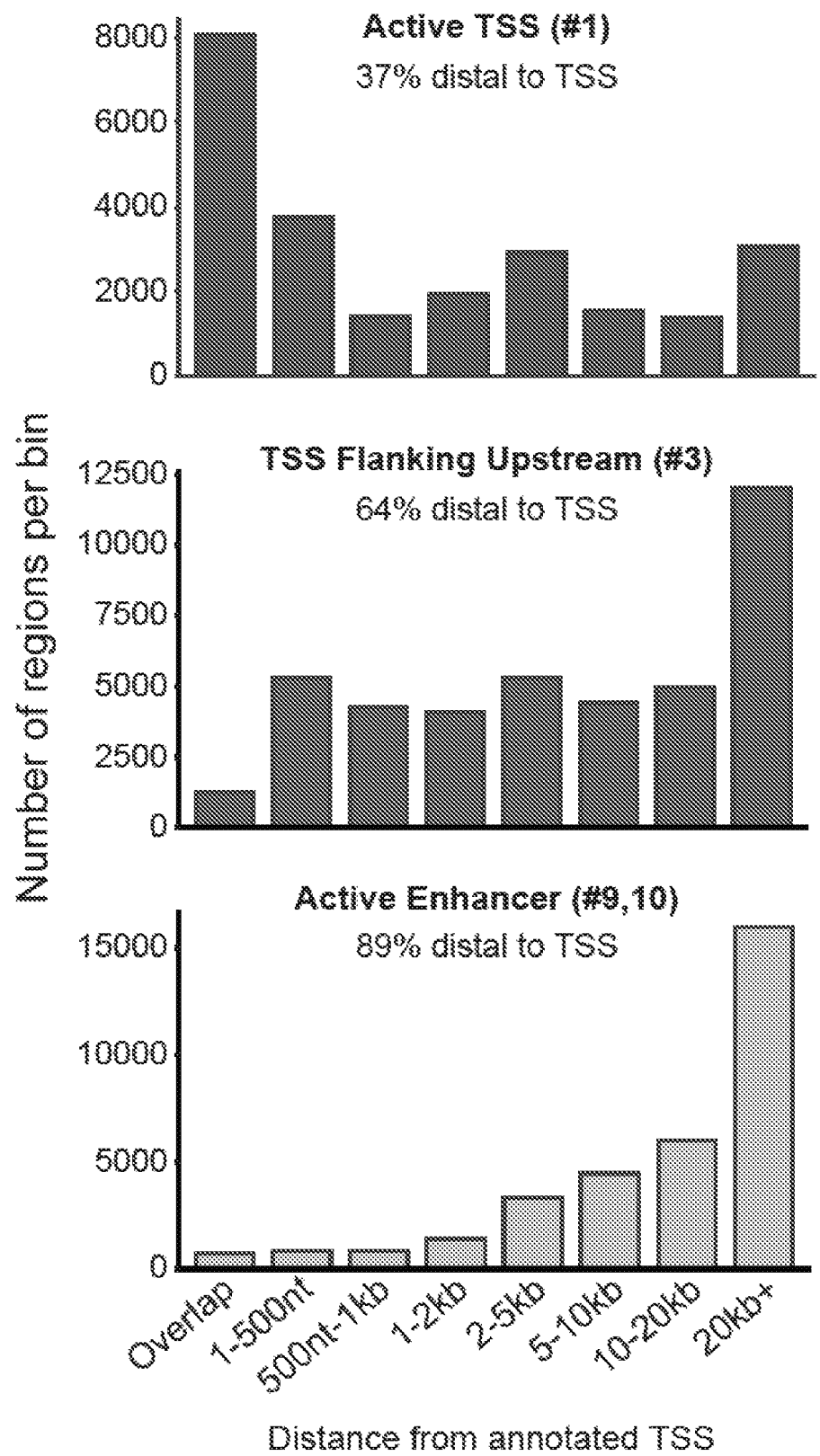

FIG. 28—Genomic distribution of TSS Flanking Upstream regions. The majority of ChromHMNI-predicted TssFlnkUp regions are not near annotated TSSs, but share a similar genomic distribution pattern to predicted active enhancers.

FIG. 29A-29F—Enrichment of motifs in active HiDRA regions. (FIG. 29A) HiDRA fragments within active enhancer state regions have greater regulatory activity than those within active TSS state regions. (FIG. 29B) Motif enrichment is calculated separately for active TSS state regions (left) and active enhancer state regions (right) that overlap active HiDRA fragments. Only top 16 motifs are shown for each group after filtering to keep only motifs corresponding to expressed TFs in GM12878 (RPKM>5). Numbers within bars correspond to false discovery rate. (FIG. 29C) Top motifs that are differentially enriched in enhancer vs. active TSS states. (FIG. 29D) Top motifs enriched in enhancer and active TSS states are largely distinct from each other (FIG. 29E) Proportion of nucleotides inside motifs for highly and lowly active fragments in enhancers and active TSS regions. (FIG. 29F) Enriched motifs in highly active enhancer (left) and active TSS (right) regions.

Figure 30:
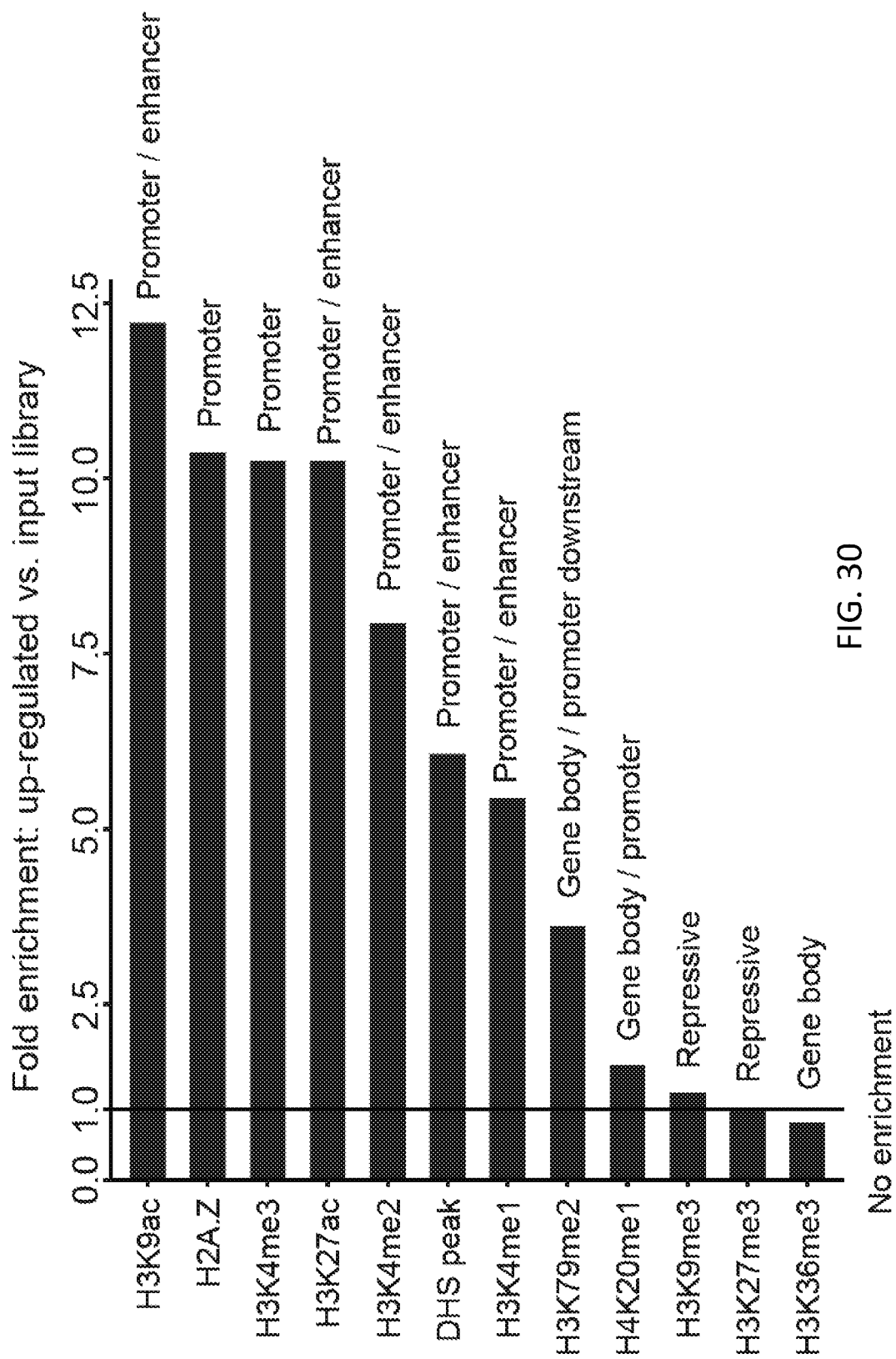

FIG. 30—Enrichment of histone modifications in active HiDRA fragments. All histone modifications and DHS data were collected from GM12878 cells by the ENCODE or Roadmap Epigenomics projects.

Figure 31:
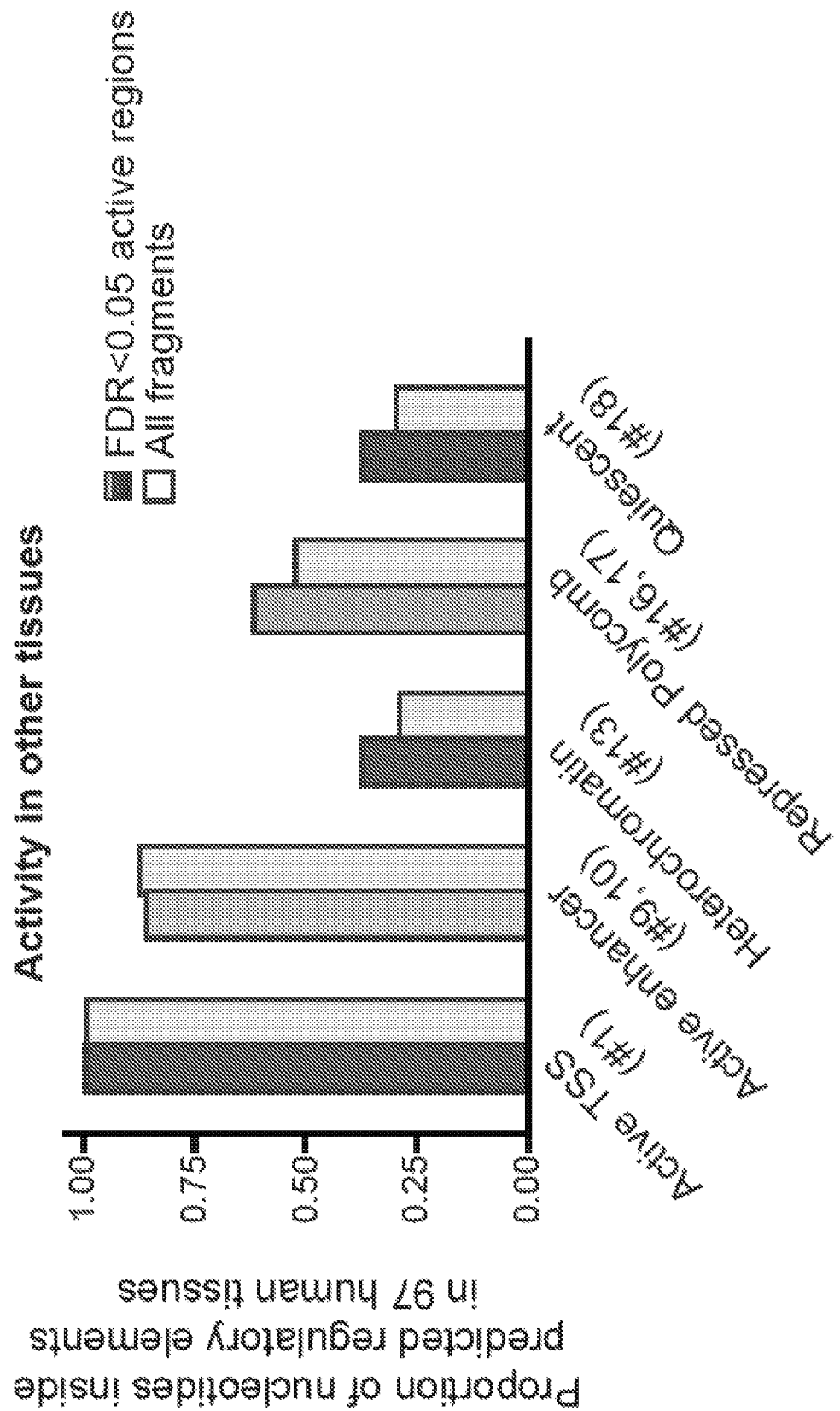

FIG. 31—Endogenously inactive chromatin states overlapping active HiDRA fragments are more likely to be active in 97 other (non-GM12878) human tissues. No difference observed for endogenously active regions. Colored bars, regions from each chromatin state overlapping active HiDRA regions. Grey bars, regions from each chromatin state overlapping all HiDRA fragments tested.

Figure 32A:
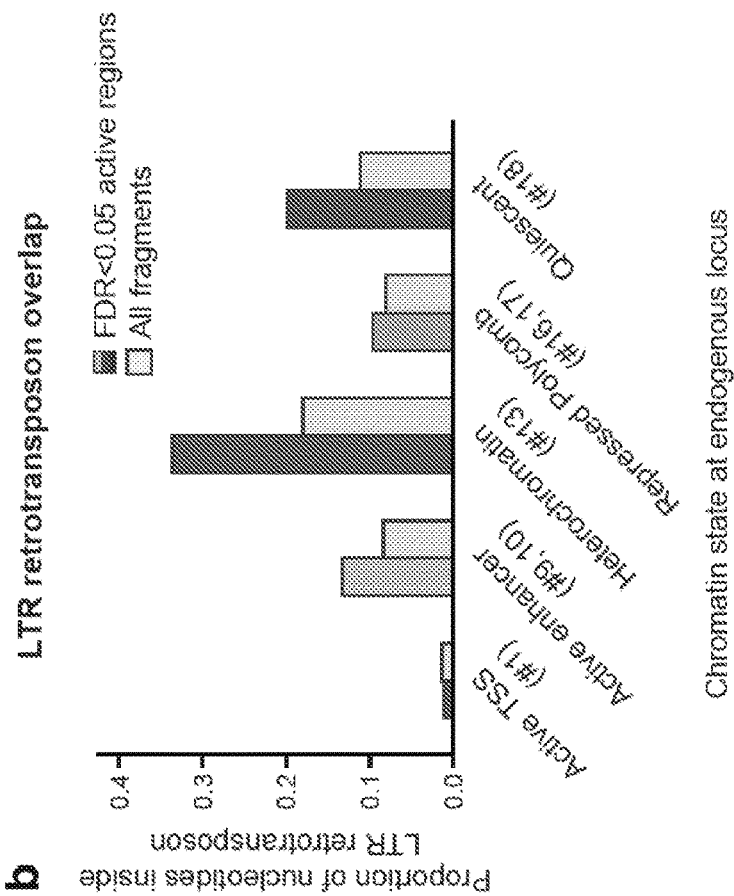
Figure 32B:
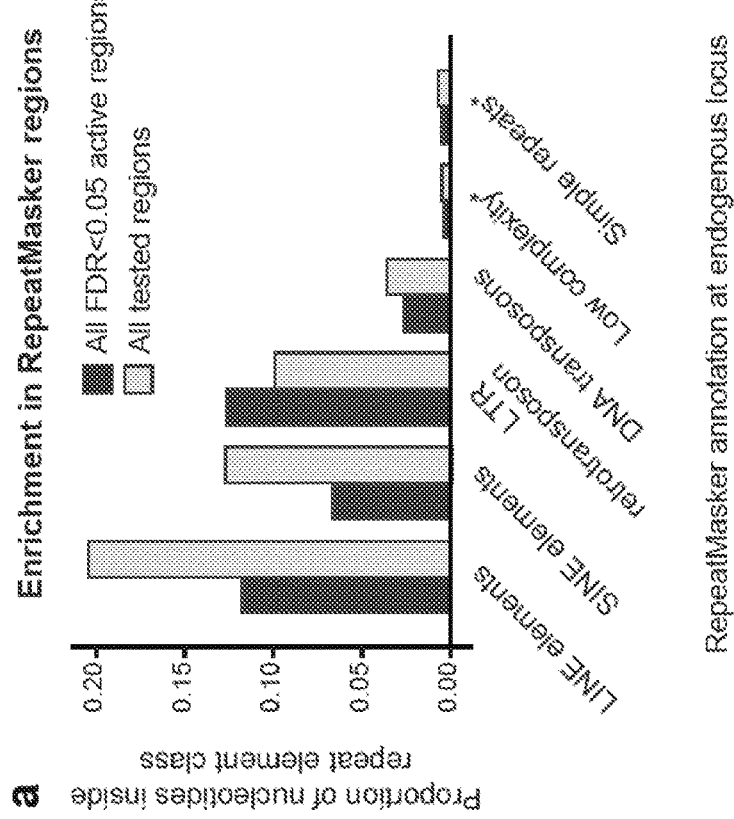

FIG. 32A-32B—LTR retrotransposon repeat elements are enriched within active HiDRA regions in endogenously inactive chromatin states. (FIG. 32A) Elements identified using RepeatMasker annotation of the hg19 human genome. (*) Low complexity and Simple Repeat classes are artificially low due to pre-filtering to remove HiDRA fragments mapping to multiple genomic locations. (FIG. 32B) Endogenously inactive chromatin states overlapping active HiDRA fragments are enriched for LTR retrotransposons compared to endogenously active regions. Colored bars, regions from each chromatin state overlapping active HiDRA regions. Grey bars, regions from each chromatin state overlapping all HiDRA fragments tested.

Figure 33:
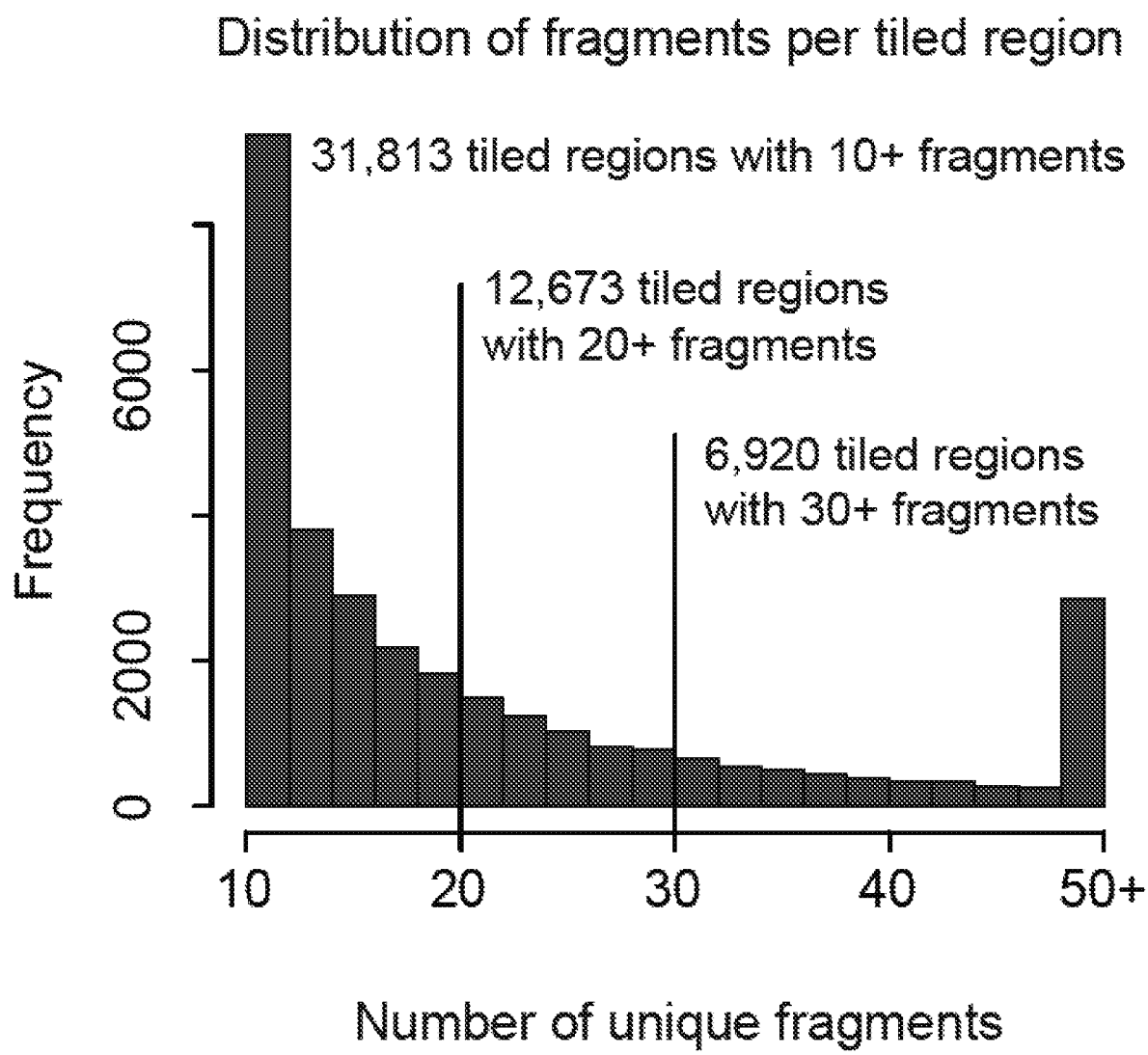

FIG. 33—Number of unique fragments per tiled region for high-resolution mapping.

Figure 34:
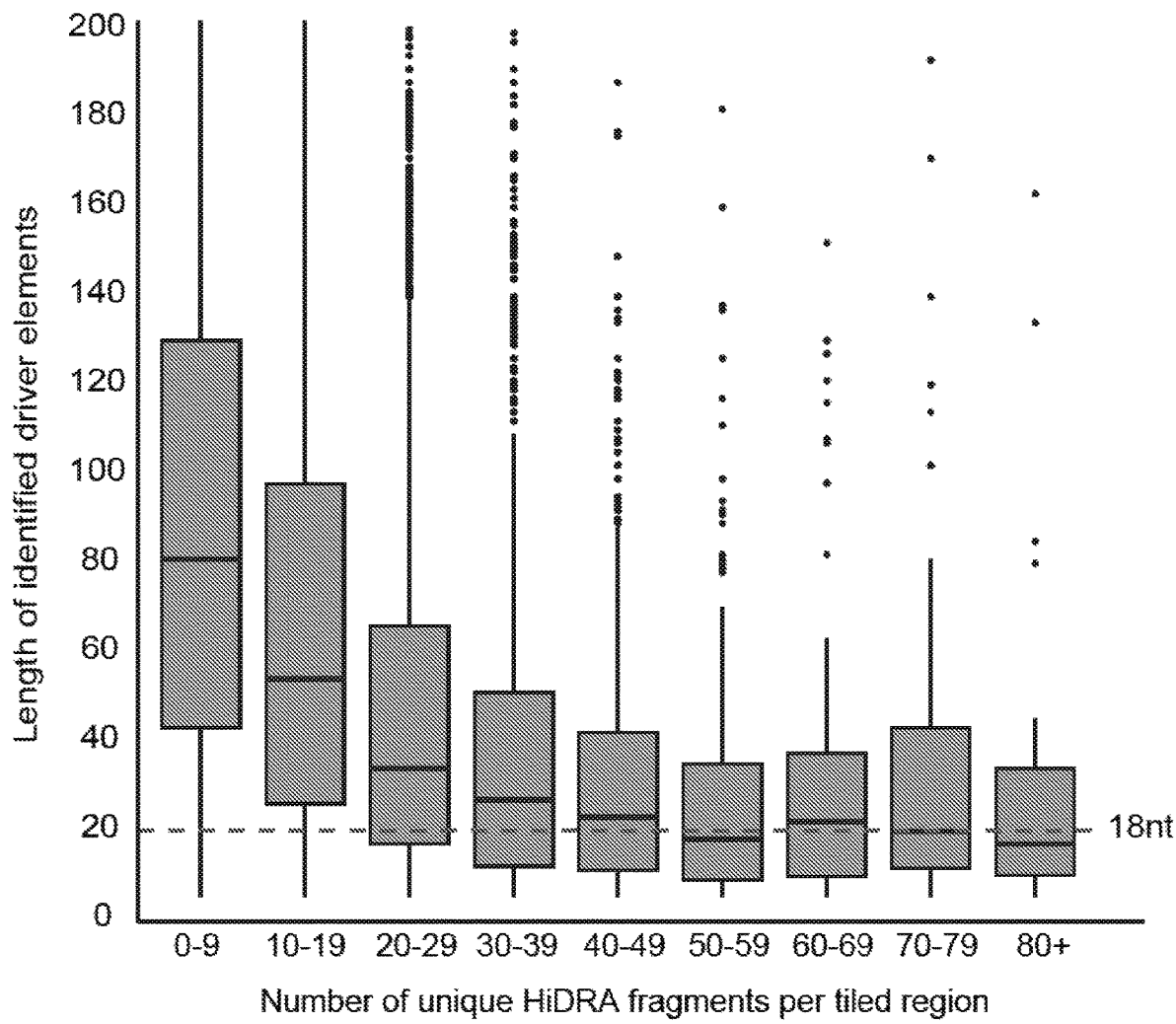

FIG. 34—Length of high-resolution driver elements depends on coverage. Driver elements identified by SHARPR-RE are smaller in size for tiled regions covered by more fragments. Decrease in driver element size plateaus around 40-50 HiDRA fragments, to reach an expected minimum size of ~18nt.

Figures 35A, 35B:
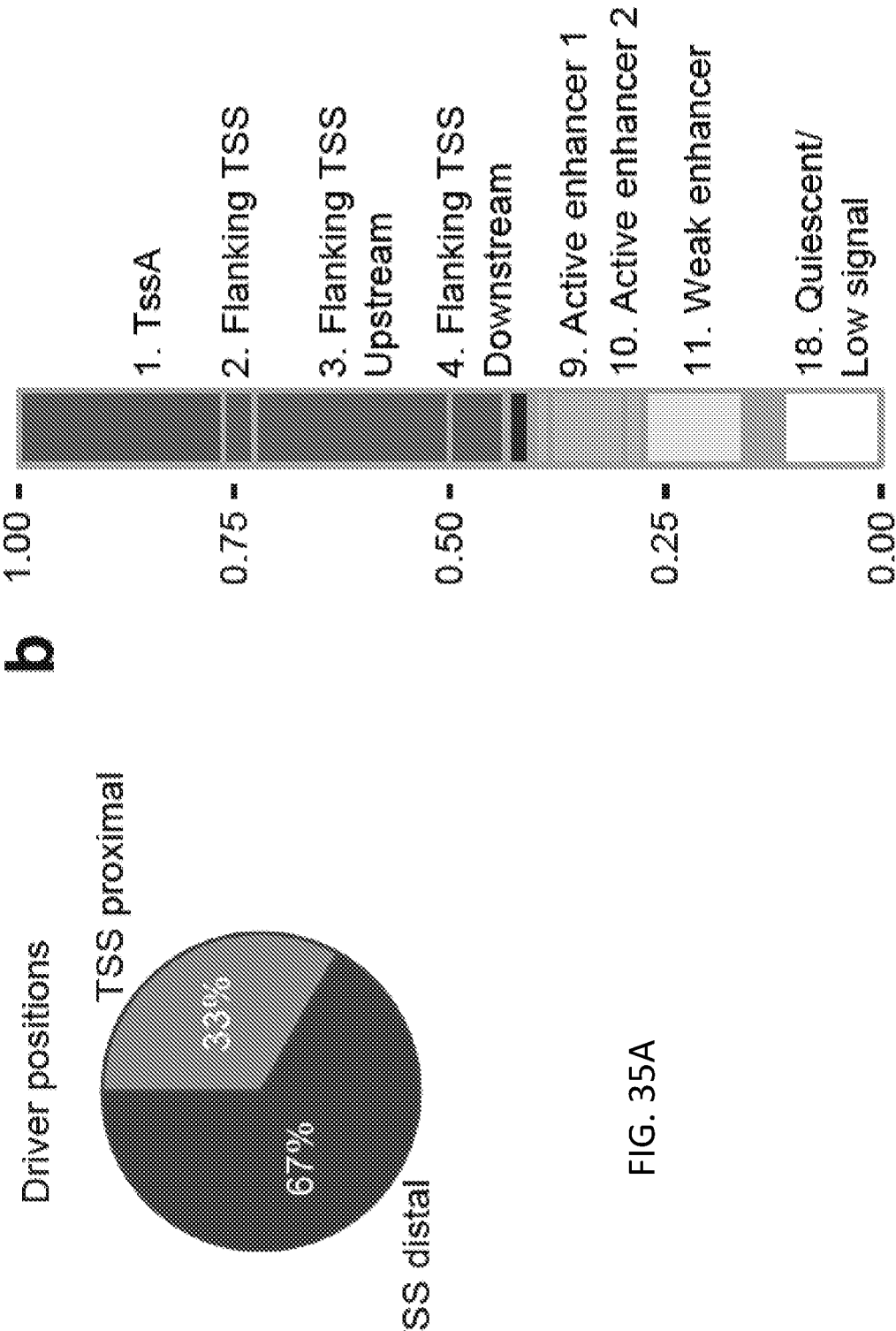

FIG. 35A-35B—Genomic distribution of HiDRA driver elements. (FIG. 35A) The majority of driver elements are distal to annotated transcription start sites (FIG. 35B) Genomic distribution of driver elements reveals that majority of driver elements are found in TSS, TSS-flanking and predicted enhancer regions.

Figures 36A, 36B:
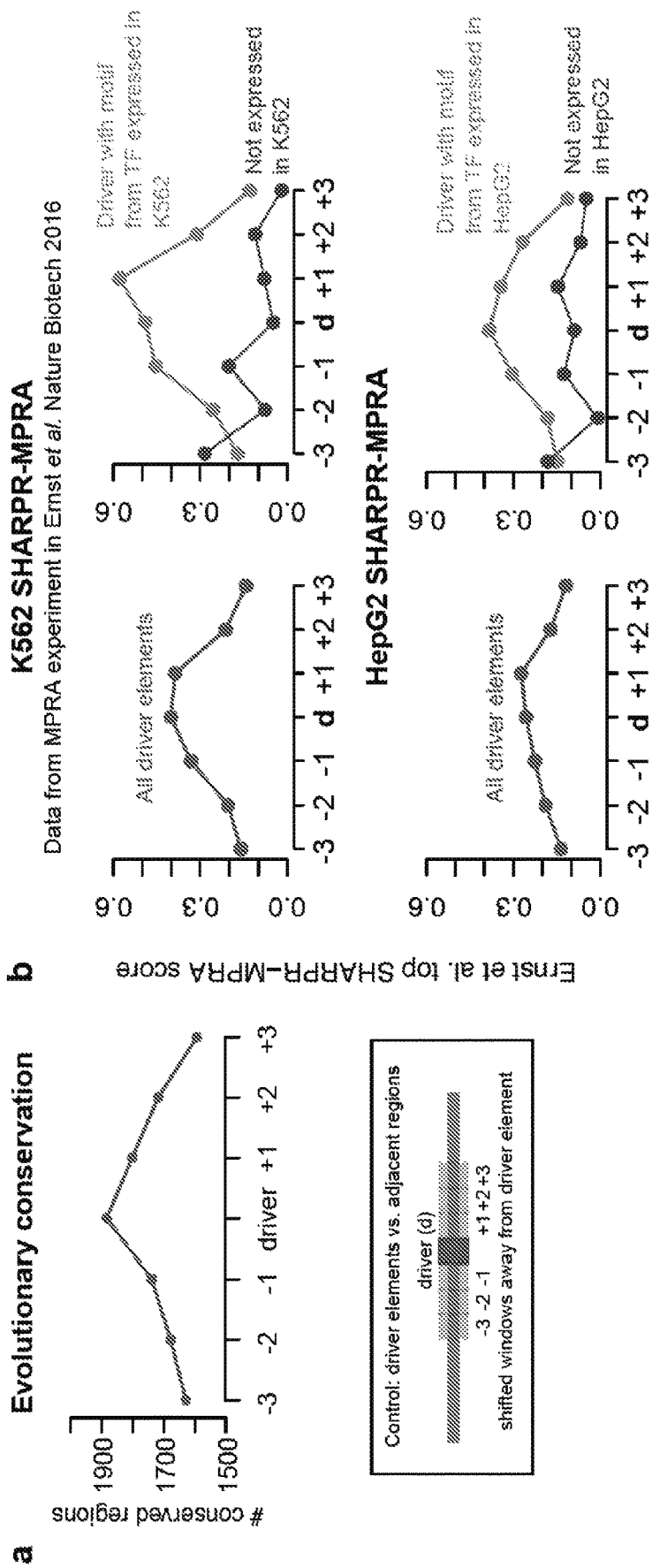

FIG. 36A-36B—Additional functional properties of driver elements. (FIG. 36A) Driver elements have greater evolutionary conservation compared to adjacent regions both upstream and downstream. +/−1,2,3 values represent control windows of equal size to the driver element shifted upstream (− values) and downstream (+ values) by the length of the driver element. (FIG. 36B) Left, Driver elements show greater functional importance scores from independent SHARPR-MPRA experiment in both K562 and HepG2. +/−1,2,3 values correspond to controls used in panel a. Right, functional importance scores for driver elements in K562 and HepG2 driven by drivers containing motifs from TFs expressed in respective cell lines.

Figure 37:
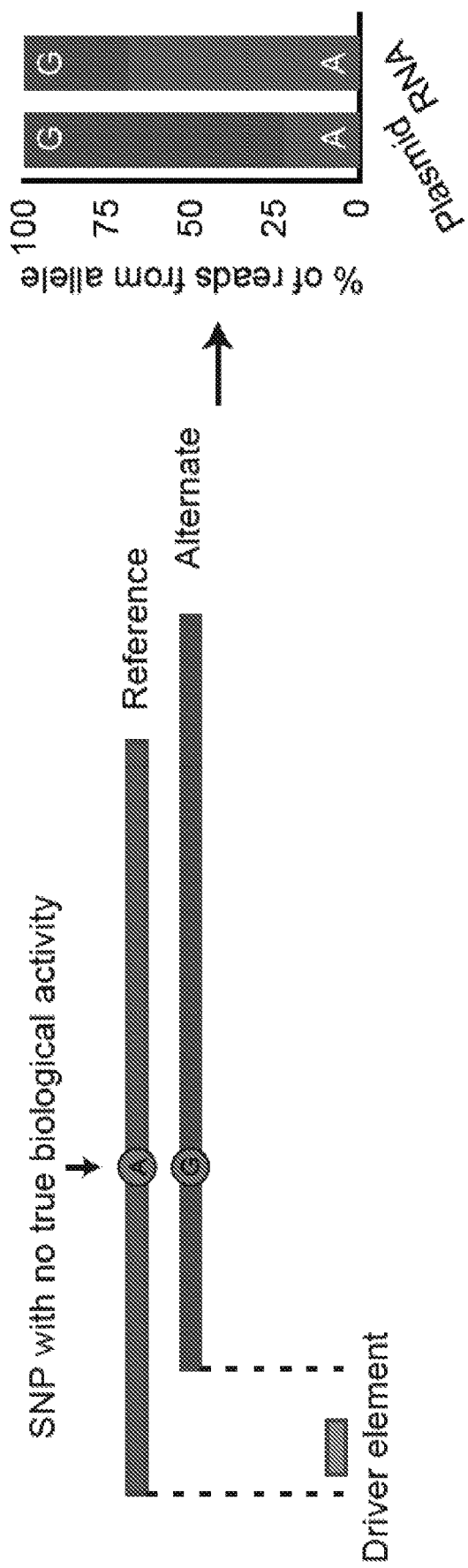

FIG. 37—Confounding effect of differing fragment positions for allelic activity analyses As HiDRA relies on random fragmentation of the genome, fragments carrying different alleles at a SNP might have differential activity due to the position of their ends, rather than due to allelic activity. In this hypothetical example, a SNP with no true allelic activity is mistakenly called as active because the fragment containing the reference allele overlaps a driver element not present in the alternate fragment.

Figure 38:
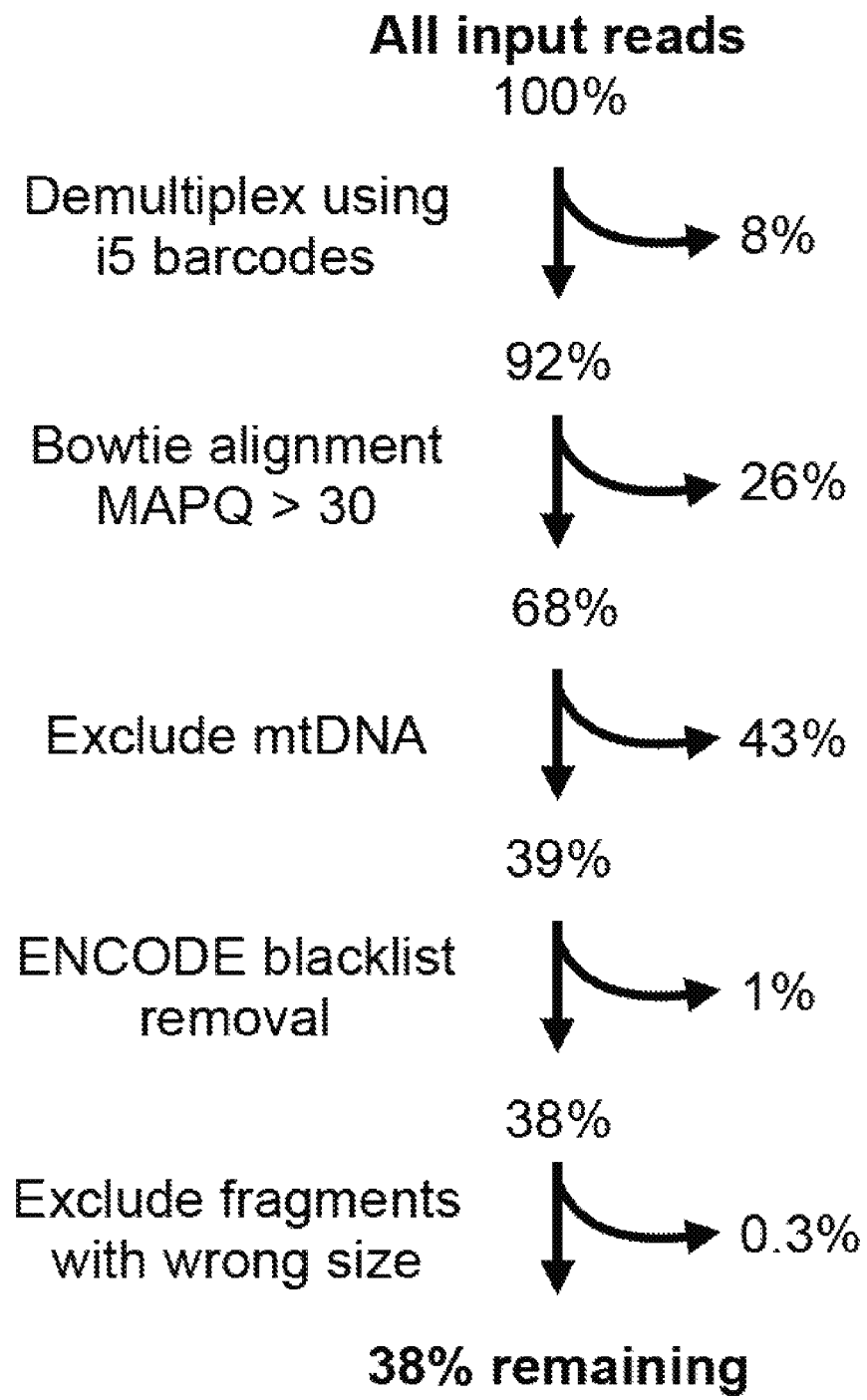

FIG. 38—Proportion of reads lost by each processing filter for HiDRA library.

Figures 39A, 39B:
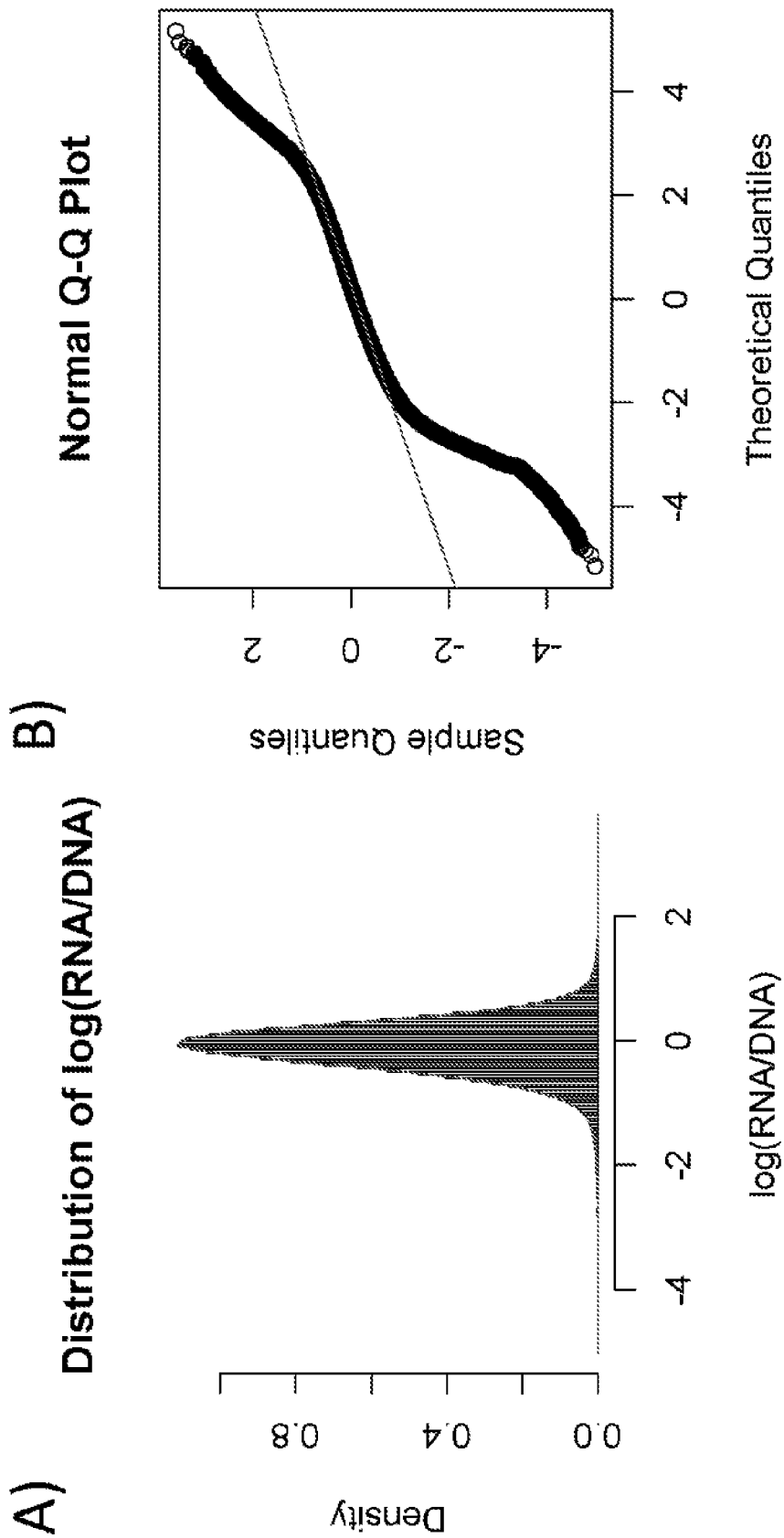

FIG. 39A-39B—FIG. 39A: A histogram with a density curve of ln(#RNA/#DNA) of the fragments from the library described in the method section. The distribution of ln(#RNA/#DNA) is closer to a normal distribution. The exclusion criteria for the fragments are length<100 or length>600. FIG. 39B: The Q-Q plot suggests that this is a heavy-tailed distribution.

Figure 40A:
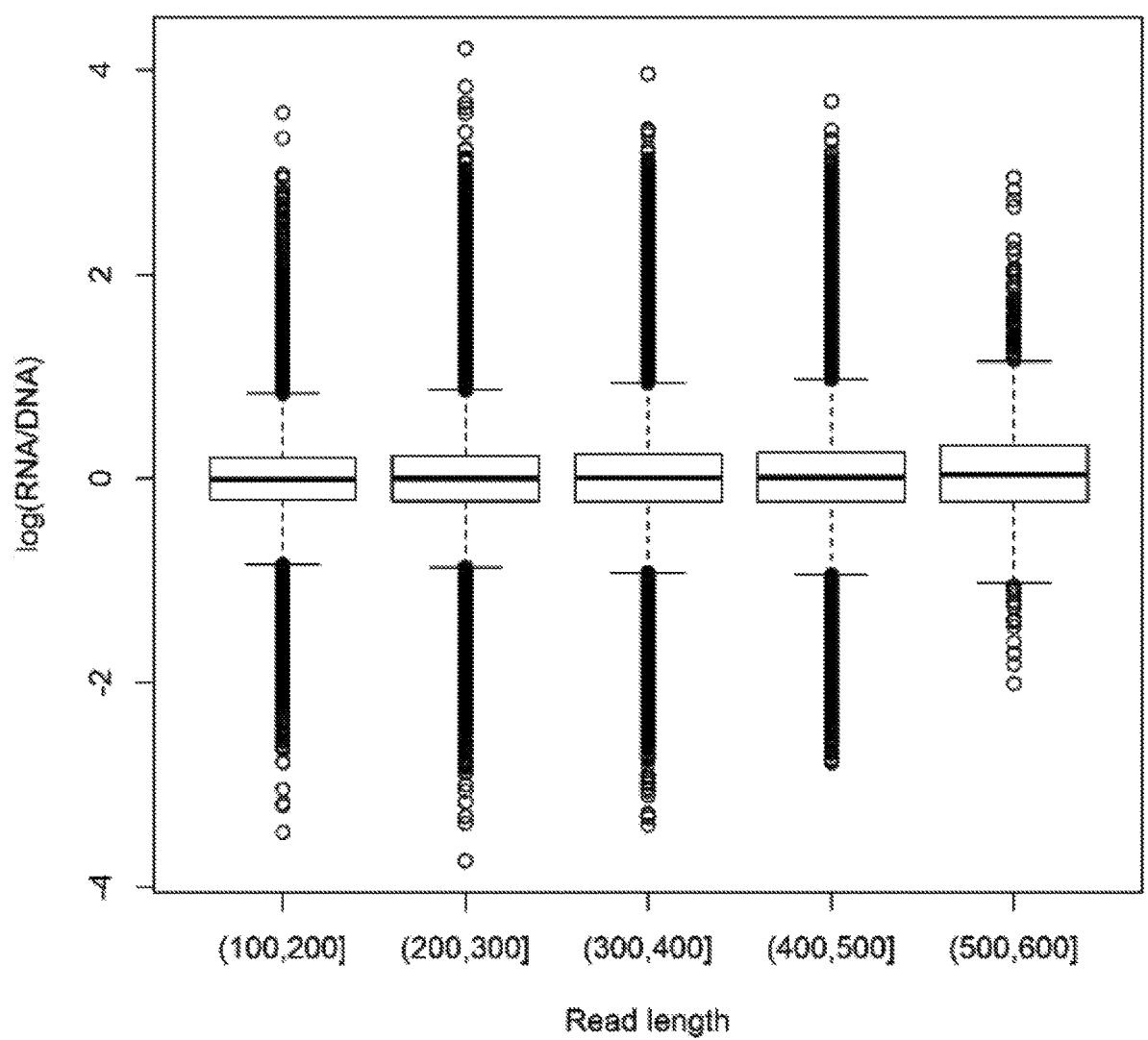
Figure 40B:
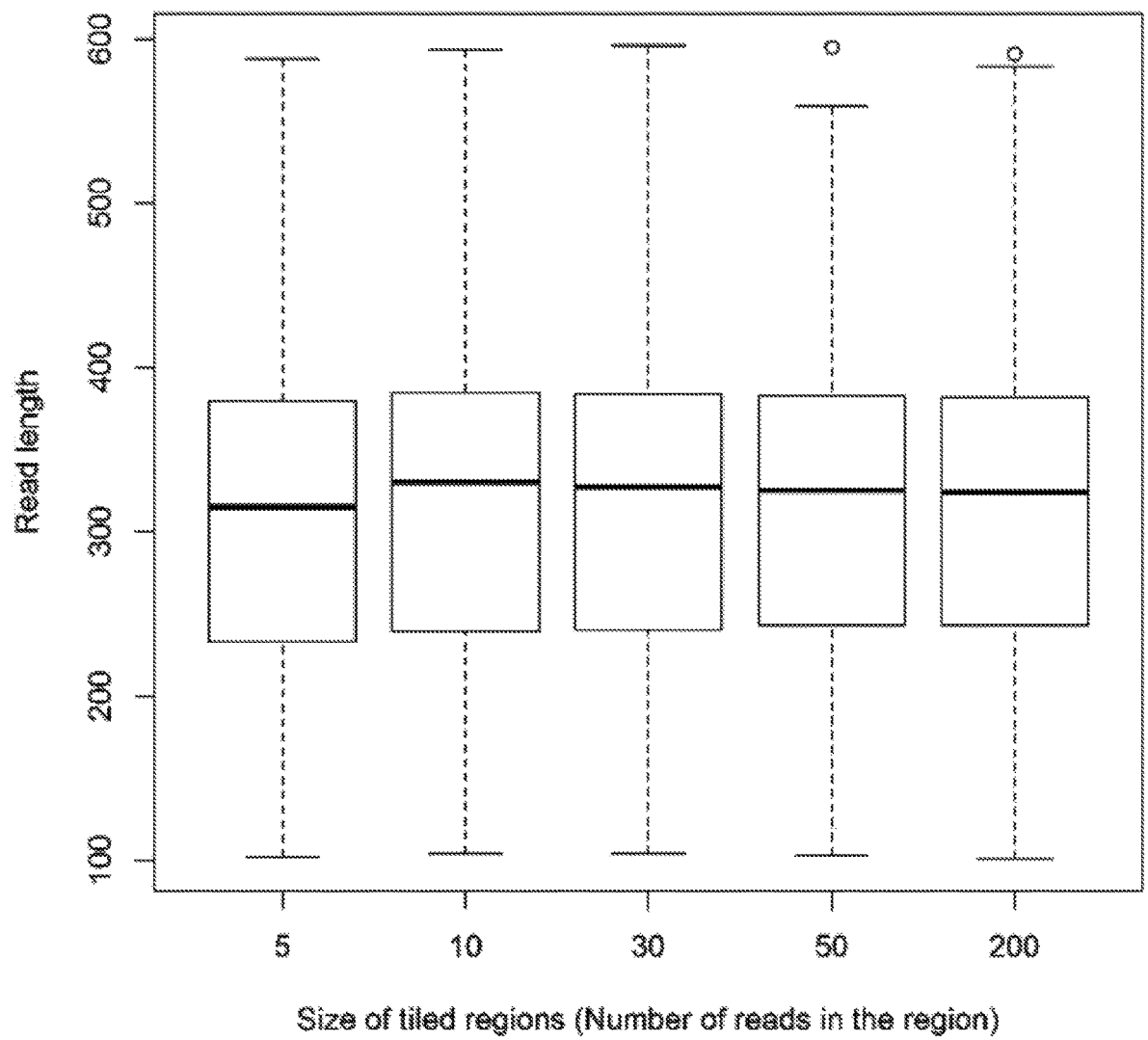

FIG. 40A-40B—Relationship between ln(#RNA/#DNA), fragment length and size of tiled regions. FIG. 40A: the distribution of ln(#RNA/#DNA) after normalization with respect to fragment length. In the plot, the fragment length is categorized into five groups. FIG. 40B: the distribution of fragment length with respect to the size of the tiled region in which the fragment is located. The size of tiled regions is defined by the number of fragments in the tiled region. The plots are based on the library described in the main text in which the fragments are ranged between 100-600nt (with 99% between 168-473nt).

Figure 41:
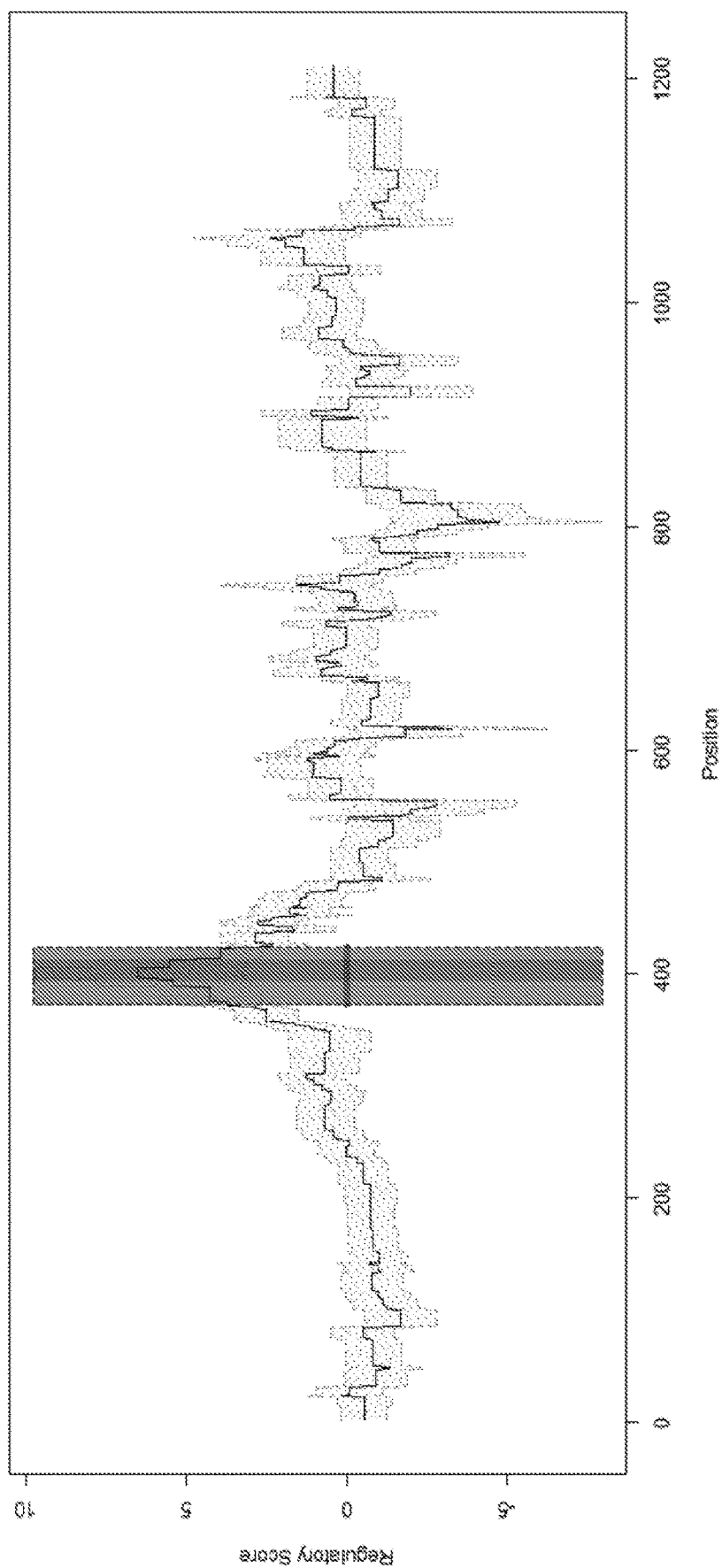

FIG. 41—An example of estimated regulatory scores from a simulated tile region of 1200nt. The data is generated within a 1200nt tile region with 50 unique HiDRA fragments ranging from 175nt to 450nt. The significant regulatory region (FWER<5%) is highlighted in red. The predicted motif region is highlighted in purple. The yellow dashed lines are the estimated scores ±MSE.

Figure 42:
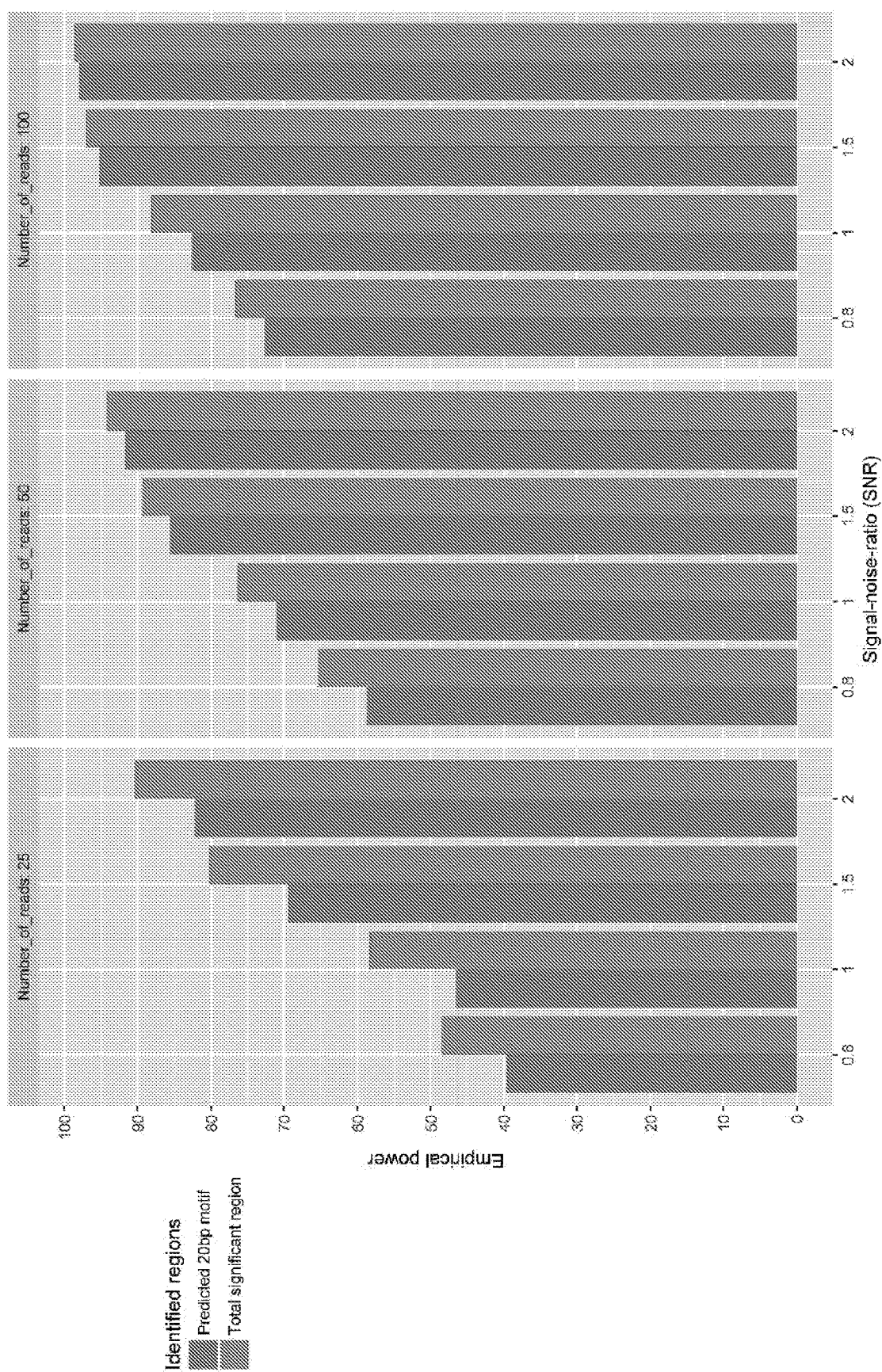

FIG. 42—Empirical statistical power according to different numbers of fragments and different SNR. Y-axis: empirical power (%). X-axis: Signal-to-noise-ratio defined by $$SNR = \frac{s_m}{\sigma_{noise}}.$$

The red bars are the empirical power for the predicted 20 bp core driver element. The blue bars are the empirical power for the identified drivers with a significant regulatory score based on a regional FWER=5%.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance, or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells, and their progeny, of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure, or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment but may. Furthermore, the particular features, structures or characteristics may be combined in any suitable manner, as would be apparent to a person skilled in the art from this disclosure, in one or more embodiments. Furthermore, while some embodiments described herein include some, but not other, features included in other embodiments, combinations of features of different embodiments are meant to be within the scope of the invention. For example, in the appended claims, any of the claimed embodiments can be used in any combination.

All publications, published patent documents, and patent applications cited herein are hereby incorporated by reference to the same extent as though each individual publication, published patent document, or patent application was specifically and individually indicated as being incorporated by reference.

Overview

Embodiments disclosed herein provide a general, scalable, high-throughput, and high-resolution approach for experimental dissection of regulatory regions and driver nucleotides in the context of human biology and disease.

The present disclosure includes methods for performing HiDRA (High-resolution Dissection of Regulatory Activity), a novel high-resolution global screen for transcriptional regulatory activity in accessible regions, enabling high-efficiency, high-throughput, and high-resolution inference of regulatory activity. The methods may comprise extracting accessible DNA regions from ATAC-Seq, size-selecting for constructs between about 150 and about 500nt long and inserting the selected constructs downstream of an episomal reporter gene to test their activity and exploit their overlapping nature for high-resolution inferences. The approach overcomes the construct-length and region count limitations of synthesis-based technologies, and the ATAC-seq selection of open chromatin regions concentrates the signal on likely regulatory regions and enables high-resolution inferences. Altogether, enhancer constructs of comparable length to low-throughput studies may be tested, achieving high resolution dissection of systematic perturbation. In some embodiments, the methods allow for testing millions of unique fragments in a single experiment.

In some embodiments, HiDRA may be applied to infer genome-wide regulatory activity across ~7 million DNA fragments, e.g., selected from accessible chromatin in the GM12878 lymphoblastoid cell line, resulting in 95,000 active fragments clustering in 65,000 regions showing significant regulatory function. These fragments may be enriched for endogenous active histone marks (including H3K9ac, H3K27ac), regulatory sequence motifs, and regions bound by immune regulators. The ATAC-based selection approach may result in highly-overlapping fragments, with up to 370 fragments per region, enabling pinpointing driver regulatory nucleotides. Overall, HiDRA may provide a general, scalable, high-throughput, high-resolution (~50 nucleotides) approach for experimental dissection of regulatory regions and driver nucleotides in the context of human biology and disease.

In some embodiments, the methods for identifying genomic enhancer regulatory elements may comprise fragmenting DNA molecules; amplifying the fragments; enriching the amplified fragments; integrating the enriched fragments into a vector to obtain a vector library; introducing (e.g., by transfecting or transducing) the vector library in a population of cells, thereby generating transcripts of one or more vector in the library; sequencing the transcripts; and identifying transcripts that have enhancer activity.

In certain embodiments, the methods for identifying genomic enhancer regulatory elements may comprise fragmenting DNA molecules to generate fragments with overhanging ends; filling in the overhanging ends with labeled nucleotide(s); joining the overhanging ends; isolating and amplifying the joined fragments; integrating the amplified fragments into a vector to generate a vector library, introducing (e.g., by transfecting or transducing) the vector library to a population of cells thereby generating transcripts of one or more vector in the library; sequencing the transcripts; and identifying transcripts that have enhancer activity.

Nucleic Acids Fragmentation

In certain embodiments, the methods herein comprise fragmenting nucleic acids from a population of cells. In some cases, the population of cells may be cells in a cell line. Any method of fragmenting DNA, such that fragments are derived from "open" (i.e., accessible) chromatin may be used. In preferred embodiments, transposition is used to fragment genomic DNA to obtain fragmented genomic DNA (tagmented fragments). Transposition is performed on a population of cells. The cells are preferably in a homogenous single cell suspension. Methods of obtaining a homogenous single cell suspension from a biological sample (e.g., cell culture, tissue sample, blood) are well known in the art. In certain embodiments, fragmenting genomic DNA at accessible chromatin is performed according to methods known in the art (see, e.g., Buenrostro et al., 2015, ATAC-seq).

In an exemplary embodiment, fragmenting the nucleic acids comprises a method comprising transposition and PCR amplification. An exemplary protocol may include any of the following reagents or steps:

Materials
  Phosphate Buffered Saline (PBS)
  Molecular biology grade IGEPAL CA-630
  Lysis buffer (10 mM Tris-HCl, pH 7.4, 10 mM NaCl, 3 mM MgCl$_2$, 0.1% IGEPAL CA-630)
  2× TD (2× reaction buffer, Illumina Cat #FC-121-1030)
  TDE1 (Nextera Tn5 Transposase, Illumina Cat #FC-121-1030)
  Qiagen MINELUTE™ PCR Purification Kit
  NEBNEXT™ High-Fidelity 2× PCR Master Mix (New England Labs Cat #M0541)
  25 uM Custom Nextera PCR Primer 1
  25 uM Custom Nextera PCR Primer 2
  100× SYBR® Green I (Invitrogen Cat #S-7563)
  0.2-ml PCR tubes
  PCR Thermal cycler
  qPCR consumables, products are specific to the instrument Cell Preparation
  1. Harvest cells, protocol to be defined by the user.
  Cells should be intact and in a homogenous single cell suspension.
  2. Spin down 50,000 cells at 500×g for 5 min, 4° C.
  The number of cells at this step is crucial as the transposase to cell ratio sets the distribution of DNA fragments generated. See Critical Parameters.
  3. Wash once with 50 μl of cold 1× PBS buffer. Spin down at 500×g for 5 min, 4° C.
  4. Gently pipette to resuspend the cell pellet in 50 μl of cold lysis buffer. Spin down immediately at 500×g for 10 min, 4° C.
  This step provides lysis of cells with non-ionic detergent and generates of a crude nuclei preparation.
  5. Discard the supernatant, and immediately continue to transposition reaction.

Transposition Reaction and Purification
  1. Make sure the cell pellet is set on ice.
  2. To make the transposition reaction mix, combine the following:
    25 μl TD (2× reaction buffer)
    2.5 μl TDE1 (Nextera Tn5 Transposase)
    22.5 μl Nuclease Free H$_2$O
  3. Resuspend nuclei in the transposition reaction mix.
  4. Incubate the transposition reaction at 37° C. for 30 min.
  Gentle mixing may increase fragment yield.
  5. Immediately following transposition, purify using a Qiagen MINELUTE™ PCR Purification Kit.
  6. Elute transposed DNA in 10 μl Elution Buffer (10 mM Tris buffer, pH 8).
  7. Purified DNA can be stored at −20° C.
  This is a convenient stopping point. Please note that these DNA fragments are not PCR amplifiable if melted at this point.

PCR Amplification
  1. To amplify transposed DNA fragments, combine the following in a 0.2 ml PCR tube:
    10 μl Transposed DNA
    10 μl Nuclease Free H$_2$O
    2.5 μl 25 μM Custom Nextera PCR Primer 1
    2.5 μl 25 μM Custom Nextera PCR Primer 2 (Contains Barcode)
    25 μl NEBNEXT™ High-Fidelity 2x PCR Master Mix
      A complete list of primers is available in Buenrostro et al. Care should be taken to ensure that samples are barcoded appropriately for subsequent pooling and sequencing.
  2. Thermal cycle as follows:
    1 cycle of 72° C. for 5 min, 98° C. for 30 sec
    5 cycles of 98° C. for 10 sec, 63° C. for 30 sec, 72° C. for 1 min
      This first 5 minute extension at 72° C. is critical to allow extension of both ends of the primer after transposition, thereby generating amplifiable fragments (see figure). This short pre-amplification step ensures that downstream quantitative PCR (qPCR) quantification will not change the complexity of the original library.
  3. To reduce GC and size bias in PCR, the appropriate number of PCR cycles is determined using qPCR allowing us to stop amplification prior to saturation. To run a qPCR side reaction, combine the following in qPCR compatible consumables:

5 µl of previously PCR amplified DNA
4.41 µl Nuclease Free H$_2$O
0.25 µl 25 µM Customized Nextera PCR Primer 1
0.25 µl 25 µm Customized Nextera PCR Primer 2
0.09 µl 100× SYBR® Green I
5 µl NEBNEXT™ High-Fidelity 2× PCR Master Mix
4. Using a qPCR instrument, cycle as follows:
1 cycle of 98° C. for 30 sec
20 cycles of 98° C. for 10 sec, 63° C. for 30 sec, 72° C. for 1 min
5. To calculate the additional number of cycles needed, plot linear Rn versus cycle and determine the cycle number that corresponds to ¼ of maximum fluorescent intensity.

The purpose of this qPCR step is to generate libraries that are minimally PCR amplified Most PCR bias comes from later PCR cycles that occur during limited reagent concentrations. This determination of the optimal number of cycles to amplify the library reduces artifacts associated with saturation PCR of complex libraries.

6. Run the remaining 45 µl PCR reaction to the cycle number determined by qPCR. Cycle as follows:
1 cycle of 98° C. for 30 sec
N cycles of 98° C. for 10 sec, 63° C. for 30 sec, 72° C. for 1 min
Cycle for an additional N cycles, where N is determined using qPCR.
7. Purify amplified library using Qiagen MINELUTE™ PCR Purification Kit. Elute the purified library in 20 µl Elution Buffer (10 mM Tris Buffer, pH 8). Be sure to dry the column before adding elution buffer.

The concentration of DNA eluted from the column ought to be approximately 30 nM, however 5-fold variation is possible and not detrimental.

Type of Nucleic Acids

The nucleic acids herein may comprise DNA, RNA, a mixture thereof, or a hybrid thereof. The nucleic acids may be genomic nucleic acids, e.g., genomic DNA. Alternatively or additionally, the nuclei acids may comprise nucleic acids from a organelle, e.g., mitochondria, ribosomes, or plastids. In some examples, the nucleic acids may comprise mitochondrial DNA. In some examples, the nucleic acids may comprise a mixture of genomic DNA and mitochondrial DNA. In some examples, the nucleic acids may comprise genomic DNA fragmented at open chromatin (e.g., tagmentation).

Methods of Fragmentation

The fragmentation can be done by a variety of methods, such as enzymatic and chemical cleavage. For example, DNA can be fragmented using an endonuclease that cuts a specific sequence of DNA and leaves behind a DNA fragment with a 5' overhang, thereby yielding fragmented DNA. In other examples an endonuclease can be selected that cuts the DNA at random spots and yields overhangs or blunt ends. In some embodiments, fragmenting the nucleic acid present in the one or more cells comprises enzymatic digestion with an endonuclease that leaves 5' overhanging ends. Enzymes that fragment, or cut, nucleic acids and yield an overhanging sequence are known in the art and can be obtained from such commercial sources as New England BioLabs® and Promega®. One of ordinary skill in the art can choose the restriction enzyme without undue experimentation. One of ordinary skill in the art will appreciate that using different fragmentation techniques, such as different enzymes with different sequence requirements, will yield different fragmentation patterns and therefore different nucleic acid ends. The process of fragmenting the sample can yield ends that are capable of being joined.

Nuclei Isolation

In some embodiments, the methods comprise isolating nuclei from the population of cells. The isolation of nuclei may be performed before fragmenting the nucleic acids. In certain embodiments, nuclei are isolated from the population of cells before fragmenting genomic DNA (e.g., a tissue sample). In certain embodiments, ATAC-seq as described herein is used to obtain fragments of genomic DNA present in accessible chromatin in a cell. The ATAC-seq protocol described herein utilizes a buffer that results in a crude nuclei preparation. In certain embodiments, tissue samples to be analyzed are frozen or fixed and nuclei are isolated from the frozen or fixed tissue. The nuclei isolated from frozen or fixed tissue may be processed according to a protocol described herein to obtain genomic fragments.

Fragment Length

The nucleic acid fragments may be from about 50 base pairs (bp) to 5000 bp in length. In some cases, the nucleic acid fragments may be from about 100 bp to about 1000 bp in length, although longer and shorter fragments are contemplated. In some embodiments, the nucleic acid fragments are from about 100 bp to about 1000 bp in length, such as about 100, about 150, about 200, about 250, about 300, about 350, about 400, about 450, about 500, about 550, about 600, about 650, about 700, about 750, about 800, about 850, about 900, about 950 or about 1000 base pairs in length, for example form about 100 to about 1000, about 200 to about 800, about 500 to about 850, about 100 to about 500 and about 300 to about 775 base pairs in length and the like. In specific examples, the nucleic acid fragments are selected for fragments that are between about 300 and 500 base pairs in length.

Overhang

In certain embodiments, nucleic acids, e.g., genomic DNA, are fragmented to yield nucleic acid fragments with overhanging ends, such as a 5' overhanging end or a 3' overhanging end. In some cases, the nucleic acids fragments have a 5' overhanging end on one end. In some cases, the nucleic acid fragments have a 3' overhanging end on one end. In some cases, the nucleic acid fragments have a 5' overhanging end on one end and a 5' overhanging end on another end. In some cases, the nucleic acid fragments have a 3' overhanging end on one end and a 3' overhanging end on another end. In some cases, the nucleic acid fragments have a 3' overhanging end on one end and a 5' overhanging end on another end.

Filling Overhang Ends

The methods may further comprise filling in one or more of the overhanging ends of the nucleic acid fragments with at least one nucleotide, e.g., labeled nucleotide. The overhanging ends may be filled in, for example using a DNA polymerase, such as available from a commercial source. The filled in nucleic acid fragments are thus blunt ended at the end filled 5' end. The at least one nucleotide filled in the fragments may be labeled nucleotide described herein that allow for capturing and detecting of the fragments.

Joining Overhang Ends

The fragments may be then end joined at the filled in end, for example, by ligation using a commercially available nucleic acid ligase, or otherwise attached to another fragment that is in close physical proximity. The ligation, or other attachment procedure, for example nick translation or strand displacement, creates one or more end joined nucleic acid fragments having a junction, for example a ligation junction, wherein the site of the junction, or at least within a few bases, includes one or more labeled nucleic acids, for example, one or more fragmented nucleic acids that have had their overhanging ends filled and joined together. While this step typically involves a ligase, it is contemplated that any means of joining the fragments can be used, for example any chemical or enzymatic means. Further, it is not necessary that the ends be joined in a typical 3'-5' ligation.

Typically, the end joined fragments are desired to be between about 100 and about 1000 bases in length, although longer and shorter fragments are contemplated. In some embodiments, the nucleic acid fragments are between about 100 and about 1000 bases in length, such as about 100, about 150, about 200, about 250, about 300, about 350, about 400, about 450, about 500, about 550, about 600, about 650, about 700, about 750, about 800, about 850, about 900, about 950 or about 1000 bases in length, for example form about 100 to about 1000, about 200 to about 800, about 500 to about 850, about 100 to about 500 and about 300 to about 775 base pairs in length and the like. In specific examples, end joined fragments are selected for fragments that are between about 300 and 500 base pairs in length.

Label and Cross-Link

To identify the created ligation junction, a labeled nucleotide may be used. In one example embodiment, one or more labeled nucleotides are incorporated into the ligated junction. For example, the overhanging ends may be filled in using a DNA polymerase that incorporates one or more labeled nucleotides during the filling in step described above.

The nucleic acid fragments may be held in a fixed position relative to one another. In some examples, the nucleic acid fragments may be fixed in position relative one another by crosslinking. In some embodiments, the nucleic acid fragments are cross-linked, either directly, or indirectly, and the information about spatial relationships between the different nucleic acid fragments in the cell, or cells, is maintained during this joining step, and substantially all of the end joined nucleic acid fragments formed at this step were in spatial proximity in the cell prior to the crosslinking step. In certain embodiments, the spatial relationships in the cell is locked in, for example cross-linked or otherwise stabilized. For example, a sample of cells can be treated with a cross-linker to lock in the spatial information or relationship about the molecules in the cells, such as the DNA in the cell.

In some embodiments, the methods further comprise reversing the crosslinking. In these cases, the crosslinking may be performed using a reversible crosslinking agent. In one example, reversing the crosslinking may be performed by contacting the sample with Proteinase K, e.g., at an elevated temperature, such as about 45° C.

Methods/Reagents of Crosslinking

In some embodiments, the crosslinking is performed by treating the nucleic acid fragments with one or more crosslinking agents. As used herein the term "crosslinking agent" refers to a chemical agent or even light, which facilitates the attachment of one molecule to another molecule. Crosslinking agents can be protein-nucleic acid crosslinking agents, nucleic acid-nucleic acid crosslinking agents, and protein-protein crosslinking agents. Examples of such agents are known in the art. In some embodiments, a crosslinking agent is a reversible crosslinking agent. In some embodiments, a crosslinking agent is a non-reversible crosslinking agent. In some cases, the crosslinking agents may be chemical crosslinkers. Examples of the chemical crosslinkers include aldehyde, epoxy, N-hydroxysuccinimide, halogen, imidate, thiol, and quinone. In some examples, the chemical crosslinker may be aldehyde. In some examples, the chemical crosslinker may be formaldehyde.

It has been found however, that in some situations, it is not necessary to hold the nucleic acids in place using a chemical fixative or crosslinking agent. Thus, in some embodiments, no crosslinking agent is used. In still other embodiments, the nucleic acids are held in position relative to each other by the application of non-crosslinking means, such as by using agar or other polymer to hold the nucleic acids in position. The labeled nucleotide is present in the junction is used to isolate or enrich the one or more end joined nucleic acid fragments using the labeled nucleotide.

In some embodiments, in order to create discrete portions of nucleic acid that can be joined together in subsequent steps of the methods, the nucleic acids present in the cells, such as cross-linked cells, are fragmented.

Isolating Joined Fragments

In some embodiments, the methods further comprise isolating the nucleic acid fragments, e.g., the joined nucleic acid fragments. The isolation may be performed using the labeled nucleotide(s) filled in the fragments, e.g., by capturing the fragments with the labeled nucleotide(s). In some embodiments, the end joined DNA that includes a labeled nucleotide is captured with a specific binding agent that specifically binds a capture moiety, such as biotin, on the labeled nucleotide. In some embodiments, the capture moiety is adsorbed or otherwise captured on a surface. In specific embodiments, the end target joined DNA is labeled with biotin, for instance by incorporation of biotin-14-CTP or other biotinylated nucleotide during the filling in of the 5' overhang, for example with a DNA polymerase, allowing capture by streptavidin. Other means for labeling, capturing, and detecting nucleic acid probes include: incorporation of aminoallyl-labeled nucleotides, incorporation of sulfhydryl-labeled nucleotides, incorporation of allyl- or azide-containing nucleotides, and many other methods described in Bioconjugate Techniques (2nd Ed), Greg T. Hermanson, Elsevier (2008), which is specifically incorporated herein by reference. In some embodiments the specific binding agent has been immobilized for example on a solid support, thereby isolating the target nucleic molecule of interest. By "solid support or carrier" is intended any support capable of binding a targeting nucleic acid. Well-known supports or carriers include glass, polystyrene, polypropylene, polyethylene, dextran, nylon, amylases, natural and modified celluloses, polyacrylamides, agarose, gabbros and magnetite. The nature of the carrier can be either soluble to some extent or insoluble for the purposes of the present disclosure. The support material may have virtually any possible structural configuration so long as the coupled molecule is capable of binding to targeting probe. Thus, the support configuration may be spherical, as in a bead, or cylindrical, as in the inside surface of a test tube, or the external surface of a rod. Alternatively, the surface may be flat such as a sheet or test strip. After capture, the end joined nucleic acid fragments are available for amplification (e.g., PCR), wherein the amplified products include universal ends for use in cloning into the regulatory element assay vector described herein.

Identifying Regulatory Elements at Genome-Wide Contact Domains

In certain embodiments, fragmenting genomic DNA is performed in order to detect regulatory elements present at contact domains (also called "topologically constrained domains", "topologically associated domains", or "physical domains") (Dixon et al., 2012 Nature 485, 376-380; Lieberman-Aiden et al., 2009 Science 326, 289-293; Nora et al., 2012 Nature 485, 381-385; Rao et al., 2014 Cell 159, 1665-1680). Contact domains as used herein refer to contiguous genomic intervals in which there is an enhanced probability of contact among all loci. Contact domains range in size from tens of kilo bases to several megabases, with a median size of 185 kb. Many contact domains are also "loop domains"—that is, contact domains whose boundaries are demarcated by the endpoints of a chromatin loop. Chromatin fibers are arranged in living cells as independent chromatin loops anchored to the nuclear matrix or chromosomal scaffold. Specific DNA sequences act as anchors for these loops. Genes are configured into looped structures or chromatin loops that juxtapose regulatory elements to activate or repress transcription. Moreover, chromatin loop formation is the result of the presence of a pair of CTCF binding motifs in the convergent orientation on opposite strands of the DNA. Not being bound by a theory, contact domains are enriched for regulatory sequences as compared to the entire genome.

In certain embodiments, regulatory elements comprising genomic contact domains in a cell may be identified. As described herein, fragments may be obtained using in situ Hi-C methods (see, e.g., WO2016089920). The methods include providing a sample of one or more cells or nuclei and following a method of Hi-C as described previously.

Amplification of Fragments

Methods herein may comprise amplifying the nucleic acid fragments. As used herein the term "amplifying" or "amplification" refers to a method to increase the number of copies of a nucleic acid molecule, such as one or more tagmented fragments or end joined nucleic acid fragments that includes a junction, such as a ligation junction. The resulting amplification products are called "amplicons." Amplification of a nucleic acid molecule (such as a DNA or RNA molecule) refers to use of a technique that increases the number of copies of a nucleic acid molecule (including fragments).

An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated.

Other examples of in vitro amplification techniques include quantitative real-time PCR; reverse transcriptase PCR (RT-PCR); real-time PCR (RT PCR); real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

In certain embodiments, the nucleic acid fragments may be amplified by an error-prone PCR. Error prone PCR is a method by which random mutants may be inserted into any piece of DNA. The technique is based on PCR (polymerase chain reaction). Normally the replication of DNA by the polymerase is extremely specific. The difference in error prone PCR is that the fidelity of the Taq DNA polymerase is modulated by alteration of the composition of the reaction buffer. In these conditions, the polymerase makes mistakes in the base paring during DNA synthesis that results in the introduction of errors in the newly synthesized complementary DNA strand. By carefully controlling the buffer composition the frequency of mis-incorporation of nucleotide bases, and therefore the number of errors introduced into the sequence may be regulated. For the technique to work properly, a Taq DNA polymerase which does not have proof-reading ability may be used. This proof-reading, or auto-correction of nucleotide sequence, is a property that is found in many commercially available Taq DNA polymerases. Use of a proof-reading DNA polymerase in an error prone PCR reaction may result in the automatic correction of the mismatched nucleotides, and any mutations introduced during the reaction may be lost.

The nucleic acid fragments may be amplified in an amplification reaction. The reaction may comprise one or more reagents for amplification. In some examples, the reaction may comprise nucleic acid polymerase, e.g., DNA polymerase. In certain examples, the reaction may comprise one or more mutagens. Examples of the mutagens include mitomycin, nitrous acid, photoactivated psoralens, sodium bisulfite, hydroxylamine, hydrazine or formic acid, analogues of nucleotide precursors, e.g., nitrosoguanidine, 5-bromouracil, 2-aminopurine, or acridine, or any combination thereof.

Enrichment and Selection

The method may comprise enriching the nucleic acid fragments, e.g., the amplified nucleic acid fragments. The enrichment may be performed by selecting the nucleic acid fragments according to certain characteristics. For example, the nucleic acid fragments may be selected by size, affinity, charge, label, or any combination thereof.

In certain embodiments, the nucleic acid fragments may be selected by size For example, the nucleic acid fragments may be selected for size between about 50 and about 5000, between about 100 and about 2000, between about 100 and about 1000, between about 150 and about 500, between about 200 and about 500, between about 230 and about 500, between about 50 and about 150, between about 100 and about 200, between about 150 and about 250, between about 200 and about 300, between about 250 and about 350, between about 300 and about 400, between about 350 and about 450, between about 400 and about 500, between about 450 and about 550, or between about 500 and about 600 nucleotides long. In certain examples, the nucleic acid fragments may be selected for size between about 150 and about 500 nucleotides long. In certain examples, the nucleic acid fragments may be selected for size between about 230 and about 500 nucleotides long.

In certain embodiments, fragments are manually loaded onto a gel and fragments corresponding to the correct size are cut from the gel and purified as is known in the art. In certain embodiments, automated size selection using precast, disposable gel cassettes may be used (see, e.g., Quail et al., (2012) Evaluation and optimisation of preparative semi-automated electrophoresis systems for Illumina library preparation. Electrophoresis. Dec; 33(23):3521-8). In certain embodiments, an automated optical electrophoretic system is used to select for fragment size (see, e.g., Pippin Prep (Sage Science; Beverly, MA, USA).

Removing Mitochondrial DNA

The methods may further comprise removing non-genomic nucleic acids from the nucleic acid fragments. In some embodiments, the methods comprise removing mitochondrial DNA from the nucleic acid fragments. In certain embodiments, mitochondrial DNA is removed to reduce the cost of a vector library containing high amounts of mitochondrial DNA. In some examples, ATAC-seq is a high-throughput sequencing technique that identifies open chromatin. Depending on the cell type, ATAC-seq samples may contain ~20-80% of mitochondrial sequencing reads.

In certain embodiments, removal of mitochondrial DNA is performed before amplifying the nucleic acid fragments. In certain embodiments, removal of mitochondrial DNA is performed after amplifying the nucleic acid fragments. In certain embodiments, removal of mitochondrial DNA is performed before the enrichment of the amplified nucleic acid fragments. In certain embodiments, removal of mitochondrial DNA is performed after the enrichment of the amplified nucleic acid fragments. In certain embodiments, removal of mitochondrial DNA is performed before the integration of the enriched nucleic acid fragments. In certain embodiments, removal of mitochondrial DNA is performed after the integration of the enriched nucleic acid fragments. In certain examples, removal of mitochondrial DNA is performed after the enrichment of the amplified nucleic acid fragments and before the integration of the enriched nucleic acid fragments.

Removal of mitochondrial DNA may be performed using a reagent targeting mitochondrial DNA. The reagent may be a CRISPR system comprising guide sequences targeting the mitochondrial DNA sequences, wherein the mitochondrial DNA is cleaved. For example, Montefiori, L. et al. 2017 describes a method of reducing mitochondrial DNA using a CRISPR/Cas9 system applicable to the present invention. Mitochondrial fragment depletion may use about 50, 75, 100, or 200 or more guide sequences. Not being bound by a theory, designing a denser set of guide sequences can achieve greater amounts of depletion to save on high-throughput sequencing costs later.

In some embodiments, removal of mitochondrial DNA may be performed by positive selection using labeled nucleic acid molecules synthesized to capture pre-determined regions of accessible chromatin or promoter and enhancer sequences. The labeled nucleic acid molecules may be nucleic fragments filled in with labeled nucleotide (s).

Integration of Fragment to Vectors

The methods may further comprise integrating the nucleic acid fragments, e.g., the enriched fragments into a vector. In some cases, such integration generates a vector library. The integration may be performed using molecular cloning methods known in the art. For example, the integration may be performed by digesting the fragments and the vector using endonuclease to great ligatable ends and ligating the digested fragments and the digested vector using ligase.

Vectors

In certain embodiments, the vectors are for delivering or introducing in a cell a reporter gene and library fragment as described herein, but also for propagating these components (e.g. in prokaryotic cells). As used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector may be capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques.

Another type of vector is a viral vector. For example, such vectors may have virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. The viral vectors may be non-integrating vectors. For example, certain vectors are capable of autonomous replication in a host cell into which they are introduced (e.g. bacterial vectors having a bacterial origin of replication and episomal mammalian vectors). The viral vectors may be integrating viral vectors. For examples, Other vectors (e.g., non-episomal mammalian vectors) are integrated into the genome of a host cell upon introduction into the host cell, and thereby are replicated along with the host genome. In certain examples, a vector may be a lentiviral vector (e.g., an integrating or non-integrating lentiviral vector). Moreover, certain vectors are capable of directing the expression of genes to which they are operatively-linked. Such vectors are referred to herein as "expression vectors." In certain embodiments, the methods utilize episomal vectors.

Exemplary vectors are described in the art (see e.g., Arnold et al., Genome-Wide Quantitative Enhancer Activity Maps Identified by STARR-seq, Science 1 Mar. 2013: Vol. 339, Issue 6123, pp. 1074-1077; and Muerdter et al., STARR-seq—Principles and applications, Genomics Volume 106, Issue 3, September 2015, Pages 145-150).

Reporter Genes

In certain embodiments, the vectors encode a reporter gene and an untranslated sequence (UTR) that when introduced into a cell of the present invention has low (basal) or non-existent expression. Upon introduction of an enhancer sequence into the vector, the vector expresses the transcript above basal levels, wherein the transcript includes the reporter gene sequence and enhancer sequence. One skilled in the art can generate a vector as described herein.

In certain embodiments, the vector may encode a reporter gene. The reporter gene encoded by the vector may encode a detectable marker. In certain embodiments, the detectable marker is a fluorescent protein such as green fluorescent protein (GFP), enhanced green fluorescent protein (EGFP), red fluorescent protein (RFP), blue fluorescent protein (BFP), cyan fluorescent protein (CFP), yellow fluorescent protein (YFP), mCherry, tdTomato, DsRed-Monomer, DsRed-Express, DSRed-Express2, DsRed2, AsRed2, mStrawberry, mPlum, mRaspberry, HcRedl, E2-Crimson, mOrange, mOrange2, mBanana, ZsYellow1, TagBFP, mTagBFP2, Azurite, EBFP2, mKalamal, Sirius, Sapphire, T-Sapphire, ECFP, Cerulean, SCFP3A, mTurquoise, mTurquoise2, monomelic Midoriishi-Cyan, TagCFP, niTFP1, Emerald, Superfolder GFP, Monomeric Azami Green, TagGFP2, mUKG, mWasabi, Clover, mNeonGreen, Citrine, Venus, SYFP2, TagYFP, Monomeric Kusabira-Orange, mKOk, mK02, mTangerine, mApple, mRuby, mRuby2, HcRed-Tandem, mKate2, mNeptune, NiFP, mKeima Red, LSS-mKatel, LSS-m ate2, mBeRFP, PA-GFP, PAmCherry1, PATagRFP, TagRFP6457, IFP1.2, iRFP, Kaede (green), Kaede (red), KikGR1 (green), KikGR1 (red), PS-CFP2, mEos2 (green), mEos2 (red), mEos3.2 (green), mEos3.2 (red), PSmOrange, Dronpa, Dendra2, Timer, AmCyan1, a variant thereof, a fragment thereof, or a combination thereof. In certain embodiments, the detectable marker is a cell surface marker. In other instances, the cell surface marker is a marker not normally expressed on the cells, such as a truncated nerve growth factor receptor (tNGFR), a truncated epidermal growth factor receptor (tEGFR), CD8, truncated CD8, CD19, truncated CD19, a variant thereof, a fragment thereof, a derivative thereof, or a combination thereof.

Enhancer activity is directly linked to the underlying DNA sequence and measured as presence of the resulting reporter transcripts among cellular RNA by deep sequencing. Specifically, DNA fragments are cloned downstream of a core promoter and into the 3' UTR of a reporter gene. Active enhancers will transcribe themselves and become part of the resulting reporter transcripts. This setup allows the simultaneous testing of millions of DNA sequences in a highly complex reporter library and also ensures that the identified sequences act as bona fide enhancers (rather than for example promoters) as they activate transcription from a remote position.

In some embodiments, the methods comprise detecting expression of the reporter gene and sorting cells in the cell line based on expression levels of the reporter gene. In certain embodiments, cell sorting (e.g., FACS) may be used for enriching cells expressing a detectable marker. Not being bound by a theory, sorting may allow for sequencing of only transcripts having specific levels of enhancer activity.

UTR

In some embodiments, a nucleic acid fragment may be integrated into an untranslated region (UTR) of the reporter gene. A UTR may be a nucleotide sequence (e.g., of a mRNA or DNA sequence or chemical analog thereof) that is transcribed into a mRNA in which the nucleotides corresponding to the open reading frame ("ORF") are not present. In some embodiments, the UTR is the region of a mRNA that is not translated into protein. In one embodiment, the UTR is either or both a 5'-UTR, i.e., upstream of the ORF coding region, or a 3'-UTR, i.e., downstream of the ORF coding region. For example, the nucleic acid fragment may be integrated into an untranslated region (UTR) downstream of the reporter gene. In certain examples, the nucleic acid fragment may be integrated into an untranslated region (UTR) upstream of the reporter gene.

Introduction of Nucleic Acids to Cells

In some embodiments, the methods may comprise introducing nucleic acids to a population of cells. The nucleic acids to be introduced may be the nucleic acid fragments, vectors, or vectors integrated with the nucleic acid fragments (e.g., the vector library described herein). In some examples, nucleic acids to be introduced may be the vector library. After introduced into cells, the nucleic acids, e.g., DNA, may express one or more transcripts.

Nucleic acids may be introduced to cells using molecular cloning techniques known in the art. Examples of methods of introducing nucleic acids into cells include transfection, transduction, electroporation, and microinjection. In some cases, the nucleic acids are introduced into cells by transfection. In some cases, the nucleic acids are introduced into cells by transduction.

Cells

Cells or the population of cells herein may be derived from cells taken from a subject, such as a tissue or cell line. A wide variety of cell lines for tissue culture models are known in the art. Examples of cell lines include, but are not limited to, HT115, RPE1, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rath, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bc1-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In certain embodiments, the population of cells may be obtained from a tissue sample. As used herein the term "tissue" refers to a plurality of functionally related cells. A tissue can be a suspension, a semi-solid, or solid. Tissue includes cells collected from a subject such as blood, cervix, uterus, lymph nodes, breast, skin, and other organs. In some cases, the population of cells may be a tissue-specific cell line.

The population of cells may comprise cells of certain type. For example, the population of cells may comprise immune cells. "Immune cells" as used herein is meant to include any cells of the immune system that may be assayed, including, but not limited to, B lymphocytes (also called B cells), T lymphocytes (also called T cells), natural killer (NK) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, myeloid cells, such as monocytes, macrophages, eosinophils, mast cells, basophils, and granulocytes, gene modified immune cells including hybridomas, drug modified immune cells, and derivatives, precursors or progenitors of the above cell types.

In certain examples, the population of cells may comprise cancer cells. Cancer cells may be cells obtained or derived from a tumor or cancer tissues. The cancer cells may be obtained or derived from leukemia, such as chronic lymphocytic leukemia, fibrosarcoma, myxo sarcoma, liposarcoma, chondrosarcoma, osteogenic sarcoma, chordoma, angiosarcoma, endotheliosarcoma, lymphangiosarcoma, lymphangioendothelioma sarcoma, synovioma, mesothelioma, Ewing's, leiomyosarcoma, rhabdomyosarcoma, gastrointestinal system carcinomas, colon carcinoma, pancreatic cancer, breast cancer, genitourinary system carcinomas, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, endocrine system carcinomas, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, or combinations thereof.

In some cases, the cells may be obtained by pooling cells or tissues from multiple individual. For example, the multiple individuals may be chosen to maximize genetic diversity at informative disease variants. In some cases, the population of cells are derived from the same cell line used for transfecting or transducing, whereby enhancer regulatory elements active in the cell line are identified.

Sequencing

In some embodiments, the methods comprise sequencing transcripts expressed by the vector library. The transcripts may comprise RNA molecules or DNA molecules derived therefrom. The sequences of the transcripts may be used for identifying nucleic acid fragments that have enhancer activity. In some examples, nucleic acid fragments with enhancer activity may be identified by measuring a ratio of a number of RNA sequencing reads comprising a fragment to the representation of the fragment in a non-transfected vector library.

In some embodiments, nucleic acid fragments with enhancer activity may be identified by comparing a sequenced fragment to the chromatin state of a genomic locus of the fragment in the cell line, where fragments present in an enhancer chromatin state are selected. For example, the enhancer chromatin state comprises H3K27ac (histone H3 lysine 27 acetylation) and H3K4me1 (histone H3 lysine 4 mono-methylation). In some embodiments, nucleic acid fragments with enhancer activity may be identified by comparing a sequenced genomic fragment to Long-Terminal-Repeat (LTR) retrotransposon sequences, wherein LTR sequences are not selected.

In preferred embodiments, the present invention uses next generation sequencing in order to detect transcripts. Exemplary next generation sequencing technologies include, for example, Illumina sequencing, Ion Torrent sequencing, 454 sequencing, SOLiD sequencing, and nanopore sequencing amongst others. Methods for constructing sequencing libraries are known in the art (see, e.g., Head et al., Library construction for next-generation sequencing: Overviews and challenges. Biotechniques. 2014; 56(2): 61-77).

The terms "depth" or "coverage" as used herein refers to the number of times a nucleotide is read during the sequencing process. Depth can be calculated from the length of the original genome (G), the number of reads(N), and the average read length(L) as N×L/G. For example, a hypothetical genome with 2,000 base pairs reconstructed from 8 reads with an average length of 500 nucleotides will have 2× redundancy. This parameter also enables one to estimate other quantities, such as the percentage of the genome covered by reads (sometimes also called coverage). A high coverage in shotgun sequencing is desired because it can overcome errors in base calling and assembly. The subject of DNA sequencing theory addresses the relationships of such quantities. Even though the sequencing accuracy for each individual nucleotide is very high, the very large number of nucleotides in the genome means that if an individual genome is only sequenced once, there will be a significant number of sequencing errors. Furthermore, rare single-nucleotide polymorphisms (SNPs) are common. Hence to distinguish between sequencing errors and true SNPs, it is necessary to increase the sequencing accuracy even further by sequencing individual genomes or libraries a large number of times.

The sequencing may be deep sequencing, e.g., ultra-deep sequencing. The term "deep sequencing" as used herein indicates that the total number of reads is many times larger than the length of the sequence under study. The term "deep" as used herein refers to a wide range of depths greater than 1× up to 100×. The term "ultra-deep" as used herein refers to higher coverage (>100-fold), which allows for detection of sequence variants in mixed populations. Alternatively or additionally, the sequencing may be low-pass sequencing or shallow sequencing. The terms "low-pass sequencing" or "shallow sequencing" as used herein refers to a wide range of depths greater than or equal to 0.1× up to 1×.

In the cases where nuclei are isolated, Nuc-seq can be used for single-nucleus isolation and RNA-Seq and is compatible with frozen or fixed tissue (see, e.g., Swiech et al., 2014, "In vivo interrogation of gene function in the mammalian brain using CRISPR-Cas9" Nature Biotechnology Vol. 33, pp. 102-106; and Habib et al., 2016, "Div-Seq: Single-nucleus RNA-Seq reveals dynamics of rare adult newborn neurons" Science, Vol. 353, Issue 6302, pp. 925-928, both of which are herein incorporated by reference in their entirety). In certain embodiments, the invention involves obtaining nuclei from a population of cells (e.g., tissues) and enriching genomic fragments from the nuclei. In certain embodiments, nuclei are isolated from cells where it is difficult to generate a single cell suspension, such as neurons, whereby a single suspension of nuclei is processed to generate fragments (e.g., from accessible chromatin).

High Resolution Mapping of Driver Elements

In certain embodiments, the method comprises high-resolution mapping of driver elements of enhancer activity within identified enhancer regulatory elements by a method comprising comparing the fragment enrichment enhancer activity of a set of overlapping fragments represented in the vector library, whereby driver elements of enhancer activity are identified for enhancer regulatory elements. As used herein the term "driver element(s)" refers to nucleotides in a genomic regulatory fragment that is required for the functional activity of the fragment. In an exemplary embodiment, the fragment may comprise transcription factor binding sites (e.g., activator, mediator complex, RUNX3 or an unknown binding site). The driver elements may be chromatin modifying or remodeling recruitment sites (e.g., histone remodeling complexes, histone modifying enzymes). The fragment may comprise more than one driver element. As used herein the terms "fragment enrichment enhancer activity" or "enhancer activity" refers to of number of transcripts sequenced. In other words, fragments having a high enhancer activity generate more transcription of the reporter. The more transcripts, the more enhancer activity. Thus, the enhancer activity can be measured by the number of transcripts including a fragment sequence. The enhancer activity may be normalized by the representation of each fragment in the input vector library.

Driver elements may be more than 10, 18, 20, 30, 40, 50, 60, 70, 80, 90 or more than 100 nucleotides in length. In certain embodiments, driver elements are greater than or equal to 18 nucleotides. In certain embodiments, overlapping fragments are represented in the input library. The enhancer activity of the overlapping fragments may be compared to identify driver elements.

An algorithm may be used to compare the overlapping fragments (e.g., SHARPR2, as described herein). The algorithm may be used by a computing system. In some examples, the algorithm may estimate regulatory scores for nucleotides in the identified set of overlapping fragments. The sequencing data from the input library and sequenced transcripts may be uploaded to a computing system and the algorithm applied to generate an output of driver elements. Not being bound by a theory, the more overlapping fragments the higher the resolution of driver elements. In certain embodiments, the minimum number of overlapping fragments is ten. Not being bound by a theory, more than 40 overlapping fragments does not provide increased resolution.

In some embodiments, the set of overlapping fragments may comprise at least 5 unique overlapping fragments, e.g., at least 10, 20, 40, 60, 80, 100 unique overlapping fragments. In certain examples, the set of overlapping fragments may comprise at least 10 unique overlapping fragments.

Identifying Sequence Variants

In certain embodiments, the method further comprises identifying driver element variants. The variants may comprise genome wide association (GWAS) variants. Variants may be identified by sequencing the transcripts. Variants may be identified by first identifying regulatory elements and second resequencing the vector library using reads sufficiently long to identify sequence variants. Not being bound by a theory, reads from sequencing transcripts may not be sufficiently long. In some embodiments, the methods further comprise correlating the driver element variants with a disease.

In certain embodiments, driver element variants may be associated with a disease. In certain examples, the GWAS variants herein may be genetic variants associated with a disease. Variants associated with a disease may be identified by comparing regulatory elements in diseased and healthy tissue samples. The variants may also be correlated with changes in gene expression. In one exemplary embodiment, differential gene expression between disease and healthy samples is determined using methods known in the art. Fragments having regulatory activity are identified using methods as described herein. Fragment sequences capable of regulating genes differentially expressed are then analyzed for sequence variants. Additionally, the sequence variants may be present in a driver element. Sequence variants may be identified that modulate expression of the differentially expressed genes.

In certain embodiments, sequence variants in regulatory elements or specifically in driver elements may be variants already associated with disease. Genome Wide Association Studies (GWASs) have identified SNPs that are associated with many complex diseases or traits. For example, as of February 2015, 2111 association studies have identified 15,396 SNPs for various diseases and traits, with the number of identified SNP-disease/trait associations increasing rapidly in recent years. However, it has been difficult for researchers to understand disease risk from GWAS results (see, e.g., Tak and Farnham, Epigenetics Chromatin. 2015 Dec. 30; 8:57). Thus, the present invention may identify functional consequences of sequence variants. In other words, a sequence variant may be identified to function in a regulatory element required for enhancer activity. In certain embodiments, a variant associated with a disease is not identified by the present invention, but a regulatory element comprising the sequence containing the variant may be identified. In certain embodiments, a fragment identified as having enhancer activity may be mutated to include the variant and enhancer activity assayed. In certain embodiments, regulatory elements are identified for a disease for which at least one genome-wide association (GWA) study (GWAS) has been performed.

In some embodiments, a gene or allele or polymorphism has been identified as contributing to disease risk or severity in at least one GWAS. See, e.g., www.genome.gov/gwastudies for examples of GWAS studies and genetic variants (alleles, polymorphisms) associated with various diseases. In some embodiments, a gene (or any sequence) is one for which an allele or polymorphism is associated with an increased or decreased risk of developing a disease of at least 1.1, 1.2, 1.5, 2, 3, 4, 5, 7.5, 10, or more, relative to individuals not having the allele or polymorphism. In some embodiments, an allele or polymorphism is associated with an increased or decreased risk of developing a disease of at least 1.1, 1.2, 1.5, 2, 3, 4, 5, 7.5, 10, or more, relative to individuals not having the allele or polymorphism. Genes, alleles, polymorphisms, or genetic loci that may contribute to any phenotypic trait of interest such as longevity, weight, resistance to infection, response or lack thereof to various therapeutic agents, resistance or susceptibility to potentially harmful substances such as toxins or infectious agents (e.g., viruses, bacteria, fungi, parasites), severity of disease or prognosis (e.g., cancer), or resistance to therapy (e.g., cancer) are of interest. A phenotypic trait may be a physical sign (such as blood pressure), a biochemical marker, which in some embodiments may be detectable in a body fluid such as blood, saliva, urine, tears, etc., such as level of a metabolite, LDL, etc., wherein an abnormally low or high level of the marker may correlate with having or not having the disease or with susceptibility to or protection from a disease.

Various additional embodiments are described in the following numbered paragraphs:

1. A method of identifying genomic enhancer regulatory elements comprising: fragmenting genomic DNA at accessible chromatin in a population of cells thereby generating genomic DNA fragments, wherein said fragmenting comprises transposition; amplifying the genomic DNA fragments; enriching the amplified genomic DNA fragments by size; integrating the enriched fragments into a vector to obtain a vector library, wherein the vector encodes a reporter gene and the enriched fragments are integrated into an untranslated region (UTR) of the reporter gene, whereby transcription of the reporter gene results in a transcript comprising the integrated fragment sequence; transfecting or transducing a cell line with the vector library, wherein the transcript comprising the integrated fragment sequences is expressed in the cell line; and sequencing the transcript expressed in the cell line, whereby integrated fragments comprising enhancer activity are identified.

2. The method according to paragraph 1, wherein the amplified genomic DNA fragments are selected for a size between about 150 and about 500 nucleotides long.

3. The method according to paragraph 1 or 2, wherein the amplified genomic DNA fragments are selected for a size between about 230 and about 500 nucleotides long.

4. The method according to any one of paragraphs 1-3, wherein the enriched fragments are integrated in a UTR downstream of the reporter gene.

5. The method according to any one of paragraphs 1-4, further comprising removing mitochondrial DNA.

6. The method according to any one of paragraphs 1-5, wherein the mitochondrial DNA is removed using a CRISPR system comprising guide sequences targeting the mitochondrial DNA sequences, wherein the mitochondrial DNA is cleaved.

7. The method according to paragraph 5 or 6, wherein mitochondrial DNA is removed after the enriching the amplified genomic DNA fragments and before the integrating the enriched fragments.

8. The method according to any one of paragraphs 1-7, wherein the vector is a plasmid.

9. The method according to any one of paragraphs 1-8, wherein the vector is a viral vector.

10. The method according to paragraph 9, wherein the viral vector is a lentiviral vector.

11. The method according to any one of paragraphs 1-10, wherein the integrated fragments comprising enhancer activity is identified by measuring a ratio of a number of RNA sequencing reads comprising a fragment to the representation of the fragment in a non-transfected vector library.

12. The method according to any one of paragraphs 1-11, wherein the integrated fragments comprising enhancer activity is identified by comparing a sequenced genomic fragment to the chromatin state of a genomic locus of the fragment in the cell line, wherein fragments present in an enhancer chromatin state are selected.

13. The method according to paragraph 12, wherein the enhancer chromatin state comprises H3K27ac (histone H3 lysine 27 acetylation) and H3K4me 1 (histone H3 lysine 4 mono-methylation).

14. The method according to any one of paragraphs 1-13, wherein the integrated fragments comprising enhancer activity is identified by comparing a sequenced genomic fragment to Long-Terminal-Repeat (LTR) retrotransposon sequences, wherein LTR sequences are not selected.

15. The method according to any one of paragraphs 1-14, further comprising detecting expression of the reporter gene in the cell line and sorting cells in the cell line based on expression levels of the reporter gene.

16. The method according to any one of paragraphs 1-15, wherein the population of cells is obtained from a tissue sample.

17. The method according to any one of paragraphs 1-16, wherein the population of cells is a tissue-specific cell line.

18. The method according to any one of paragraphs 1-17, wherein the population of cells is obtained by pooling cells or tissues from more than one individual.

19. The method according to any one of paragraphs 1-18, wherein the population of cells comprise immune cells.

20. The method according to any one of paragraphs 1-19, wherein the population of cells comprise cancer cells.

21. The method according to any one of paragraphs 1-20, wherein the population of cells are derived from the same cell line used for transfecting or transducing, whereby enhancer regulatory elements active in the cell line are identified.

22. The method according to any one of paragraphs 1-21, further comprising isolating nuclei from the population of cells before fragmenting the genomic DNA.

23. The method according to any one of paragraphs 1-22, wherein the fragments are amplified by error-prone PCR.

24. The method according to any one of paragraphs 1-23, wherein the fragments are amplified in an amplification reaction comprising a mutagen.

25. The method according to any one of paragraphs 1-24, further comprising high-resolution mapping of driver elements of enhancer activity within identified enhancer regulatory elements by a method comprising comparing the fragment enrichment enhancer activity of a set of overlapping fragments represented in the vector library, whereby driver elements of enhancer activity are identified for enhancer regulatory elements.

26. The method according to paragraph 25, wherein the driver element comprises a minimum of 18 driver nucleotides.

27. The method according to paragraph 25 or 26, wherein the comparing comprises uploading the overlapping fragment sequences into a computing system and applying an algorithm, wherein the algorithm compares the fragment enrichment enhancer activity of the overlapping fragments.

28. The method according to paragraph 27, wherein the algorithm estimates regulatory scores for nucleotides in the identified set of overlapping fragments.

29. The method according to any one of paragraphs 25-28, wherein the set of overlapping fragments comprises at least 10 unique overlapping fragments.

30. The method according to any one of paragraphs 25-29, further comprising identifying driver element variants.

31. The method according to paragraph 30, wherein the driver element variants comprise genome wide association (GWAS) variants.

32. The method according to paragraph 31, wherein the GWAS variants are genetic variants associated with a disease.

33. The method according to paragraph 32, wherein identifying driver element variants comprises resequencing the vector library using reads sufficiently long to identify sequence variants.

34. The method according to any one of paragraphs 30-33, further comprising correlating the driver element variants with a disease.

35. A method of identifying genomic enhancer regulatory elements comprising: fragmenting genomic DNA in a population of cells, thereby generating genomic DNA fragments comprising overhanging ends; filling in the overhanging ends with at least one labeled nucleotide; joining the filled in overhanging ends of the fragmented genomic DNA, wherein the joined fragments comprise contact domains; isolating the joined genomic DNA fragments using the labeled nucleotide; amplifying the isolated joined genomic DNA fragments; integrating the amplified fragments into a vector to obtain a vector library, wherein the vector encodes a reporter gene and the amplified fragments are integrated into an untranslated region (UTR) of the reporter gene, whereby transcription of the reporter gene results in a transcript comprising the integrated fragment sequence; transfecting or transducing a cell line with the vector library, wherein the transcript comprising the integrated fragment sequence is expressed in the cell line; and sequencing the transcripts expressed in the cell line, whereby integrated fragments comprising enhancer activity are identified.

36. The method according to paragraph 35, wherein the genomic DNA fragments are held in a fixed position relative to one another.

37. The method according to paragraph 35 or 36, wherein the genomic DNA fragments are fixed in position relative to one another by crosslinking.

38. The method according to paragraph 37, wherein the crosslinking comprises treating the genomic DNA fragments with a chemical crosslinker.

39. The method according to paragraph 38, wherein the chemical crosslinker comprises an aldehyde.

40. The method according to paragraph 39, wherein the aldehyde comprises formaldehyde.

41. The method according to any one of paragraphs 37-40, further comprising reversing the crosslinking.

42. The method according to paragraph 41, wherein the reversing the crosslinking comprises contacting the sample with Proteinase K.

The invention is further described in the following examples, which do not limit the scope of the invention described in the claims.

EXAMPLES

Figure 1A:
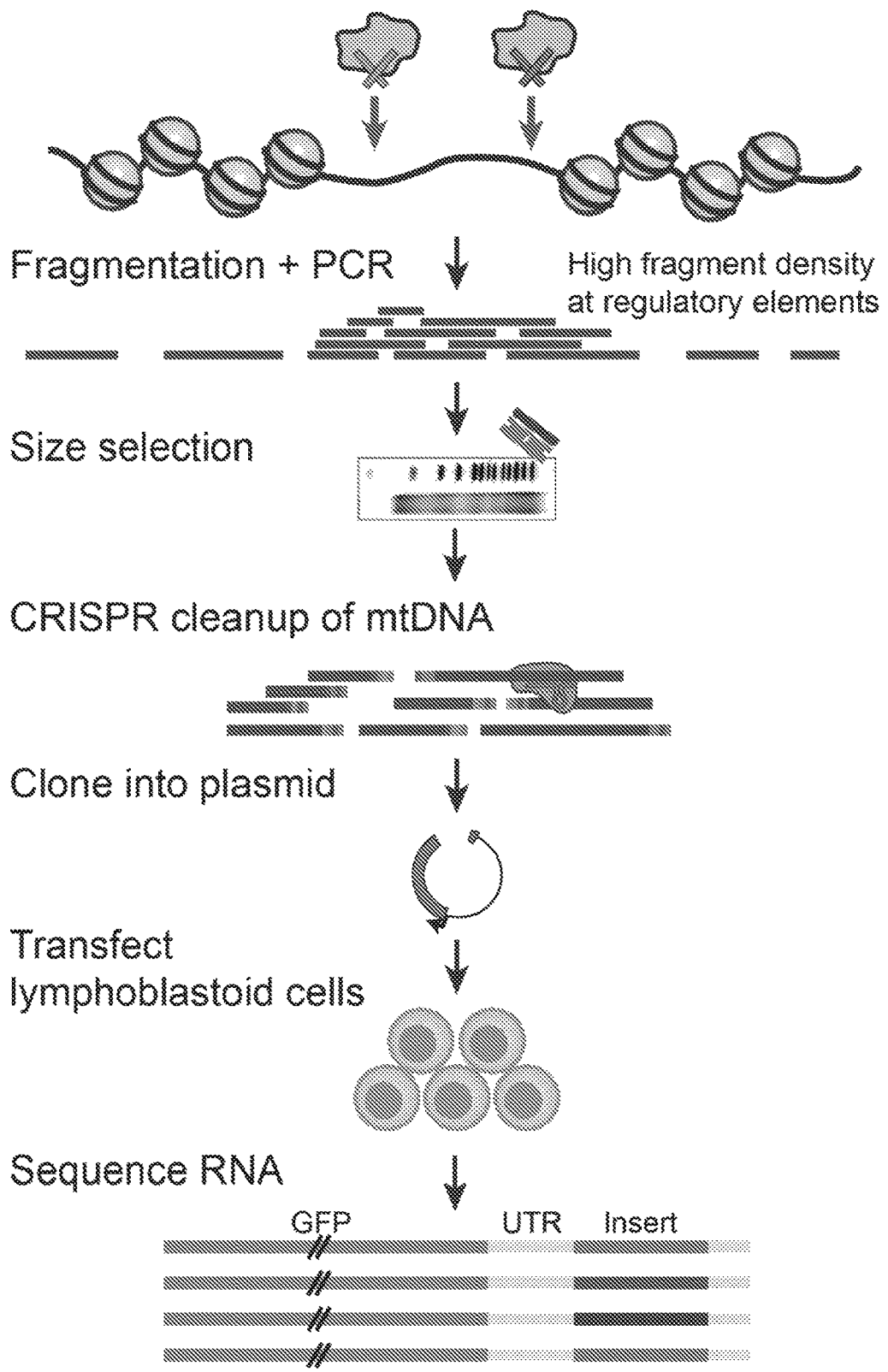
FIG. 1A-1D—Overview of HiDRA library preparation.

Example 1—HiDRA Experimental Method Overview and Plasmid Library Construction HiDRA leverages the selective fragmentation of genomic DNA at regions of open chromatin to generate fragment libraries that densely cover putative transcriptional regulatory elements. Fragments are enriched from open chromatin and regulatory regions using ATAC-seq (Assay for Transposase-Accessible Chromatin with high throughput sequencing) and subsequently cloned into the 3' untranslated region (UTR) of a reporter gene on the self-transcribing enhancer reporter vector used in STARR-seq[3, 4]. Fragments with transcriptional regulatory activity promote self-transcription such that active segments of DNA can be identified and quantified by high-throughput RNA sequencing to produce a quantitative readout of enhancer activity (FIG. 1A). Library construction can be completed in 2-3 days and requires as few as $10^4$-$10^5$ cells as input starting material.

Figure 1B:
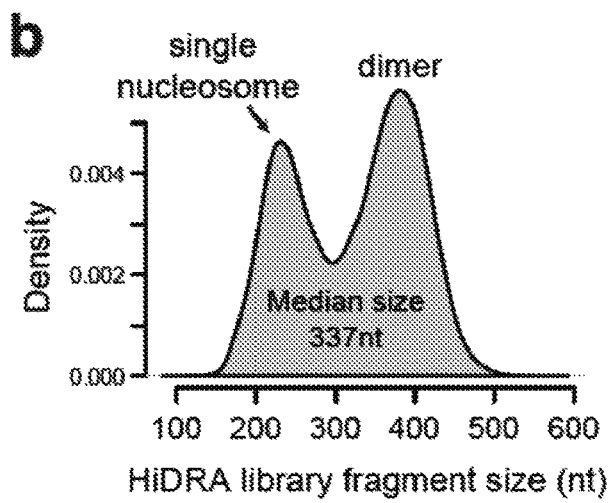
Figure 1C:
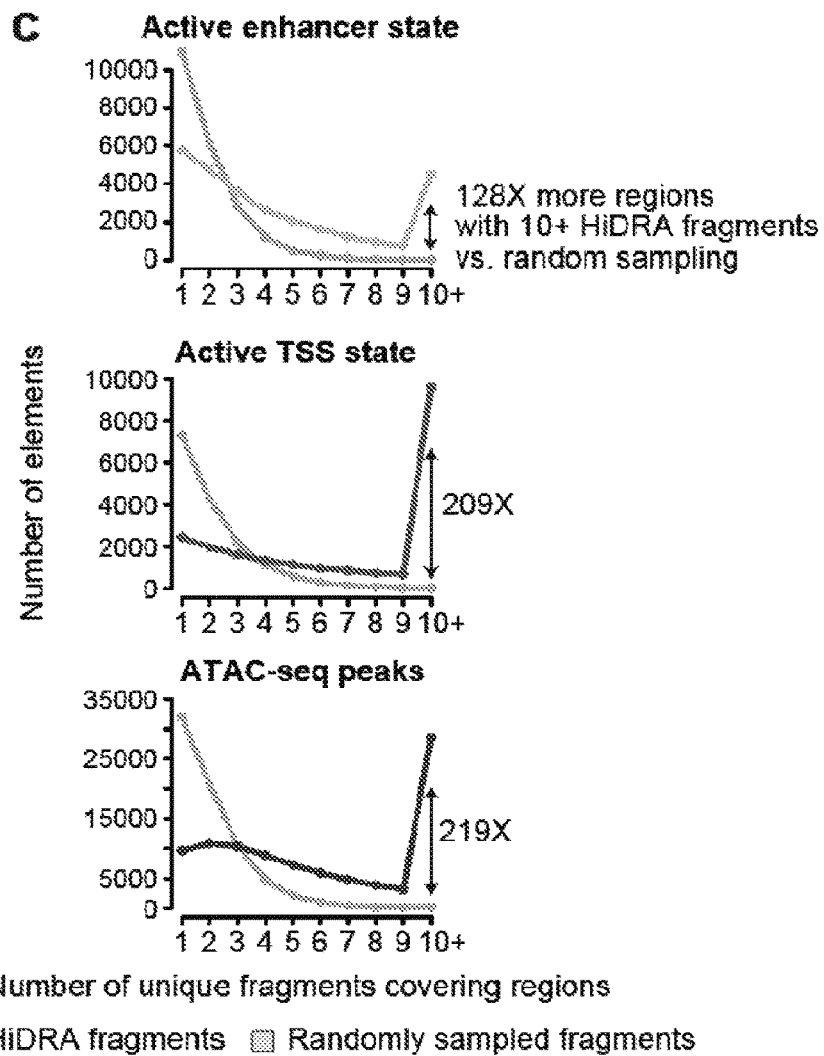
Figure 8:
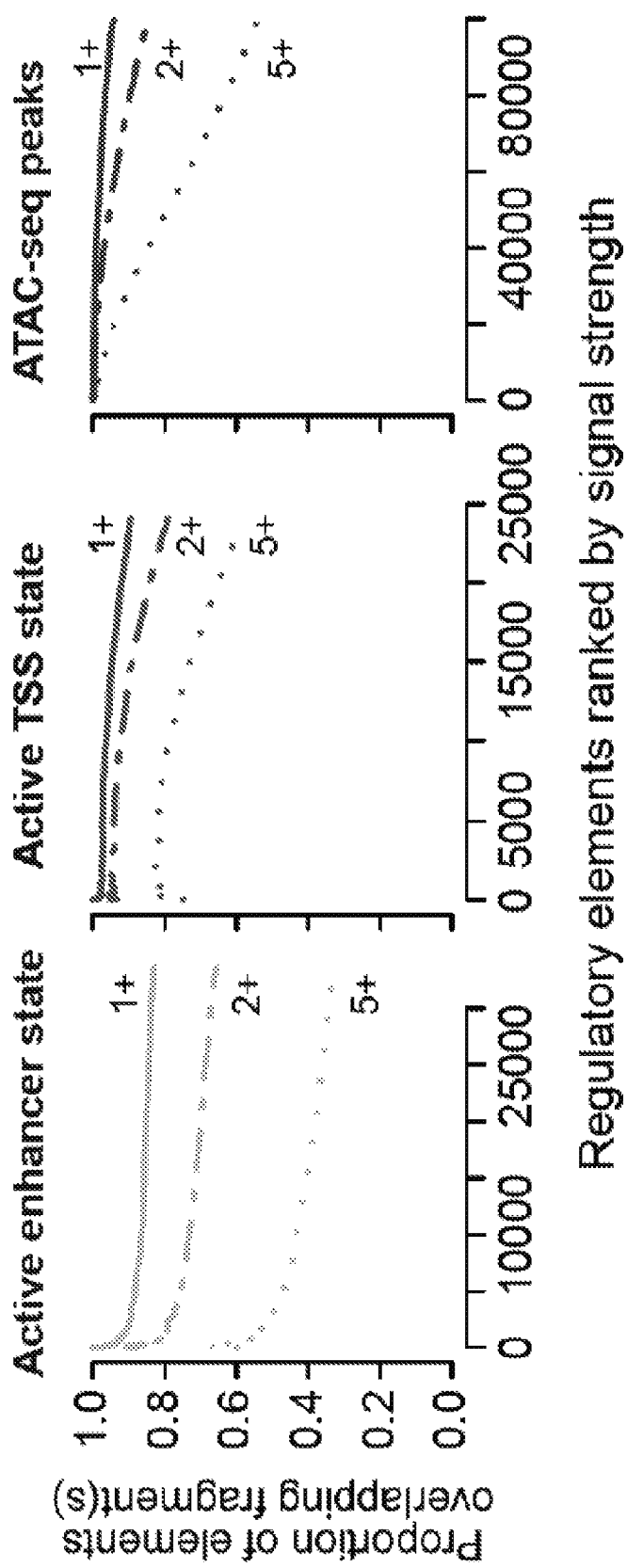
FIG. 8—HiDRA coverage is greater for highly active regulatory elements. Active enhancer and active TSS chromatin states were ranked by H3K27ac signal strength, and ATAC-seq peaks were ranked by density of ATAC-seq reads from Buenrostro et al. (2013). Solid, dashed and dotted lines correspond to coverage with at least 1, 2 and 5 unique HiDRA fragments.
Figure 9A:
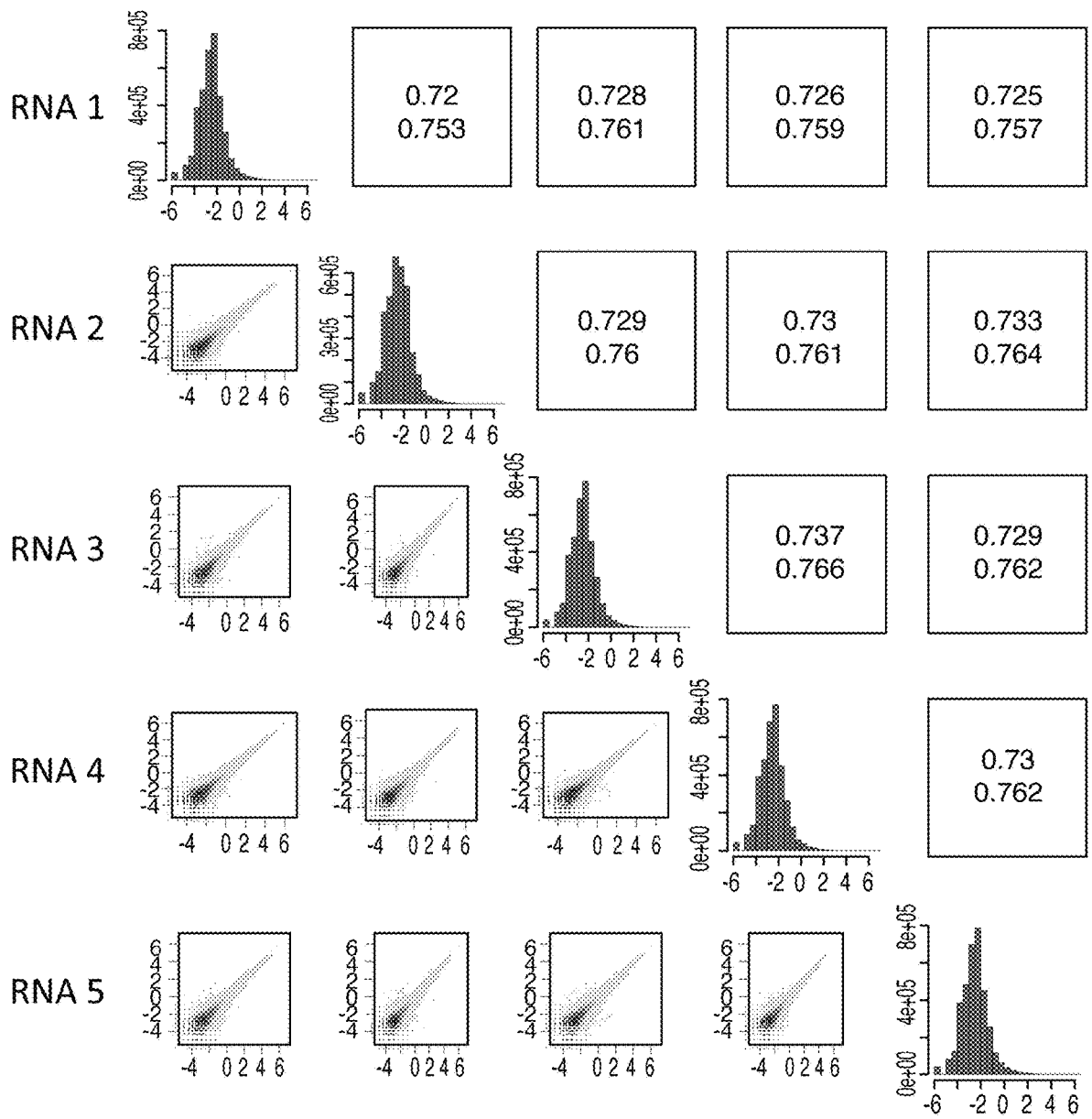
FIG. 9A-9D—Correlation between RNA samples from HiDRA. Correlation is shown at four different RPM cut-offs (FIG. 9A for 0.1 RPM cutoff, FIG. 9B for 0.2 PRM cutoff, FIG. 9C for 0.5 RPM cutoff, and FIG. 9D for 1.0 RPM cutoff). Only fragments passing the minimum RPM cut-off in plasmid samples are shown. Unlike gene expression analysis where read counts from many unique fragments are collapsed into one gene expression value, in HiDRA Applicants consider each fragment on its own. Given the high number of unique features in HiDRA, Poisson "shot noise" will decrease correlations between replicates for low RPM cut-offs.
Figure 9B:
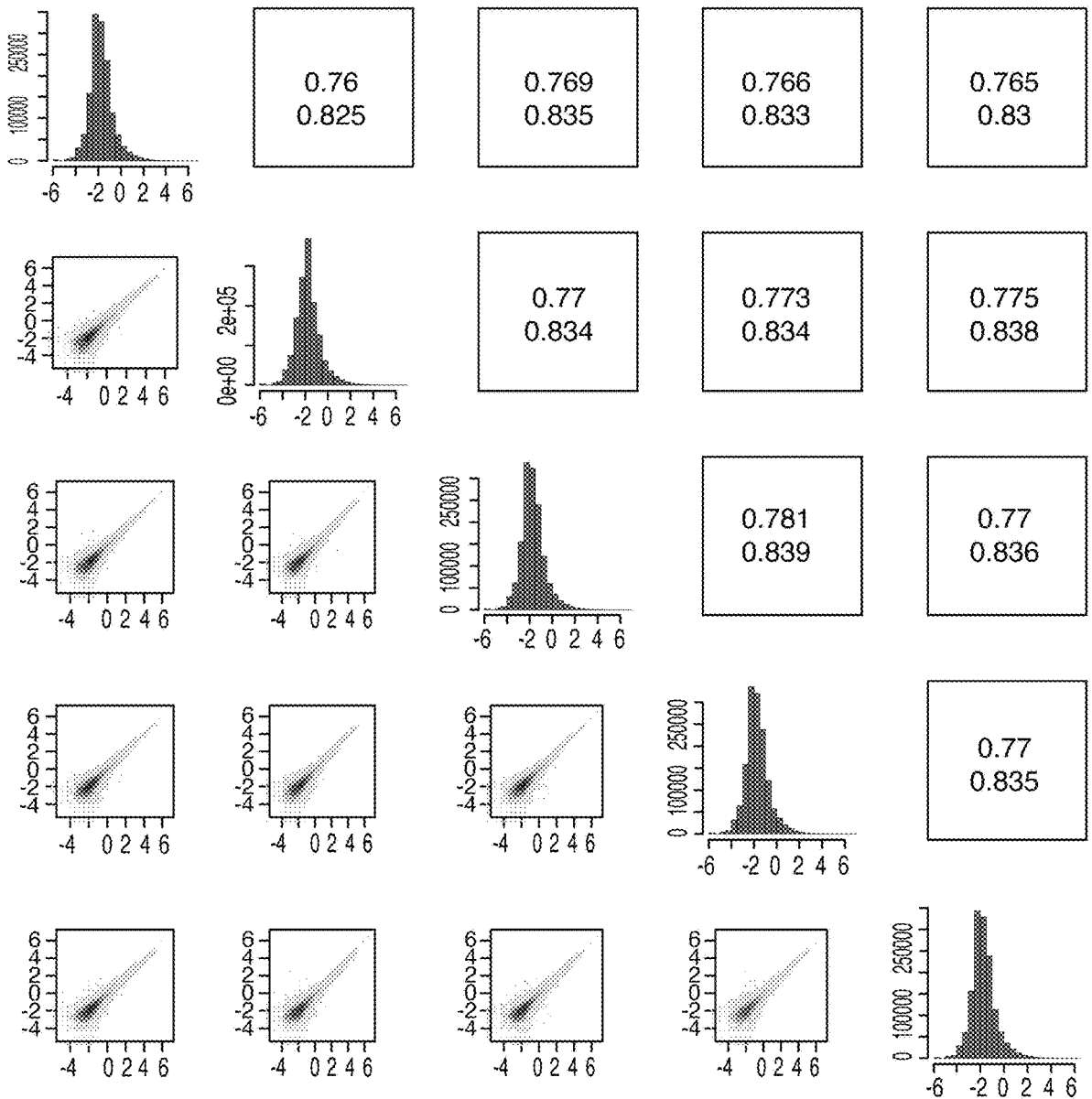
Figure 9C:
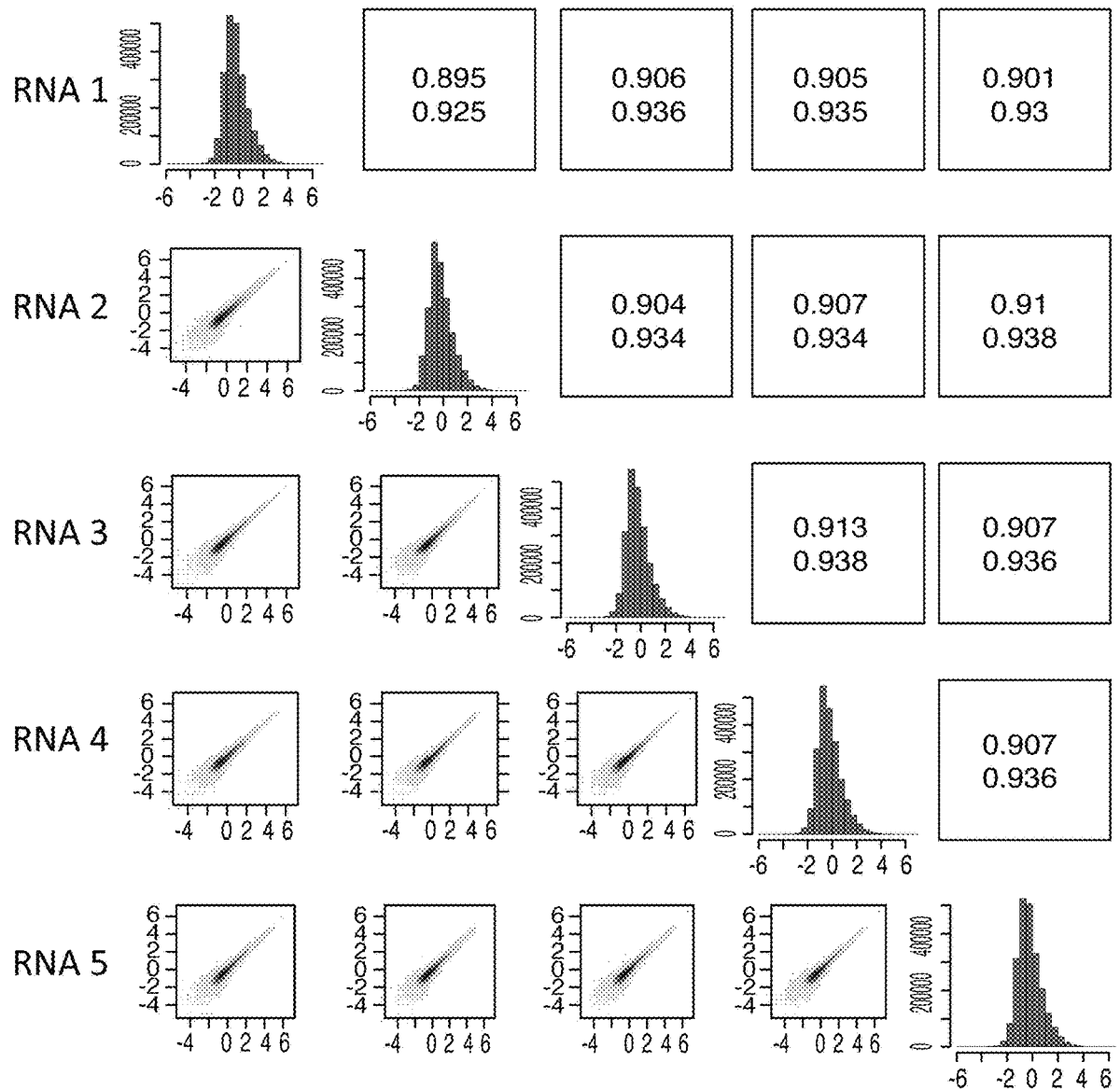
Figure 9D:
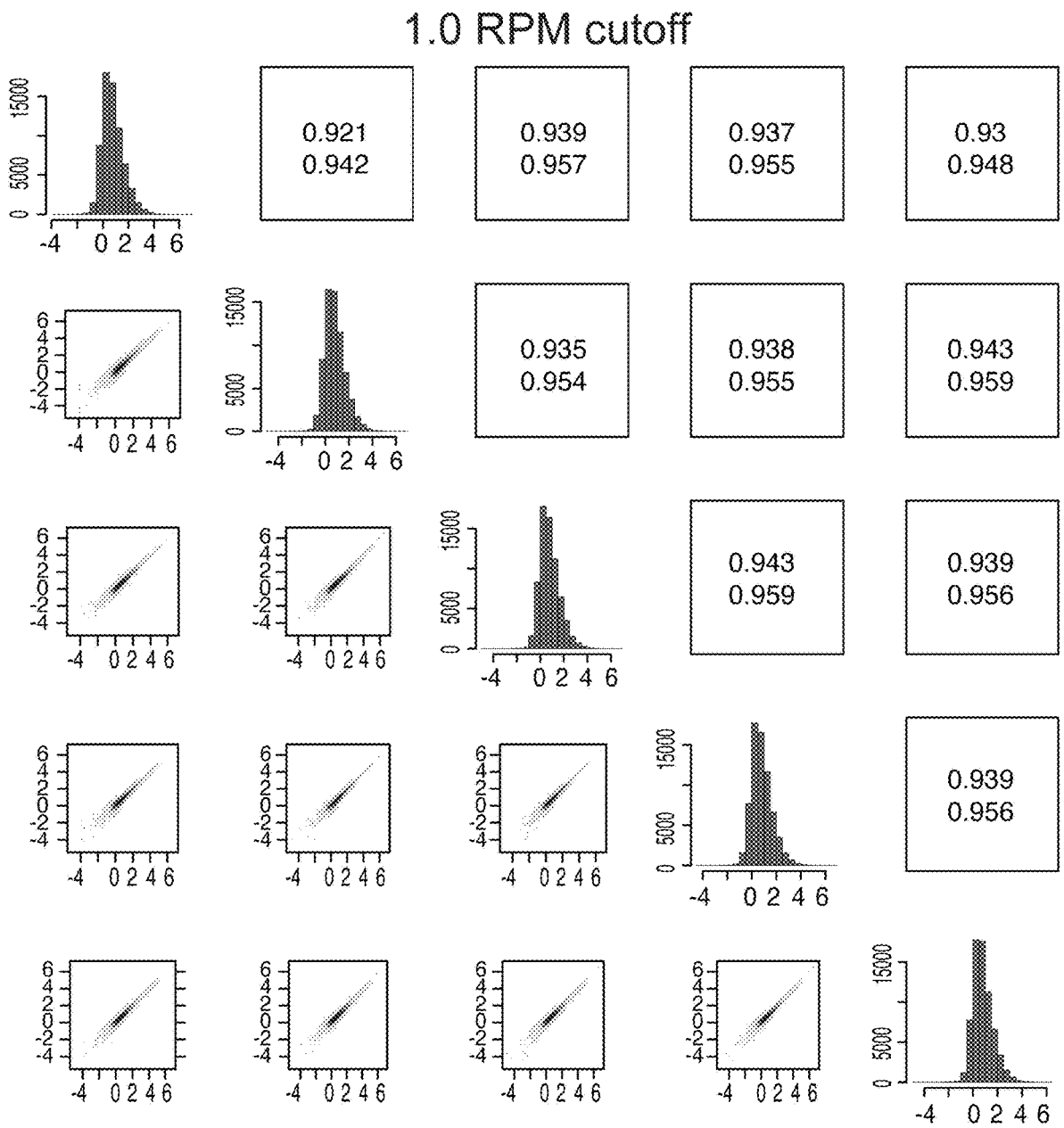

Applicants constructed a HiDRA library with 9.7 million total unique mapping fragments, of which 4 million had a frequency greater than 0.1 reads per million (RPM; non-mitochondrial reads). More than 99% of fragments had lengths between 169nt and 477nt (median: 337nt), with the fragment length distribution showing two peaks spaced by ~147nt, corresponding to the length of DNA wrapped around each nucleosome (FIG. 1B). In contrast to unbiased fragmentation of the genome, the library has much higher efficiency for selectively targeting accessible DNA regions that are more likely to play gene-regulatory roles. The HiDRA library covers 4486 predicted enhancers and 9631 predicted promoters ("Active Transcription Start Site (TSS)" state) with more than 10 unique fragments (FIG. 1C, colored lines), a ~130-fold and ~210-fold enrichment compared to 35 enhancer and 46 promoter regions expected to be covered by chance at the same coverage, indicating that HiDRA library construction successfully targets predicted regulatory regions. Even among enhancer and promoter regions, those with higher expected activity are preferentially selected by HiDRA, as they show higher accessibility and are thus more likely to be cloned in our library and tested by our episomal reporters (FIG. 8).

Figure 1D:
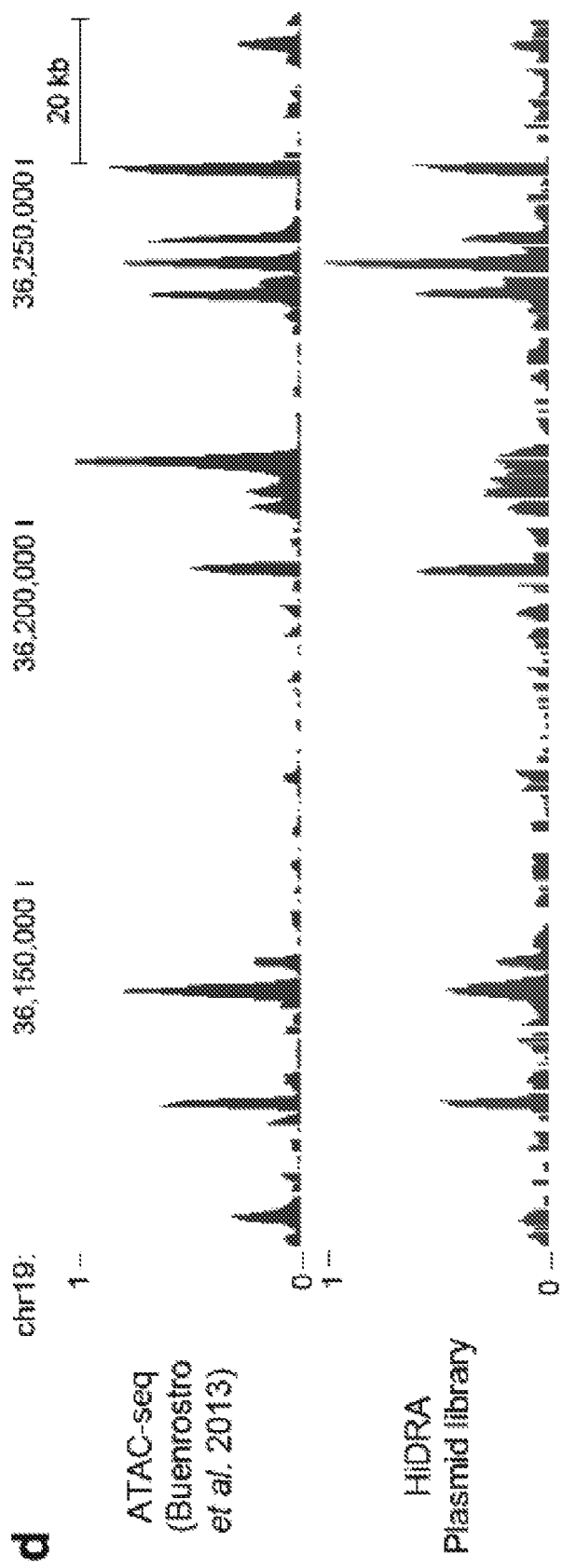

The cloning strategy is specifically designed to densely sample regulatory regions, in order to enable high resolution inference of regulatory activity from highly-overlapping fragments. Indeed, Applicants found up to 370 unique fragments per region in our HiDRA libraries, with 32,000 genomic intervals containing at least 10 overlapping fragments and 2750 containing at least 50 fragments, compared to 180 and 0 that would be expected by randomly-selected fragments, respectively. In addition to clustering of tested fragments within the same region, high-resolution inference relies on partially-overlapping rather than fully-overlapping fragments, which requires a random fragmentation pattern. Indeed, the Tn5 transposase Applicants used here inserts randomly into the genome, and indeed the resulting DNA fragments provide a dense sampling of start and end positions that mirrors the peaks of ATAC-seq experiments (FIG. 1D), indicating that accessible regions most likely to show regulatory activity will have both higher representation in our libraries, and also more starting and ending positions that can help identify driver nucleotides.

Example 2— Identification of DNA Fragments with Transcriptional Regulatory Activity To evaluate the ability of each cloned DNA fragment to promote gene expression, Applicants transfected the HiDRA library into GM12878 lymphoblastoid cells, collected RNA 24 hours post-transfection, and measured the abundance of transcribed fragments by high-throughput RNA sequencing. Applicants carried out 5 replicate transfection experiments from the same plasmid library, each into ~120 million cells, and observed a high degree of correlation in the RNA counts between replicates (0.95 Pearson correlation on average for fragments >1 RPM; 0.76 for >0.1 RPM; FIGS. 9A-9D). To quantify the regulatory activity of tested elements, Applicants compared the number of RNA reads obtained for a fragment (corresponding to the expression level of the reporter gene, as the constructs are self-transcribing), relative to representation of that fragment in the non-transfected input plasmid library (thus normalizing the differential abundance of each fragment in our library). Applicants observed a substantial number of fragments that are more prevalent in RNA than DNA, indicating capability of many HiDRA fragments to drive reporter gene expression (FIG. 2A).

Given the intentionally high initial complexity of the HiDRA library, many fragments are sequenced with a relatively low depth of coverage. Applicants therefore grouped fragments with a 75% reciprocal overlap to boost the read coverage of genomic regions and increase statistical power. This yielded 7.1 million unique "fragment groups" generated from merging 9.7 million HiDRA fragments. In total, Applicants identified 95,481 fragment groups that promote reporter gene expression at an FDR cut-off of 0.05, which Applicants refer to as 'active HiDRA fragments' (FIG. 2A, red dots). These 95,481 active HiDRA fragments are located within 66,254 unique genomic intervals that Applicants subsequently refer to as "active HiDRA regions".

Applicants found that active HiDRA fragments showed a wide range of input DNA levels in the plasmid library, indicating that regulatory function and DNA accessibility rely on complementary sequence signals, and that DNA accessibility alone is not sufficient to predict episomal regulatory function. Applicants also found that active HiDRA regions are predominantly distal to annotated transcription start sites (TSSs) (FIG. 2B), validating the utility of HiDRA for pinpointing distal regulatory regions that are particularly challenging to identify.

As proof-of-concept that HiDRA is capable of identifying true enhancer elements, Applicants examined the well-studied immunoglobulin heavy chain enhancer within the intron of the immunoglobulin heavy constant epsilon (IGHE) gene[18]. Applicants observed that the peak of HiDRA activity is centered precisely within the region previously identified as driving enhancer activity in low-throughput luciferase assays (FIG. 2C).

Figure 2E:
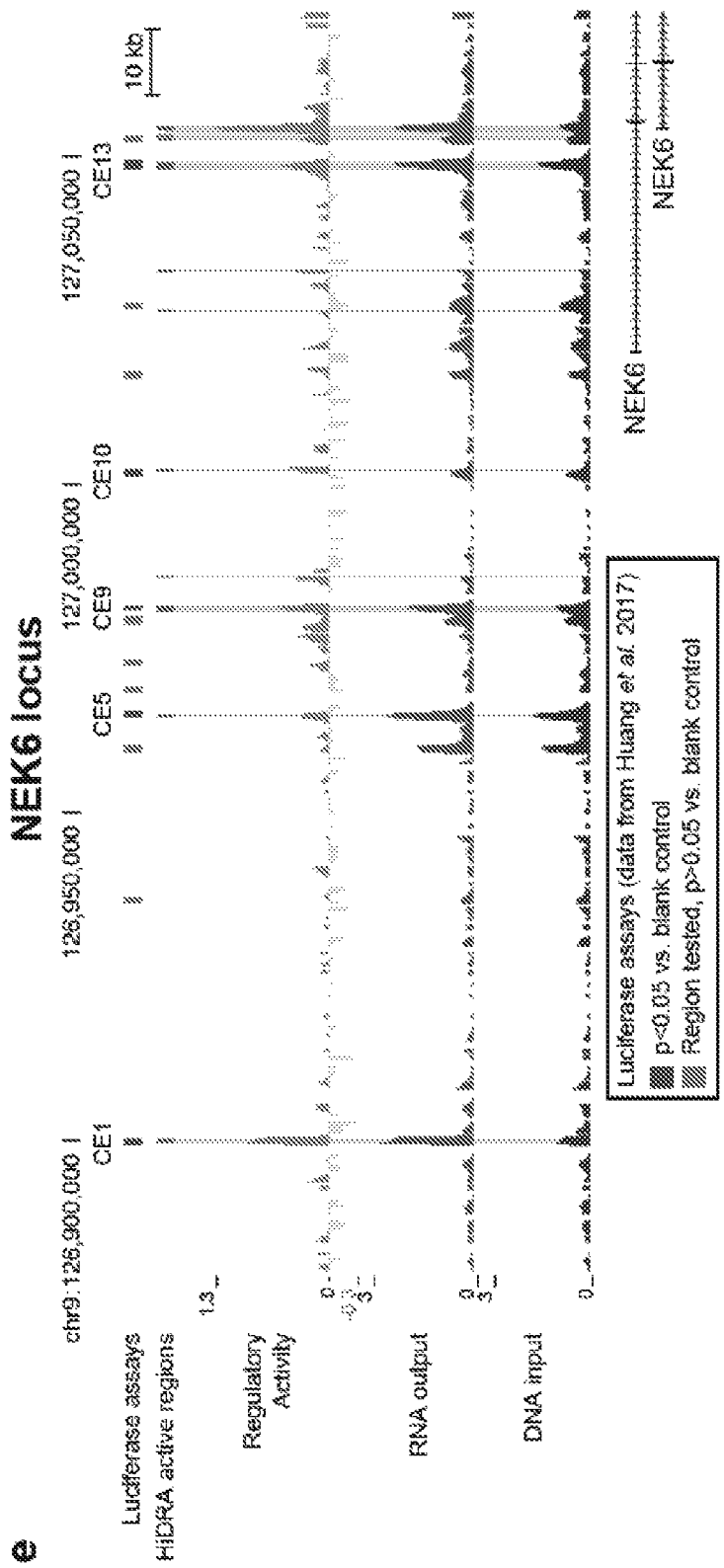

To assess the quantitative accuracy of HiDRA relative to luciferase assays, Applicants compared active HiDRA regions and luciferase results across 21 putative enhancers predicted and tested independently by Huang et al.[19]. Applicants found a 0.88 Pearson correlation between measured luciferase activity and HiDRA activity, confirming the accuracy and quantitative nature of the high-throughput approach (FIG. 2D). A visualization of 14 luciferase-tested enhancers in the serine/threonine kinase NEK6 locus shows a strong correspondence between luciferase assay results and HiDRA active regions (FIG. 2E).

Figure 3A:
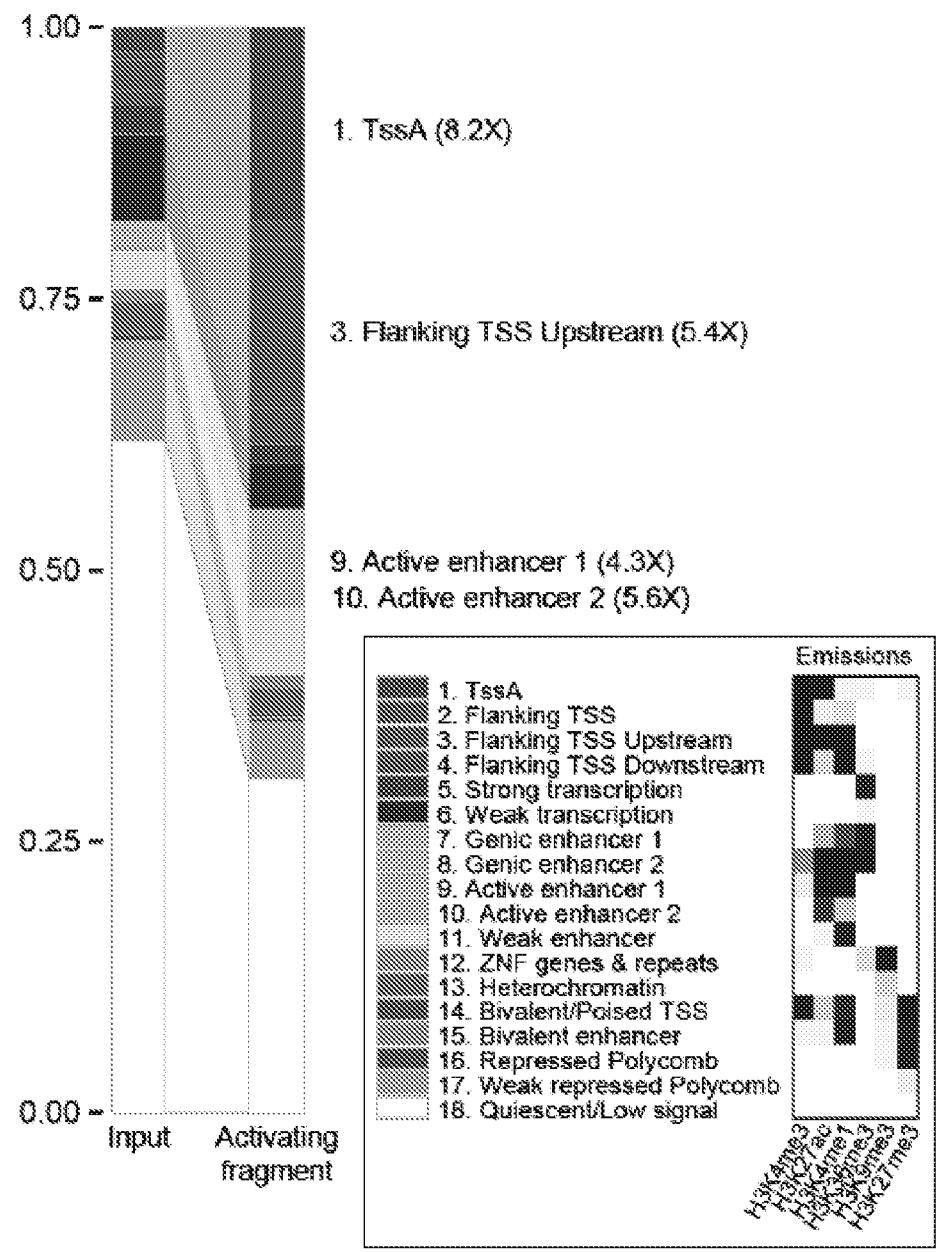
FIG. 3A-3B—Active HiDRA fragments are enriched in endogenously active regulatory regions.
Figure 3B:
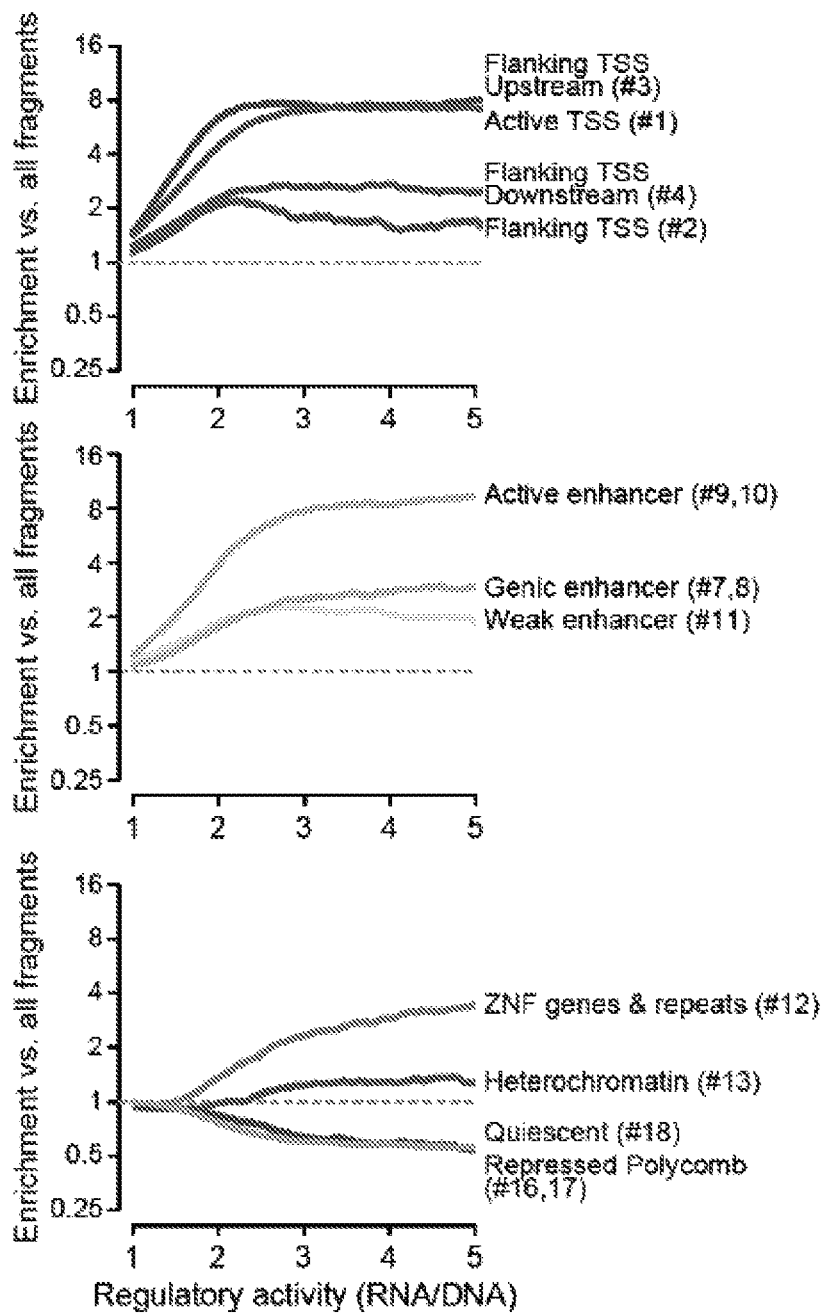

Example 3— HiDRA Regulatory Elements are Enriched in Promoter and Enhancer Elements Applicants next surveyed the 95,481 active HiDRA fragments identified in GM12878 to assess shared common genomic or epigenomic characteristics. In comparison to the set of all HiDRA fragments tested, active fragments were 12 times more likely to overlap an active promoter "TssA" chromatin state (marked by H3K4me3 and H3K27ac, FIG. 3A inset) and 5 times more likely to overlap an "Active Enhancer" chromatin state (marked by H3K4me1 and H3K27ac, FIG. 3A). By contrast, "Weak Enhancer" chromatin states (marked by H3K4me1 but lack of H3K27ac) showed substantially weaker enrichment (2.2-fold) within active HiDRA fragments than active enhancers, consistent with previous literature indicating that presence of H3K27ac correlates with higher greater expression of nearby genes (FIG. 3B). Overall, 35% of all predicted active promoters (8355 regions) and 16% of all predicted active enhancers (5276 regions) overlapped at least one active HiDRA fragment.

Figure 4A:
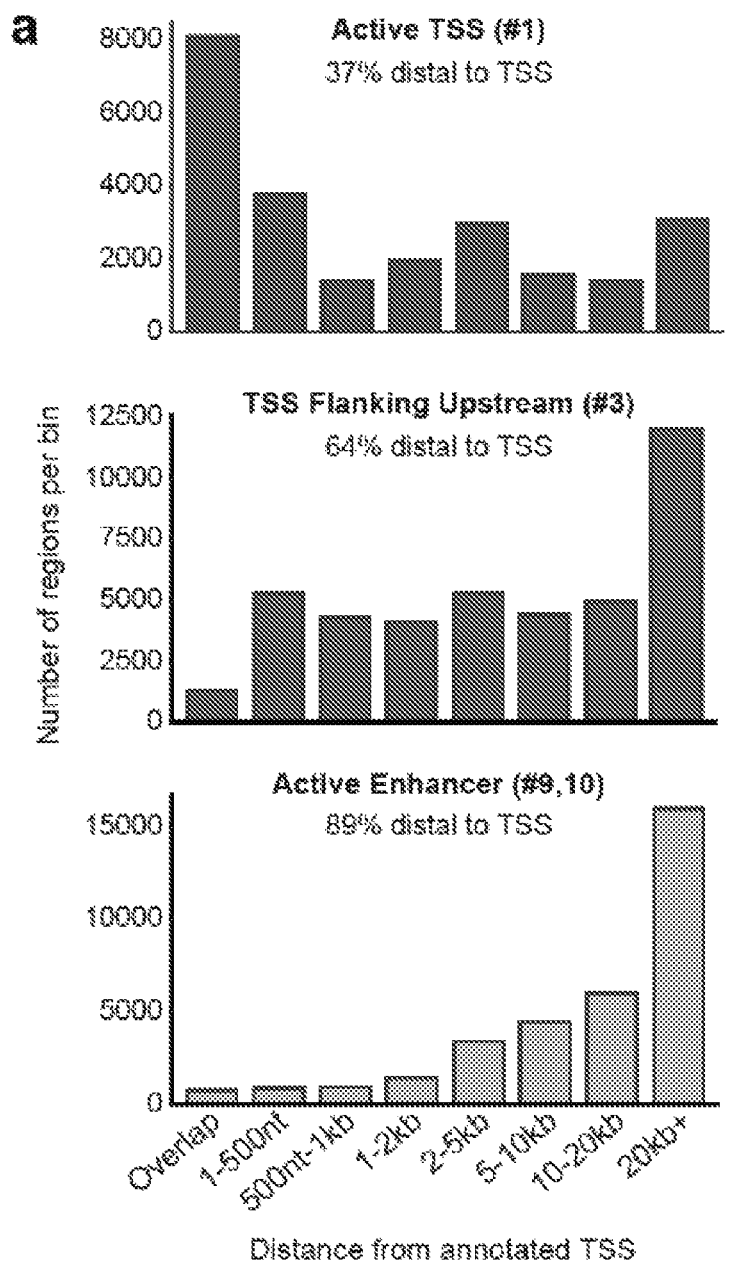
FIG. 4A-4E—HiDRA activity outside of promoter and enhancer elements and in endogenously inactive regions.

In addition to active promoter and active enhancer chromatin states, the "TSS Flanking Upstream" chromatin state showed strong enrichment for active HiDRA fragments (7.3-fold higher than expected from the input library). This chromatin state is defined by the presence of both promoter and enhancer histone marks H3K4me1, H3K4me3, and H3K27ac, and was named "TSS Flanking" due its depletion at exactly the TSS position, but its enrichment 400nt-1kb upstream of annotated transcription start sites[9]. However, 64% of its occurrences are >2 kb from the nearest transcription start site, suggesting that a portion of genomic regions annotated as "TSS Flanking Upstream" may function biologically as distal enhancers (FIG. 4A).

When Applicants computed enrichment of chromatin states as a function of HiDRA activity strength, Applicants found a linear quantitative relationship for HiDRA activity levels up to ~2.5-fold RNA/DNA ratios, with increasing activity showing increasing chromatin state enrichment for both promoter and enhancer chromatin states (FIG. 3B). Surprisingly, this enrichment stayed constant thereafter for promoter regions, and increased modestly for enhancer regions, ultimately surpassing the enrichment seen for promoters. In fact, even though promoter chromatin states were more enriched at intermediate HiDRA activity levels, enhancer chromatin states were the most enriched at the highest HiDRA activity levels ($p=9.3 \times 10^{-102}$, FIG. 10A), suggesting that enhancer elements have a greater dynamic range of regulatory activity potential, which has implications for the regulatory architecture of genes.

At the other end of the spectrum, Quiescent and Polycomb-repressed chromatin states showed a 2-fold depletion for HiDRA active elements, but heterochromatin-associated chromatin states showed a modest enrichment, indicating that they may contain regulatory signals that become active once taken outside their repressive endogenous chromosomal context. The ZNF/repeats-associated chromatin state (marked by H3K36me3 and H3K9me3) showed a modest enrichment for lower HiDRA activity levels but continued to increase linearly even at the highest activity levels, possibly due to active repetitive elements, as Applicants discuss below.

Figure 11:
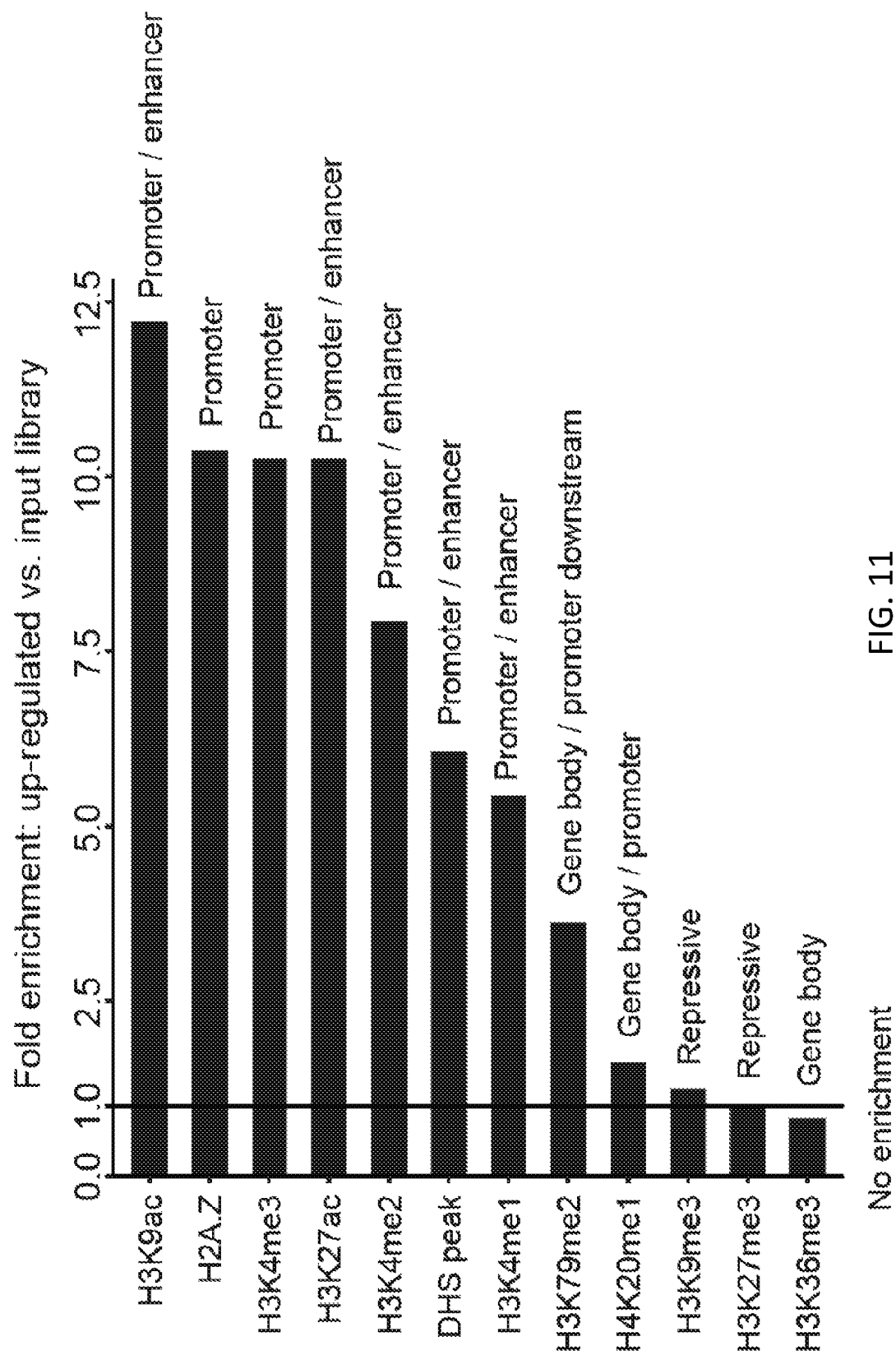
FIG. 11—Enrichment of histone modifications in active HiDRA fragments. All histone modifications and DHS data were collected from GM12878 cells by the ENCODE or Roadmap Epigenomics projects.

Applicants also studied the enrichment of HiDRA regions for individual histone marks profiled by the ENCODE project in GM12878[9]. Active promoter- and active-enhancer-associated acetylation marks H3K9ac and H3K27ac, histone turnover-associated H2A.Z, promoter- and enhancer-associated H3K4me3 and H3K4me1, and DNase I accessible chromatin were the most enriched individual marks within active HiDRA regions, while Polycomb-repression-associated H3K27me3, heterochromatin-associated H3K9me3, and transcription-associated H3K36me3 were the least enriched compared to the input library (FIG. 11).

Figures 10A, 10B:
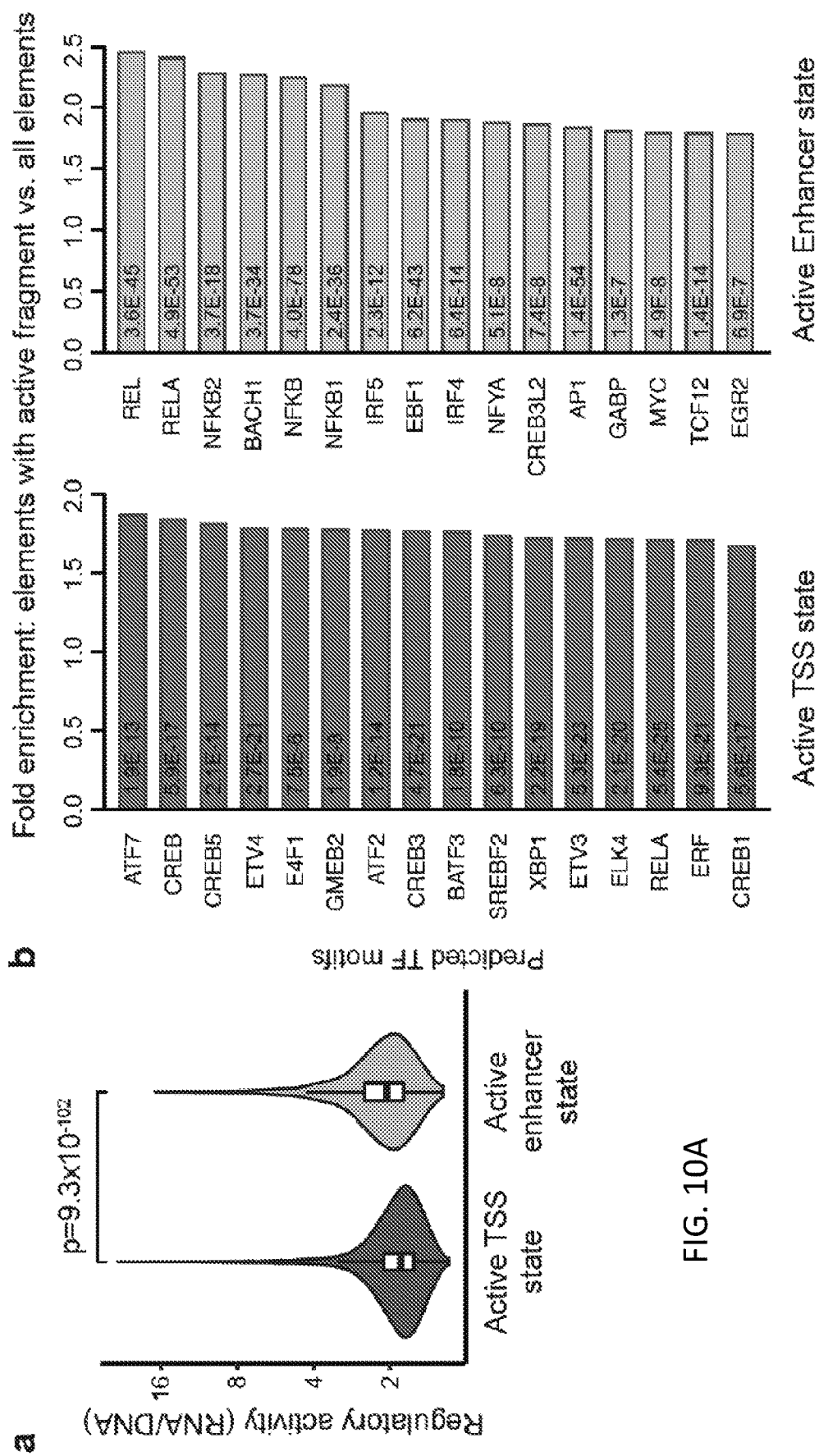
FIG. 10A-10B—Enrichment of motifs in active HiDRA regions.

As these elements are tested outside their endogenous chromatin context, Applicants expect that they drive reporter gene transcription by recruiting transcriptional regulators in a sequence-specific way, and Applicants sought to gain insights into the recruited factors. Applicants calculated the overrepresentation of 651 transcription factor sequence motifs assembled by ENCODE in active HiDRA regions and found enrichment for many distinct motifs for immune transcription factors (FIG. 10B), including IRF, NFKB1, and RELA, corresponding to transcriptional regulators known to function in GM12878 compared to other human cell lines. The motifs enriched in promoter chromatin states were largely distinct from those enriched in enhancer chromatin states, highlighting the differential regulatory control of the two types of regions (FIG. 10A). These differences in motif content indicate that the two types of regions recruit different sets of transcriptional regulators both in their endogenous context and in our episomal assays, consistent with their distinct endogenous chromatin state and their distinct properties in our HiDRA assays.

Example 4— HiDRA Regulatory Activity Outside Promoter and Enhancer Regions

Even though HiDRA active regions were most enriched for enhancer and promoter states, they were not exclusive to them. In fact, approximately half of active HiDRA regions (52%) showed endogenous epigenomic signatures characteristic of repressed and inactive chromatin states, including Quiescent, Repressed Polycomb, Weak Repressed Polycomb, and Heterochromatin.

Figure 4B:
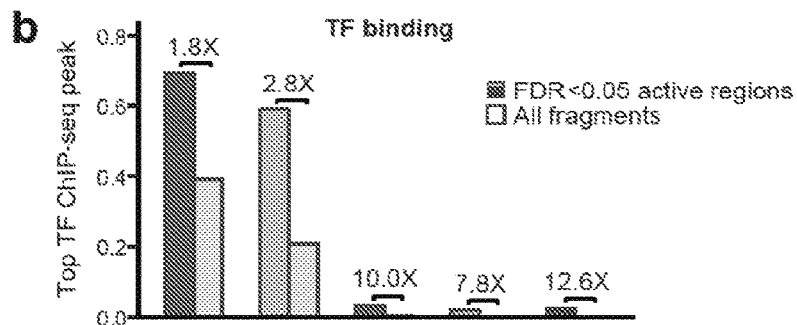

As active chromatin states were defined based on the profiling of only a subset of known chromatin marks in GM12878, Applicants reasoned that perhaps other marks may be marking these regions active, but that they were perhaps not profiled in GM12878 and thus missed by the reference genome annotations. For example, a recent study identified subclasses of active enhancer elements marked with H3K122ac or H3K64ac but not H3K27ac[14]. While these marks were not profiled in GM12878, inactive chromatin states that showed HiDRA activity were 8-fold to 13-fold more likely to be bound by transcription factors in ChIP-seq experiments in GM12878 than inactive chromatin states that lacked HiDRA activity (FIG. 4B), indicating that the assays can successfully recover active regions even outside active chromatin states, and highlighting the importance of the unbiased survey of open chromatin regions regardless of their endogenous chromatin marks.

Figure 4C:
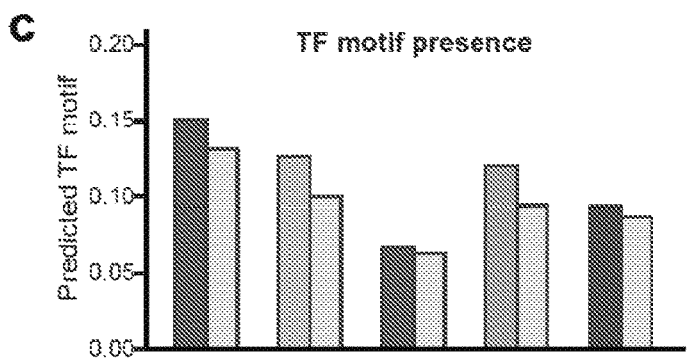
Figure 4D:
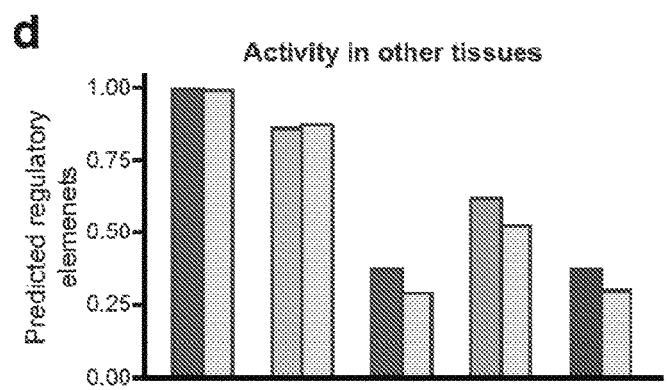

As both high-throughput and low-throughput episomal assays test regions outside their endogenous chromatin context, Applicants reasoned that some active HiDRA regions with inactive chromatin signatures may reflect endogenously-inactive regions that become active when removed from the influence of nearby repressive effects. Applicants reasoned that these regions would contain sequence motifs of TFs active in GM12878, but that these sequence motifs would be less likely to be bound in vivo, compared to motifs in active states. Indeed, Applicants found that active HiDRA regions from endogenously-inactive chromatin states showed similar enrichments in regulatory motif occupancy to that of enhancer and promoter chromatin states (FIG. 4C), but substantial differences in their endogenous TF binding (FIG. 4B), consistent with endogenous repression due to their genomic context. These regions were also ~30% more likely to be active in another human tissue, compared to HiDRA-inactive regions (FIG. 4D), consistent with cell-type specific repression in their endogenous chromatin context.

Figure 4E:
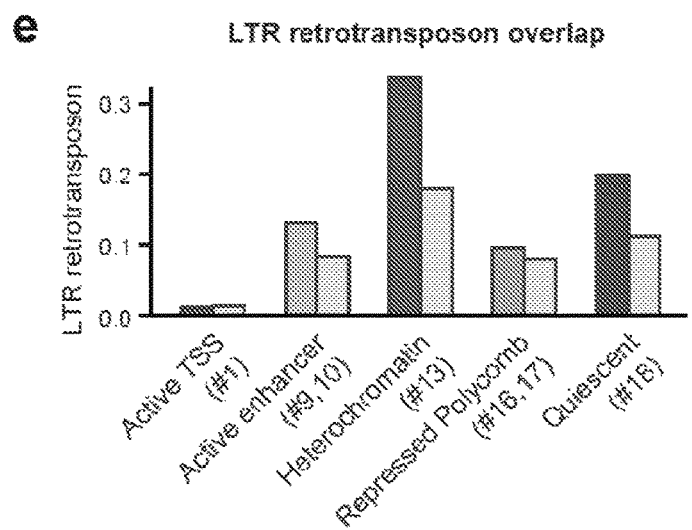
Figure 12:
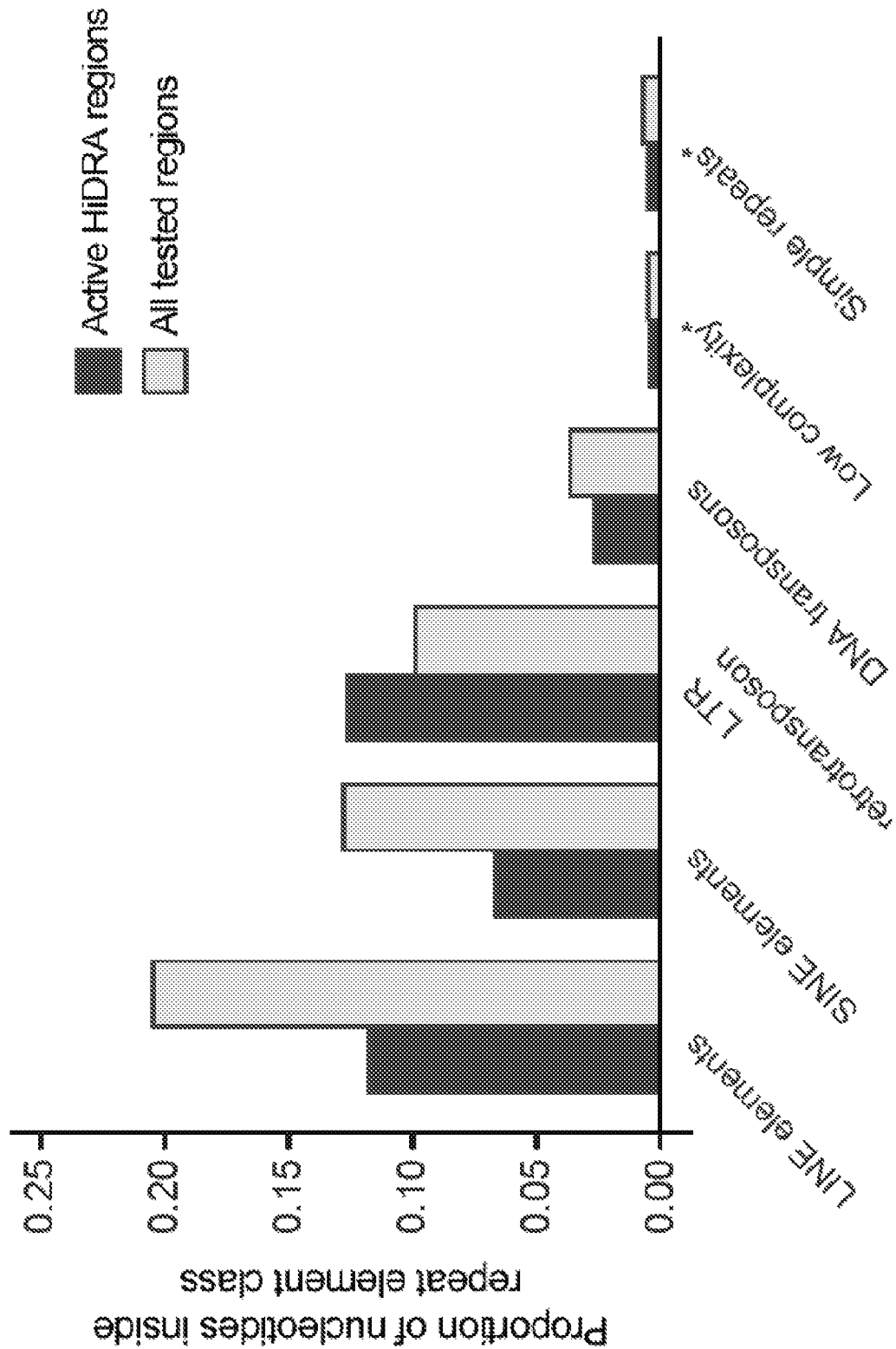
FIG. 12—LTR retrotransposon repeat elements are enriched within active HiDRA regions. Elements identified using RepeatMasker annotation of the hg19 human genome. Low complexity and Simple Repeat classes are artificially low due to pre-filtering to remove HiDRA fragments mapping to multiple genomic locations.

In addition to the presence of regulatory motifs for known regulators active in GM12878, Applicants sought additional driver elements that may be responsible for the episomal activity of endogenously-inactive regions. In particular, Applicants considered the presence of Long-Terminal-Repeat (LTR) retrotransposons, which have been previously shown to have regulatory activity potential and were enriched in the set of all active HiDRA regions unlike other repetitive elements in the genome (FIG. 12)[2, 20]. Indeed, Applicants found that active HiDRA regions from endogenously-inactive regions showed substantial enrichment for LTR retrotransposons. In fact, Quiescent and Heterochromatin states were more enriched for LTR retrotransposons than either Enhancer or Promoter chromatin states (FIG. 4E, FIG. 12). As LTRs are motif-rich and often act as the substrate for recently evolved enhancers, these endogenously inactive but episomally-active HiDRA regions may represent a reservoir for the emergence of new regulatory elements[6].

Example 5— High-Resolution Mapping of Regulatory Activity with HiDRA

Figure 5A:
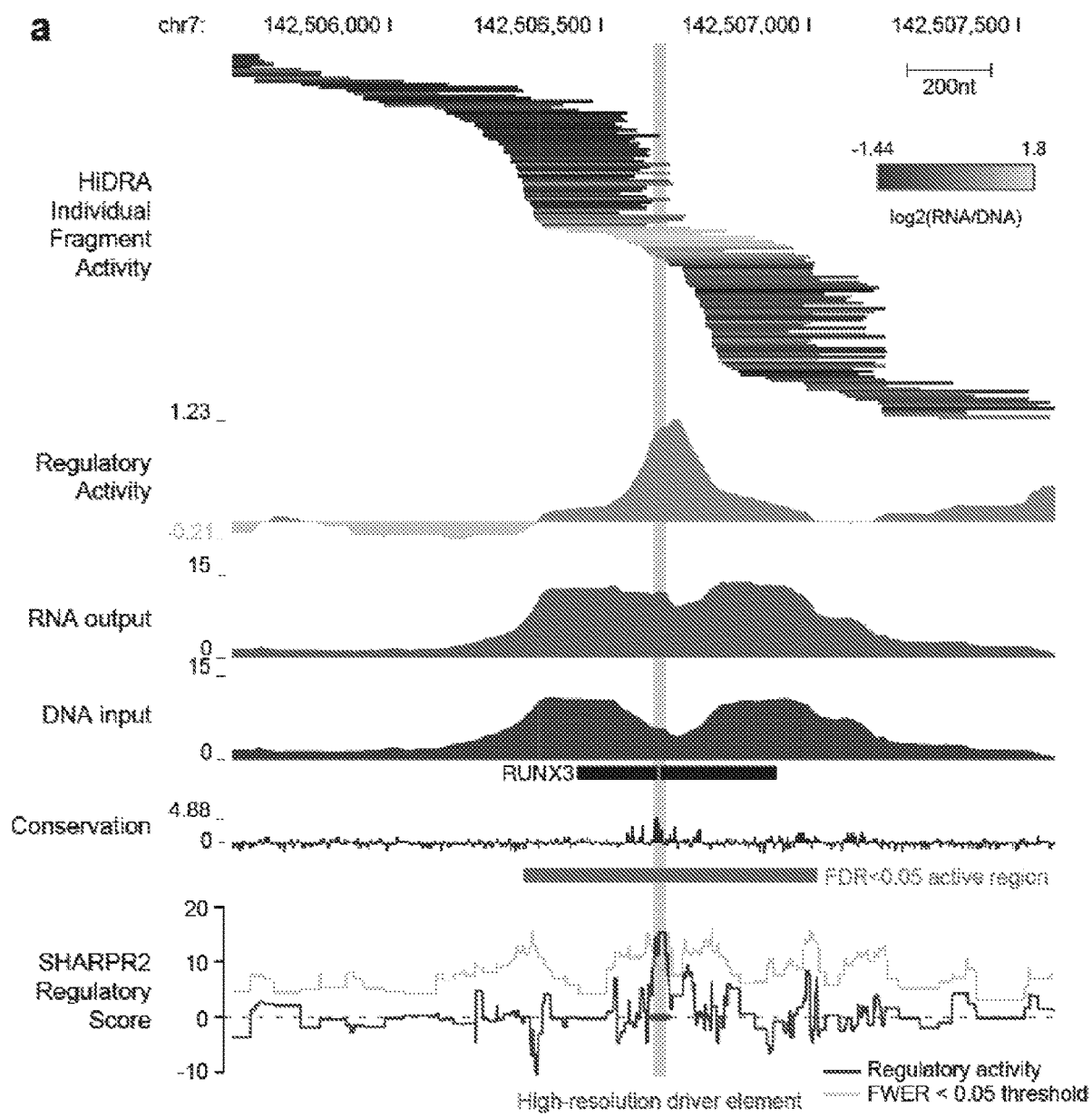
FIG. 5A-5E—High-resolution mapping of transcriptional regulatory elements with SHARPR2.

Applicants next sought to exploit the highly overlapping nature of tested HiDRA fragments to increase the resolution of regulatory inferences by exploiting subtle differences between neighboring fragments that only overlap partially. As an example, Applicants considered a 3 kb region on chromosome 7 that is covered by 134 distinct HiDRA fragments. When Applicants examined every fragment in this region, Applicants observed that fragments overlapping the known RUNX3 motif showed substantially higher regulatory activity (FIG. 5A). This motif is bound by the RUNX3 protein in GM12878 cells and shows increased evolutionary conservation (FIG. 5A). These properties suggest that the driver regulatory nucleotides within this region are tightly concentrated surrounding the RUNX3 motif, and that on the global level the differential activity of HiDRA-tested segments should enable us to systematically discover these driver nucleotides in an unbiased way based on the relative activity of fragments that do or do not overlap them.

As part of the development of Sharpr-MPRA[2], Applicants had previously developed the SHARPR algorithm, a graphical probabilistic model that inferred high-resolution activity from MPRA tiling experiments by reasoning about the differential activity of partially-overlapping microarray spots. Intuitively, SHARPR allowed us to transform measurements from the 145-bp resolution of individually tested tiles to the 5-bp resolution of the offset between consecutive tiles. The SHARPR algorithm relies on synthesized oligos that uniformly tile regions at regularly spaced intervals, and thus is not applicable for the random fragmentation nature of HiDRA experiments where both the length and the spacing of neighboring fragments can vary. To address this challenge, Applicants developed a new algorithm, SHARPR2, which estimates regulatory scores underlying any set of randomly-positioned and variable-length segments, by appropriately scaling the segments by their varying lengths, and enabling inferences at variable-length offsets between them (Appendix A).

Applying the SHARPR2 algorithm to the RUNX3 example above, Applicants found that the 3 kb region was narrowed down to a single 'driver' element of 27nt (FIG. 5A). These captured the known RUNX3 motif shown experimentally by ChIP-Seq to be bound by the RUNX3 regulator in GM12878[9], and also the independently-determined high-resolution region of evolutionary conservation, even though neither line of evidence was used in the inferences.

Figure 5B:
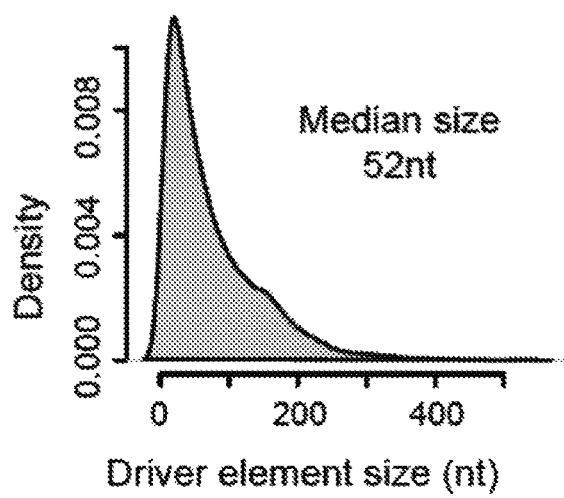
Figure 13:
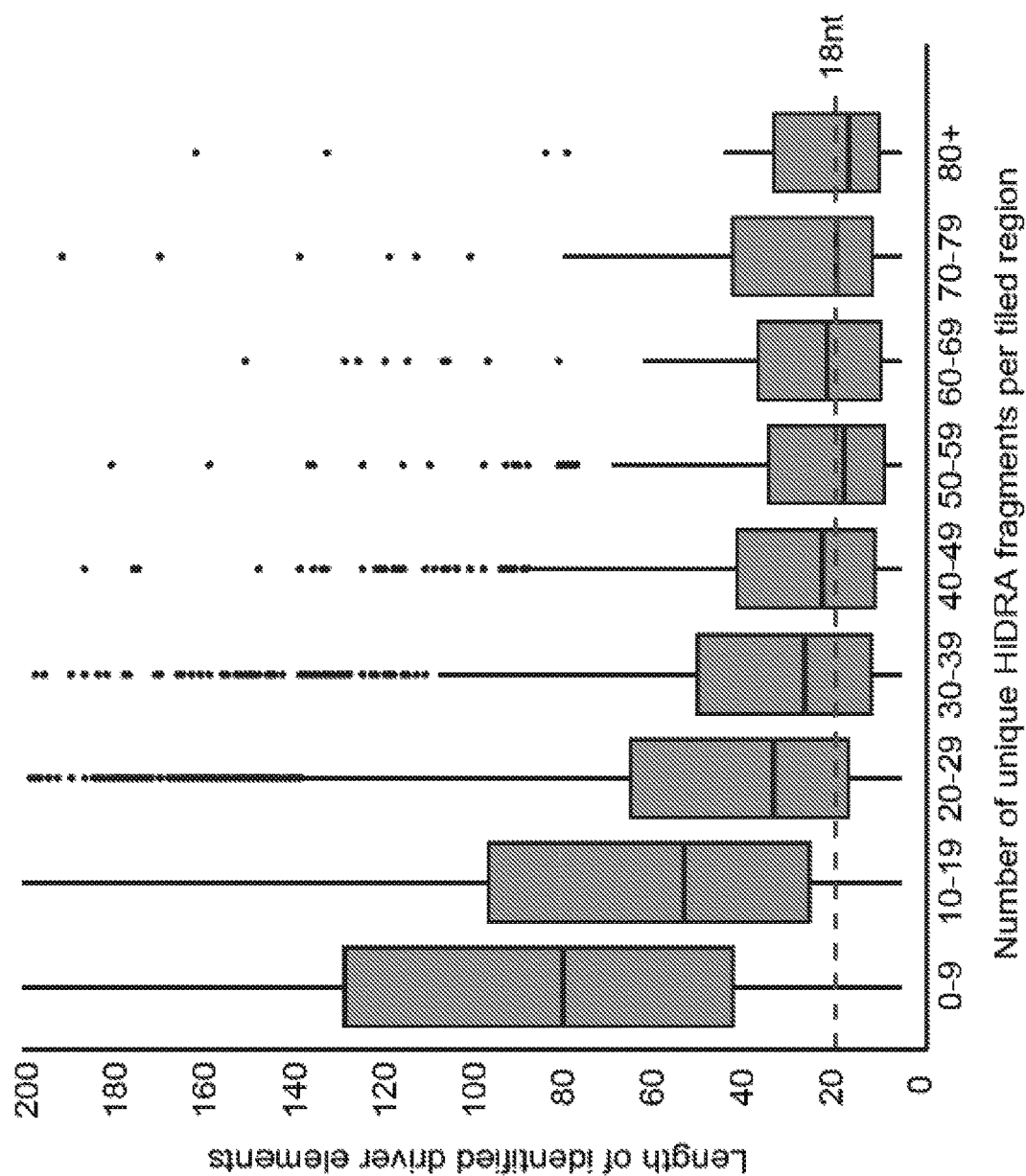
FIG. 13—Length of high-resolution driver elements depends on coverage. Driver elements identified by SHARPR2 are smaller in size for tiled regions covered by more fragments. Decrease in driver element size plateaus around 40-50 HiDRA fragments, to reach an expected minimum size of ~18nt.
Figures 14A, 14B:
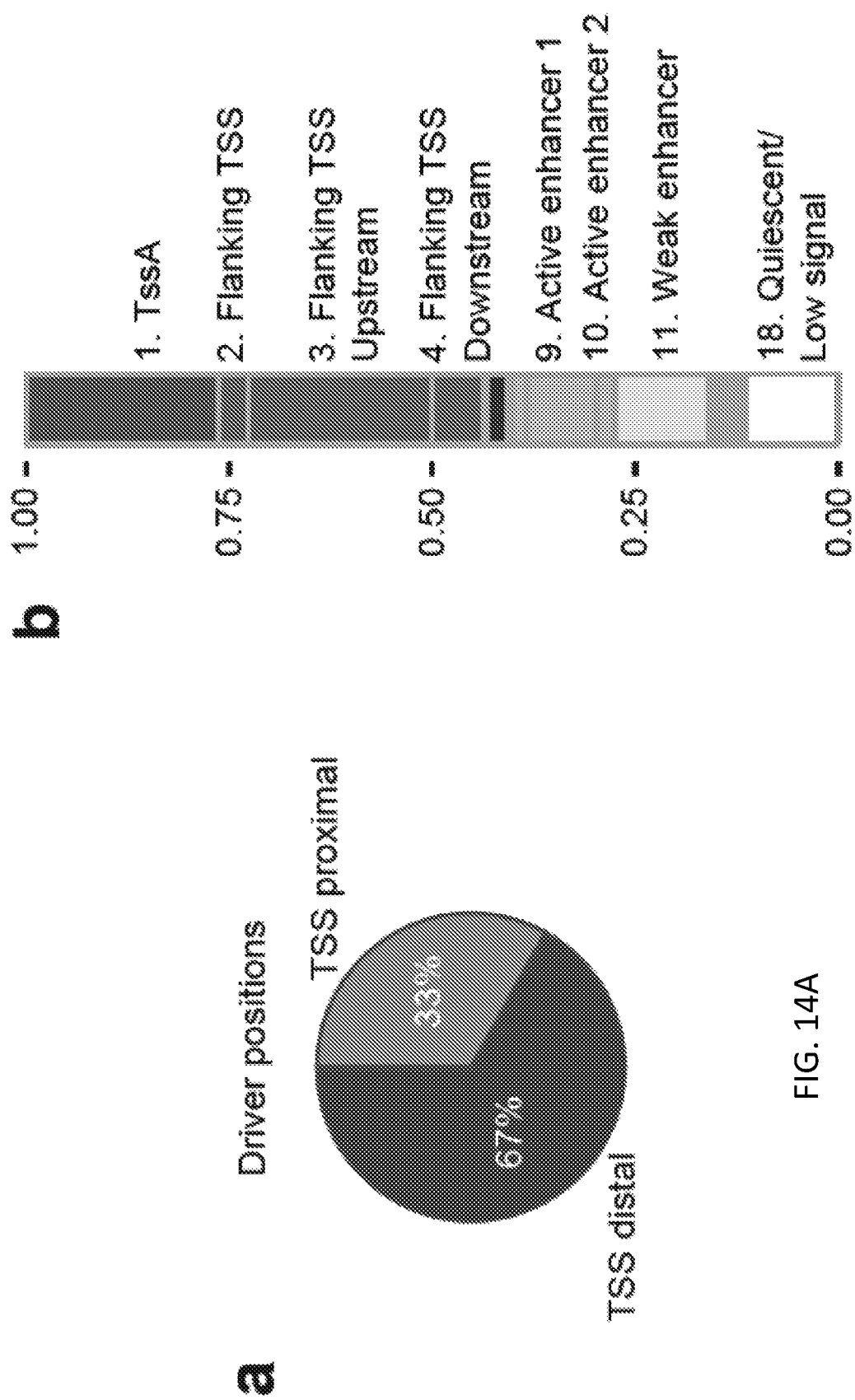
FIG. 14A-14B—Genomic distribution of HiDRA driver elements.

Across all ~32,000 "tiled regions" that are covered by at least 10 unique HiDRA fragments, SHARPR2 predicted ~13,000 driver elements of median length 52nt, using a regional family-wise error rate of 5% (FIG. 5B). With increasing coverage, the resolution of driver regions also increased, from ~50nt for regions with 10-20 fragments to ~20nt for regions with 40 or more fragments (FIG. 13). The length of driver elements did not further decrease between 40 and 80 fragments per tiled region, suggesting a minimum number of ~18 driver nucleotides necessary to drive regulatory activity. Similar to active HiDRA regions, driver elements were also mostly distal from annotated TSS regions and were preferentially found in endogenously active chromatin states (active promoters, TSS-flanking, and active enhancer regions, FIGS. 14A-14B).

Figure 5C:
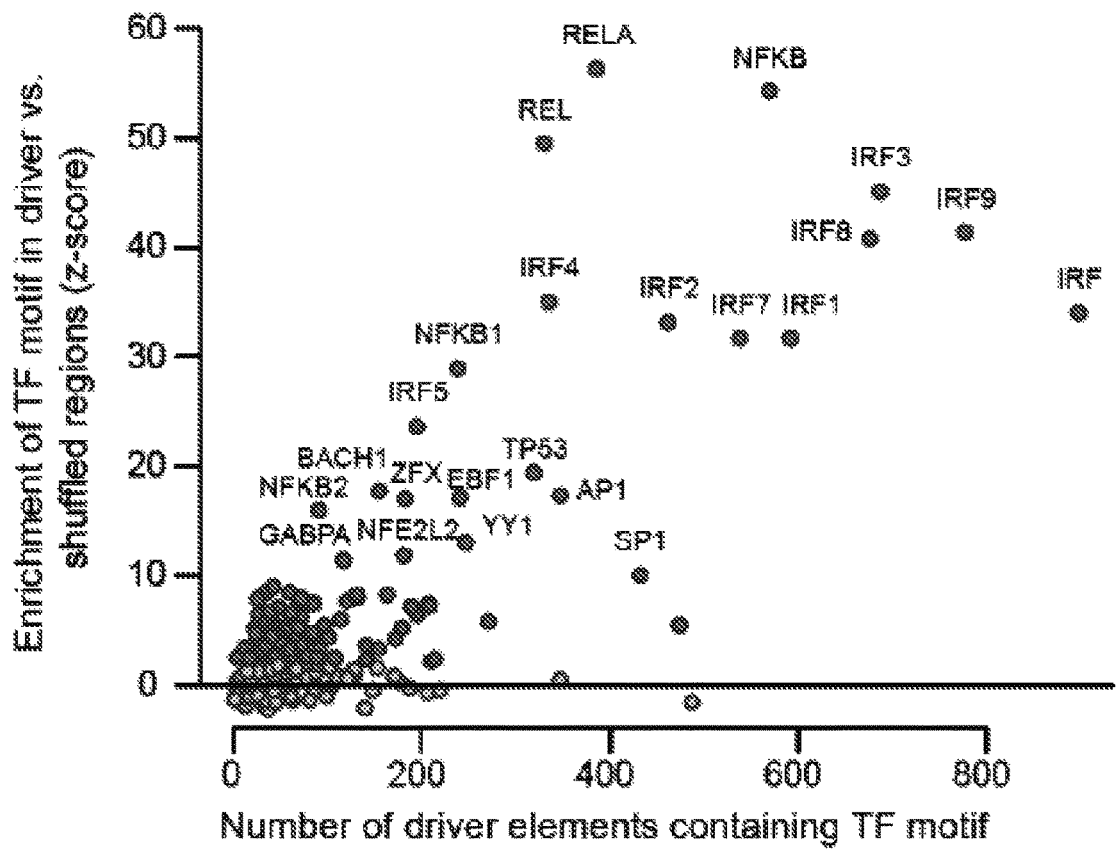
Figure 5D:
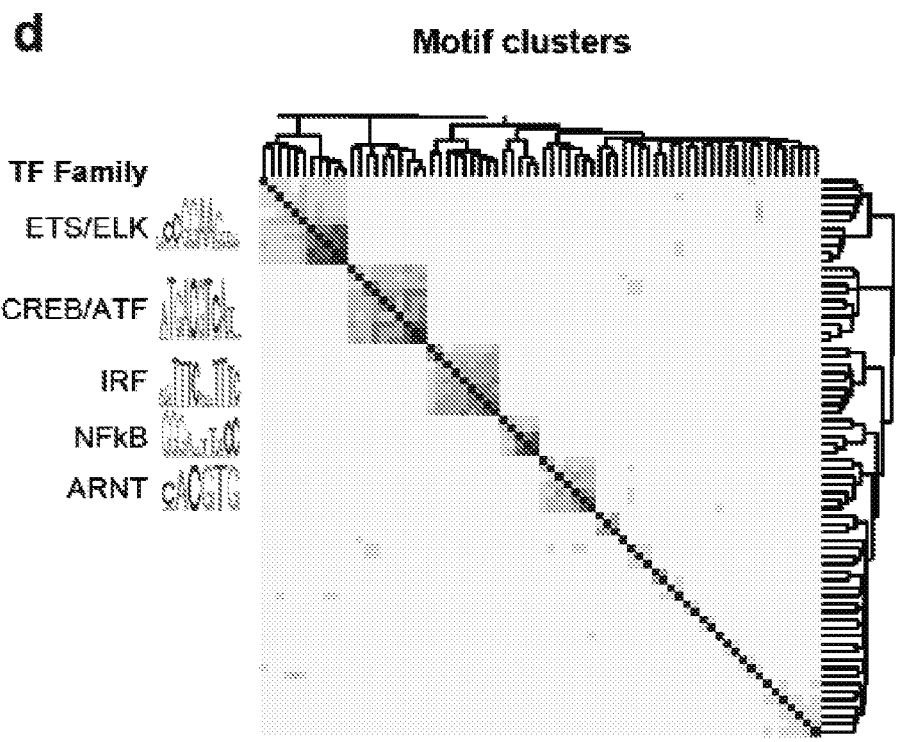
Figure 5E:
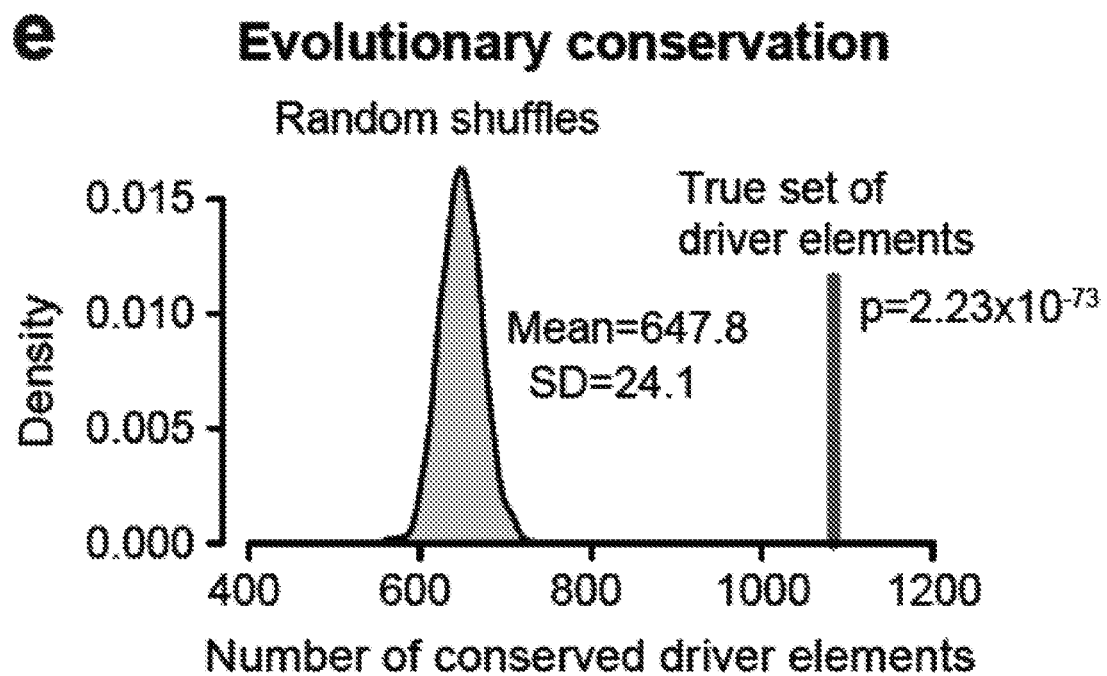

Applicants found that predicted driver nucleotides were significantly more enriched for regulatory motifs than shuffled controls (obtained by randomly shuffling driver positions within tiled regions). The enriched motifs consisted of regulators known to be active in GM12878, including several critical B-cell and immune transcription factor including NF-kB and the IRF family (FIG. 5C). A total of 98 motifs were enriched in driver elements (FDR<0.05), clustering into several distinct groups with little overlap between groups, suggesting a wide range of distinct transcription factors act to regulate GM12878 gene expression (FIG. 5D). Applicants also found that driver nucleotides are significantly more likely to be evolutionarily-conserved across vertebrates than randomly-shuffled controls (FIG. 5E), with ~1080 driver elements overlapping conserved regions, compared to only ~650 expected by chance ($p=2.23\times10^{-73}$). These results indicate that our high-resolution inferences are biologically meaningful and can help pinpoint driver nucleotides among larger regions.

Figure 6A:
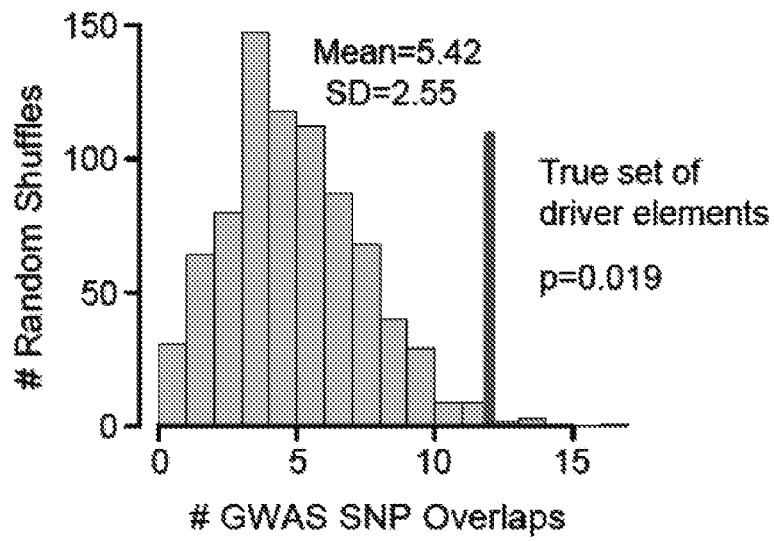
FIG. 6A-6B—High-resolution driver elements are enriched for fine-mapped GWAS SNPs.
Figure 6B:
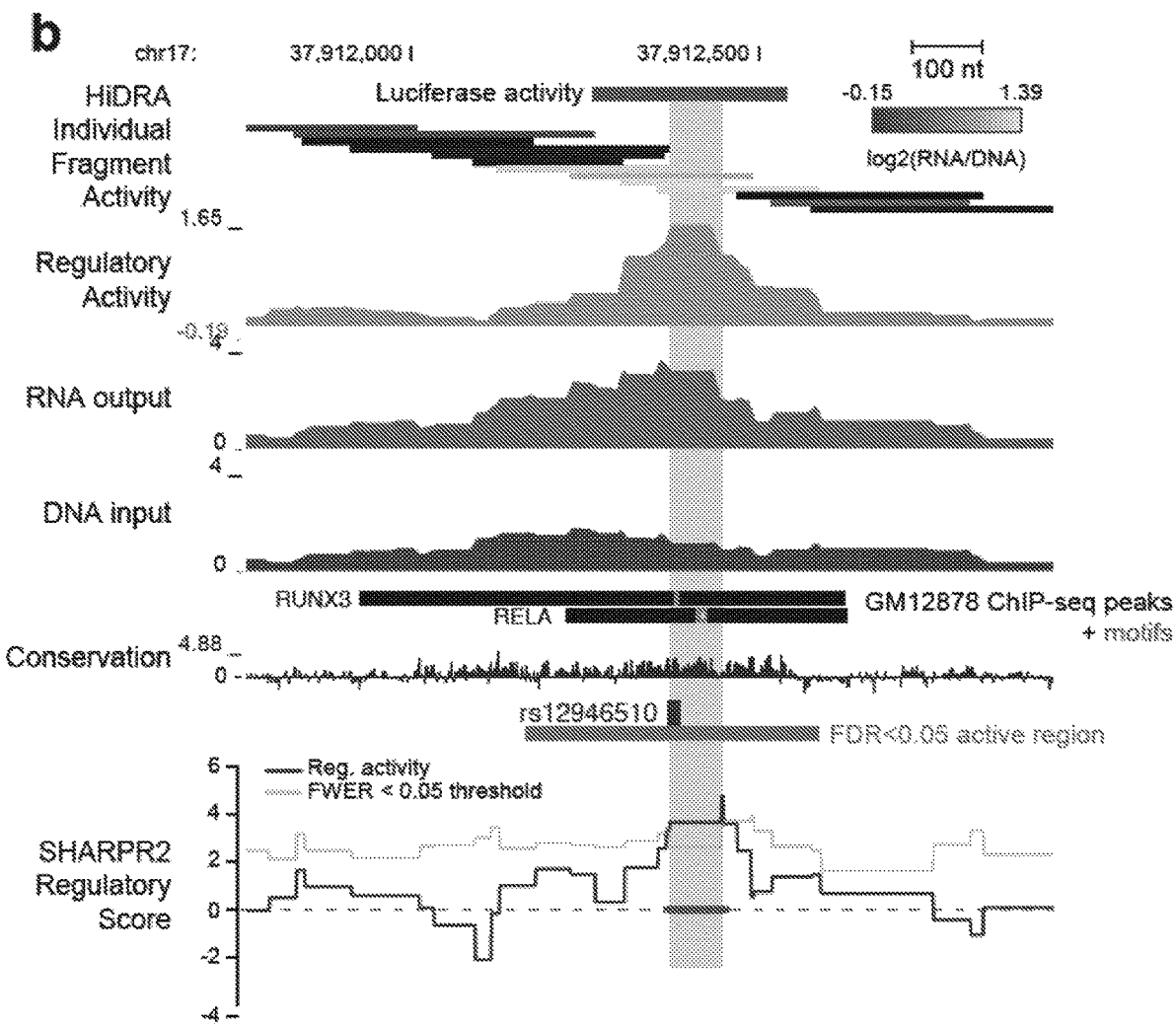

Example 6— Prioritization and Characterization of GWAS Variants Affecting Regulatory Activity Applicants next sought to use the predicted active regions and driver nucleotides to gain insights into non-coding variation. Applicants studied the overlap between genetic variants associated with immune disorders and our high resolution predicted driver nucleotides. Even though driver nucleotides only cover 0.032% of the genome, Applicants found 12 cases where they overlap fine-mapped SNPs associated with 21 immune-related traits' predicted to be causal (~5 expected by chance inside tiled regions, p=0.012, FIG. 6A). For example, Applicants predict a 76-nt driver element overlapping rs12946510 in the IKZF3 locus associated with multiple sclerosis in a tiled region of 3 kb (FIG. 6B), suggesting this may be the causal variant. The SNP overlaps a 76-nt driver element that contains a RUNX3 motif and a RELA motif, both bound by the respective TFs in GM12878[9]. Indeed, rs12946510 is predicted to be causal based on genetic fine-mapping[21], with a posterior probability of 0.314 of being causal with the next strongest signal showing only 0.067 posterior probability. rs12946510 is also an eQTL for the IKZF3 gene[21,22], and was recently shown to disrupt enhancer activity for the surrounding 279-nt region using a luciferase reporter assay[23], consistent with the prediction that rs12946510 is a causal SNP.

Figure 7F:
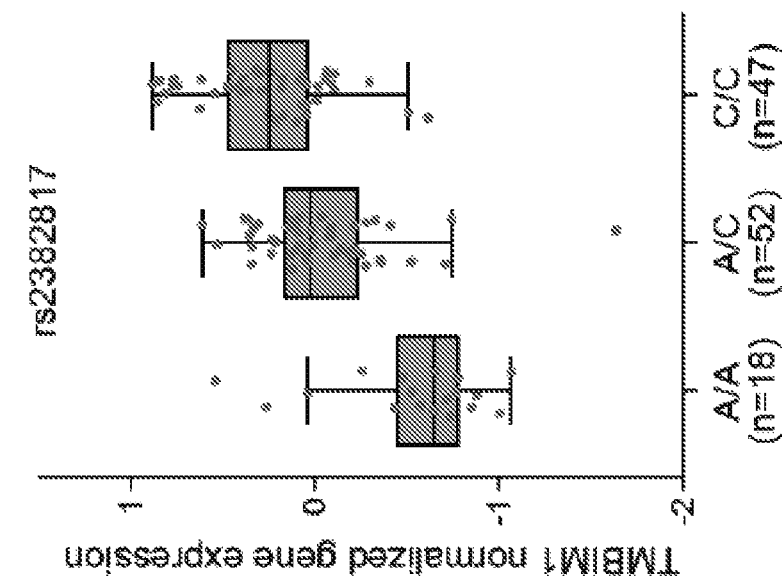

To recognize regions that showed differential activity between risk and non-risk alleles of common genetic variants, Applicants first inferred the genotype of all RNA fragments profiled. As HiDRA is a sequencing-based assay, where the expression of reporter genes is quantified based on the number of sequencing reads, allele-specific differences in HiDRA activity between risk and non-risk haplotypes should be detectable in principle by using heterozygous positions to distinguish reads coming from the 275 paternal or the maternal allele. In practice however, HiDRA fragments are much longer (~337 median length) than the typical sequencing reads Applicants used for quantification (37nt, paired end), and thus 78% of genetic variants will not be covered by the sequencing reads (if they fall in the inner ~260nt not captured by our paired-end sequencing). To overcome this limitation and to determine allele-specific activity scores for all of the fragments, Applicants used low-depth re-sequencing of the input library using long reads, thus revealing the genotype associated with each start/end position in our library (FIG. 7A). Applicants augmented this information with 4-nt random i7 barcodes that were added by PCR during the initial HiDRA library construction, thus ensuring that the [start, end, i7] triplet is almost guaranteed to be unique, by resolving the cases where both start and end positions are identical between paternal and maternal alleles. This strategy enabled Applicants to resolve the genotype of all previously quantified HiDRA fragments without having to sequence both the plasmid and RNA libraries to full length at high depth, which would be too costly.

Figure 15:
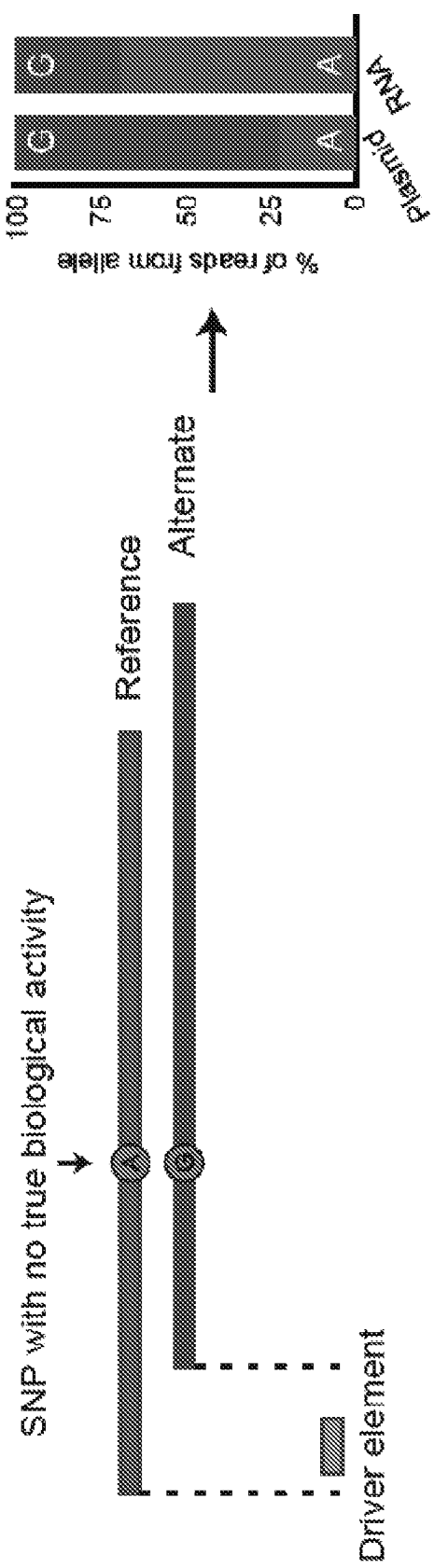
Fig. 15—Confounding effect of differing fragment positions for allelic activity analyses. As HiDRA relies on random fragmentation of the genome, fragments carrying different alleles at a SNP might have differential activity due to the position of their ends, rather than due to allelic activity. In this hypothetical example, a SNP with no true allelic activity is mistakenly called as active because the fragment containing the reference allele overlaps a driver element not present in the alternate fragment.
Figures 16A, 16B:
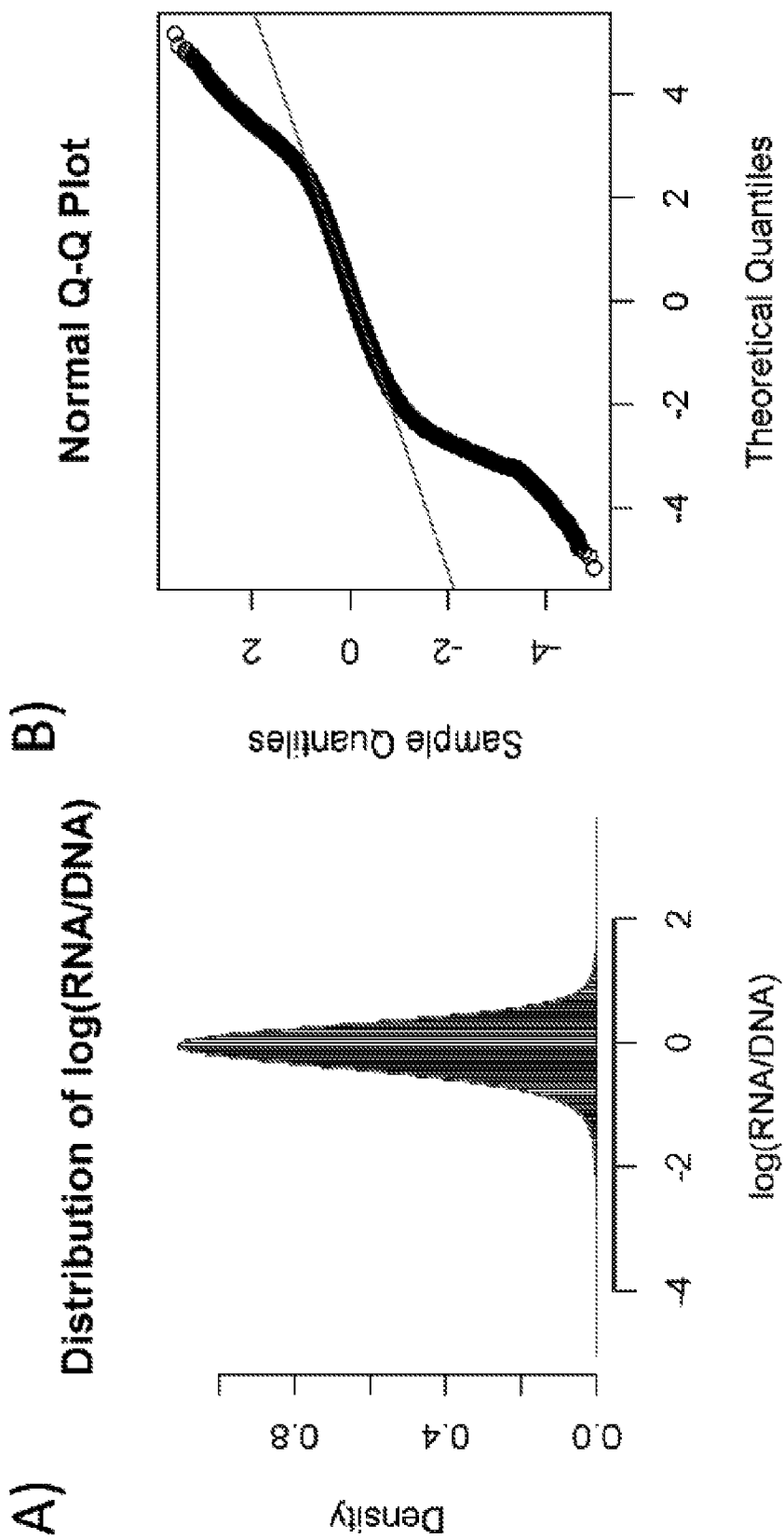
FIG. 16A-16B— FIG. 16A shows a histogram with a density curve of ln(#RNA/#DNA) of the fragments from the library described in the method section. The distribution of ln(#RNA/#DNA) is closer to a normal distribution. The exclusion criteria for the fragments are length<100 or length>600.
Figure 17A:
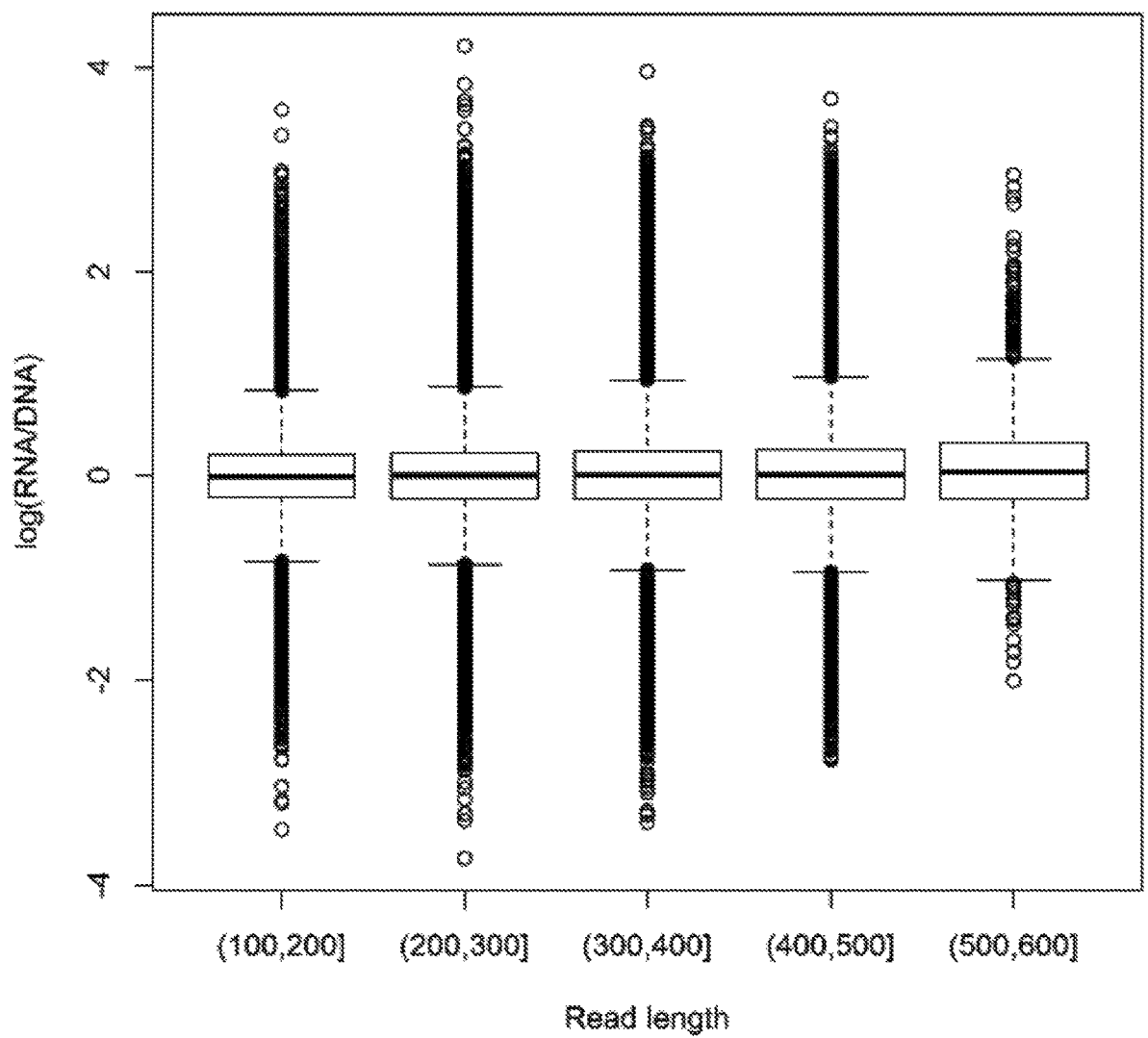
FIG. 17A-17B—Relationship between ln(#RNA/#DNA), fragment length and size of tiled regions.
Figure 17B:
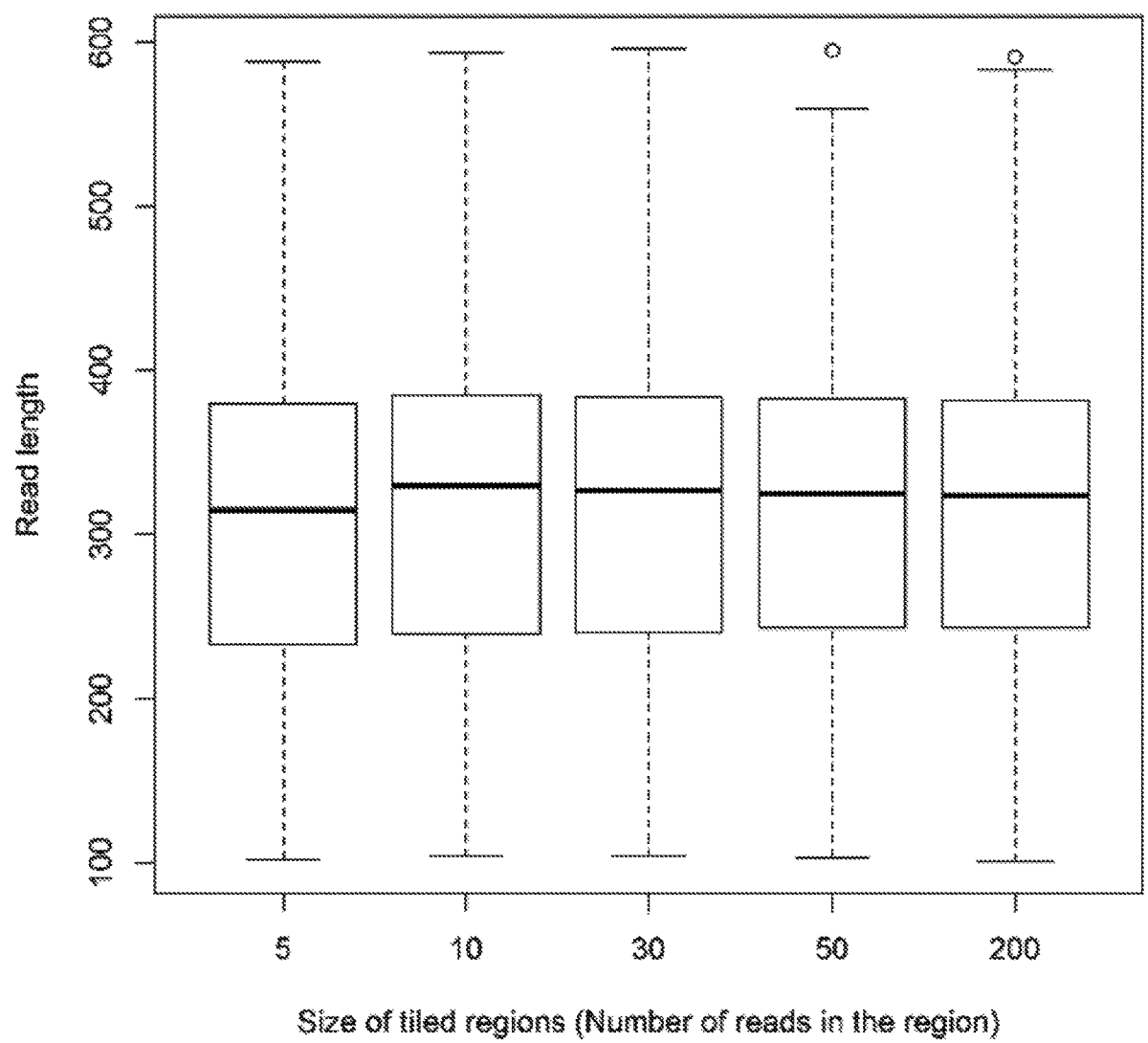
Figure 18:
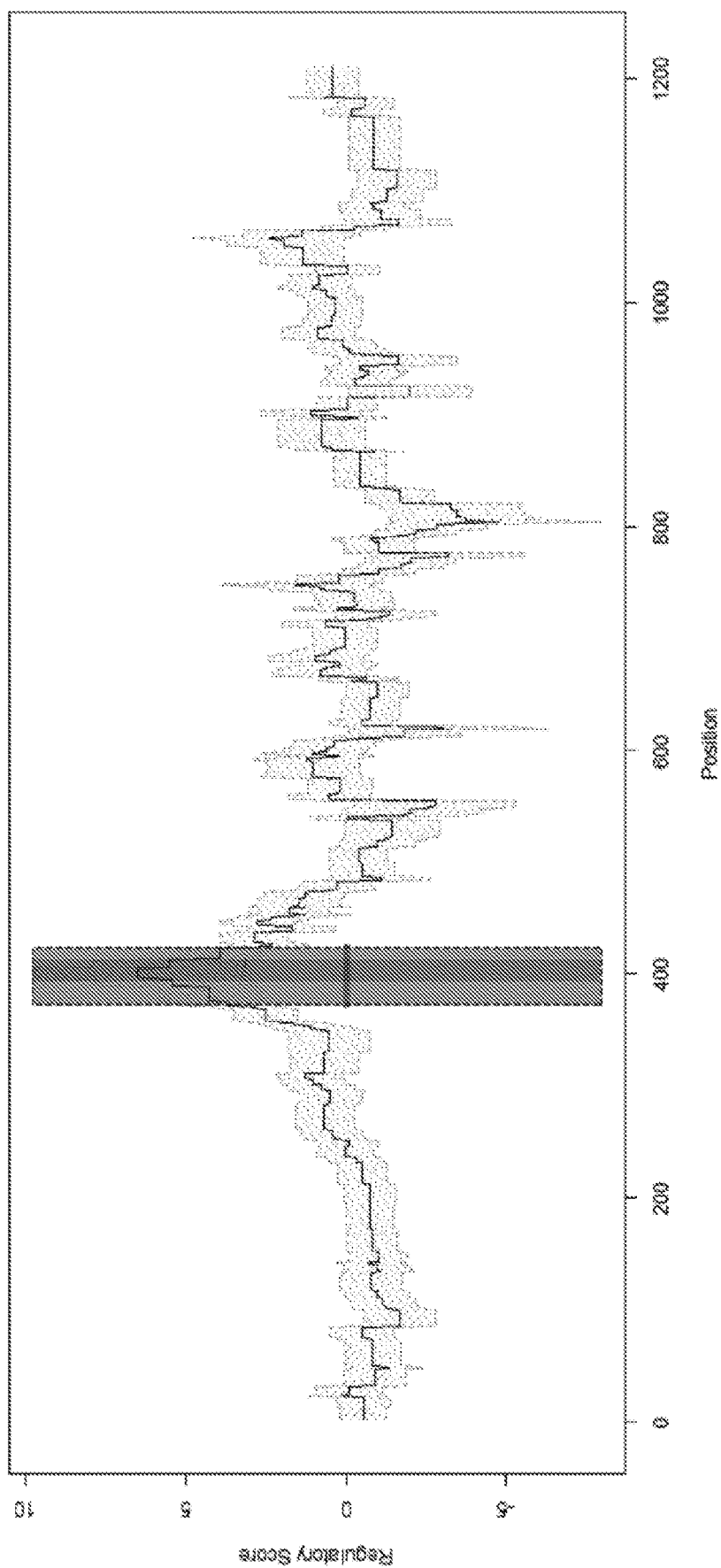
FIG. 18—An example of estimated regulatory scores from a simulated tile region of 1200nt. The data is generated within a 1200nt tile region with 50 unique HiDRA fragments ranging from 175nt to 450nt. The significant regulatory region (FWER<5%) is highlighted in red. The predicted motif region is highlighted in purple. The yellow dashed lines are the estimated scores ±MSE.
Figure 19:
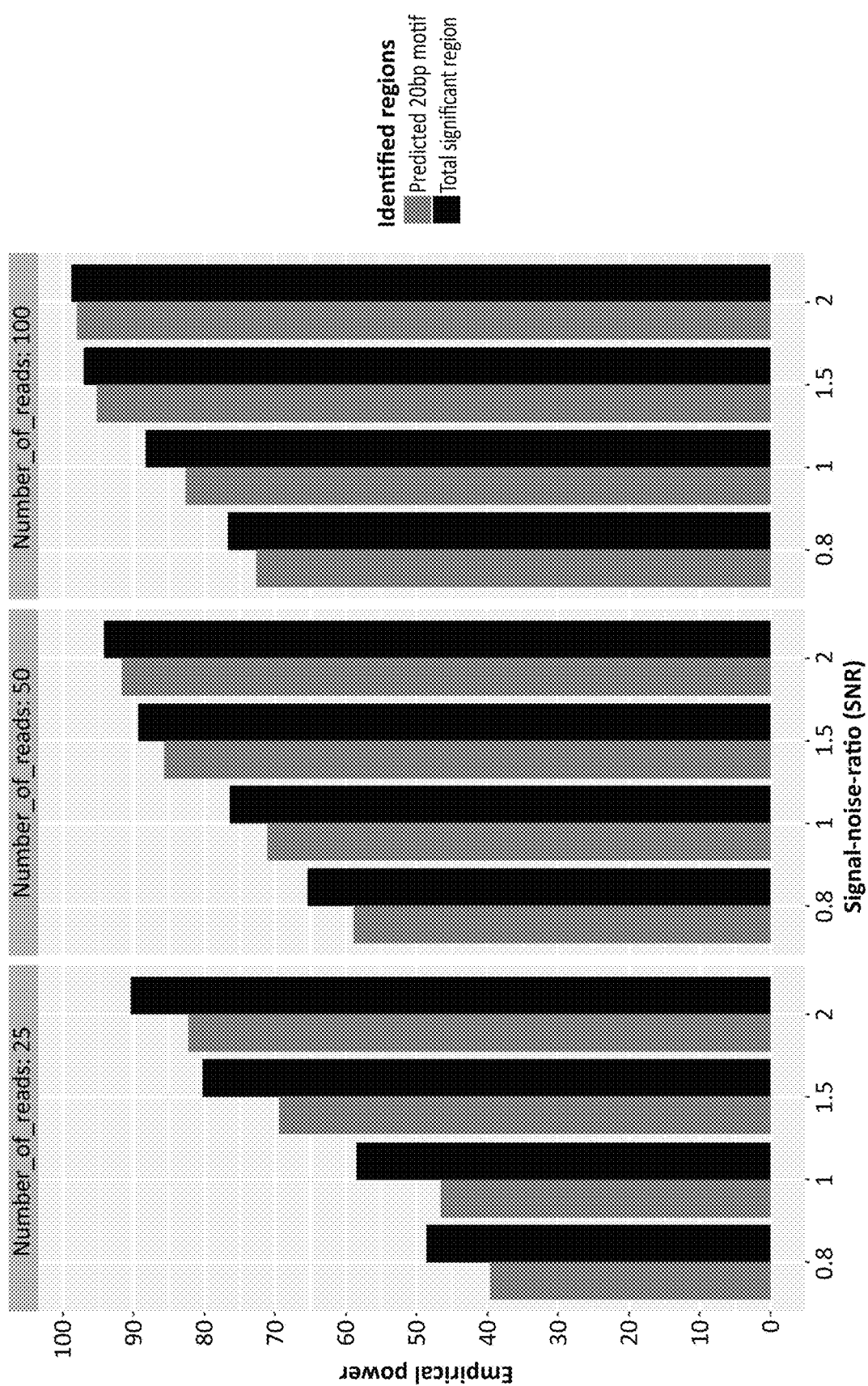
FIG. 19—Empirical statistical power according to different numbers of fragments and different SNR. Y-axis: empirical power (%). X-axis: Signal-to-noise-ratio defined by $$SNR = \frac{s_m}{\sigma_{noise}}.$$

In a proof-of-concept analysis to assess the ability of HiDRA to detect allelic activity, Applicants applied this approach systematically to all heterozygous positions known in the genotyped GM12878 cell lines. Applicants found ~180,000 heterozygous SNPs that were represented by at least one HiDRA fragment at either allele in our library. Applicants realized that fragments carrying the maternal or paternal alleles of a SNP may also differ at their start and end positions, and that differences at fragment ends may cause SNPs with no true biological activity to falsely appear to disrupt HiDRA activity (FIG. 15). Applicants attempted to filter out these cases by only comparing fragments that show 90% mutual overlap, and where the start and end of the fragment is more than 25nt from a high-resolution driver element, thus ensuring that allelic differences are not due to differential inclusion of driver elements (~16,000 SNPs remained after filtering). At an uncorrected nominal p-value cut-off of 0.05, Applicants found 880 'allelic' HiDRA SNPs where paternal and maternal alleles showed differences in activity, 25 of which had a corrected FDR<0.1 (beta-binomial model[24]). The corresponding SNPs in these 880 allelic HiDRA regions were more frequently found in HiDRA active regions and more frequently predicted to have strong regulatory effects in open chromatin regions by an independent study[25] (FIGS. 7B, 7C), suggesting they are biologically meaningful.

Figure 7E:
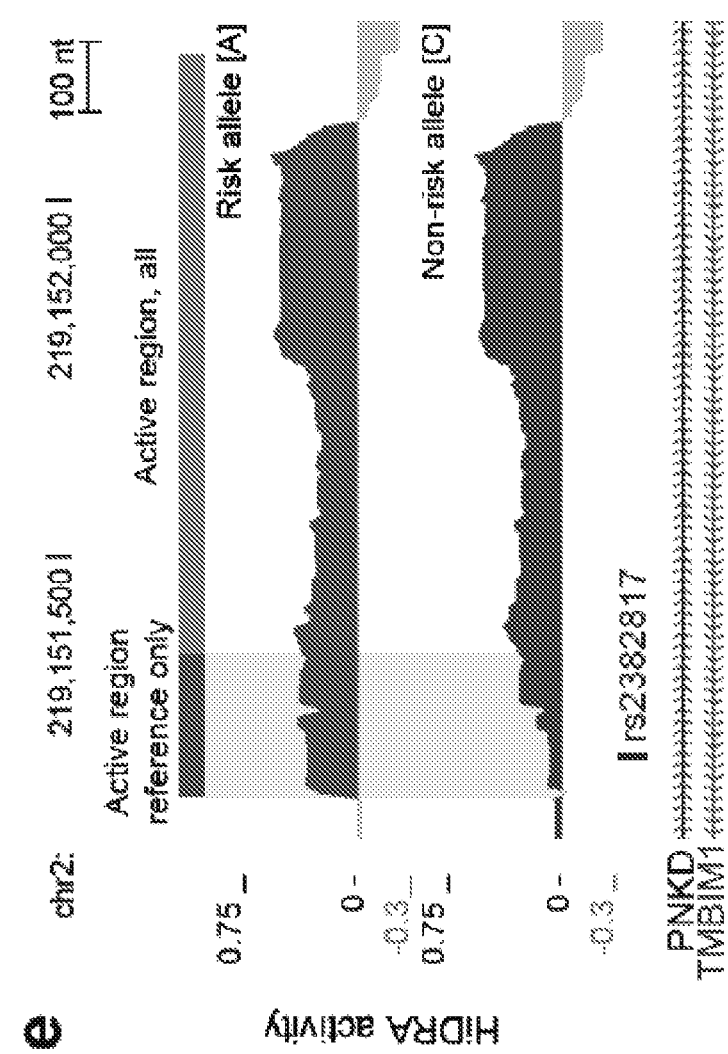

For example, Applicants found that rs2382817, a SNP associated with inflammatory bowel disease[22] (pG-WAS=$1.13 \times 10^{-13}$), shows differential HiDRA activity between paternal and maternal alleles. The risk allele shows increased regulatory activity upstream of a HiDRA-annotated active region (nominal p=$8.7 \times 10^{-4}$, FDR=0.25, FIGS. 7D, 7E). In a panel of human individuals from the GTEx project[26], rs2382817 was an eQTL for TMBIM1 in EBV-transformed lymphocytes (the same cell type as GM12878, FIG. 7F), and for TMBIM1 and other nearby genes PNKD, ARPC2 and GPBAR1 in other tissues, consistent with a role of rs2382817 in gene expression regulation and illustrating the possibility of using HiDRA to detect SNPs with allelic effects on regulatory activity.

These results indicate that HiDRA can help shed light on disease-associated variants, by either narrowing down the set of candidate causal SNPs using the high-resolution driver nucleotide inferences, or by directly observing differential activity between risk and non-risk alleles using allele-specific activity inferences.

Example 7—Discussion

Applicants presented a high-throughput experimental assay, HiDRA, to test transcriptional regulatory activity for millions of DNA fragments preferentially generated from regions of open chromatin and discover high resolution driver elements. Applicants performed HiDRA mapping of regulatory activity using a library of sequences from the GM12878 lymphoblastoid cell line ranging from 169-477nt in length. Applicants found that the endogenous loci of up-regulated HiDRA fragments are significantly more likely to be classified as promoter and enhancer elements, contain motifs for immune transcription factors and be marked by activating histone modifications. Applicants also leverage the dense tiling of HiDRA fragments at regulatory regions to perform a high-resolution mapping of regulatory activity to identify short DNA segments that act as drivers of regulatory activity, including one 76nt driver element that overlaps a SNP, rs12946510, associated with multiple sclerosis risk.

While Applicants performed the study in the GM12878 cell line, the HiDRA methodology can be readily applied to study the transcriptional regulatory architecture of any cell line. For cell lines with poor transfection efficiencies, a non-integrating lentiviral infection method can be used instead of transfection, as both approaches have shown highly similar results in other high-throughput reporter assays 27. HiDRA libraries can also be transfected in a different cell line than was used for library generation. For example, libraries could be generated from limited patient tissue, and subsequently transfected into a relevant immortalized cell line.

Applicants also demonstrate a proof-of-concept application of HiDRA to identify SNPs that alter regulatory element activity by mapping reads in an allele-specific manner, as well as illustrate potential confounding factors for analyzing allelic HiDRA and STARR-seq data when fragments mapping to either allele have different genomic positions. Moving forward, construction of libraries with higher coverage at relevant SNPs should mitigate this concern. HiDRA also relies on the presence of different alleles in the input genomic DNA. While no human individual or cell line exists that is heterozygous at every clinically important genetic variant, future studies can pool cells or tissue from multiple individuals to generate a HiDRA library heterozygous at more loci. As recent studies have also shown that cancer driver mutations are enriched inside promoter elements, HiDRA may also be applied to pools of tumor samples to identify promoter variants that experimentally alter regulatory activity and gene expression[28].

One limitation of HiDRA is the use of genomic DNA, while technologies involving in vitro synthesis can readily introduce changes to DNA not observed in the human population to better fine-map regulatory subregions of enhancers[15,29]. HiDRA fragment libraries can be modified to introduce non-existing mutations through error-prone PCR or introduction of mutagens during fragment amplification. Another improvement to the assay is to further enrich for fragments from active regulatory regions, by coupling with a fragment capture technology similar to those used in Capture Hi-C to selectively test a subset of enhancers or promoters at higher resolution while retaining the advantages of having larger fragment sizes and high library complexity[30]. Finally, the SHARPR2 high-resolution mapping algorithm can be applied to other STARR-seq experiments. For example, investigators interested in only a specific locus could perform STARR-seq on a bacterial artificial chromosome clone ("BAC-STARR-seq") that contains the region of interest[3]. SHARPR2 high-resolution mapping will then readily be capable of mapping regulatory activity of this specific locus with single nucleotide resolution.

In summary, Applicants present HiDRA, a high-throughput method to assay the regulatory activity of millions of open chromatin-derived fragments located genome-wide. As HiDRA can be readily applied to any eukaryotic cell type, Applicants envision this approach or similar technologies being used to quantify the transcriptional regulatory landscape of DNA sequences for a variety of tissues from multiple organisms.

Example 8—Methods

HiDRA Library Construction

Applicants performed 16 ATAC-seq reactions on 50,000 GM12878 cells each using a modified protocol based upon Buenrostro et al. (Supplemental Note 1). Applicants performed cell collection, lysis, and Tn5 digestion as described by Buenrostro et al., Tn5-fragmented DNA was cleaned up using a MINELUTE™ PCR purification kit (Qiagen #28004, four reactions per column eluted in 20 uL EB buffer) and the resulting 80 uL of eluate was split into 16 PCR reactions (Supplemental Note 2). PCR was performed using custom HPLC-purified primers (F: 5'-TAGAG-CATGCACCGGCAAGCAGAAGACGGCAT-ACGAGATNNNNATGTCTCGTGGGC TCGGAGATGT-3' (SEQ ID NO: 1, R: 5'-GGCCGAATTCGTCGATCGTCGGCAGCGTCA-GATGTG-3' (SEQ ID NO: 2), NNNN corresponds to random 4nt i7 barcode sequence) and NEBNEXT™ Ultra II Q5 DNA polymerase master mix (NEB #M0544L). Thermocycler conditions were: 65C for 5 min, 98C for 30 sec, 8 cycles of: 98C for 10 sec and 65C for 90 sec. PCR reactions were pooled and 385 cleaned up with a Qiagen MINELUTE™ PCR purification kit (two PCR reactions per column eluted in 20 uL EB buffer) and run on a 1% agarose E-Gel EX with SYBR® Gold II stain (Thermo Fisher #G402001). Size selection of ATAC-seq fragments was performed by gel excision using a razor blade. Gel slabs were pooled into <300 mg groups and DNA was purified using a MIN-ELUTE™ Gel Extraction kit (Qiagen #28604) and eluted in 20 uL of buffer EB per column following modified guidelines described in Box 2 of Taiwo et al. (2012)[31]. The resulting size-selected ATAC-seq fragment library was treated with an anti-mitochondrial DNA CRISPR/Cas9 library following the protocol outlined in Montefiori et al. using 10× excess of Cas9 protein (Supplemental Note 3)[32]. Applicants cleaned up the reaction with a Qiagen MIN-ELUTE™ PCR purification kit and split into 8 PCR reactions for a second round of PCR using the same conditions and primers described above. PCR products were cleaned up using two rounds of AMPure bead selection (0.8× ratio of beads to input) to size-select against small fragments, eluted in 40 uL of dH2O and quantified using a Qubit dsDNA HS Assay kit (Thermo Fisher #Q32854).

The pSTARR-seq_human plasmid used for generating the plasmid library was a gift from Alexander Stark (Addgene plasmid #71509). The linear backbone used for the subsequent cloning steps was generated by digesting 4 ug of circular pSTARR-seq_human for 4-6 hours with AgeI and SalI restriction enzymes (NEB #R3552S and R3138S), followed by gel excision under a dark reader transilluminator (Clare Chemical #DR22A) to extract a linear 3.5 kb fragment corresponding to the human STARR-seq plasmid backbone. Applicants performed cloning of the fragment library into the plasmid backbone approximately following the Methods section from Arnold et al. (2013) 3. For each library, Applicants performed 20 individual InFusion HD cloning reactions (Takara Bio #638911) using a 3.5:1 molar ratio of insert to vector backbone, following manufacturer's instructions (Supplemental Note 4). Each group of five InFusion reactions was collected and cleaned up using the Qiagen MINELUTE™ Enzymatic Reaction cleanup kit, eluted in 10 uL of dH2O, and transformed into four 20 uL aliquots of MegaX DH10B T1R electrocompetent bacteria. The bacteria were thawed on ice for 10 min and mixed with eluted DNA (five InFusion reactions per 100 uL of bacteria). 22 uL of bacteria/DNA mixture were pipetted into a 0.1 cm electroporation cuvette (Thermo Fisher Scientific #P41050) and tapped repeatedly against a hard surface to remove bubbles. Cuvettes were electroporated using a Bio-Rad Gene Pulser Xcell Microbial Electroporation System (Bio-Rad #1652662) using the conditions: 2.0 kV, 200 S2, 25 g (Supplemental Note 5). For high-yield transformations, Applicants observed electroporation time constants between 4.8 and 5.1 ms. After electroporation, bacteria were immediately collected in 750 uL pre-warmed SOC media, pooled, and incubated for 1 hr in a 37C shaker. After recovery, serial dilutions of bacteria were plated to estimate the number of clones in the library. Recovered bacteria were diluted in 2 L of pre-warmed luria broth and 100 ug/mL of carbenicillin and grown overnight (8-10 hours while shaking). Plasmids were collected from bacteria using the Plasmid Plus Mega-Prep kit (Qiagen #12981) following manufacturer's instructions. Plasmid concentration was quantified using a Nanodrop One machine (Thermo Scientific) and diluted to a 3 ug/uL concentration for subsequent transfection steps. To ensure plasmid library quality and diversity, a small aliquot of the fragment library was amplified by PCR using i5 and i7 primers, run on an Illumina MiSeq machine using the 50-cycle v2 kit as per manufacturer's instructions, and aligned to the human genome to ensure correct complexity and sufficient proportions of reads within predicted transcriptional regulatory elements (Supplemental Note 6, see subsequent Methods sections for details on processing of sequencing libraries).

Cell Culture and Transfections

GM12878 cells were obtained from the Coriell biorepository and grown in RPMI 1640 Medium with GlutaMAX Supplement (Thermo Fisher #61870127), 15% fetal bovine serum (Sigma Aldrich #F2442), and 1% pen/strep at a density of between $2 \times 10^5$ and $1 \times 10^6$ cells/mL with regular media changes every 2-3 days. Approximately 24 hours before transfection, GM12878 cells were split to a density of $4 \times 10^5$ cells/mL to ensure the presence of actively dividing cells for increased transfection efficiency. For transfection, cells were collected by centrifugation for 5 min at 300 g, washed once with pre-warmed PBS, and collected again for 5 min at 300 g. PBS was aspirated, and cell pellets were re-suspended in Resuspension Buffer R (Thermo Fisher Scientific #MPK10096) at a concentration of 7.5 million cells per 100 uL. DNA was added to cells at a concentration of 5 ug of plasmid per 1 million cells. In total, Applicants transfected between 120-130 million cells per replicate using 100 uL tips from the Neon Transfection System at 1200V with 3 pulses of 20 ms. Transfected cells were immediately recovered in pre-warmed GM12878 media without antibiotic and recovered at a density of $1 \times 10^6$ cells/mL for 24 hours. In parallel, Applicants performed two transfections of GM12878 cells with a positive control GFP plasmid to assess transfection efficiency using the same conditions.

RNA Isolation and cDNA Generation

GM12878 cells were collected 24 hours post-transfection, washed twice in pre-chilled PBS (collecting for 5 min at 300 g) and RNA was purified using the Qiagen RNEasy Maxi kit (Qiagen #75162) following manufacturer's instructions and performing the optional on-column DNase treatment step (Qiagen #79254). Poly A+ RNA was extracted from total RNA using the Oligotex mRNA Midi kit (Qiagen #70042, two columns per RNA sample), and any remaining DNA was digested with a second DNase treatment step using Turbo DNase (Thermo Fisher #AM2238) following manufacturer's instructions (Supplemental Note 7). Treated mRNA was cleaned up and concentrated using the Qiagen RNEasy MINELUTE™ Cleanup kit (Qiagen #74204). Applicants generated cDNA from mRNA using Superscript III Reverse Transcriptase (Thermo Fisher #18080085) with a gene-specific RT primer located in the 3'UTR of the sgGFP reporter gene downstream from the inserted fragments (5'-CAAACTCATCAATGTATCTTATCATG-3') (SEQ ID NO: 3). Reverse transcription was performed following manufacturer's recommendations except with 2 ug of poly A+ mRNA and 1 uL of 12.5 uM primer per 20 uL reaction, and extension was performed for 60 minutes at 50C (Supplemental Note 8). Reverse transcription reactions were cleaned up using a MINELUTE™ PCR purification kit (Qiagen #28106, two reactions per column) and eluted in 15 uL of pre-warmed buffer EB.

Library Construction and High-Throughput Sequencing

Applicants performed a qPCR to test the number of cycles needed for amplification of single-stranded cDNA as well as input material of plasmid DNA needed such that both reactions had the same Ct values. Applicants used 1 uL of ssDNA and dilutions of plasmid DNA similar to the method described by Tewhey et al. Cell 2016. qPCRs were performed in 10 uL reactions with all reagents scaled down proportionally from a normal 50 uL PCR reaction (1 uL of DNA, 5 uL of Ultra II Q5 master mix, 0.4 uL of 25 uM primer mix, 0.2 uL of 10X SYBRL dye, 3.4 uL of dH2O) with thermocycler conditions: 98C for 30 s, 20 cycles of: 98C for 10 s, 65C for 90 s. Applicants proceeded to perform eight regular 50 uL PCR reactions (each scaled up 5× from the 10 uL PCR reactions) using the same thermocycler conditions except using the Ct value for the cycle number (F: 5'-CAAGCAGAAGACGGCATACGAGAT-3', (SEQ ID NO: 4 R: 5'-AATGATACGGCGACCACCGAGATCTA-CAC[$X^8$]TCGTCGGCAGCGTC-3', "X8" sequence corresponds to sample barcode, chosen from Illumina Nextera barcode list) (SEQ ID NO: 5). PCR reactions were cleaned up using Qiagen MINELUTE™ PCR purification kits and balanced for sequencing using the Kapa Library Quantification Kit (Kapa Biosystems #KK4824, Supplemental Note 9).

Each library batch (five transfected RNA biological replicates, five plasmid controls) was sequenced by the Broad Institute Walk-Up Sequencing Facility on four flowcells on a NextSeq 500 machine using the 75-cycle kit as per manufacturer's instructions for 2×37nt paired-end reads with 2×8nt barcodes.

Read mapping, data processing and identification of significantly up-regulated fragment groups Reads were labelled by a random 4nt P7 barcode and an 8nt P5 barcode for sample ID. Reads were split into the ten samples (5 plasmid replicates and 5 RNA replicates) by P5 barcode and aligned to the human genome (hg19 assembly) using bowtie2 v2.2.9. Alignment files were filtered to (i) keep only aligned fragments, (ii) remove reads mapping to chrM, (iii) select reads passing the -q 30 filter in samtools, and (iv) remove reads aligning to the ENCODE hg19 blacklist regions (Supplemental Note 10). Applicants identified unique fragments using the bamtobed command in BEDTools (v2.26.0) and filtered to keep only fragments between 100 and 600nt.

In analyzing results from HiDRA, Applicants track the abundance of each individual fragment between the input (plasmid DNA) and output (RNA). Applicants grouped fragments into "fragment groups" by 75% mutual overlap (bedtools v2.26.0), removed redundant fragment groups and summed counts of all fragments per group. To control for length-dependent biases, Applicants split fragment groups into bins of 100nt (100-200, 200-300, etc.) and used DEseq2 (v1.10.1) to identify FDR<0.05 significantly up-regulated fragment groups[33].

Analysis of Active HiDRA Regions

All overlap and shuffle analyses performed using the BEDTools suite, v2.26.0[34]. Most colors for plots chosen with guidance from the wesanderson R package (github-.com/karthik/wesanderson). For chromatin state annotations, Applicants used the 18-state output model generated by the Roadmap Epigenomics Consortium[1]. Active enhancer states were merged from states #9 and #10 (EnhA1 and EnhA2). ATAC-seq peaks positions were obtained from Buenrostro et al. (2013)[4].

Signal tracks: Signal tracks for regulatory activity calculated as (RNA-DNA)/DNA after adding a pseudocount of 0.1 to both plasmid and RNA samples, and drawn in UCSC Genome browser showing only means (no whiskers) and with 5-pixel smoothing.

Correlation between RNA samples: Applicants show correlations for fragments selected by four different cut-offs of minimum RPM. Pearson and Spearman correlations were calculated on log2-transformed data. Matrix of graphs drawn using layout and grid. arrange functions in R from the gridExtra library. Scatterplot between RNA samples drawn using the hexbinplot function from the hexbin library in R with xbins=100.

Proximal vs. distal: TSS regions were defined using the UCSC Genome Browser's Table Browser tool for hg19. Distances to nearest annotated TSS were taken using closestBed tool in the BEDTools2 suite.

TF motif enrichment: Applicants obtained the hg19 TF motif catalog from the ENCODE project[9]. Applicants only considered motifs corresponding to transcription factors expressed in GM12878 (RPKM>5 using processed RNA-seq data from the Roadmap Epigenomics Consortium).

Activity of HiDRA regions in other tissues: Applicants set a lenient definition for active in other tissues as the union of regions annotated in 97 non-GM12878 tissues from epigenome roadmap predicted with 18-state ChromHMA/I model. For active regions Applicants considered states "TssA" (state #1), "TssFlnkU" (state #3), and "EnhA" (states #9 and 10).

SHARPR2 activity plots: Tracks were drawn in the UCSC Genome Browser using "Custom Tracks". Coloring of individual fragments was performed by setting maximum and minimum colors (RGB 0,0,0 and RGB 255,255,0, respectively) to log2(RNA/DNA) values of 3rd lowest and 3rd highest fragments (two strongest and weakest fragments were removed to avoid strong outliers), and scaling colors of all other fragments linearly between these extremes. Applicants chose to include only ChIP-seq bound TF bars for ChIPseq experiments performed in GM12878 cells by the ENCODE project and where the motif (green bar) overlapped driver nucleotides.

SHARPR2 Identification of High-Resolution Driver Elements

See Appendix A for details and more information on SHARPR2.

Read mapping and data analysis for allele-specific regulatory activity

Applicants used vcf-consensus (VCFTools) to mask the hg19 genome assembly by replacing heterozygous nucleotides identified by the Illumina NA12878 Platinum Genome with N's. 250nt paired-end MiSeq reads were trimmed using cutadapt to remove Illumina primer sequences, mapped to the NA12878-masked hg19 assembly using bowtie2 v2.2.9 (settings: —end-to-end—phred33—sensitive-p 7-N 1—no-unal), and filtered using the steps described above for 37nt reads. As some long reads have poor quality scores at their 3' end, Applicants trimmed low quality sequences (quality value <38) to reduce the proportion of sequencing errors at SNPs that could lead to incorrect allelic assignment of fragments. Fragments were then assigned to a SNP based on genotype at the position. For comparisons of SNP activity, Applicants only considered fragments with 90% mutual overlap to reduce the confounding effect of fragments that differ by both allele and position. Applicants also removed fragments if either end was within 25nt of a driver element, as in these cases small differences in end position could artificially lead to large effects. After assigning fragment abundances (from high-depth 37nt PE read sequencing) to each allele of a SNP, Applicants identified SNPs with significant differential activity using QuASAR-1VIPRA. CENTIPEDE SNPs were identified by Moyerbrailean et al. (2016) using an effect-size cut-off of >3 or <−3, following the cut-offs used by Kalita et al. (2017)[24,25].

URLs and Data Availability

All high-throughput sequencing data generated by this study has been deposited in NCBI GEO with accession GSE104001. Processed HiDRA plasmid input, RNA output, activity, as well as active fragments and driver elements can be visualized on the UCSC genome browser at:

genome.ucsc.edu/cgibin/
hgTracks?hgSdoOtherUser=submit&hgS_otherUser
Name=xinchenw&
hgS_otherUserSessionName=HiDRA_GM12878_
092617.

The SHARPR2 R package is currently available from R-forge at: r-forge.rproject.org/R/?group_id=2288, and will also be available from CRAN pending package approval.

Supplementary Notes for Methods Section

0) Note on HiDRA insert size—Applicants recommend caution before trying very large fragments (e.g. 800nt and above) in HiDRA or STARR-seq. If sequencing on an Illumina machine, fragments of this size do not cluster efficiently and can lead to poor sequencing results. Applicants tried a library with a wide length distribution of 600-1.5 kb, and found that large fragments (800nt and above) were very poorly represented in plasmid samples. Surprisingly, some of the strongest "active" regions in RNA output were large fragments (1 kb and above)—this is likely an artificial signal due to internal splicing of some large fragments, creating a smaller fragment that is very efficiently sequenced. A more detailed study of this artifact could yield insights into RNA splicing of nongenic regions and the evolution of new genes.

1) Applicants performed 16 ATAC-seq reactions on 50,000 GM12878 cells each. Applicants chose to perform extra ATAC-seq reactions to ensure high library complexity, but performing so many reactions is not necessary if initial cell/tissue amount is an issue.

2) 16 reactions chosen to maintain high library complexity and allow for low cycle number based on slide 67 from www.broadinstitute.org/files/shared/illuminavids/SamplePrepSlides.pdf. Applicants did not quantify library complexity with fewer reactions, but if reagents or time are an issue, reducing number of reactions will probably have minimal effect on the library.

3) Mitochondrial fragment depletion was useful, however for future studies Applicants recommend designing a denser set of gRNAs to achieve greater amounts of depletion to save on high-throughput sequencing costs later.

4) In subsequent tests Applicants found that in our hands that the NEBuilder HiFi DNA Assembly enzyme (NEB #e5520) yielded approximately 8-10× more bacterial colonies per reaction using the same primers as described here, in our hands. Based on manufacturer's' literature, primers with longer homology arms (20-25nt overlaps) should yield even greater efficiency.

5) Applicants recommend using MegaX DH10B T1R cells or performing extensive tests if changing to a different line of bacteria. In our hands, Applicants experienced substantially lower transfection efficiencies and greater degree of arcing when using other electrocompetent cells (e.g. NEB 10-beta). Also, if this is your first time performing bacterial electroporations, Applicants recommend practicing a few times with the pUC19 positive control plasmid under different conditions.

6) The most important consideration for HiDRA library preparation is the expected complexity (number of unique fragments). If the complexity is too low, there will be insufficient fragments in most regulatory regions for high-resolution mapping. If library complexity is too high, more cells may need to be transfected for reliable activity readings, and DNA and RNA libraries will need to be sequenced to greater depth. While developing HiDRA, Applicants were able to generate plasmid libraries with over 30-50 million unique fragments (almost an order of magnitude greater than the data presented here), however this would require very large sequencing runs. In our experience, library complexity can be controlled in the (bottleneck) homology-based cloning step. Before proceeding through time-consuming and expensive transfection, RNA collection & RNA sequencing steps, Applicants recommend sequencing the plasmid library (MiSeq or spiking into a larger run) to estimate library complexity and proportion of reads within interesting regions (enhancers, promoters, etc).

7) As the Oligotex mRNA kits are fairly expensive, another option is to synthesize biotin-labelled capture probes against the reporter gene transcript and perform streptavidin bead pull-down, as described by Tewhey et al. (Cell, 2016), but modifying the probe sequences to match the sgGFP reporter gene on pSTARR-seq_human.

8) The Superscript III RT manual recommends using no more than 500 ng of polyA RNA for reverse transcription reactions. As Applicants are only reverse transcribing a single gene and not the entire transcriptome, Applicants reasoned Applicants could use add more polyA RNA per reaction. Applicants selected 2 ug of polyA RNA after performing reverse transcription reactions with increasing amounts of RNA followed by reaction cleanup and 6-cycle PCR to quantify yield.

9) If possible, Applicants recommend balancing libraries on either a MiSeq or by spiking in on a sequencing run. Applicants have tried Kapa kits, Bioanalyzer and Qubit/Nanodrop, and balancing by MiSeq/sequencing is the best option.

10) Applicants always recommend filtering against the ENCODE blacklist regions, especially for ATACseq or ATAC-seq-esque libraries due to the presence of a pseudo-mitochondrial region near the beginning of chr1 that will otherwise substantially affect downstream analyses. Adapter removal is also important if read length is greater than minimum fragment size.

TABLE 1

Empirical FWER for the proposed local multiple testing procedure. The empirical FWER was calculated from 500 replicates under each setting. The theoretical FWER α is 5%. Applicants examined the empirical FWER with respect to a max tiled region length (between 900 nt and 1500 nt) and the number of fragments in the tiled region.

| Number of fragments | Max length of tiled region | | | |
|---|---|---|---|---|
| | 900 | 110 | 1300 | 1500 |
| 25 | 7.6% | 9.0% | 7.0% | 7.6% |
| 50 | 7.2% | 6.0% | 4.8% | 4.0% |
| 75 | 7.0% | 5.2% | 5.8% | 6.4% |
| 100 | 6.8% | 5.0% | 6.0% | 6.7% |
| 125 | 6.4% | 5.4% | 6.4% | 5.0% |

REFERENCES

1. Consortium, R. E. et al. Integrative analysis of 111 reference human epigenomes. Nature 518, 317—330 (2015).
2. Ernst, J. et al. Genome-scale high-resolution mapping of activating and repressive nucleotides in regulatory regions. Nat Biotechnol 34, 1180-1190 (2016).
3. Arnold, C. D. et al. Genome-wide quantitative enhancer activity maps identified by STARR-seq. Science 339, 1074-1077 (2013).
4. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nature Methods 10, 1213-1218 (2013).
5. Nord, A. S. et al. Rapid and Pervasive Changes in Genome-wide Enhancer Usage during Mammalian Development. Cell 155, 1521-1531 (2013).
6. Long, H. K., Prescott, S. L. & Wysocka, J. Ever-Changing Landscapes: Transcriptional Enhancers in Development and Evolution. Cell 167, 1170-1187 (2016).
7. Wang, X. et al. Discovery and validation of sub-threshold genome-wide association study loci using epigenomic signatures. eLife Sciences 5, e10557 (2016).
8. Ernst, J. & Kellis, M. Discovery and characterization of chromatin states for systematic annotation of the human genome. Nat Biotechnol 28, 817-825 (2010).
9. ENCODE Project Consortium et al. An integrated encyclopedia of DNA elements in the human genome. Nature 489, 57-74 (2012).
10. Rada-Iglesias, A. et al. A unique chromatin signature uncovers early developmental enhancers in humans. Nature 470, 279-283 (2010).
11. Ernst, J. et al. Mapping and analysis of chromatin state dynamics in nine human cell types. Nature 473, 43-49 (2011).
12. Visel, A., Minovitsky, S., Dubchak, I. & Pennacchio, L. A. VISTA Enhancer Browser—a database of tissue-specific human enhancers. Nucleic Acids Res. 35, D88—D92 (2007).
13. Taylor, G. C. A., Eskeland, R., Hekimoglu-Balkan, B., Pradeepa, M. M. & Bickmore, W. A. H4K16 acetylation marks active genes and enhancers of embryonic stem cells, but does not alter chromatin compaction. Genome Res. 23, 2053-2065 (2013).
14. Pradeepa, M. M. et al. Histone H3 globular domain acetylation identifies a new class of enhancers. Nature Genetics 48, 681-686 (2016).
15. Tewhey, R. et al. Direct Identification of Hundreds of Expression-Modulating Variants using a Multiplexed Reporter Assay. Cell 165, 1519-1529 (2016).
16. Melnikov, A. et al. Systematic dissection and optimization of inducible enhancers in human cells using a massively parallel reporter assay. Nat Biotechnol 30, 271-277 (2012).
17. Kwasnieski, J. C., Mogno, I., Myers, C. A., Corbo, J. C. & Cohen, B. A. Complex effects of nucleotide variants in a mammalian cis-regulatory element. Proceedings of the National Academy of Sciences 109, 19498-19503 (2012).
18. Gillies, S. D., Morrison, S. L., 0i, V. T. & Tonegawa, S. A tissue-specific transcription enhancer element is located in the major intron of a rearranged immunoglobulin heavy chain gene. Cell 33, 717-728 (1983).
19. Huang, Y. et al. cis -Regulatory Circuits Regulating NEK6 Kinase Overexpression in Transformed B Cells Are Super-Enhancer Independent. Cell Reports 18, 2918-2931 (2017).
20. Barakat, T. S. et al. Functional dissection of the enhancer repertoire in human embryonic stem cells. biorxiv.org Available at: www.biorxiv.org/content/biorxiv/early/2017/07/04/146696.full.pdf.
21. Farh, K. K.-H. et al. Genetic and epigenetic fine mapping of causal autoimmune disease variants. Nature (2014). doi:10.1038/nature13835
22. Jostins, L. et al. Host—microbe interactions have shaped the genetic architecture of inflammatory bowel disease. Nature 491, 119-124 (2012).
23. Hitomi, Y. et al. Identification of the functional variant driving ORMDL3 and GSDMB expression in human chromosome 17q12-21 in primary biliary cholangitis. Sci Rep 7, 2904 (2017).
24. Kalita, C. A. et al. QuASAR-MPRA: Accurate allele-specific analysis for massively parallel reporter assays. biorxiv.org Available at: www.biorxiv.org/content/biorxiv/early/2017/07/12/105627.full.pdf.
25. Moyerbrailean, G. A. et al. Which Genetics Variants in DNase-Seq Footprints Are More Likely to Alter Binding? PLoS Genet 12, e1005875 (2016).
26. GTEx Consortium. Human genomics. The Genotype-Tissue Expression (GTEx) pilot analysis: multitissue gene regulation in humans. Science 348, 648-660 (2015).

27. Inoue, F. et al. A systematic comparison reveals substantial differences in chromosomal versus episomal encoding of enhancer activity. Genome Res. 27, 38-52 (2017).
28. Khurana, E. et al. Role of non-coding sequence variants in cancer. Nat Rev Genet 17, 93-108 (2016).
29. Kheradpour, P. & Kellis, M. Systematic discovery and characterization of regulatory motifs in ENCODE TF binding experiments. Nucleic Acids Res. (2013). doi: 10.1093/nar/gkt1249
30. Mifsud, B. et al. Mapping long-range promoter contacts in human cells with high-resolution capture Hi-C. Nature Genetics 47, 598-606 (2015).
31. Taiwo, O. et al. Methylome analysis using MeDIP-seq with low DNA concentrations. Nat Protoc 7, 617-636 (2012).
32. Montefiori, L. et al. Reducing mitochondrial reads in ATAC-seq using CRISPR/Cas9. Sci Rep 7, 1213 (2017).
33. Michael I Love, W. H. S. A. Moderated estimation of fold change and dispersion for RNA-seq data with DESeq2. Genome Biol 15, (2014).
34. Quinlan, A. R. & Hall, I. M. BEDTools: a flexible suite of utilities for comparing genomic features. Bioinformatics 26, 841-842 (2010).

Appendix A—Methodological Details of SHARPR2

A1. Model specification

Basic Model

We define a tiled region" as a continuous region in which each position is covered by at least one HiDRA fragment Suppose that a tiled region containing P positions is covered by R fragments. The regulatory activity of each fragment j with a length $l_j$, $j \in \{1, \ldots, R\}$ can be measured by the ratio $$\frac{RNA_j}{DNA_j}$$

between me counts of sequenced RNA and DNA. For a design with multiple replicates, the ratio is calculated from the average counts of RNA and DNA across the replicates. In this paper, we calculate RNA/DNA ratios for each fragment after normalization of RNA & DNA by DESeq2 with the library split into 100nt bins (100-200nt, 2013-300nt, etc). We expect that the ratio fora fragment containing one or more functional driver element site is larger than those not overlapping a driver element We use the transformed observation $M_j^o$ by taking the log-transformation with base e of $$\frac{RNA_j}{DNA_j}$$

for the downstream analysis, i.e., $$M_j^o = \ln\left(\frac{RNA_j}{DNA_j}\right).$$

For the HiDRA library described in the Methods section, we observed that the empirical distribution of $M_j^o$ from the whole genome (approximately 4 million fragments after quality control and filtering for minimum expression) is nearly symmetrically centered at zero but with heavy tails (Supplemental Figure S8).

In HiDRA, the length of a general tiled region is much larger than the number of fragments (P»R). The basic idea of SHARPR2 is to use a shrinkage prior to tackle this large p small n problem. We first compute a centered variable $M_j$ for each fragment j by subtracting $\mu_a$ the mean of the background signal (i.e., $M_j = M_j^o - \mu_a$). The mean of the background signal $\mu_a$ is the average signal intensity from fragments not overlapping a driver element Thus, we estimate $\mu_a$ by the mean value of the observations taken from all tiled regions covered by <5 fragments across the whole chromosome, With the assumption that the majority of these k tiled regions do not contain a driver element. More specifically, suppose that there are K tiled regions on a Chromosome and each tiled region is covered by $R_k$ fragments each of Which has an observation $M_{jk}^o$, $j \in \{1, \ldots R_k\}$ and $k \in \{1, \ldots, K\}$. Thus, we have $\hat{\mu}_a = \Sigma_{k \in B} \Sigma_{j=1}^{R_k} M_{jk}^o / \Sigma_{k \in B} R_k$, where B is the set of all tiled regions covered by <5 fragments (B={k|$R_k$<5}).

Within one tiled region, we assume that $M_j$ (we omit the index k whenever the formula only involves a specific tiled region) follows an i.i.d. normal distribution with a mean equal to a scaled sum of those regulatory scores $A_i$ that are covered by fragment j, that is, $$M \sim \mathcal{N}(L^{-1}TA, \Sigma_m) \quad (1)$$

where T is an indicator matrix, i.e., $T_{ij}=1$ if position i, $i \in \{1, \ldots, P\}$, is covered by fragment j; otherwise $T_{ij}=0$, and L is a diagonal matrix for scaling each fragment. Note that this specification of T assumes that each position in the tiled region contributes identically to the regulatory activity measurement of the fragments. If, for example, driver elements at the ends of a fragment may contribute less to the regulatory activity, smaller weights can be assigned according to its distance to the middle of the fragment. For the purpose of regularization, we impose an $\ell_2$ penalty on A, which is equivalent to a normal prior from the Bayesian perspective. Generalizing MPRA-SHARPR (Ernst et al., 2016) from 5 bp to 1 bp, the regulatory score $A_i$ at each position i, which is a latent variable, is assigned by a univariate normal prior $$A_i \sim \mathcal{N}(0, \sigma_a^2), \quad (2)$$

where u is a hyper-parameter, which is defined by users and is tested for 1 and 50 in Ernst et al., 2016_ In MPRA-SHARPR, it is assumed that $L_{jj}=l_j$. Because each fragment has the same length in MPRA-SHARPR, we end up with $$L = lI \text{ and } M \sim \mathcal{N}\left(\frac{TA}{l}, \Sigma_m\right)$$

Ernst et al., 2016), where I is the identity matrix. In contrast, each fragment has a different length in HiDRA ranging from 150nt to 500nt. In SHARPR2, we use a uniform scale coefficient $L_{jj}=\bar{l}$, where $\bar{l}=\Sigma_{k=1}^K \Sigma_{j=1}^{R_k} l_{jk}/\Sigma_{k=1}^K R_k$ is the average length of all fragments on the chromosome. Under this modeling of L, the signal of a fragment depends only on the sum of the regulatory scores at all positions that the fragment covers but not on the fragment length. $\Sigma_m$ is a covariance matrix with non-zero diagonal elements equal to $\sigma_m^2$, which is set to be the sample variance of $M_j$ in (Ernst et al., 2016). The marginal distribution of M after integrating out A from (1) follows $$M \sim \mathcal{N}(0, L^{-1}T\Sigma_a(L^{-1}T)' + \Sigma_m), \quad (3)$$

where $$\Sigma_a = \begin{pmatrix} \sigma_a^2 & \cdots & 0 \\ \vdots & \ddots & \vdots \\ 0 & \cdots & \sigma_a^2 \end{pmatrix}$$

is a diagonal matrix. Thus, the ridge estimate or the posterior mean of A given the observed M is $$\hat{A} = \Sigma_a (L^{-1}T)'(L^{-1}T\Sigma_a(L^{-1}T) + \Sigma_m)^{-1}M. \quad (4)$$

After some rearrangement to merge $\Sigma_a$ and $\Sigma_m$, we end up with the following equation $$\hat{A}_\lambda = ((L^{-1}T)'L^{-1}T + \lambda I)^{-1}(L^{-1}T)'M \quad (5)$$

where $$\lambda = \frac{\sigma_m^2}{\sigma_a^2}$$

is the penalizing coefficient

Selection of Penalizing Coefficient

Instead of letting $\sigma_a^2$ and thus the penalizing coefficient $\lambda$ be defined by users as in (Ernst et al., 2016), we select $\lambda$ in a data-driven way. This is because the choice of $\lambda$ substantially affects the estimates and thus the following hypothesis testing procedure. This means that $\lambda$ should be selected carefully. Note that although the formula (4) is the same as the posterior mean in the Bayesian framework used in MPRA-SHARPR, we instead regard (5) as a ridge estimate under the classical framework in SHARPR2. In this case, we only assume that (1) is the true model in which A are parameters rather than random variables, and (2) is used for the purpose of regularization. Note that in this case the choice of $\lambda$ has significant influence on the estimation of A. If $\lambda$ is too small, the estimates would be unstable, while an overly large $\lambda$ would bring more bias. A handful of strategies have been proposed to select an optimal and stable $\lambda$, including cross-validation (Golub et al., 1979; Hastie et at, 2009), the Hoerl-Kennard-Baldwin plug-in method (Cule and De Iorio, 2013; Hoed and Kennard, 1970; Hoeft et al., 1975), and the Markov chain Monte Carlo (MCMC) methods (Denison, 2002). We select $\lambda$ by following the strategy proposed by Cule and De Iorio, 2013, which generalizes the idea of (Hoer) et al., 1915) to the large p small n problem and shows stable estimation in simulation and real data studies. More specifically, we first perform the singular value decomposition (SVD) for $L^{-1}T$:

$$L^{-1}T = UDV',$$

where D is a diagonal matrix with t non-zero diagonal elements $d_{ij}$, and $t \leq \min(P,R)$ We select $r^* \in \{1, \ldots, t\}$, so that $$r^* = \mathrm{argmin}_r r - \sum_{j=1}^{t} \frac{d_{jj}^4}{(d_{jj}^2 + \lambda_r)^2},$$

where we have $$\lambda_r = \frac{r\hat{\sigma}_r^2}{\hat{\eta}_r'\hat{\eta}_r'},$$

-continued $$\hat{\eta} = D^{-2}V'(L^{-1}T)'M, \text{ and}$$

$$\hat{\sigma}_r^2 = \frac{(M - (L^{-1}T)_r V_r \hat{\eta}_r)'(M - (L^{-1}T)_r V_r \hat{\eta}_r)}{R - r},$$

where $\hat{\eta}_r$, is an r-vector of the first r elements in $\hat{\eta}$.

Given $r^*$, we choose $\lambda$ as $$\lambda_{r^*} = \frac{r^*\hat{\sigma}_{r^*}^3}{\hat{\eta}_{r^*}'\hat{\eta}_{r^*}},$$

and the estimate at A in SHARPR2 is $$\hat{A}_\lambda = ((L^{-1}T)'L^{-1}T + \lambda_{r^*}*I)^{-1}(L^{-1}T)'M = HM, \quad (6)$$

where $H = \{(L^{-1}\,T'L^{-1}T + \lambda_{r^*}*1\}^{-1}(L^{-1}T)'$ is the hat matrix. For HIDRA dataset, it is usually the case that the number of fragments R is much smaller than the length of a tiled region P. We apply SVD to the hat matrix to avoid the inversion of a large-scale matrix After SVD, we have $$H = ((L^{-1}T)'L^{-1}T + \lambda_{r^*}I)^{-1}(L^{-1}T)'$$
$$= (VD'U'UDV + \lambda_{r^*}VV')^{-1}VD'U'$$
$$= V(D'U'UD + \lambda_{r^*}I)^{-1}V'VD'U'$$
$$= V(D'U'UD + \lambda_{r^*}I)^{-1}D'U',$$

in which the computation of LID is dramatically faster as D has at mast R non-zero diagonal elements. In the analysis of the example HiDRA library, we observed that this algorithm of selecting $\lambda^{r*}$ produced stable estimates of the regulatory scores. We also noticed that the algorithm would produce an overly small $\lambda_r*$ if in a tiled region two or more fragments are mapped to almost the same position (the difference is only a couple of nucleotides) and have large opposite values of $$\ln\left(\frac{\#RNA_j}{\#DNA_j}\right).$$

This phenomenon may suggest a potential data problem. Note that this algorithm estimates a unique $\lambda_r*$ for each tiled region, and thus the estimated regulatory scores cannot be compared directly across regions. If the comparison across regions is the major concern (e.g., using the estimated regulatory scores as a training set in deep learning such as convolutional neural networks (CNN) for other downstream analysis), studentized estimates $Z_{\lambda,i}$ can be used (described in the next section).

Accuracy of Estimation

To provide a measure of the accuracy of the estimates, we compute the pointwise mean square error (MSE) of $\hat{A}_\lambda$. As we assume that (1) is the true model, $\hat{A}_\lambda$ is a biased estimate of A, and the MSE of $\hat{A}_\lambda$ should take into account both variance and bias. That is, we are interested in finding not only Var($\hat{A}$) but $E(\hat{A}_\lambda - A)^2$ as well. Note that the MSE can be decomposed into $$MSE(\hat{A}_\lambda) = \mathrm{Var}(\hat{A}_\lambda) + \mathrm{Bias}(\hat{A}_{80})^2,$$

where $\mathrm{Bias}(\hat{A}_{\lambda)=E(\hat{A}\lambda)} - A$ measures the bias between the true value of A and the mean of $\hat{A}_\lambda$. The bias term is given by $Bias(\hat{A}_\lambda)^2 = (E(\hat{A}_\lambda)-A)(E(\hat{A}_\lambda)-A)' = (((L^{-1}T)'L^{-1}T+\lambda_r*I)^{-1}(L^{-1}T)'L^{-1}T-I)AA'(((L^{-1}T)'L^{-1}T+\lambda_r*I)^{-1}(L^{-1}T)'L^{-1}T-I)' = (W_r*-I)AA'(W_r*-I)'$, where $W_r* = ((L^{-1}T)'L^{-1}T+\lambda_r*I)^{-1}(L^{-1}T)'L^{-1}T$.

The variance $Var(\hat{A}_\lambda)$ can be shown as $$Var(\hat{A}_\lambda) = Var(((L^{-1}T)'L^{-1}T+\lambda_r*I)^{-1}(L^{-1}T)'M) =$$
$$((L^{-1}T)'L^{-1}T+\lambda_r*I)^{-1}(L^{-1}T)'Var(M)(((L^{-1}T)'L^{-1}T+\lambda_r*I)^{-1}(L^{-1}T)')' =$$
$$\sigma_m^2((L^{-1}T)'L^{-1}T+\lambda_r*I)^{-1}(L^{-1}T)'L^{-1}T(((L^{-1}T)'L^{-1}T+\lambda_r*I)^{-1})' = \sigma_m^2 HH'.$$

The true value of $\sigma_m^2$ is unknown, but can be estimated from the residuals $$\hat{\sigma}_m^2 = \frac{(M-L^{-1}T\hat{A}_\lambda)'(M-L^{-1}T\hat{A}_\lambda)}{R-df},$$

where $df = R-2tr(H)+tr(HH)'$ is the residual degrees of freedom (Hastie and Tibshirani, 1990). Plugging in the ridge estimate (5) for A and the sample estimate $\hat{\sigma}_m^2$ for $\sigma_m^2$, the estimated point wise MSE is $$\widehat{MSE}(\hat{A}_\lambda) = \hat{\sigma}_m^2 W_r*(((L^{-1}T)'L^{-1}T+\lambda_r*I)^{-1})'+(W_r*-I)\hat{A}_\lambda \hat{A}_\lambda'(W_r*-I)', \quad (7)$$

Pointwise confidence intervals (CIs) can be calculated from $\widehat{Var}(\hat{A}_\lambda)$, e.g., 95% CI $\hat{A}_\lambda \pm 1.96 \times \sqrt{\widehat{Var}(\hat{A}_\lambda)}$. Note that the bias term $Bias(\hat{A}_\lambda)$ is non-zero if A of $\lambda_r*$ is non-zero. Therefore, it is not straightforward to interpret the CIs obtained from $Var(\hat{A}_\lambda)$. Instead, the following 95% CI $$CI_{adj} = \hat{A}_\lambda - \widehat{Bias}(\hat{A}_\lambda) \pm 1.96 \times \sqrt{\widehat{Var}(\hat{A}_\lambda)}$$

can be used (De Brabanter et al., 2011), which adjusts for the bias. One problem of the adjusted CI is that the true bias is unknown and its estimate $\widehat{Bias}(\hat{A}_\lambda)$ might not be accurate A1 Identifying High-Resolution Driver Elements Regional FWER Controlling Procedure Given the estimated regulatory scores $\hat{A}_\lambda$ for each nucleotide within a specific tiled region, we then aim at finding a regional threshold to declare the significant regulatory regions (regulatory drivers) at which an active motif is located. More specifically, we need to make the inference for nucleotide i by testing the following hypothesis, $H_0: A_i = 0 \text{ vs. } H_a: A_i > 0.$ For this hypothesis testing, we are only interested in finding activating regulatory elements but not repressive ones. For a specific tiled region containing P positions, we want to find a cutoff $c_i$ so that the family-wise error rate (FWER) $\alpha$ is bounded below a given value (e.g., 0.05). The value of $\alpha$ can be set, differently among different tiled regions. This amounts to a multiple testing problem of performing P one-sided tests of the estimated regulatory scores $\hat{A}_\lambda = (\hat{A}_{\lambda,1}, \ldots, \hat{A}_{\lambda,P})' = 0$ simultaneously. One way can be computing a p-value for each $\hat{A}_{\lambda,i}$ and use the simple Bonferroni correction to obtain a local significance level $$\alpha_i = \frac{\alpha}{P}$$

from which $c_i$ can be computed. This approach would be overly conservative as $\hat{A}_{\lambda,i}$ was not independent of each other in this case. A more accurate cutoff should take into account the correlation structure of the estimated regulatory scores. On the other hand, performing a permutation test for each tiled region would be too time consuming for a library of the whole genome albeit more accurate. Following the strategy described by (Dickhaus and Gierl, 2012; Stange et al., 2015), we thus propose a fast multiple testing procedure based on Gaussian copula to find region-specific cutoffs for controlling FINER $\alpha$. Note that under the null hypothesis A=0, the bias term in (7) disappears. We use the studentized estimate as the test statistics $$Z_{\lambda i} = \frac{\hat{A}_{\lambda i}}{\sqrt{\widehat{Var}(\hat{A}_{\lambda i})}} = \frac{\hat{A}_{\lambda i}}{\hat{\sigma}_m \sqrt{diag(HH')_i}},$$

where $diag()_i$ stands for the ith element in the vector of the diagonal elements of a matrix. It has been shown that under the null hypothesis, $Z_{\lambda,i}$ follows a Student t-distribution and can be approximated by a standard normal distribution under a large sample size (Cule et al., 2011; Halawa and Bassiouni, 2000). (Cule et al., 2011) find through simulation studies that the type I error rate and the power using the normality approximation are comparable to those from permutation tests for a wide range of $\lambda$. This observation motivates us to assume that under the null hypothesis, $Z_\lambda$ follows a multivariate normal distribution $$Z_\lambda = \hat{\sigma}_m^{-1}(HH \mathsf{L} I)^{-1/2}\hat{A}_\lambda = S\hat{A}_\lambda \sim N(0, S\widehat{Var}(\hat{A}_\lambda)S), \quad (8)$$

where $\mathsf{L}$ is the Hadamard product. In the simulation studies provided in the next section, we will investigate the potential influence on the empirical FINER induced by the multivariate normal approximation under a small sample size. As the marginal cumulative density function (CDF) $F_i(x_i)$ of $Z_\lambda$ is continuous, according to Sklar's theorem (Nelsen, 1999), there exist a unique copula $\mathcal{C}: [0,1]^P \to [0,1]$ such that $\forall (x_1, \ldots, x_P)' \in \mathbb{R}^P: F(x_1, \ldots, x_P) = \mathcal{C}(F_1(x_1), \ldots, F_P(x_P))$, where $F(x_1, \ldots, x_P)$ is the joint CDF. Hence, for a one-sided test we have $$\alpha = FWER = \mathbb{P}_{H_0}\left(\bigcup_{i=1}^{P} Z_{\lambda i} > c_i\right) = 1 - \mathbb{P}_{H_0}\left(\bigcap_{i=1}^{P} Z_{\lambda i} \leq c_i\right) =$$
$$1 - \mathbb{P}_{H_0}(Z_{\lambda 1} \leq c_1, \ldots, Z_{\lambda P} \leq c_P) = 1 - C(F_1(c_1), \ldots, F_1(c_1))$$

Under the multivariate normality approximation of (8), we have $$\alpha = 1 - \mathcal{C}(F_1(c_1), \ldots, F_P(c_P)) = 1 - \mathcal{C}_{s\widehat{Var}(\hat{A}_\lambda)S}(\Phi_1(c_1), \ldots, \Phi_P(c_P)) \quad (9)$$

where $\mathcal{C}_{s\widehat{Var}(\hat{A}_\lambda)S}(u_1, \ldots, U_P)$ is a Gaussian copula with a correlation parameter matrix of $S\widehat{Var}(\hat{A}_\lambda)S$, and $\Phi(c)$ is the CDF of a standard normal distribution. Given a specific value of $\alpha$, there are infinite many solutions $(u_1, \ldots, u_P) = \mathcal{C}_{s\widehat{Var}(\hat{A}_\lambda)S}^{-1}(1-\alpha)$. However, if we treat every position as equally important and pursue a single-step common-quantile cutoff ((Dudoit and van der Laan, 2008), Chapter 4) c, i.e., $c_1 = \ldots = c_P = c$, we can find a unique solution $$u* = \mathcal{C}_{s\widehat{Var}(\hat{A}_\lambda)S}(1-\alpha), \text{ at } u_1 = \ldots = u^P = u*,$$

and $$c* = \Phi^{-1}(u*)$$

So, we reject $H_0$ for the positions in $\mathcal{H} = \{i \in (1, \ldots, P): Z_{\lambda,i} > c*\}$, which we term as high-resolution "driver" elements. The common-quantile cutoff $c^*$ can be calculated, for example, by the function qmvnorm in the R package mvtnorm (Genz and Bretz, 2002). The similar idea can also be used to obtain adjusted p-values for controlling regional FWER as shown in (Conneety and Boehnke, 2007). In real data analysis, the estimated covariance matrix $\widehat{Var}(\hat{A}_\lambda)$ is often degenerated and the estimates of adjacent positions are completely correlated when P>R. Therefore, we trim the number of the estimates by selecting one position from each group in which the estimates for the positions are completely correlated. This also dramatically reduces the computational intensity for finding the solution to (9y identifying the driver elements, we can further attempt to pinpoint the location of the most possible occurrence of a 20nt "core" driver element (see section A4 below for rationale for choosing ~20nt as the estimated "core" region). We predict the center position $i_m$ of a 20 bp core driver element by the highest regulatory scores over its 20 bp flanking region, i.e., $$i_m = \operatorname{argmax}_{i \in \mathcal{H}} \frac{\sum_{k=(i-9)v1}^{(i+10)\wedge P} \hat{A}_{\lambda i}}{(i+10) \wedge P - (i-9)v1 + 1}.$$

Supplemental Figure S10 gives an illustration of the significant regulatory region and the predicted motif region. In this example, the true motif is located at position 400-420nt and is covered by an identified significant driver element by SHARPR2 (highlighted in red). The predicted core driver region (highlighted in purple) further pinpoints the location of the motif at ~400 bp.

Global FDR Controlling Procedure

The above regional procedure calls significant driver elements for a specific tiled region. To identify driver elements across an entire genome, it may be preferable to control the global false discovery rate (FDR). We thus propose a global p-value correction procedure for this purpose by taking into account the p-values observed from the whole genome. We first calculate the pointwise p-values for all positions in all filed regions across the genome based on the t-distribution $$Z_{\lambda i} = \frac{\hat{A}_{\lambda i}}{\sqrt{\widehat{Var}(\hat{A}_{\lambda i})}} \sim t_{R-tr(H)},$$

where $R-tr(H)$ is the sample size minus the effective degrees of freedom. As mentioned in the local controlling procedure, we select one position from a consecutive region in which the estimate for these positions are completely correlated. Then, the Benjamini-Hochberg procedure (Benjamini and Hochberg, 1995) is performed on the pointwise p-values to control the global FDR at level $\alpha$. As the p-values from different filed regions are independent, the p-values can be regarded as dependent in finite blocks when the number of fragments $R_k$ within each tiled region K is large $$\left(\text{assuming } \frac{K}{\sum_{k=1}^{K} R_k} \to 0\right).$$

Thus, under this assumption, the estimate of FDR is consistent (Schwartzman and Lin, 2011; Storey et al., 2004).

A3. Evaluation of Empirical Statistical Power and FWER Simulation Settings

We assessed the performance of the proposed SHARPR2 algorithm in terms of empirical statistical power estimated from our simulation studies. To mimic the current version of the HIDRA library, we randomly generated a number R of fragments (R between 25-100) in a P=1 kb tiled region. The length of each fragment was sampled from a uniform distribution $l_j \sim U(175,450)$, $j \in \{1, \ldots, R\}$. We randomly selected a 20 bp driver element from a 400 bp window in the middle of the tiled region. For any fragment that covers the driver element, we generated its signal from a normal distribution $\mathcal{N}(\mu_{motif}=S_m, \sigma_{motif}=0.1)$, where $S_m$ is the true signal varying across different simulation scenarios. For the rest of the fragments, we generated the signal from a normal distribution $\mathcal{N}(\mu_{noise}=0, \sigma_{noise}=1)$. We defined the signal-to-noise-ratio (SNR) as $$SNR = \frac{S_m}{\sigma_{noise}}.$$

We examined the empirical FWER and empirical statistical power under different SNR and numbers of fragments. For each simulation selling, we generated 500 replicates to obtain the estimates of empirical FWER and statistical power.

Evaluation of Empirical Type I Error Rate

Our results in Table 1 show that generally the empirical regional FWER was controlled at ~5% when the number of fragments was above 50. We observed mild inflation of empirical FWER especially in the case of small sample size (e.g., 25), but the inflation diminished with the sample size increasing. This inflation should be due to the discrepancy between the true null distribution of the statistic and the asymptotic normal distribution at the tails (Han et al., 2009). This indicates that the error introduced by the multivariate normality approximation should be taken into account when the sample size is overly small (e.g., by setting a more stringent cutoff for a tiled region covered by very few fragments). In addition, we also found that overall the shortest tiled region (900 kb) in the simulation yielded the largest FWER. One possible justification is that in a shorter tiled region, fragments are more frequently overlapped. Thus, the estimates of the regulatory scores are more closely correlated with each other, which results in a denser correlation matrix that requires more samples for an accurate estimate Evaluation of Empirical Statistical Power Next, we examined the statistical power for pinpointing a driver element under the condition of $\alpha=5\%$, i.e., the FINER <5%. In this investigation, a true positive is counted if an identified driver element or a predicted 20 bp functional motif region overlapping the true driver element region. The results in Supplemental Figure S11 show that the statistical power for both regions consistently increases with respect to the number of fragments and the SNR If there are 100 fragments in a tiled region, SHARPR2 can achieve more than 80% power under SNR=1. When the number of fragments is small (e.g., 25), SNR>1.5 is needed to achieve a power of 80. Higher SNR requires that the biological experiments have higher precision and sensitivity., so that significantly more RNAs can be sequenced when the DNA region covers a true driver element A4. Analysis of a HiDRA Library We applied SHARPR2 to a HIDRA library prepared from the GM12878 lymphoblastoid cell line. The library contains 3,896,416. fragments after quality control, with the length of fragments ranging from 100-600nt (99% of fragments between 168-413nt). We first identified 645,936 tiled regions that are covered by at least two fragments across the whole genome, among which 28,092 were are by more than 10 fragments. The distribution of the signals (ln(#RNA/#DNA)) of these fragments are almost symmetrically centered at zero with heavy tails (Supplemental Figure S8). The average and the variance of the signals are constant across the length of fragments after normalization (Supplemental Figure S9).

We estimated the regulator scores for the 22 chromosomes separately and called driver elements based on a cutoff controlling regional FWER<0.05 for the positions in each tiled region. We found that the tiled regions covered by larger numbers of HiDRA fragments were more likely to have a driver element called, which is likely a combination of greater statistical power and enrichment for regions more likely to contain drivers As shown in FIG. 5C, most driver elements are found within active TSS, TSS Flanking Upstream and active enhancers chromatin states. The median size of driver elements identified from the tiled regions covered by >10 fragments was 52nt after filtering to remove drivers smaller than 5nt. The average size of drivers decreased with an increase in number of fragments in a tiled region, suggesting that more complex libraries with greater numbers of unique fragments should be able to detect shorter driver elements (Supplemental Figure S6), The average size of a driver element converges to ~18nt after the depth of unique HiDRA fragment coverage reaches 50 fragments/kb (Supplemental Figure S6).

APPENDIX A REFERENCES

Benjamini, Y., and Hochberg, Y. (1995). Controlling the false discovery rate: a practical and powerful approach to multiple testing. J. R. Stat. Soc. Ser. B Methodol. 289-300.
Conneely, K. N., and Boehnke, M. (2007). So many correlated tests, so little time! Rapid adjustment of P values for multiple correlated tests. Am. J. Hum. Genet. 81, 1158-1168.
Cule, E., and De Iorio, M. (2013). Ridge regression in prediction problems: automatic choice of the ridge parameter. Genet. Epidemiol. 37, 704-714.
Cule, E., Vineis, P., and De Iorio, M. (2011). Significance testing in ridge regression for genetic data. BMC Bioinformatics 12, 372.
De Brabanter, K., De Brabanter, J., Suykens, J. A., and De Moor, B. (2011). Approximate confidence and prediction intervals for least squares support vector regression. IEEE Trans. Neural Netw. 22, 110-120.
Denison, D. G. T. (2002). Bayesian Methods for Nonlinear Classification and Regression (John Wiley & Sons).
Dickhaus, T., and Gierl, J. (2012). Simultaneous test procedures in terms of p-value copulae.
Dudoit, S., and van der Laan, M. J. (2008). Multiple Testing Procedures with Applications to Genomics (New York, NY: Springer New York).
Ernst, J., Melnikov, A., Zhang, X., Wang, L., Rogov, P., Mikkelsen, T. S., and Kellis, M. (2016). Genome-scale high-resolution mapping of activating and repressive nucleotides in regulatory regions. Nat. Biotechnol. 34, 1180-1190.
Genz, A., and Bretz, F. (2002). Comparison of methods for the computation of multivariate t probabilities. J. Comput. Graph. Stat. 11, 950-971.
Golub, G. H., Heath, M., and Wahba, G. (1979). Generalized Cross-Validation as a Method for Choosing a Good Ridge Parameter. Technometrics 21, 215-223.
Halawa, A. M., and Bassiouni, M. Y. E. (2000). Tests of regression coefficients under ridge regression models. J. Stat. Comput. Simul. 65, 341-356.
Han, B., Kang, H. M., and Eskin, E. (2009). Rapid and Accurate Multiple Testing Correction and Power Estimation for Millions of Correlated Markers. PLOS Genet. 5, e1000456.
Hastie, T. J., and Tibshirani, R. J. (1990). Generalized Additive Models (CRC Press). Hastie, T., Tibshirani, R., and Friedman, J. (2009). The Elements of Statistical Learning: Data
Mining, Inference, and Prediction, Second Edition (Springer Science & Business Media). Hoerl, A. E., and Kennard, R. W. (1970). Ridge regression: Biased estimation for non-orthogonal problems. Technometrics 12, 55-67.
Hoerl, A. E., Kannard, R. W., and Baldwin, K. F. (1975). Ridge regression: some simulations. Commun. Stat. 4, 105-123. Nelsen, R. B. (1999). An Introduction to Copulas. In An Introduction to Copulas, (Springer), pp. 1-4.
Schwartzman, A., and Lin, X. (2011). The effect of correlation in false discovery rate estimation. Biometrika 98, 199-214.
Stange, J., Bodnar, T., and Dickhaus, T. (2015). Uncertainty quantification for the family-wise error rate in multivariate copula models. AStA Adv. Stat. Anal. 99, 281-310.
Storey, J. D., Taylor, J. E., and Siegmund, D. (2004). Strong control, conservative point estimation and simultaneous conservative consistency of false discovery rates: a unified approach. J. R. Stat.aSoc. Ser. B Stat. Methodol. 66, 187-205.

Example 9—High-Resolution Genome-Wide Functional Dissection of Transcriptional Regulatory Regions and Nucleotides in Human Genome-wide epigenomic maps have revealed millions of putative enhancers and promoters, but experimental validation of their function and high-resolution dissection of their driver nucleotides remain limited. Here, this example shows HiDRA (High-resolution Dissection of Regulatory Activity), a combined experimental and computational method for high-resolution genome-wide testing and dissection of putative regulatory regions. Applicants tested ~7 million accessible DNA fragments in a single experiment, by coupling accessible chromatin extraction with self-transcribing episomal reporters (ATAC-STARR-seq). By design, fragments were highly overlapping in densely-sampled accessible regions, enabling us to pinpoint driver regulatory nucleotides by exploiting differences in activity between partially-overlapping fragments using a machine learning model (SHARPR-RE). In GM12878 lymphoblastoid cells, Applicants found 65,000 regions showing enhancer function, and pinpoint ~13,000 high-resolution driver elements. These were enriched for regulatory motifs, evolutionarily-conserved nucleotides, and disease-associated genetic variants from genome-wide association studies. Overall, HiDRA provided a high-throughput, high-resolution approach for dissecting regulatory regions and driver nucleotides.

Introduction

Precise spatiotemporal control of gene expression was achieved by the interplay between non-coding regulatory elements, including distal enhancers and proximal promoters, and the transcriptional regulators they helped recruit or repel, thus modulating the expression of nearby genes (1-3). Unlike protein-coding genes, which can be readily identified by their sequence properties and evolutionary signatures, gene-regulatory elements lack highly-predictive sequence patterns and show only modest evolutionary conservation at the nucleotide level (1,4). Thus, systematic recognition of gene-regulatory elements has relied on mapping of their epigenomic signatures, including DNA accessibility, histone modifications, and DNA methylation (5-7). For example, both enhancers and promoters have high DNA accessibility and low H3K27me3, but distal enhancers show relatively higher H3K27ac and H3K4me1 while promoters show relatively higher H3K9ac and H3K4me3 (8,9). However, many regions showing such epigenomic marks do not experimentally drive reporter gene expression, and some regions driving gene expression lack endogenous signatures (10-12). Moreover, epigenomic signatures are often low-resolution, with important driver regulatory nucleotides comprising only a small subset of the larger regions showing epigenomic signatures (13).

Experimental dissection of enhancer and promoter regions has been traditionally expensive, laborious, low-throughput, and low-resolution, lacking the resolution to pinpoint individual regulatory driver nucleotides without recourse to extensive mutagenesis. Several recent high-throughput reporter assays for enhancer function enable testing of thousands of distinct DNA sequences simultaneously, by cloning variable DNA fragments into common reporter constructs, and using high-throughput sequencing to quantify fragment activity. Synthesis-based approaches (e.g. MPRA (14), CRE-seq (15)) use oligonucleotide synthesis technology to generate elements and coupled barcodes. Genome-fragmentation approaches (e.g. STARR-seq (16), Cap-STARR-seq (17,18), ChIP-STARR (1-3,19)) use DNA fragments collected or captured from genomic DNA. For synthesis-based approaches, technical limitations of oligonucleotide synthesis technology restrict the tested DNA fragment lengths to 130-230 nucleotides, and the number of tested constructs to 100,000-200,000 sequences per array. For genome-fragmentation approaches, random fragmentation of the entire genome results in only shallow coverage of regulatory elements, while synthesis-based capture is limited in the number of regions interrogated due to its reliance on oligonucleotide synthesis, and ChIP-based capture is limited in only one or few transcription factors at a time. To recognize driver nucleotides within tested regions, synthesis-based approaches have used systematic mutagenesis (1, 4, 20) or tiling at regularly-spaced intervals (5-7, 13), but both require synthesis of many constructs for fine-mapping each region, thus reducing the number of regions that can be dissected at high resolution.

Here, Applicants present HiDRA (High-resolution Dissection of Regulatory Activity), a method for high-resolution inference of transcriptional regulatory activity across all accessible regions of the genome. HiDRA overcomes the limitations of previous technologies and combine their advantages, enabling high-throughput and high-resolution inference of regulatory activity. Briefly, Applicants first extracted accessible DNA regions using ATAC-seq (10-12, 21), size-selected for constructs 150-500nt long, and incorporated them in self-reporting episomal constructs (ATAC-STARR-seq), by insertion in the 3' untranslated region (3' UTR) of reporter genes, thus enabling them to drive their own transcription and serve as their own barcodes, providing a quantitative readout of their activity. Applicants then exploited the dense sampling of accessible regions and the partially-overlapping nature of tested fragments for high-resolution inferences using a machine-learning approach (SHARPR-RE). The approach overcome the construct-length and region-count limitations of synthesis-based technologies at substantially lower cost, and the ATAC-based selection of open chromatin regions concentrated the signal on likely regulatory regions and enabled high-resolution inferences. Altogether, in a single experiment Applicants tested millions of enhancer constructs of comparable length to low-throughput studies while achieving the high-resolution dissection of systematic perturbation studies.

Applicants applied HiDRA to infer genome-wide regulatory activity across ~7 million DNA fragments preferentially selected from accessible chromatin in the GM12878 lymphoblastoid cell line, resulting in ~65,000 discrete genomic regions showing significant regulatory function. These were enriched for endogenous active histone marks (including H3K9ac, H3K27ac), regulatory sequence motifs, and regions bound by immune regulators. Applicants' selection approach resulted in highly-overlapping fragments (~32,000 regions covered by 10+ unique fragments, ~12,500 by 20+ fragments), enabling Applicants to pinpoint "driver" regulatory nucleotides that are critical for transcriptional enhancer activity. Applicants discover ~13,000 of these high-resolution driver elements, which were enriched for regulatory motifs and evolutionarily conserved nucleotides, and helped predict causal genetic variants underlying disease from genome-wide association studies. Overall, HiDRA provided a general, scalable, and high-throughput approach for the high-resolution experimental dissection of regulatory regions and driver nucleotides in the context of human biology and disease.

Results

HiDRA Experimental Method Overview

HiDRA leverages the selective fragmentation of genomic DNA at regions of open chromatin to generate fragment libraries that densely cover putative transcriptional regulatory elements. The experimental component of HiDRA was the combination of ATAC-seq and STARR-seq (i.e. ATAC-STARR-seq): fragments were enriched from open chromatin and regulatory regions using ATAC-seq (Assay for Transposase-Accessible Chromatin with high throughput sequencing) and subsequently cloned into the 3' UTR of a reporter gene on the self-transcribing enhancer reporter vector used in self-transcribing active regulatory region sequencing (STARR-seq) (13, 16, 21). Fragments with transcriptional regulatory activity promoted self-transcription such that active segments of DNA can be identified and quantified by high-throughput RNA sequencing to produce a quantitative readout of enhancer activity (FIG. 20A). Library construction can be completed in 2-3 days and requires as few as 104-105 cells as input starting material.

Applicants constructed a HiDRA library with 9.7 million total unique mapping fragments, of which 4 million had a frequency greater than 0.1 reads per million (RPM; non-mitochondrial reads). More than 99% of fragments had lengths between 169nt and 477nt (median: 337nt), with the fragment length distribution showing two peaks spaced by –147nt, corresponding to the length of DNA wrapped around each nucleosome (FIG. 20B). In contrast to unbiased fragmentation of the genome, the library had much higher efficiency for selectively targeting accessible DNA regions that are more likely to play gene-regulatory roles. The HiDRA library covers 4486 predicted enhancers and 9631 predicted promoters ("Active Transcription Start Site (TSS)" state (5, 6, 14) with more than 10 unique fragments (FIG. 20C, colored lines), a ~130-fold and ~210-fold enrichment compared to 35 enhancer and 46 promoter regions expected to be covered by chance at the same coverage. This indicated that HiDRA library construction successfully targeted predicted regulatory regions rather than randomly fragmenting the genome. Even among enhancer and promoter regions and ATAC-seq peaks, those with higher expected activity were preferentially selected by HiDRA, as they showed higher accessibility and were thus more likely to be cloned in our library and tested by our episomal reporters (FIGS. 26A-26C).

The cloning strategy was specifically designed to densely sample regulatory regions, in order to enable high-resolution inference of regulatory activity from highly-overlapping fragments. Indeed, Applicants found up to 370 unique fragments per region in our HiDRA libraries, with ~32,000 genomic intervals containing at least 10 overlapping fragments and ~2750 containing at least 50 fragments, compared to 180 and 0 that would be expected by randomly-selected fragments, respectively. In addition to clustering of tested fragments within the same region, high-resolution inference relied on partially-overlapping rather than fully-overlapping fragments, which required a random fragmentation pattern. Indeed, the Tn5 transposase used here inserted randomly into the genome, and indeed the resulting DNA fragments provided a dense sampling of start and end positions that mirrored the peaks of ATAC-seq experiments (FIG. 20D), indicating that accessible regions most likely to show regulatory activity would have both higher representation in our libraries, and also more starting and ending positions that can help identify driver nucleotides.

Identification of DNA Fragments with Regulatory Activity

To evaluate the ability of each cloned DNA fragment to promote gene expression, Applicants transfected our HiDRA library into GM12878 lymphoblastoid cells, collected RNA 24 hours post-transfection, and measured the abundance of transcribed fragments by high-throughput RNA sequencing. Applicants carried out 5 replicate transfection experiments from the same plasmid library, each into ~120 million cells, and Applicants observed a high degree of correlation in the RNA counts between replicates (0.95 Pearson correlation on average for fragments ≥1 RPM; 0.76 for ≥0.1 RPM; FIGS. 27A-27D). To quantify the regulatory activity of tested elements, Applicants compared the number of RNA reads obtained for a fragment (corresponding to the expression level of the reporter gene, as the constructs are self-transcribing), relative to representation of that fragment in the non-transfected input plasmid library (thus normalizing the differential abundance of each fragment in our library). Applicants observed a substantial number of fragments that were more prevalent in RNA than DNA, indicating capability of many HiDRA fragments to drive reporter gene expression (FIG. 21A).

Given the intentionally high initial complexity of the HiDRA library, many fragments would be sequenced with a relatively low depth of coverage. Applicants therefore grouped fragments with a 75% reciprocal overlap to boost the read coverage of genomic regions and increased statistical power. This yielded 7.1 million unique "fragment groups" generated from merging 9.7 million HiDRA fragments. In total, Applicants identified 95,481 fragment groups that promote reporter gene expression at an FDR cut-off of 0.05, which is referred to as 'active HiDRA fragments' (FIG. 21A, red dots, see Methods). These 95,481 active HiDRA fragments were located within 66,254 unique genomic intervals that were subsequently referred to as "active HiDRA regions". Active HiDRA fragments showed a wide range of input DNA levels in the plasmid library, indicating that regulatory function and DNA accessibility relied on complementary sequence signals, and that DNA accessibility alone was not sufficient to predict episomal regulatory activity. Applicants also found that active HiDRA regions were predominantly distal to annotated transcription start sites (TSSs) (FIG. 21B), validating the utility of HiDRA for pinpointing distal regulatory regions that were particularly challenging to identify.

As proof-of-concept that HiDRA was capable of identifying true enhancer elements, Applicants examined the immunoglobulin heavy chain enhancer within the intron of the immunoglobulin heavy constant epsilon (IGHE) gene (15, 22). Applicants observed that the peak of HiDRA activity was centered precisely within the region previously identified as driving enhancer activity in low-throughput luciferase assays (FIG. 21C). To assess the quantitative accuracy of HiDRA relative to luciferase assays, Applicants compared active HiDRA regions and luciferase results across 21 putative enhancers predicted and tested independently by Huang et al. (16, 23). Applicants found a 0.88 Pearson correlation between measured luciferase activity and HiDRA activity, confirming the accuracy and quantitative nature of our high-throughput approach (FIG. 21D). A visualization of 14 luciferase-tested enhancers in the serine/threonine kinase NEK6 locus showed a strong correspondence between luciferase assay results and HiDRA active regions (FIG. 21E).

HiDRA Elements were Enriched in Promoters and Enhancers

Applicants surveyed the 95,481 active HiDRA fragments identified in GM12878 to assess shared common genomic or epigenomic characteristics. In comparison to the set of all HiDRA fragments tested, active fragments were 8-times more likely to overlap regions annotated as Active Promoter chromatin states by ChromHMM based on the presence of H3K4me3 and H3K27ac, and 5-times more likely to overlap annotated Active Enhancer chromatin states, marked by H3K4me1 and H3K27ac (FIG. 22A). By contrast, Weak Enhancer chromatin states marked by H3K4me1 and absence of H3K27ac had substantially weaker enrichment (1.7-fold) within active HiDRA fragments than active enhancers, consistent with previous literature indicating that presence of H3K27ac correlates with higher greater expression of nearby genes (FIG. 22B). Overall, 35% of all predicted active promoters (8355 regions) and 16% of all predicted active enhancers (5276 regions) overlapped at least one active HiDRA fragment.

In addition to active promoter and active enhancer chromatin states, the "TSS Flanking Upstream" chromatin state showed strong enrichment for active HiDRA fragments (7.3-fold higher than expected from the input library). This chromatin state was defined by the presence of both promoter and enhancer histone marks H3K4me1, H3K4me3, and H3K27ac, and was named "TSS Flanking" due its depletion at exactly the TSS position, but its enrichment 400nt-1kb upstream of annotated transcription start sites 7, 17, 18. However, 64% of its occurrences are >2 kb from the nearest transcription start site, suggesting that a portion of genomic regions annotated as "TSS Flanking Upstream" may function biologically as distal enhancers (FIG. 28).

When Applicants computed enrichment of chromatin states as a function of HiDRA activity strength, Applicants found a linear quantitative relationship for HiDRA activity levels up to ~2.5-fold RNA/DNA ratios, with increasing activity showing increasing chromatin state enrichment for both promoter and enhancer chromatin states (FIG. 22B). Surprisingly, this enrichment stayed constant thereafter for promoter regions, and increased modestly for enhancer regions, ultimately surpassing the enrichment seen for promoters. In fact, even though promoter chromatin states were more enriched at intermediate HiDRA activity levels, enhancer chromatin states were the most enriched at the highest HiDRA activity levels (p=9.3×10-102, Mann-Whitney U test, FIG. 29A), suggesting that enhancer elements have a greater dynamic range of regulatory activity potential, which has implications for the regulatory architecture of genes.

Surprisingly, fragments from heterochromatin-associated chromatin states showed a modest enrichment in active elements, indicating that DNA kept in an endogenous heterochromatic state may contain regulatory signals that become active once taken outside their repressive endogenous chromosomal context. The ZNF/repeats-associated chromatin state (marked by H3K36me3 and H3K9me3) showed a modest enrichment for lower HiDRA activity levels, but continued to increase linearly even at the highest activity levels, possibly due to active repetitive elements, as discussed below. In contrast, Quiescent and Polycomb-repressed chromatin states showed a 2-fold relative depletion for HiDRA active elements, accounting for the enrichments found in other states. The depletion of Polycomb-repressed chromatin states may reflect Polycomb repression on the episomal plasmid.

Applicants also studied the enrichment of HiDRA regions for individual hi stone marks profiled by the ENCODE project in GM128787. Active promoter- and active-enhancer-associated acetylation marks H3K9ac and H3K27ac, histone turnover-associated H2A. Z, promoter- and enhancer-associated H3K4me3 and H3K4me1, and DNase I accessible chromatin were the most enriched individual marks within active HiDRA regions, while Polycomb-repression-associated H3K27me3, heterochromatin-associated H3K9me3, and transcription-associated H3K36me3 were the least enriched compared to the input library (FIG. 30).

Figures 29A, 29B:
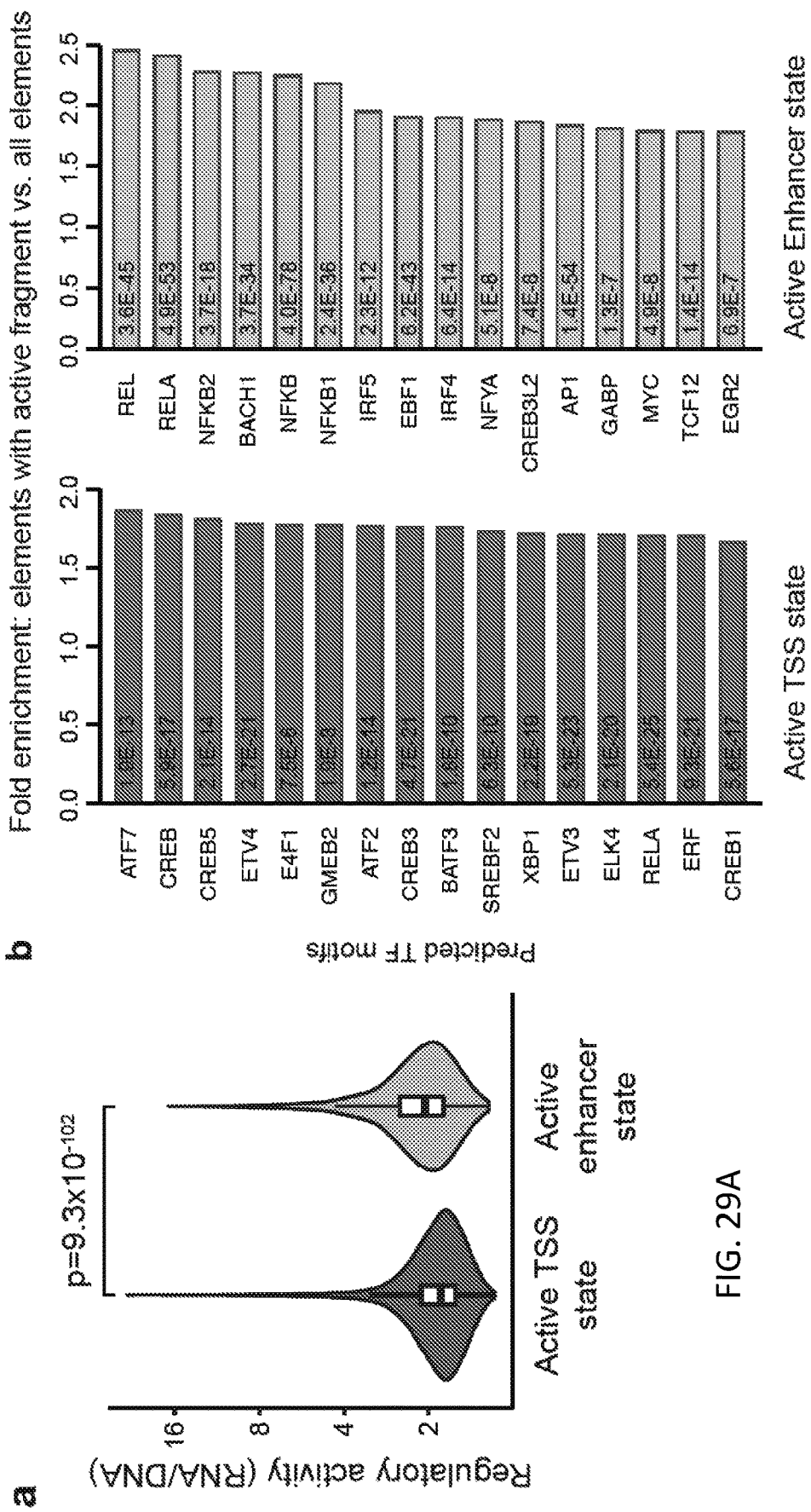
Figure 29C:
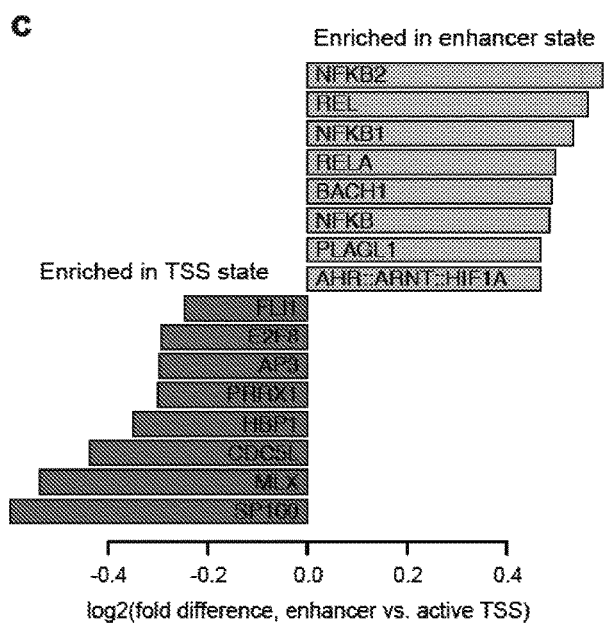
Figure 29D:
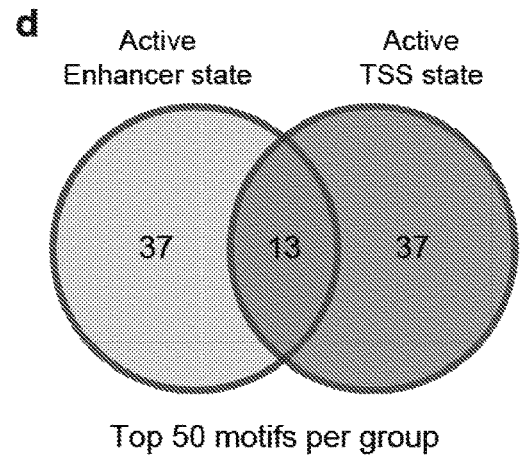
Figure 29E:
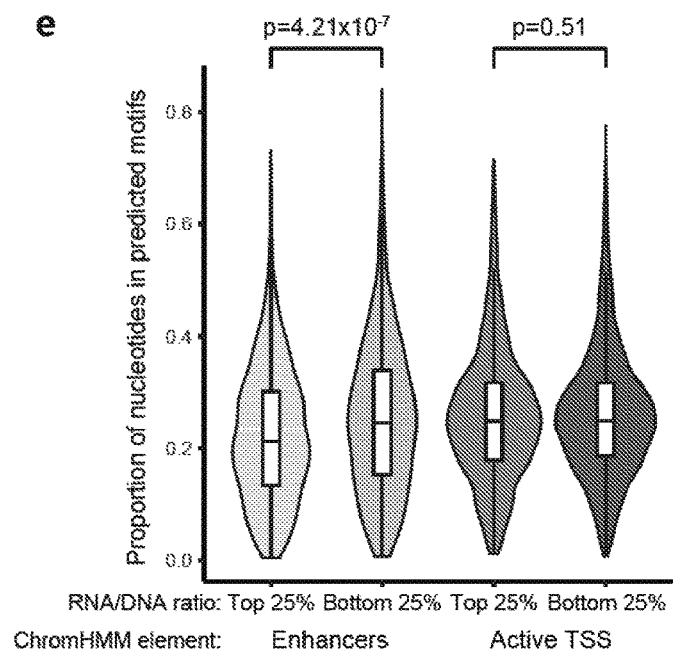
Figure 29F:
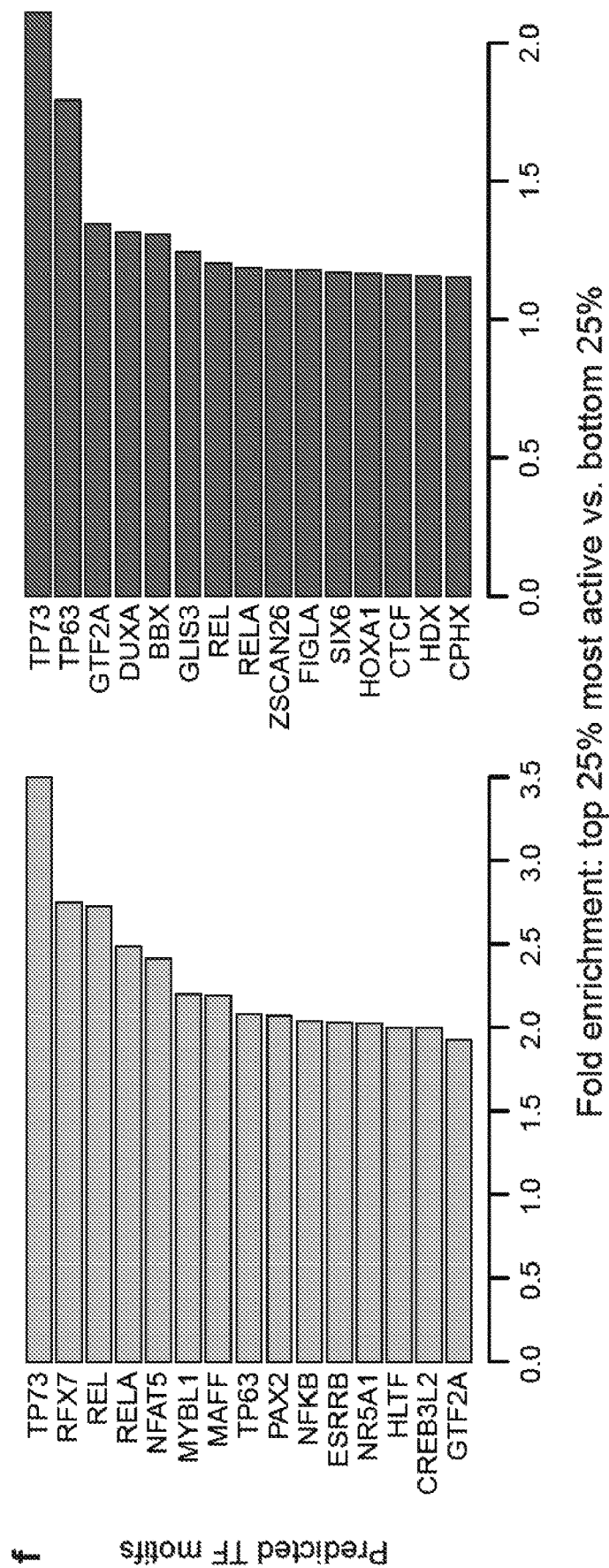

As these elements were tested outside their endogenous chromatin context, Applicants expected that they drive reporter gene transcription by recruiting transcriptional regulators in a sequence-specific way, and Applicants sought to gain insights into the recruited factors. Applicants calculated the overrepresentation of 651 transcription factor sequence motifs assembled by ENCODE in active HiDRA regions, and found enrichment for many distinct motifs for immune transcription factors (FIG. 29B), including IRF, NFKB1, and RELA, corresponding to transcriptional regulators known to function in GM12878 compared to other human cell lines. The motifs enriched in promoter chromatin states were largely distinct from those enriched in enhancer chromatin states, highlighting the differential regulatory control of the two types of regions (FIGS. 29B-29D). High-activity fragments showed distinct motif composition, and were enriched for GM12878 regulators including NF-kB (FIGS. 29E, 29F). These differences in motif content indicated that the two types of regions recruit different sets of transcriptional regulators both in their endogenous context and in the episomal assays, consistent with their distinct endogenous chromatin state and their distinct properties in our HiDRA assays.

Regulatory Activity Outside Promoters and Enhancers

Even though HiDRA active regions were most enriched for enhancer and promoter states, they were not exclusive to them. In fact, consistent with recent studies (24, 25), approximately half of active HiDRA regions (52%) showed endogenous epigenomic signatures characteristic of repressed and inactive chromatin states, including Quiescent, Repressed Polycomb, Weak Repressed Polycomb, and Heterochromatin.

As active chromatin states were defined based on the profiling of only a subset of known chromatin marks in GM12878, Applicants reasoned that perhaps other marks may be marking these regions active, but that they were perhaps not profiled in GM12878 and thus missed by the reference genome annotations. For example, a recent study identified subclasses of active enhancer elements marked with H3K122ac or H3K64ac but not H3K27ac12. While these marks were not profiled in GM12878, inactive chromatin states that showed HiDRA activity were 8-fold to 13-fold more likely to be bound by transcription factors in ChIP-seq experiments in GM12878 than inactive chromatin states that lacked HiDRA activity (FIG. 22D), indicating that our assays can successfully recover active regions even outside active chromatin states, and highlighting the importance of the unbiased survey of open chromatin regions regardless of their endogenous chromatin marks.

As both high-throughput and low-throughput episomal assays test regions outside their endogenous chromatin context, Applicants reasoned that some active HiDRA regions with inactive chromatin signatures may reflect endogenously-inactive regions that become active when removed from the influence of nearby repressive effects. Applicants reasoned that these regions would contain sequence motifs of TFs active in GM12878, but that these sequence motifs would be less likely to be bound in their endogenous chromatin context, compared to motifs in active states. Indeed, Applicants found that active HiDRA regions from endogenously-inactive chromatin states showed similar enrichments in regulatory motif sequence coverage to that of enhancer and promoter chromatin states (FIG. 22C), but substantial differences in their endogenous TF binding (FIG. 22D), consistent with endogenous repression due to their genomic context. These regions were also ~30% more likely to be active in another human tissue, compared to HiDRA-inactive regions (FIG. 31), consistent with cell-type-specific repression in their endogenous chromatin context.

In addition to the presence of regulatory motifs for known regulators active in GM12878, Applicants sought additional driver elements that may be responsible for the episomal activity of endogenously-inactive regions. In particular, Applicants considered the presence of Long-Terminal-Repeat (LTR) retrotransposons, which had been previously shown to have regulatory activity potential and were enriched in the set of all active HiDRA regions unlike other repetitive elements in the genome (FIG. 32A) (13, 26). Indeed, Applicants found that active HiDRA regions from endogenously-inactive regions showed substantial enrichment for LTR retrotransposons. In fact, Quiescent and Heterochromatin states were more enriched for LTR retrotransposons than either Enhancer or Promoter chromatin states (FIG. 32B). These regions were endogenously inactive despite their seeming regulatory activity potential, likely due to the effect of repressive chromatin in their endogenous loci. As LTRs are motif-rich and often act as the substrate for recently evolved enhancers, these endogenously-inactive but episomally-active HiDRA regions may represent a reservoir for the emergence of new regulatory elements (2).

High-Resolution Mapping of Regulatory Activity with HiDRA

Applicants sought to exploit the highly overlapping nature of tested HiDRA fragments to increase the resolution of regulatory inferences by exploiting subtle differences between neighboring fragments that only overlap partially. As an example, Applicants considered a 3 kb region on chromosome 7 that is covered by 134 HiDRA fragments with distinct start and end positions. When Applicants examined every fragment in this region, Applicants observed that fragments overlapping a known RUNX3 motif showed substantially higher regulatory activity (FIG. 23A). This motif was bound by the RUNX3 protein in GM12878 cells and showed increased evolutionary conservation (FIG. 23A). These properties suggested that the driver regulatory nucleotides within this region were tightly concentrated surrounding the RUNX3 motif, and that on the global level the differential activity of HiDRA-tested segments would allow for systematically discover these driver nucleotides in an unbiased way based on the relative activity of fragments that do or do not overlap them.

As part of the development of Sharpr-MPRA13, Applicants had previously developed the SHARPR algorithm (Systematic High-resolution Activation and Repression Prediction from Reporter assays), a graphical probabilistic model that inferred high-resolution activity from MPRA tiling experiments by reasoning about the differential activity of partially-overlapping microarray spots. SHARPR allowed Applicants to transform measurements from the 145-bp resolution of individually tested tiles to the 5-bp resolution of the offset between consecutive tiles. The SHARPR algorithm relied on synthesized oligos that uniformly tiled regions at regularly spaced intervals. Applicants developed a new algorithm, SHARPR-RE (for SHARPR with Random Endpoints), which estimated regulatory scores underlying any set of randomly-positioned and variable-length segments, by appropriately scaling the segments by their varying lengths, and enabling inferences at variable-length offsets between them (Supplementary Methods).

Applying the SHARPR-RE algorithm to the RUNX3 example above, Applicants found that the 3 kb region was narrowed down to a single 'driver' element of 27nt (FIG. 23A). These captured the known RUNX3 motif shown experimentally by ChIP-seq to be bound by the RUNX3 regulator in GM128787, and also the independently-determined high-resolution region of evolutionary conservation, even though neither line of evidence was used in our inferences.

Across all ~32,000 "tiled regions" that were covered by at least 10 unique HiDRA fragments (FIG. 33), SHARPR-RE predicted ~13,000 driver elements of median length 52nt, using a regional family-wise error rate of 5% (FIG. 23B, see Supplementary Methods and Supplementary Datasets 2 and 3). The resolution with which driver elements could be resolved increased with the number of unique HiDRA elements spanning a tiled region, reflecting both the increased number of breakpoints in densely-tiled regions, and the increased discovery power afforded by the SHARPR-RE algorithm. Regions tiled by 40 or more fragments showed ~20nt resolution (FIG. 34). Regions tiled by fewer fragments (10-20) showed lower resolution (~50nt), but resolution only increased to ~18nt with higher fragment density, suggesting the minimum size of driver elements detectable by the HiDRA assay that resulted in regulatory activity was only slightly longer than individual regulatory motifs. Similar to active HiDRA regions, driver elements were also mostly distal from annotated TSS regions, and were preferentially found in endogenously active chromatin states (active promoters, TSS-flanking, and active enhancer regions, FIG. 35).

Compared to a background of all tiled regions, which were specifically enriched for GM12878 regulatory regions, Applicants found that predicted driver nucleotides were significantly more enriched for regulatory motifs than shuffled controls (obtained by randomly shuffling driver element positions within the same set of tiled regions with at least 10 unique HiDRA fragments). The enriched motifs consisted of regulators known to be active in GM12878, including several critical B-cell and immune transcription factor including NF-kB and the IRF family (FIG. 23C). A total of 98 motifs were enriched in driver elements (FDR<0.05 vs. random shuffling of driver elements in tiled regions, see Methods), clustering into several distinct groups with little overlap between groups, suggesting a wide range of distinct transcription factors act to regulate GM12878 gene expression (FIG. 23D). Applicants also found that driver nucleotides were significantly more likely to be evolutionarily-conserved across vertebrates than randomly-shuffled controls in tiled regions (FIG. 23E), with 1080 driver elements overlapping conserved regions, compared to only ~650 expected by random shuffling of driver elements within tiled regions (p=2.23×10−73). Driver elements were also more evolutionarily conserved than equally-sized segments residing directly upstream or downstream (FIG. 36A), supporting the biological importance of the high-resolution inferences.

Applicants also validated our high-resolution predictions using an independent high-resolution experimental method based on 1VIPRA array synthesis and high-resolution tiling (Sharpr-MPRA13). As the original SHARPR algorithm did not include the functionality to call discrete driver elements, Applicants compared Sharpr-MPRA activity scores within driver elements identified in this study compared to equally-sized segments shifted upstream and downstream. Applicants found that HiDRA driver elements were much more likely to show Sharpr-MPRA activity than these shifted segments. Sharpr-MPRA activity scores peaked for HiDRA driver elements, and were lower in flanking regions (256 regions tested in both HepG2 and K562, FIG. 36B), supporting the functional importance of HiDRA driver nucleotides (FIG. 36B, left panels). The agreement was stronger for Sharpr-MPRA scores in K562 than HepG2 (FIG. 36B), consistent with its higher similarity to GM12878. Specifically distinguishing accessible DNA sites based on their motif content (and thus the trans-acting TFs predicted to target them), Applicants found that predicted targets of K562 and HepG2 TFs that were also expressed in GM12878 showed even higher Sharpr-MPRA scores, whereas targets of TFs that were not expressed in GM12878 showed nearly complete loss of any enrichment signal (FIG. 36B, right panels), thus providing a mechanistic explanation for their similarity in activity.

Applicants also evaluated whether disruption of regulatory motifs within predicted driver elements reduced their activity. Applicants selected HiDRA driver elements whose disruption had previously been tested in K562 and HepG2 using a synthesis-based MPRA27. In all four cases, shuffling motif-containing nucleotides within predicted driver regions showed reduced 1VIPRA activity in one or both cell types tested (FIG. 36C, Mann-Whitney U test), confirming the functionality of our predicted driver nucleotides for enhancer activity. Applicants also evaluated whether genetic variants in predicted driver nucleotides were more likely to result in differential activity between the two alleles, compared to other genetic variants. Applicants used the results of an independent experimental study that quantified allelic enhancer activity for 4,335 single-nucleotide polymorphisms (SNPs) across the genome (28), of which 24 overlap driver elements identified by our assay. Genetic variants inside driver elements indeed showed significantly stronger allelic skews compared to all variants tested by MPRA (p=1.62×10−4, Mann-Whitney U test), and also compared to all tested variants inside HiDRA-tiled regions but outside driver elements (p=9.20×10−4, Mann-Whitney U test) (FIG. 23F), supporting the functional importance of our predictions, and the high-resolution nature of our driver elements.

Taken together, these results indicated that the high-resolution inferences were biologically meaningful and could help pinpoint driver nucleotides among larger regions.

Characterization of GWAS SNPs Affecting Enhancer Activity

Applicants next sought to use our predicted active regions and driver nucleotides to gain insights into non-coding variation, as past work has demonstrated that disease-associated variants are preferentially localized to regulatory elements (4, 29, 30). Applicants studied the overlap between genetic variants associated with immune disorders and the high-resolution predicted driver nucleotides. Even though driver nucleotides only covered 0.032% of the genome, Applicants found 12 cases where they overlapped fine-mapped SNPs associated with 21 immune-related traits (31) predicted to be causal (~5 expected by chance inside tiled regions, p=0.012 vs. random shuffling, FIG. 24A). For example, Applicants predicted a 76-nt driver element overlapping rs12946510 in the IKZF3 locus associated with multiple sclerosis in a tiled region of 3 kb (FIG. 24B), suggesting this may be the causal variant. The SNP overlapped a 76-nt driver element that contains a RUNX3 motif and a RELA motif, both bound by the respective TFs in GM128787. Indeed, rs12946510 was predicted to be causal based on genetic fine-mapping (31), with a posterior probability of 0.314 of being causal with the next strongest signal showing only 0.067 posterior probability. rs12946510 was also an eQTL for the nearby IKZF3 gene (31, 32), and was recently shown to disrupt enhancer activity for the surrounding 279-nt region using a luciferase reporter assay (33), consistent with the prediction that rs12946510 was a causal SNP.

To recognize regions that showed differential activity between risk and non-risk alleles of common genetic variants, Applicants first inferred the genotype of all RNA fragments profiled. As HiDRA was a sequencing-based assay, where the expression of reporter genes was quantified based on the number of sequencing reads, allele-specific differences in HiDRA activity between risk and non-risk haplotypes would be detectable in principle by using heterozygous positions to distinguish reads coming from the paternal or the maternal allele. In practice however, HiDRA fragments were much longer (~337 median length) than the typical sequencing reads we used for quantification (37nt, paired end), and thus 78% of genetic variants may not be covered by our sequencing reads (if they fell in the inner ~260nt not captured by the paired-end sequencing). To overcome this limitation and to determine allele-specific activity scores for all the fragments, Applicants used low-depth re-sequencing of our input library using long reads, thus revealing the genotype associated with each start/end position in our library (FIG. 25A). Applicants augmented this information with 4-nt random i7 barcodes that were added by PCR during the initial HiDRA library construction, thus ensuring that the [start, end, i7] triplet was almost guaranteed to be unique, by resolving the cases where both start and end positions were identical between paternal and maternal alleles. This strategy enabled us to resolve the genotype of all previously quantified HiDRA fragments without having to sequence both the plasmid and RNA libraries to full length at high depth, which would be too costly.

In a proof-of-concept analysis to assess the ability of HiDRA to detect allelic activity, Applicants applied this approach systematically to all heterozygous positions known in the genotyped GM12878 cell lines. Applicants found 180,000 heterozygous SNPs that were represented by at least one HiDRA fragment at either allele in the library. Detection of allelic activity with random fragmentation was subject to confounders, as fragments carrying the maternal or paternal allele of a SNP may also differ at their start and end positions, which may result in activity differences independent of SNP effects (FIG. 37). To minimize such effects, Applicants only compared fragments with 90% mutual overlap, and with driver elements at least 25nt from fragment ends. Additionally, statistical power to detect allelic differences may be limited for many SNPs. Applicants also only consider SNPs that have >20 read coverage for both fragments (reference and non-reference alleles). In total, 16,000 SNPs remained after applying these three filters. At an uncorrected nominal p-value cut-off of 0.05, Applicants found 880 'allelic' HiDRA SNPs where paternal and maternal alleles showed differences in activity, 25 of which had a corrected FDR<0.1 (beta-binomial model (34), Supplementary Dataset 4). The corresponding SNPs in these 880 allelic HiDRA regions were more frequently found in HiDRA active regions and more frequently predicted to have strong regulatory effects in open chromatin regions by an independent study (35) (FIG. 25B, 25C), suggesting they are biologically meaningful. As an example, Applicants found that rs2382817, a SNP associated with inflammatory bowel disease (32) (GWAS p=1.13×10−13), showed differential HiDRA activity between paternal and maternal alleles. The risk allele showed increased regulatory activity upstream of an HiDRA-annotated active region (nominal p=8.7×10−4, FDR=0.25, p-values from QuASAR-MPRA, FIG. 25D, 25E), illustrating the possibility of using HiDRA to detect SNPs with allelic effects on regulatory activity.

These results indicated that HiDRA would shed light on disease-associated variants, by either narrowing down the set of candidate causal SNPs using our high-resolution driver nucleotide inferences, or by directly observing differential activity between risk and non-risk alleles using allele-specific activity inferences.

DISCUSSION

In this example, Applicants introduced a high-throughput experimental assay, HiDRA, for testing transcriptional regulatory activity across millions of DNA fragments, and for inferring high-resolution driver elements within them. In the experimental component of HiDRA, Applicants captured regions of open chromatin, size selecting them, and inserting them downstream of transcription start in an episomal reporter construct, thus driving their own transcription and serving as their own barcodes (ATAC-STARR-seq). By concentrating the signal on open-chromatin regions, HiDRA enabled high-resolution inference of driver nucleotides within these regions using a machine-learning model (SHARPR-RE), by exploiting subtle differences in the reporter activity driven by partially-overlapping tested fragments. Applicants referred to the combined SHARPR-RE-ATAC-STARR-seq method as the "High-resolution Dissection of Regulatory Activity", or HiDRA. By capturing putative regulatory regions directly from open chromatin regions, HiDRA had the advantage of foregoing oligonucleotide synthesis, and thus enabling testing of much longer fragments, and testing many more regions in a single experiment.

Applicants applied HiDRA on the GM12878 lymphoblastoid cell line, revealing a global map of regulatory elements and their sequence-driven effects on transcription. Applicants showed that HiDRA provided a quantitative assay with strong sensitivity and specificity, compared to low-throughput luciferase assays. Applicants showed that fragments with the strongest activity show endogenous promoter and enhancer signatures, contain motifs for immune transcription factors, and showed in vivo binding by immune regulators. Applicants also showed that driver nucleotides inferred by the high-resolution mapping were enriched for evolutionarily-conserved regions, known regulatory motifs for immune regulators, and for genetic variants associated with immune traits. Applicants also showed that long-read resequencing of the HiDRA library can distinguish allele-specific activity of risk vs. non-risk fragments derived from heterozygous loci associated with disease, enabling directionality-of-effect inference and providing mechanistic insights on disease loci.

Another method that enables the high-resolution dissection of thousands of putative regulatory regions is Sharpr-MPRA13. Sharpr-MPRA and HiDRA differ in key several respects: Sharpr-1VIPRA selects regions based on prior computational predictions, requiring microarray-based synthesis. This in vitro synthesis step limits the number of nucleotides and regions tested by Sharpr-MPRA (4.6 Mb in 15,720 regions for Sharpr-MPRA vs. 46.3 Mb in 31,813 regions for HiDRA). Moreover, Sharpr-MPRA uses fixed 5-bp increments (vs. random increments for HiDRA, stemming from the transposase fragmentation pattern), 145-bp fragments (vs. random lengths for HiDRA, 335-bp on average), and Sharpr-MPRA tests elements upstream of the TSS using 3'UTR barcodes (vs. testing elements downstream, thus enabling them to serve as their own barcodes).

Figure 20C:
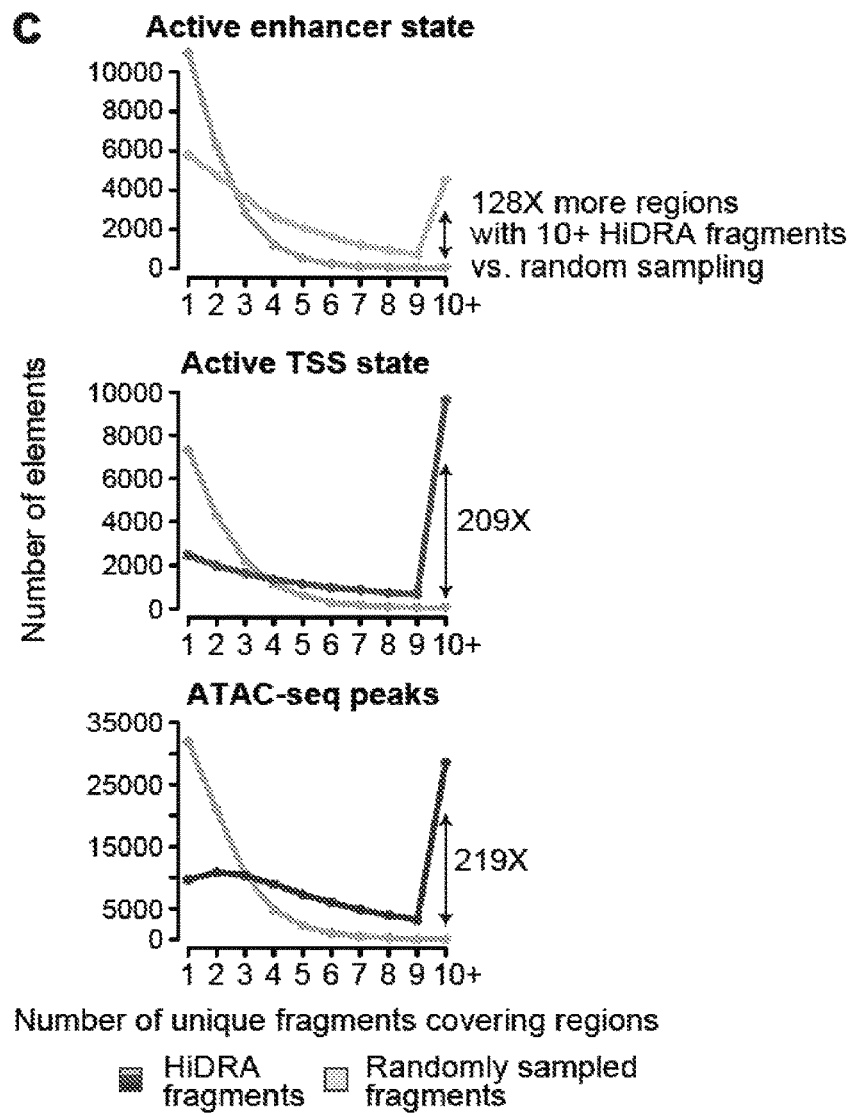
Figure 20D:
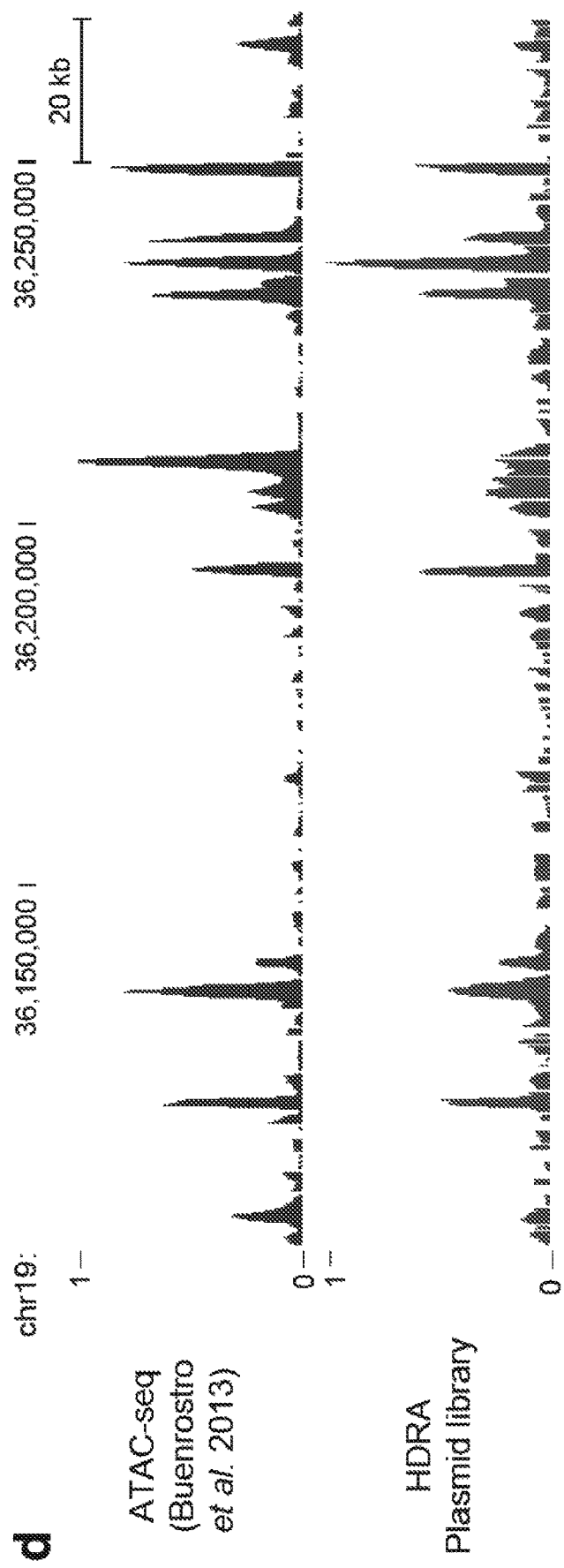

The ATAC-STARR-seq step in HiDRA had many benefits compared to regular STARR-seq without fragment selection. ATAC-STARR-seq preferentially tested the activity of fragments derived from open chromatin, and the HiDRA library Applicants developed achieves 130-220× more highly covered regulatory elements than random genome fragmentation (FIG. 20C). This facilitated both higher confidence discovery of regulatory elements, and the high-resolution dissection of regulatory elements by comparing the relative activity of partially-overlapping fragments. This latter application using the newly developed SHARPR-RE algorithm permitted the genome-wide mapping of high-resolution driver elements, and would not be possible with regular STARR-seq unless extremely complex fragment libraries were used (at least 15 or 20-fold more complex than this current library). HiDRA may therefore be feasibly and readily applied across a wide range of tissues for high-resolution mapping without the limitations that regular STARR-seq would entail (e.g. >109 cells per tissue, and high depth of sequencing to quantify a library with ~20-fold more fragments).

The HiDRA approach was general and can be readily adapted for other applications. While Applicants performed our study using ATAC regions from the GM12878 cell line and re-transfection of constructs in the same cell line, the approach may be applicable to any cell type, and to combining of different source and target cells. For example, libraries may be generated from limited patient tissue, or a pool of multiple donors to increase heterozygous loci, and subsequently transfected into a relevant immortalized cell line that can be easily grown to high cell quantities. Here, Applicants used transfection to introduce episomal plasmid reporters, but lentiviral methods may be used in cell lines with lower transfection efficiencies. Applicants chose non-integrating episomal reporters to focus more directly on sequence function independently of its broader chromatin context, however the HiDRA approach may be used with an integrating lentiviral vector to also incorporate the effect of chromosomal context, with the understanding that previous analyses used up to ~100 integration sites per tested element to accurately quantify activity 36. Moreover, integrating reporter techniques may require cell sorting using fluorescent reporter activity, which limits the number of constructs that can be tested (37).

The HiDRA approach can also be specifically tuned for mapping differential allele activity in regulatory regions associated with human disease SNPs from GWAS. At the library construction stage, capture probes can be used to further increase coverage at known polymorphic SNPs of interest, thus increasing fine-mapping resolution, facilitating comparison of fragments with alternate alleles but matching start and end positions, and increasing statistical power to detect differential activity between risk and non-risk alleles. For cancer mutations and other somatic mutations, HiDRA may also be applied to pools of tumor samples, or pools of disease tissue, to identify variants that alter regulatory activity and gene expression (39). For systematic mutagenesis, HiDRA libraries can also processed to introduce new mutations through error-prone PCR or introduction of mutagens during amplification.

We also envision modifications of the HiDRA assay presented here for testing specific subsets of the genome. A modified HiDRA assay may be used to enrich for fragments from active regulatory regions, by coupling HiDRA with a fragment capture technology similar to those used in Capture Hi-C to selectively test a subset of enhancers or promoters at higher resolution while retaining the advantages of having larger fragment sizes and high library complexity 40. To test regions associated with specific chromatin states, capture could be performed using the output of chromatin immunoprecipitation experiments (ChIP) using histone modifications, thus preferentially sequencing genomic regions that were also pulled down with ChIP. Finally, the SHARPR-RE high-resolution mapping algorithm developed here can be applied to perform high-resolution mapping of genomic regions for high-complexity libraries with sufficient fragment density (e.g. testing of individual large regions using bacterial artificial chromosome clones with "BAC-STARR-seq" (16), or high-resolution mapping of transcription factor binding sites with ChIP-STARR-seq (19). Applicants envision that HiDRA and such modified approaches can be used to quantify the transcriptional regulatory landscape of DNA sequences for a variety of tissues from multiple organisms.

URLs and Data Availability

All high-throughput sequencing data generated by this study has been deposited in NCBI GEO with accession GSE104001. Processed HiDRA plasmid input, RNA output, activity, as well as active fragments and driver elements can be directly visualized on the UCSC genome browser at: genome.ucsc.edu/cgi-bin/hgTracks?hgS_doOtherUser=submit&hg_otherUserName=xinchenw&hgS_otherUserSessionName=HiDRA_GM12878_092617. These bigWig files can also be downloaded at the NCBI GEO repository (GSE104001). The SHARPR-RE R package is available on CRAN (CRAN.R-project.org/package=sharpr2).

Methods

Method Considerations and Detailed Information

Additional information and considerations in applying the method are provided in Supplementary Notes.

HiDRA Library Construction

Applicants performed 16 ATAC-seq reactions on 50,000 GM12878 cells each using a modified protocol based upon Buenrostro et al. (Supplementary Note 1). Initial steps of ATAC-seq (cell collection, lysis, and Tn5 digestion) followed the protocol in Buenrostro et al: each batch of 50,000 cells was collected by spinning at 500 g for 5 min in a 4° C. cold room, washed with 50 µL of 1×PBS, and resuspended in ATAC-seq lysis buffer (10 mM Tris-HCl, pH 7.4, 10 mM NaCl, 3 mM MgCl2, 0.1% IGEPAL CA-630); a pellet was collected by spinning at 500 g for 10 min, and was resuspended in 25 µL TD buffer (Illumina #FC-121-1030), 2.54, Tn5 transposase (Illumina #FC-121-1030) and 22.5 µL dH2O; the transposition reaction proceeded for 30 minutes at 37° C. on a shaker (300 rpm). Tn5-fragmented DNA was cleaned up using a MINELUTE™ PCR purification kit (Qiagen #28004, four reactions per column eluted in 20 µL EB buffer) and the resulting 80 uL of eluate was split into 16 PCR reactions (Supplementary Note 2). PCR was performed using custom HPLC-purified primers (F: 5'-TAGAGCATGCACCGGCAAGCAGAAGACGGCATACGAGATNNNNATGTCTCGTGGGC TCGGAGATGT-3' (SEQ ID NO: 1), R: 5'-GGCCGAATTCGTCGATCGTCGGCAGCGTCAGATGTG-3', where NNNN corresponded to a random 4nt i7 barcode sequence) (SEQ ID NO: 2) and NEBNEXT™ Ultra II Q5 DNA polymerase master mix (NEB #M0544L). Thermocycler conditions were: 65° C. for 5 min, 98° C. for 30 sec, 8 cycles of: 98° C. for 10 sec and 65° C. for 90 sec. PCR reactions were pooled and cleaned up with a Qiagen MINELUTE™ PCR purification kit (two PCR reactions per column eluted in 20 uL EB buffer) and run on a 1% agarose E-Gel EX with SYBRL Gold II stain (Thermo Fisher #G402001). Size selection of ATAC-seq fragments was performed by gel excision using a razor blade to select fragments between 150-500nt. Gel slabs were pooled into <300 mg groups and DNA was purified using a MINELUTE™ Gel Extraction kit (Qiagen #28604) and eluted in 20 µL of buffer EB per column following modified guidelines described in Box 2 of Taiwo et al. (2012) (41). The resulting size-selected ATAC-seq fragment library was treated with an anti-mitochondrial DNA CRISPR/Cas9 library following the protocol outlined in Montefiori et al. using 10× excess of Cas9 protein (Supplementary Note 3) (42). Applicants cleaned up the reaction with a Qiagen MINELUTE™ PCR purification kit and split into 8 PCR reactions for a second round of PCR using the same conditions and primers described above. PCR products were cleaned up using two rounds of AMPure bead selection (0.8× ratio of beads to input) to size-select against small (<150nt) fragments, eluted in 404, of dH2O and quantified using a Qubit dsDNA HS Assay kit (Thermo Fisher #Q32854).

The pSTARR-seq_human plasmid used for generating the plasmid library was a gift from Alexander Stark (Addgene plasmid #71509). The linear backbone used for the subsequent cloning steps was generated by digesting 4 µg of circular pSTARR-seq_human for 4-6 hours with AgeI and SalI restriction enzymes (NEB #R3552S and R3138S), followed by gel excision under a dark reader transilluminator (Clare Chemical #DR22A) to extract a linear 3.5 kb fragment corresponding to the human STARR-seq plasmid backbone. Applicants performed cloning of the fragment library into the plasmid backbone approximately following the Methods section from Arnold et al. (2013) (16). For each library, we performed 20 individual InFusion HD cloning reactions (Takara Bio #638911) using a 3.5:1 molar ratio of insert to vector backbone, following manufacturer's instructions (Supplementary Note 4). Each group of five InFusion reactions was collected and cleaned up using the Qiagen MINELUTE™ Enzymatic Reaction cleanup kit, eluted in 10 uL of dH$_2$O, and transformed into four 20 uL aliquots of MegaX DH10B T1R electrocompetent bacteria. The bacteria were thawed on ice for 10 min and mixed with eluted DNA (five InFusion reactions per 100 of bacteria). 22 uL of bacteria/DNA mixture were pipetted into a 0.1 cm electroporation cuvette (Thermo Fisher Scientific #P41050) and tapped repeatedly against a hard surface to remove bubbles. Cuvettes were electroporated using a Bio-Rad Gene Pulser Xcell Microbial Electroporation System (Bio-Rad #1652662) using the conditions: 2.0 kV, 200 Ω, 25 µF (Supplementary Note 5). For high-yield transformations, Applicants observed electroporation time constants between 4.8 and 5.1 ms. After electroporation, bacteria were immediately collected in 750 uL pre-warmed SOC media, pooled, and incubated for 1 hr in a 37° C. shaker. After recovery, serial dilutions of bacteria were plated to estimate the number of clones in the library. Recovered bacteria were diluted in 2 L of pre-warmed Luria broth and 100 µg/mL of carbenicillin and grown overnight (8-10 hours while shaking). Plasmids were collected from bacteria using the Plasmid Plus MegaPrep kit (Qiagen #12981) following manufacturer's instructions. Plasmid concentration was quantified using a Nanodrop One machine (Thermo Scientific) and diluted to a 3 µg/µL concentration for subsequent transfection steps. To ensure plasmid library quality and diversity, a small aliquot of the fragment library was amplified by PCR using i5 and i7 primers, run on an Illumina MiSeq machine using the 50-cycle v2 kit as per manufacturer's instructions, and aligned to the human genome to ensure correct complexity and sufficient proportions of reads within predicted transcriptional regulatory elements (Supplementary Note 6, see subsequent Methods sections for details on processing of sequencing libraries).

Cell Culture and Transfections

GM12878 cells were obtained from the Coriell biorepository and grown in RPMI 1640 Medium with GlutaMAX Supplement (Thermo Fisher #61870127), 15% fetal bovine serum (Sigma Aldrich #F2442), and 1% pen/strep at a density of between $2\times10^5$ and $1\times10^6$ cells/mL with regular media changes every 2-3 days. Approximately 24 hours before transfection, GM12878 cells were split to a density of 4×105 cells/mL to ensure the presence of actively dividing cells for increased transfection efficiency. For transfection, cells were collected by centrifugation for 5 min at 300 g, washed once with pre-warmed PBS, and collected again for 5 min at 300 g. PBS was aspirated and cell pellets were re-suspended in Resuspension Buffer R (Thermo Fisher Scientific #MPK10096) at a concentration of 7.5 million cells per 100 µL. DNA was added to cells at a concentration of 5 µg of plasmid per 1 million cells. In total, Applicants transfected 5 replicates with 120-130M million cells per replicate using 1004, tips from the Neon Transfection System at 1200V with 3 pulses of 20 ms. Replicate number was chosen based on other high-throughput reporter assay studies (e.g. Vockley et al. and Tewhey et al.). Transfected cells were immediately recovered in pre-warmed GM12878 media without antibiotic and recovered at a density of $1 \times 10^6$ cells/mL for 24 hours. In parallel, Applicants performed two transfections of GM12878 cells with a positive control GFP plasmid to assess transfection efficiency using the same conditions.

RNA Isolation and cDNA Generation

GM12878 cells were collected 24 hours post-transfection, washed twice in pre-chilled PBS (collecting for 5 min at 300 g) and RNA was purified using the Qiagen RNEasy Maxi kit (Qiagen #75162) following manufacturer's instructions and performing the optional on-column DNase treatment step (Qiagen #79254). Poly A+ RNA was extracted from total RNA using the Oligotex mRNA Midi kit (Qiagen #70042, two columns per RNA sample), and any remaining DNA was digested with a second DNase treatment step using Turbo DNase (Thermo Fisher #AM2238) following manufacturer's instructions (Supplementary Note 7). Treated mRNA was cleaned up and concentrated using the Qiagen RNEasy MINELUTE™ Cleanup kit (Qiagen #74204). We generated cDNA from mRNA using Superscript III Reverse Transcriptase (Thermo Fisher #18080085) with a gene-specific RT primer located in the 3'UTR of the sgGFP reporter gene downstream from the inserted fragments (5'-CAAACTCATCAATGTATCTTATCATG-3'(SEQ ID NO: 3)). Reverse transcription was performed following manufacturer's recommendations except with 2 µg of poly A+ mRNA and 1 uL of 12.504 primer per 20 µL reaction, and extension was performed for 60 minutes at 50° C. (Supplementary Note 8). Reverse transcription reactions were cleaned up using a MINELUTE™ PCR purification kit (Qiagen #28106, two reactions per column) and eluted in 15 µL of pre-warmed buffer EB.

Library Construction and High-Throughput Sequencing

We performed a qPCR to test the number of cycles needed for amplification of single-stranded cDNA as well as input material of plasmid DNA needed such that both reactions had the same Ct values. Applicants used 1 µL of ssDNA and dilutions of plasmid DNA similar to the method described by Tewhey et al. Cell 2016. qPCRs were performed in 10 µL reactions with all reagents scaled down proportionally from a normal 50 uL PCR reaction (1 uL of DNA, 5 uL of Ultra II Q5 master mix, 0.44 µL of 25 µM primer mix, 0.2 µL of 10x SYBR® dye, 3.44, of $dH_2O$) with thermocycler conditions: 98° C. for 30 s, 20 cycles of: 98° C. for 10 s, 65° C. for 90 s. Applicants proceeded to perform eight regular 50 uL PCR reactions (each scaled up 5x from the 104, PCR reactions) using the same thermocycler conditions except using the Ct value for the cycle number (F: 5'-CAAGCAGAAGACGGCATACGAGAT-3' (SEQ ID NO: 4), R: 5'-AATGATACGGCGACCACCGAGATCTA-CAC[X8]TCGTCGGCAGCGTC-3', "X8" sequence corresponds to sample barcode, chosen from Illumina Nextera barcode list (SEQ ID NO: 5)). PCR reactions were cleaned up using Qiagen MINELUTE™ PCR purification kits and balanced for sequencing using the Kapa Library Quantification Kit (Kapa Biosystems #KK4824, Supplementary Note 9).

Each library batch (five transfected RNA biological replicates, five plasmid controls) was sequenced by the Broad Institute Walk-Up Sequencing Facility on four flowcells on a NextSeq 500 machine using the 75-cycle kit as per manufacturer's instructions for 2×37nt paired-end reads with 2×8nt barcodes.

Fragment Data Processing and Calling Active Fragment Groups

Reads were labelled by a random 4nt P7 barcode and an 8nt P5 barcode for sample ID. Reads were split into the ten samples (5 plasmid replicates and 5 RNA replicates) by P5 barcode and aligned to the human genome (hg19 assembly) using bowtie2 v2.2.9. Alignment files were filtered to (i) keep only aligned fragments, (ii) remove reads mapping to chrM, (iii) select reads passing the -q 30 filter in samtools, and (iv) remove reads aligning to the ENCODE hg19 blacklist regions (Supplementary Note 10). Applicants identified unique fragments using the bamtobed command in BEDTools (v2.26.0) and filtered to keep only fragments between 100 and 600nt. A diagram illustrating proportion of reads lost to each filter step is available in FIG. 38.

In analyzing results from HiDRA, Applicants tracked the abundance of each individual fragment between the input (plasmid DNA) and output (RNA). Applicants grouped fragments into "fragment groups" by 75% mutual overlap (bedtools v2.26.0, intersect Bed command), removed redundant fragment groups and summed counts of all fragments per fragment group. As Applicants detected active fragments by comparing RNA signal to the non-transfected DNA library, Applicants controlled for the possible length-dependent biases in transfection efficiency of plasmids by splitting fragment groups into separate bins of 100nt (100-200nt, 200-300nt, etc.) and used DEseq2 (v1.10.1) to identify FDR<0.05 significantly up-regulated fragment groups in each bin43.

Analysis of Active HiDRA Regions

All overlap and shuffle analyses performed using the BED Tools suite, v2.26.044. Most colors for plots chosen with guidance from the wesanderson R package (github.com/karthik/wesanderson). For chromatin state annotations Applicants used the 18-state output model generated by the Roadmap Epigenomics Consortium6. Active enhancer states were merged from states #9 and #10 (EnhA1 and EnhA2). ATAC-seq peaks positions were obtained from Buenrostro et al. (2013)21.

Signal tracks: Signal tracks for regulatory activity calculated as (RNA-DNA)/DNA after adding a pseudocount of 0.1 to both plasmid and RNA samples, so that fragments with no activity have a regulatory activity value of 0. Signal tracks were drawn in UCSC Genome browser showing only means (no whiskers) and with 5-pixel smoothing.

Correlation between RNA samples: Applicants showed correlations for fragments selected by four different cut-offs of minimum RPM. Pearson and Spearman correlations were calculated on log2-transformed data. Matrix of graphs drawn using layout and grid.arrange functions in R from the gridExtra library. Scatterplot between RNA samples drawn using the hexbinplot function from the hexbin library in R with xbins=100.

Proximal vs. distal: TSS regions were defined using the UCSC Genome Browser's Table Browser tool for hg19. Distances to nearest annotated TSS were taken using closestBed tool in the BEDTools2 suite.

TF motif enrichment: Applicants obtained the hg19 TF motif catalog from the ENCODE project7. Applicants only considered motifs corresponding to transcription factors expressed in GM12878 (RPKM>5 using processed GM12878 RNA-seq data from the Roadmap Epigenomics Consortium). TF motifs in driver elements were compared against motifs found in shuffled driver elements within the same set of tested tiled regions (regions with at least 10 HiDRA fragments).

Random shuffling of driver elements: To assess significance of TF motifs, evolutionary conservation and fine-mapped GWAS SNPs in driver elements, Applicants shuffled the positions of driver elements within tiled regions (genomic segments with at least 10 HiDRA fragments) using shuffleBed with the -incl flag to force driver elements to be shuffled within tiled regions. To assess the significance of enrichment, Applicants performed 1,000 shuffles of driver elements and calculated z-score of true driver elements compared to shuffled driver elements. The p-value of this difference was calculated in R from this z-score under a normal distribution (2-sided) with mean and standard deviation calculated from random shuffles.

Activity of HiDRA regions in other tissues: Applicants set a lenient definition for active in other tissues as the union of regions annotated in 97 non-GM12878 tissues from epigenome roadmap predicted with 18-state ChromHMA/I model. For active regions Applicants considered states "TssA" (state #1), "TssFlnkU" (state #3), and "EnhA" (states #9 and 10).

SHARPR-RE activity plots: Tracks were drawn in the UCSC Genome Browser using "Custom Tracks". Coloring of individual fragments was performed by setting maximum and minimum colors (RGB 0,0,0 and RGB 255,255,0, respectively) to log2(RNA/DNA) values of 3rd lowest and 3rd highest fragments (two strongest and weakest fragments were removed to avoid strong outliers), and scaling colors of all other fragments linearly between these extremes. Applicants chose to include only ChIP-seq bound TF bars for ChIP-seq experiments performed in GM12878 cells by the ENCODE project and where the motif (green bar) overlapped driver nucleotides.

Comparison of driver elements vs. 1VIPRA allelic skew: Applicants used allelic skew data from Supplemental Table S1 from Tewhey et al. (2016). In total, 39,500 SNPs were tested by Tewhey et al. for allelic activity, of these 4,335 SNPs had enhancer activity in MPRA fragments containing either allele so that allelic skew can be calculated. 3,291 SNPs remained after using dbSNP142 and the corresponding RsMergeArch file to assign coordinates for these SNPs. Applicants used this set of 3,291 SNPs to assess the degree of allelic skew inside driver elements.

Comparison of driver elements vs. Sharpr-MPRA activity: Applicants used Sharpr-MPRA activity scores from the basepredictions_*_ScaleUpDesign1 and2_combinedP.txt files provided by Ernst et al. (2016). Applicants identified the top Sharpr-MPRA activity score per driver element and compared these to activity scores for control, shifted elements.

SHARPR-RE Identification of High-Resolution Driver Elements

See Supplementary Methods for details and more information on SHARPR-RE.

Read Mapping and Data Analysis for Allele-Specific Activity

Applicants used vcf-consensus (VCFTools) to mask the hg19 genome assembly by replacing heterozygous nucleotides identified by the Illumina NA12878 Platinum Genome with N's. 250nt paired-end MiSeq reads were trimmed using cutadapt to remove Illumina primer sequences, mapped to the NA12878-masked hg19 assembly using bowtie2 v2.2.9 (settings: —end-to-end—phred33—sensitive -p 7-N 1—no- unal), and filtered using the steps described above for 37nt reads. As some long reads have poor quality scores at their 3' end, Applicants trimmed low quality sequences (quality value <38) to reduce the proportion of sequencing errors at SNPs that could lead to incorrect allelic assignment of fragments. Fragments were then assigned to a SNP based on genotype at the position. For comparisons of SNP activity, Applicants only considered fragments with 90% mutual overlap to reduce the confounding effect of fragments that differ by both allele and position. Applicants also removed fragments if either end was within 25nt of a driver element, as in these cases small differences in end position could artificially lead to large effects. After assigning fragment abundances (from high-depth 37nt PE read sequencing) to each allele of a SNP, Applicants identified SNPs with significant differential activity using QuASAR-1VIPRA. CENTIPEDE SNPs were identified by Moyerbrailean et al. (2016) using an effect-size cut-off of >3 or <−3, following the cut-offs used by Kalita et al. (2017) (34, 35).

REFERENCES

1. Nord, A. S. et al. Rapid and Pervasive Changes in Genome-wide Enhancer Usage during Mammalian Development. Cell 155, 1521-1531 (2013).
2. Long, H. K., Prescott, S. L. & Wysocka, J. Ever-Changing Landscapes: Transcriptional Enhancers in Development and Evolution. Cell 167, 1170-1187 (2016).
3. Wamstad, J. A., Wang, X., Demuren, O. O. & Boyer, L. A. Distal enhancers: new insights into heart development and disease. Trends in Cell Biology 24, 294-302 (2014).
4. Wang, X. et al. Discovery and validation of sub-threshold genome-wide association study loci using epigenomic signatures. eLife 5, e10557 (2016). doi:10.7554/eLife.10557
5. Ernst, J. & Kellis, M. Discovery and characterization of chromatin states for systematic annotation of the human genome. Nat Biotechnol 28, 817-825 (2010).
6. Consortium, R. E. et al. Integrative analysis of 111 reference human epigenomes. Nature 518, 317-330 (2015).
7. ENCODE Project Consortium et al. An integrated encyclopedia of DNA elements in the human genome. Nature 489, 57-74 (2012).
8. Rada-Iglesias, A. et al. A unique chromatin signature uncovers early developmental enhancers in humans. Nature 470, 279-283 (2010).
9. Ernst, J. et al. Mapping and analysis of chromatin state dynamics in nine human cell types. Nature 473, 43-49 (2011).
10. Visel, A., Minovitsky, S., Dubchak, I. & Pennacchio, L. A. VISTA Enhancer Browser—a database of tissue-specific human enhancers. Nucleic Acids Res. 35, D88—D92 (2007).
11. Taylor, G. C. A., Eskeland, R., Hekimoglu-Balkan, B., Pradeepa, M. M. & Bickmore, W. A. H4K16 acetylation marks active genes and enhancers of embryonic stem cells, but does not alter chromatin compaction. Genome Res. 23, 2053-2065 (2013).
12. Pradeepa, M. M. et al. Histone H3 globular domain acetylation identifies a new class of enhancers. Nature Genetics 48, 681-686 (2016).
13. Ernst, J. et al. Genome-scale high-resolution mapping of activating and repressive nucleotides in regulatory regions. Nat Biotechnol 34, 1180-1190 (2016).

14. Melnikov, A. et al. Systematic dissection and optimization of inducible enhancers in human cells using a massively parallel reporter assay. Nat Biotechnol 30, 271-277 (2012).
15. Kwasnieski, J. C., Mogno, I., Myers, C. A., Corbo, J. C. & Cohen, B. A. Complex effects of nucleotide variants in a mammalian cis-regulatory element. Proceedings of the National Academy of Sciences 109, 19498-19503 (2012).
16. Arnold, C. D. et al. Genome-wide quantitative enhancer activity maps identified by STARR-seq. Science 339, 1074-1077 (2013).
17. Vanhille, L. et al. High-throughput and quantitative assessment of enhancer activity in mammals by CapStarr-seq. Nat Comms 6, 6905 (2015).
18. Dao, L. T. M. et al. Genome-wide characterization of mammalian promoters with distal enhancer functions. Nature Genetics 49, 1073-1081 (2017).
19. Vockley, C. M. et al. Direct GR Binding Sites Potentiate Clusters of TF Binding across the Human Genome. Cell 166, 1269-1281.e19 (2016).
20. Patwardhan, R. P. et al. Massively parallel functional dissection of mammalian enhancers in vivo. Nat Biotechnol 30, 265-270 (2012).
21. Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. Nature Methods 10, 1213-1218 (2013).
22. Gillies, S. D., Morrison, S. L., Oi, V. T. & Tonegawa, S. A tissue-specific transcription enhancer element is located in the major intron of a rearranged immunoglobulin heavy chain gene. Cell 33, 717-728 (1983).
23. Huang, Y. et al. cis -Regulatory Circuits Regulating NEK6 Kinase Overexpression in Transformed B Cells Are Super-Enhancer Independent. Cell Reports 18, 2918-2931 (2017).
24. Liu, Y. et al. Functional assessment of human enhancer activities using whole-genome STARR-sequencing. Genome Biol 18, 219 (2017). doi:10.1186/s13059-017-1345-5
25. Muerdter, F. et al. Resolving systematic errors in widely used enhancer activity assays in human cells. Nature Methods 15, 141-149 (2018).
26. Barakat, T. S. et al. Functional dissection of the enhancer repertoire in human embryonic stem cells. Cell Stem Cell 23, 276-288 (2018).
27. Kheradpour, P. & Kellis, M. Systematic discovery and characterization of regulatory motifs in ENCODE TF binding experiments. Nucleic Acids Res 42, 2976-2987 (2013).
28. Tewhey, R. et al. Direct Identification of Hundreds of Expression-Modulating Variants using a Multiplexed Reporter Assay. Cell 165, 1519-1529 (2016).
29. Maurano, M. T. et al. Systematic Localization of Common Disease-Associated Variation in Regulatory DNA. Science 337, 1190-1195 (2012).
30. Gusev, A. et al. Partitioning heritability of regulatory and cell-type-specific variants across 11 common diseases. American Journal of Human Genetics 95, 535-552 (2014).
31. Farh, K. K.-H. et al. Genetic and epigenetic fine mapping of causal autoimmune disease variants. Nature 518, 337-343 (2014).
32. Jostins, L. et al. Host—microbe interactions have shaped the genetic architecture of inflammatory bowel disease. Nature 491, 119-124 (2012).
33. Hitomi, Y. et al. Identification of the functional variant driving ORMDL3 and GSDMB expression in human chromosome 17q12-21 in primary biliary cholangitis. Sci Rep 7, 2904 (2017). doi: 10.1038/s41598-017-03067-3
34. Kalita, C. A. et al. QuASAR-MPRA: accurate allele-specific analysis for massively parallel reporter assays. Bioinformatics 34, 787-794 (2018).
35. Moyerbrailean, G. A. et al. Which Genetics Variants in DNase-Seq Footprints Are More Likely to Alter Binding? PLoS Genet 12, e1005875 (2016). doi:10.1371/journal.pgen.1005875
36. Inoue, F. et al. A systematic comparison reveals substantial differences in chromosomal versus episomal encoding of enhancer activity. Genome Res. 27, 38-52 (2017).
37. Murtha, M. et al. FIREWACh: high-throughput functional detection of transcriptional regulatory modules in mammalian cells. Nature Methods 11, 559-565 (2014).
38. Zabidi, M. A. et al. Enhancer—core-promoter specificity separates developmental and housekeeping gene regulation. Nature 518, 556-559 (2014).
39. Khurana, E. et al. Role of non-coding sequence variants in cancer. Nat Rev Genet 17, 93-108 (2016).
40. Mifsud, B. et al. Mapping long-range promoter contacts in human cells with high-resolution capture Hi-C. Nature Genetics 47, 598-606 (2015).
41. Taiwo, O. et al. Methylome analysis using MeDIP-seq with low DNA concentrations. Nat Protoc 7, 617-636 (2012).
42. Montefiori, L. et al. Reducing mitochondrial reads in ATAC-seq using CRISPR/Cas9. Sci Rep 7, 1213 (2017). doi:10.1038/s41598-017-02547-w
43. Michael I Love, W. H. S. A. Moderated estimation of fold change and dispersion for RNA-seq data with DESeq2. Genome Biol 15, (2014). doi:10.1186/s13059-014-0550-8
44. Quinlan, A. R. & Hall, I. M. BEDTools: a flexible suite of utilities for comparing genomic features. Bioinformatics 26, 841-842 (2010).

Methodological Details of SHARPR-RE

A1. Model Specification Basic Model

Applicants defined a "tiled region" as a continuous region in which each position was covered by at least one HiDRA fragment. Suppose that a tiled region containing P positions was covered by R fragments. The regulatory activity of each fragment j with a length $l_j$, $j \in \{1, \ldots, R\}$ was measured by the ratio $$\frac{\#RNA_j}{\#DNA_j}$$

between the counts of sequenced RNA and DNA. For a design with multiple replicates, the ratio can be calculated from the average counts of RNA and DNA across the replicates. In this example, Applicants calculated RNA/DNA ratios for each fragment after normalization of RNA & DNA by DESeq2 with the library split into 100nt bins (100-200nt, 200-300nt, etc). The ratio for a fragment containing one or more functional driver element site was larger than those not overlapping a driver element. For the downstream analysis, Applicants used the transformed observation $M_j^o$ by taking the log-transformation with base e of $$\frac{\#RNA_j}{\#DNA_j}, \text{ i.e., } M_j^o = \ln\left(\frac{\#RNA_j}{\#DNA_j}\right).$$

For the HiDRA library described in the Methods section, Applicants observed that the empirical distribution of $M_j^o$ across the whole genome (approximately 4 million fragments after quality control and filtering for minimum expression) was nearly symmetrically centered at zero but with heavy tails that indicate regulatory activity (FIGS. 39A-39B).

In HiDRA, the length of a tiled region was generally much larger than the number of fragments (P»R). The basic idea of SHARPR-RE was to use a shrinkage prior to tackle this large p small n problem. Applicants first computed a centered variable $M_j$ for each fragment j by subtracting $\mu_\alpha$, the mean of the background signal (i.e., $M_j = M_j^o - \mu_\alpha$). The mean of the background signal $\mu_\alpha$ is the average signal intensity from fragments not overlapping a driver element. We estimate $\mu_\alpha$ by the mean of the observations taken from all tiled regions covered by <5 fragments across the whole chromosome, with the assumption that the majority of these tiled regions do not contain a driver element. More specifically, suppose that there are ! tiled regions on a chromosome and each tiled region is covered by $R_k$ fragments each of which has an observation $M_{jk}^o$, $j \in \{1, \ldots, R_k\}$ and $k \in \{1, \ldots, K\}$. Thus, we have $\mu_a = \Sigma_{k \in B} \Sigma_{i=1}^{R_k} M_{jk}^o / \Sigma_{k \in B} R_k$ where B was the set of all tiled regions covered by <5 fragments (B={K|$R_k$<5}).

Within one tiled region, Applicants assumed that $M_j$ (Applicants omitted the index k whenever the formula only involved a specific tiled region) followed an i.i.d. normal distribution with a mean equal to a scaled sum of those regulatory scores $A_i$ that are covered by fragment j, that is, $$M \sim \mathcal{N}(L^{-1}TA, \Sigma E_m), \quad (1)$$

where $T \in \{0,1\}^{R \times P}$ was an indicator matrix, i.e., $T_{ij}=1$ if position i, $i \in \{1, \ldots, P\}$, was covered by fragment j; otherwise $T_{ij}=0$, and $L \in \mathbb{R}^{R \times R}$ was a diagonal matrix for scaling each fragment. Note that this specification of T assumed that each position in the tiled region contributed identically to the regulatory activity measurement of the fragments. If, for example, driver elements at the ends of a fragment may contribute less to the regulatory activity, smaller weights can be assigned according to its distance to the middle of the fragment. For the purpose of regularization, Applicants imposed an $\ell_2$ penalty on A, which was equivalent to a normal prior from the Bayesian perspective. Generalizing SHARPR-MPRA1 from 5nt to 1nt, the regulatory score A at each position i, which was a latent variable, is assigned by a univariate normal prior $$A_i \sim \mathcal{N}(0, \sigma_a^2), \quad (2)$$

where $\sigma_a^2$ was a hyper-parameter, which was defined by users and was tested for specific values in SHARPR-MPRA 1. In SHARPR-MPRA, it was assumed that $L_{jj}=l_j$. Because each fragment had the same length in SHARPR-MPRA, Applicants ended up with L=l1 and $$M \sim \mathcal{N}\left(\frac{TA}{i}, \Sigma_m\right), \quad (1)$$

where I was the identity matrix. In contrast, each fragment had a different length in HiDRA ranging from 150nt to 500nt. In SHARPR-RE, Applicants chose a uniform scale coefficient $L_{jj}=\bar{l}$, where $\bar{l}=\Sigma_{k=1}^K \Sigma_{j=1}^{R_k} l_{jk}/\Sigma_{k=1}^K R_k$ was the average length of all fragments on the chromosome. Under this modeling of L, the signal of a fragment depended only on the sum of the regulatory scores at all positions that the fragment covered but not on the fragment length. $\Sigma_m \in \mathbb{R}^{R \times R}$ was a covariance matrix with non-zero diagonal elements equal to $\sigma_m^2$, which was set to be the sample variance of $M_j$ in SHARPR-MPRA (1). Thus, the marginal distribution of M after integrating out A from (1) follows $$M \sim \mathcal{N}(0, L^{-1}T\Sigma_a(L_{-1}T)' + \Sigma_m), \quad (3)$$

where $$\Sigma_a = \begin{pmatrix} \sigma_a^2 & \cdots & 0 \\ \vdots & \ddots & \vdots \\ 0 & \cdots & \sigma_a^2 \end{pmatrix}$$

was a diagonal matrix and the prime stands for transpose. Thus, the ridge estimate or the posterior mean of A given the observed M was $$\hat{A} = \Sigma_a (L^{-1}T)'(L^{-1}T\Sigma_a(L^{-1}T)' + \Sigma_m)^{-1} M. \quad (4)$$

After some rearrangement to merge $\Sigma^a$ and $\Sigma_m$, Applicants ended up with the following equation $$\hat{A}_\lambda = ((L^{-1}T)'L^{-1}T + \lambda I)^{-1}(L^{-1}T)'M \quad (5)$$

where $$\lambda = \frac{\sigma_m^2}{\sigma_a^2}$$

was the penalizing coefficient.

Selection of Penalizing Coefficient

Instead of letting $\sigma_a^2$ and thus the penalizing coefficient $\lambda$ be defined by users as in Ernst et al. (11), Applicants selected A in a data-driven way. This was because the choice of $\lambda$ substantially affected the estimates and the performance of the following hypothesis testing procedure. This meant that $\lambda$ should be selected carefully. Note that although the formula (4) was essentially the same as the posterior mean in the Bayesian framework used in SHARPR-MPRA, Applicants instead regarded (5) as a ridge estimate under the classical framework in SHARPR-RE. In this case, we only assume that (1) was the true model in which A were parameters rather than random variables, and (2) was used for the purpose of regularization. Note that in this case the choice of $\lambda$ had significant influence on the estimation of A. If $\lambda$ was too small, the estimates would be unstable, while an overly large $\lambda$ would bring more bias. A handful of strategies have been proposed to select an optimal and stable $\lambda$, including cross-validation (2), the Hoerl-Kennard-Baldwin plug-in method (3-5), and a Markov chain Monte Carlo (MCMC) method (6). In SHARPR-RE, Applicants selected $\lambda$ by following the strategy proposed by Cule and De Iorio, 2013, which generalized the idea of Hoerl et al. 1975 (5) to the large p small n problem and shows fast and stable estimation in simulation and real data studies. More specifically, Applicants first performed a singular value decomposition (SVD) for $L^{-1}T$:

$$L^{-1}T = UDV',$$

where D was a diagonal matrix with t non-zero diagonal elements $d_{jj}$, and t≤min (P,R) Applicants selected $r^* \in \{1, \ldots, t\}$, so that $$r^* = \mathrm{argmin}_r r - \sum_{j=1}^t \frac{d_{jj}^4}{(d_{jj}^2 + \lambda_r)^2},$$

where we have $$\lambda_r = \frac{r\sigma_r^2}{\hat{\eta}_r'\hat{\eta}_r},$$

$$\hat{\eta} = D^{-2}V^{-2}(L^{-1}T)'M,$$

$$\text{and } \hat{\sigma}_r^2 = \frac{(M-L^{-1}TV_r\hat{\eta}_r)'(M-L^{-1}TV_r\hat{\eta}_r)}{R-r},$$

where $\hat{\eta}r$ was an r-vector of the first r elements in $\ddot{\eta}r$, and $V_r$ was the first r column of V.

Given r*, we choose $\lambda$ as $$\lambda_{r^*} = \frac{r^*\sigma_{r^*}^2}{\hat{\eta}_{r^*}'\hat{\eta}_{r^*}},$$

and the estimate of ! in SHARPR-RE is $$\hat{A}_{r^*} = ((L^{-1}T)'L^{-1}T + \lambda_{r^*}I)^{-1}(L^{-1}T)'M = H_{\lambda_{r^*}}M, \quad (6)$$

where $H_{\lambda_{r^*}} \beta((L^{-1}T)'L^{-1}T + \lambda_{r^*}I)^{-1}(L^{-1}T)'$ was the hat matrix. For HiDRA datasets, it was often the case that the number of fragments R was much smaller than the length of a tiled region P. To make the computation more efficient, Applicants applied SVD to the hat matrix to avoid the inversion of a large-scale matrix, so that Applicants had $$H = ((L^{-1}T)'L^{-1}T + \lambda_{r^*}I)^{-1}(L^{-1}T)'$$

$$= (VD'U'UDV' + \lambda_{r^*}VV')^{-1}VD'U'$$

$$= V(D'U'UD + \lambda_{r^*}I)^{-1}V'VD'U'$$

$$= V(D'U'UD + \lambda_{r^*}I)^{-1}D'U',$$

in which the computation of UD was dramatically faster as D had at most R non-zero diagonal elements. In the analysis of the example, HiDRA library, Applicants observed that this algorithm of selecting $\lambda_{r^*}$ produced stable estimates of the regulatory scores. We also noticed that the algorithm would produce an overly small $\lambda$ if two or more fragments in a tiled region were mapped to almost the same position (the difference was only a couple of nucleotides) and had large opposite values of $$\ln\left(\frac{\#RNA_j}{\#DNA_j}\right).$$

This phenomenon may suggest a potential data problem.

Note that this algorithm estimated a unique $\lambda_r^*$ for each tiled region, and thus the estimated regulatory scores cannot be compared directly across tiled regions. If the comparison across regions was the major concern (e.g., using the estimated regulatory scores as a training set in deep learning such as convolutional neural networks (CNN) for other downstream analysis), studentized estimates $Z_{\lambda,i}$ can be used (described in the next section).

Accuracy of Estimation

To measure the accuracy of the estimates, Applicants computed the pointwise mean square error (MSE) of $\hat{A}_\lambda$. As Applicants assumed that (1) was the true model, $\hat{A}_\lambda$ was a biased estimate of A if A≠0, and the MSE of $\overline{A}_\lambda$ should take into account both variance and bias. That was, Applicants were interested in finding not only Var ($\hat{A}$) but $E(\hat{A}_\lambda - A)^2$ as well. Note that the MSE can be decomposed into $$MSE(\hat{A}_\lambda) = Var(\hat{A}_\lambda) + Bias(\hat{A}_\lambda)^2$$

where $Bias(\hat{A}_\lambda) = E(\hat{A}_\lambda) - A$ measured the bias between the true value of A and the mean of $\hat{A}_\lambda$. The bias term was given by $$Bias(\hat{A}_\lambda)^2 = (E(\hat{A}_\lambda) - A)(E(\hat{A}_\lambda) - A)' = ((L^{-1}T)'L^{-1}T + \lambda I)^{-1}$$
$$(L^{-1}T)'L^{-1}T - I)AA'(((L^{-1}T)'L^{-1}T + \lambda I)^{-1}(L^{-1}T)'L^{-1}$$
$${}_1T - I)' = (W_\lambda - I)AA'(W_\lambda - I)',$$

where $W_\lambda = H_\lambda L^{-1}T$

The variance var=($\hat{A}_\lambda$) can be shown as $$Var(\hat{A}_\lambda) = Var\left(((L^{-1}T)'L^{-1}T + \lambda I)^{-1}(L^{-1}T')M\right)$$

$$= ((L^{-1}T)'L^{-1}T + \lambda I)^{-1}(L^{-1}T)'Var(M)$$

$$\left(((L^{-1}T)'L^{-1}T + \lambda I)^{-1}(L^{-1}T)'\right)'$$

$$= \sigma_m^2((L^{-1})'L^{-1}T + \lambda I)^{-1}(L^{-1}T)'L^{-1}T$$

$$\left(((L^{-1}T)'L^{-1}T + \lambda I)^{-1}\right)'$$

$$= \sigma_m^2 H_\lambda H_\lambda'.$$

The true value of $\sigma_m^2$ is unknown, but can be estimated from the residuals $$\hat{\sigma}_m^2 = \frac{(M - L^{-1}T\hat{A}_\lambda)'(M - L^{-1}T\hat{A}_\lambda)}{R - df},$$

where $df = R - 2tr(H_\lambda) + tr(H_\lambda H_\lambda')$ was the residual degrees of freedom (7) and tr ( ) stands for the trace. Plugging in the ridge estimate (5) to A and the sample estimate $\hat{\sigma}_m^2$ to $\sigma_m^2$, the estimated MSE was $$\widehat{MSE}(\hat{A}_\lambda) = \widehat{Var}(\hat{A}_\lambda) + \widehat{Bias}(\hat{A}_\lambda)^2 = \hat{\sigma}_m^2 H_\lambda H_\lambda' + (W_\lambda - I)\hat{A}_\lambda \hat{A}_\lambda'(W_\lambda - I), \quad (7)$$

Pointwise confidence intervals (CIs) can be calculated from $\widehat{Var}(\hat{A}_\lambda)$, e.g., 95% CI≈$\hat{A}_\lambda \pm 1.96 \times \sqrt{\widehat{Var}(\hat{A}_\lambda)}$. Note that the bias term $Bias(\hat{A}_\lambda)$ was non-zero if A or $\lambda$ was non-zero. Therefore, it was not straightforward to interpret the CIs obtained from $Var(\hat{A}_\lambda)$. Instead, the following adjusted 95% CI $$CI_{adj} = \hat{A}_\lambda - \widehat{Bias}(\hat{A}_\lambda) \pm 1.96 \times \sqrt{\widehat{Var}(A_\lambda)}$$

was proposed (8), which adjusted for the bias. One problem of the adjusted CI was that the true bias was unknown and its estimate $\widehat{Bias}(\hat{A}_\lambda)$ might not be accurate.

A2. Identifying High-Resolution Driver Elements

Regional FWER Controlling Procedure

Given the estimated regulatory scores $\hat{A}_\lambda$ for each nucleotide within a specific tiled region, Applicants then aimed at finding a regional threshold to declare significant regulatory regions, which were term as high-resolution "driver" elements at which an active motif was located. More specifically, Applicants made the inference for each nucleotide i by testing the following hypothesis, $$H_0: A_i = vs. \; H_a: A_i > 0.$$

For this hypothesis testing, Applicants focused only on finding activating regulatory elements but not repressive ones; however, generalization to a two-sided test was straightforward. For a specific tiled region containing P positions, Applicated wanted to find a cutoff $C_i$ so that the family-wise error rate (FWER) α was bounded below a given value (e.g., 0.05). The value of α can be set differently among different tiled regions. This amounts to a multiple testing problem of performing P one-sided tests of the estimated regulatory scores $\hat{A}_\lambda=(\hat{A}_{\lambda 1}, \ldots, \hat{A}_{\lambda P})'=0$ simultaneously. One way can be computing a p-value for each $\hat{A}_{\lambda i}$ and using the simple Bonferroni correction to obtain a local significance level $$\alpha_i = \frac{\alpha}{P}$$

from which $C_i$ can be computed. This approach would be overly conservative as $\hat{A}_{\lambda i}$ was not independent of each other in this case. A more accurate cutoff should take into account the correlation structure of the estimated regulatory scores. On the other hand, performing a permutation test for each tiled region would be too time consuming for a library comprising the whole genome albeit more accurate. Following the strategy described by (9,10), Applicants thus proposed a fast multiple testing procedure based on Gaussian copula to find region-specific cutoffs for controlling FWER α. Note that under the null hypothesis $A_i=0$, the bias term in (7) disappeared. Applicants used the studentized estimate as the test statistics $$Z_{\lambda i} = \frac{\hat{A}_{\lambda i}}{\sqrt{\widehat{\mathrm{Var}}(A_{\lambda i})}} = \frac{\hat{A}_{\lambda i}}{\hat{\sigma}_m \sqrt{\mathrm{diag}(H_\lambda H'_\lambda)_i}},$$

where $\mathrm{diag}(\ )_i$ stands for the ith element in the vector of the diagonal elements of a matrix. It had been shown that under the null hypothesis, $Z_{\lambda i}$ followed a Student t-distribution and can be approximated by a standard normal distribution under a large sample size (11,12). Cule et al. 2011 found through simulation studies that the type I error rate and the statistical power using the normality approximation were comparable to those from permutation tests for a wide range of A. Applicants assumed that under the null hypothesis, $Z_\lambda$ approximately followed a multivariate normal distribution $$Z_\lambda = \delta_m^{-1}(H_\lambda H_\lambda' \odot I)^{-1/2} \hat{A}_\lambda = S\hat{A}_\lambda \sim \mathcal{N}(0, S\widehat{\mathrm{Var}}(\hat{A}_\lambda)S), \quad (8)$$

where $\odot$ was the Hadamard product and $S=\delta_m^{-1}(H_\lambda H_\lambda' \odot I)^{-1/2}$. In the simulation studies provided in the next section, Applicants investigated the empirical FWER based on this multivariate normal approximation under small sample size and high-dimensional cases. Denote by $F_i(x_i)$ the marginal cumulative density function (CDF) of $Z_\lambda$ which was continuous. According to Sklar's theorem (13), there existed a unique copula $\mathcal{C}:[0,1]^P \to [0,1]$, such that
$\forall (x_1, \ldots, x_P)' \in \mathbb{R}^P: F(x_1, \ldots, x^P) = \mathcal{C}(F_1(x_1), \ldots, F_P(x_P))$, where $F(x_1, \ldots, x_P)$ was the joint CDF. Hence, for the one-sided test we had $$\alpha = FWER$$
$$= \mathbb{P}_{H_0}\left(\bigcup_{i=1}^P Z_{\lambda i} > c_i\right)$$
$$= 1 - \mathbb{P}_{H_0}\left(\bigcap_{i=1}^P Z_{\lambda i} \le c_i\right)$$
$$= 1 - \mathbb{P}_{H_0}(Z_{\lambda 1} \le c_1, \ldots, Z_{\lambda P} \le c_P)$$
$$= 1 - C(F_1(c_1), \ldots, F_P(c_P))$$

Under the multivariate normality approximation of (8), we had $$\alpha = 1 - \mathcal{C}(F_1(c_1), \ldots, F_P(c_P)) = 1 - \mathcal{C}_s\widehat{\mathrm{Var}}_{(\hat{A}_\lambda)S}(\Phi_1(c_1), \ldots, \Phi_P(c_P)), \quad (9)$$

where $\mathcal{C}_s\widehat{\mathrm{Var}}_{(\hat{A}_\lambda)S}(u_1, \ldots, u_P)$ was a Gaussian copula with a correlation parameter matrix of $S\widehat{\mathrm{Var}}(\hat{A}_\lambda)S$, and $\Phi(c)$ is the CDF of a standard normal distribution. Given a specific value of α, there were infinite many solutions $(u_1, \ldots, u_P) = \mathcal{C}_s\widehat{\mathrm{Var}}_{(\hat{A}_\lambda)S}^{-1}(1-\alpha)$. However, if we treated every position as equally important and pursued a single-step common-quantile cutoff (Dudoit and van der Laan, 2008, Chapter 4) c, i.e., $c_1 = \ldots = c_P = c$, we can find a unique solution $$u^* = \mathcal{C}_s\widehat{\mathrm{Var}}_{(\hat{A}_\lambda)S}^{-1}(1-\alpha), \text{ at } u_1 = \ldots = u_P = u^*$$

And $$c^* = \Phi^{-1}(u^*).$$

So, Applicants rejected $H_0$ for the positions in $\mathcal{H} = \{i \in (1, \ldots, P): Z_{\lambda i} > c^*\}$. The common-quantile cutoff $c^*$ can be calculated, for example, by the function qmvnorm in the R package mvtnorm (14). The similar idea can also be used to obtain adjusted p-values for controlling regional FWER as shown in Conneely and Boehnke, 2007 (15). In real data analysis, the estimated) covariance matrix $\widehat{\mathrm{Var}}(\hat{A}_\lambda)$ was often degenerated and the estimates of adjacent positions were completely correlated when P>R. Therefore, Applicants trimmed the number of the estimates by selecting one position from each group in which the estimates for the positions were completely correlated. This also dramatically reduced the computational intensity for finding the solution to (9). After identifying the driver elements, we can further attempt to pinpoint the location of the most possible occurrence of a 20nt "core" driver element (see section A4 below for rationale for choosing ~20nt as the estimated "core" region). We predicted the center position $i_m$ of a 20nt core driver element by the highest regulatory scores over its 20nt flanking region, i.e., $$i_m = \mathrm{argmax}_{i \in \mathcal{H}} \frac{\sum_{n=(i-9)}^{(i+10) \wedge P} \hat{A}_{\lambda n}}{(i+10) \wedge P - (i-9) \vee 1 + 1}.$$

FIG. 41 gives an illustration of the significant regulatory region and the predicted motif region. In this example, the true motif was located at position 400-420nt and was covered by an identified significant driver element by SHARPR-RE (highlighted in red). The predicted core driver region (highlighted in purple) further pinpoints the location of the motif at ~400nt.

Global FDR Controlling Procedure

The above regional procedure called significant driver elements for a specific tiled region. If we want to identify driver elements across an entire genome, it may be preferable to control the global false discovery rate (FDR). Applicants thus proposed a global multiple testing correction procedure for this purpose by taking into account the p-values observed from the whole genome. Applicants first calculated the pointwise p-values for all positions in each tiled region across the genome based on the t-distribution $$Z_{\lambda i} = \frac{\hat{A}_{\lambda i}}{\sqrt{\hat{\text{Var}}(\hat{A}_{\lambda i})}} \sim t_{R-tr(H_\lambda)},$$

where R−tT(H$_\lambda$) was the sample size minus the effective degrees of freedom. As mentioned in the local controlling procedure, Applicants selected one position from a consecutive region in which the estimates for these positions were completely correlated. Then, Applicants applied the Benjamini-Hochberg procedure to the pointwise p-values to control the global FDR at level α. As p-values from different tiled regions were independent, the p-values across the genome can be regarded being dependent in finite blocks if the size of the largest tiled region is limited. More specifically, Applicants assumed that the ratio between max(R$_k$) and the total number of fragments $\Sigma_{k=1}^{K} R_k$ went to zero as $$\sum_{k=1}^{K} R_k \to \infty \text{(i.e., } \frac{\max(R_k)}{\sum_{k=1}^{K} R_k} \to 0 \text{ as } \sum_{k=1}^{K} R_k \to \infty,$$

and R$_k$ is used instead of P$_k$ because the number of tests in a tiled region was related to R$_k$ when P$_k$»R$_k$). Thus, under this assumption, which was biologically reasonable, the estimate of FDR was consistent (16, 17).

A3. Evaluation of Empirical Statistical Power and FWER

Simulation Settings

Applicants assessed the performance of the proposed SHARPR-RE algorithm in terms of empirical statistical power estimated from our simulation studies. To mimic the current version of the HiDRA library, Applicants randomly generated a number ! of fragments (R between 25-100) in a tiled region with P=1 kb. The length of each fragment was sampled from a uniform distribution l$_j$~U(175,450), j∈ {1, . . . , R}. Applicants randomly selected a 20nt driver element from a 400nt window in the middle of the tiled region. For any fragment that covers the driver element, Applicants generated its signal from a normal distribution $\mathcal{N}(\mu_{driver}=S_m\sigma_{driver}=0.1)$, where S$_m$ was the true signal varying across different simulation scenarios. For the rest of the fragments, Applicants generated signals from a normal distribution $\mathcal{N}(\mu_{noise}=0, \sigma_{noise}=1)$. Applicants defined the signal-to-noise-ratio (SNR) as $$SNR = \frac{S_m}{\sigma_{noise}}.$$

Applicants examined the empirical FWER and empirical statistical power under different SNR and numbers of fragments. Under each simulation setting, Applicants generated 500 replicates to obtain the estimated of the empirical FWER and statistical power.

Evaluation of Empirical Type I Error Rate

The results in Table 2 below show that generally the empirical regional FWER was controlled at ~5%, which was the theoretical FWER, when the number of fragments was above 50. Applicants observed mild inflation of the empirical FWER especially in the case of small sample size (e.g., 25), but the inflation diminished with the sample size increasing in most situations. This inflation can be due to the discrepancy between the true null distribution of the statistics and the asymptotic multivariate normal distribution at the tails as shown in 18. This indicates that the error introduced by the multivariate normality approximation should be taken into account when the sample size is overly small (for example, by using a similar scaling procedure as proposed in 18 or by setting a more stringent cutoff for a tiled region covered by a small number of fragments).

TABLE 2

Empirical FWER for the proposed local multiple testing procedure. The empirical FWER was calculated from 500 replicates under each setting. The theoretical FWER ! is 5%. Applicants examined the empirical FWER with respect to a max tiled region length (between 900 nt and 1500 nt ) and the number of fragments in the tiled region.

| Number of | Max length of a tiled region | | | |
|---|---|---|---|---|
| fragments | 900 | 1100 | 1300 | 1500 |
| 25 | 7.6% | 9.0% | 7.0% | 7.6% |
| 50 | 7.2% | 6.0% | 4.8% | 4.0% |
| 75 | 7.0% | 5.2% | 5.8% | 6.4% |
| 100 | 6.8% | 5.0% | 6.0% | 6.7% |
| 125 | 6.4% | 5.4% | 6.4% | 5.0% |

Evaluation of Empirical Statistical Power

Next, Applicants examined the statistical power for pinpointing a driver element under the condition of !=5%, i.e., the FWER <5%. In this investigation, a true positive was counted if an identified driver element or a predicted 20 bp functional motif region overlapping the true driver element region. The results in FIG. 42 show that the statistical power for both regions consistently increased with respect to the number of fragments and the SNR. If there were 100 fragments in a tiled region, SHARPR-RE can achieve more than 80% power under SNR=1.

When the number of fragments was small (e.g., 25), SNR>1.5 was needed to achieve a power of 80%. Higher SNR required that the biological experiments had higher precision and sensitivity, so that significantly more RNAs can be sequenced when the DNA region covers a true driver element.

A4. Analysis of an HiDRA Library

Applicants applied SHARPR-RE to an HiDRA library prepared from the GM12878 lymphoblastoid cell line. The library contained 3,896,416 fragments after quality control, with the length of fragments ranging from 100-600nt (99% of fragments between 168-473nt). Applicant first identified 645,936 tiled regions that were covered by at least two fragments across the whole genome, among which 28,092 regions were covered by more than 10 fragments. The distribution of the signals (ln(#RNA/#DNA)) of these fragments are almost symmetrically centered at zero with heavy tails (FIGS. 39A-39B). The average and the variance of the signals are constant across the length of HiDRA fragments after normalization (Materials and Methods, FIG. 15). Applicants estimated the regulatory scores for the 22 chromosomes separately and called driver elements based on a cutoff controlling regional FWER<0.05 for the positions in each tiled region. Applicants found that the tiled regions covered by larger numbers of HiDRA fragments were more likely to have a driver element called, which was likely a combination of greater statistical power and enrichment for regions more likely to contain drivers.

As shown in FIG. 24C, most driver elements were found within active TSS, TSS Flanking Upstream and active enhancer chromatin states. The median size of driver elements identified from the tiled regions covered by >10 fragments was 52nt after filtering to remove drivers smaller than 5nt. The average size of drivers decreased with an increase in number of fragments in a tiled region, suggesting that more complex libraries with greater numbers of unique fragments should be able to detect shorter driver elements (FIG. 34). The average size of a driver element converged to ~18nt after the depth of unique HiDRA fragment coverage reaches 50 fragments/kb (FIG. 34).

REFERENCES

1. Ernst, J. et al. Genome-scale high-resolution mapping of activating and repressive nucleotides in regulatory regions. Nat Biotechnol 34, 1180-1190 (2016).
2. Golub, G. H., Heath, M. & Wahba, G. Generalized Cross-Validation as a Method for Choosing a Good Ridge Parameter. Technometrics 21, 215 (1979).
3. Cule, E. & De Iorio, M. Ridge regression in prediction problems: automatic choice of the ridge parameter. Genet. Epidemiol. 37, 704-714 (2013).
4. HOERL, A. E. & KENNARD, R. W. Ridge Regression—Biased Estimation for Nonorthogonal Problems. Technometrics 12, 55-& (1970).
5. HOERL, A. E., KENNARD, R. W. & BALDWIN, K. F. Ridge Regression—Some Simulations. Communications in Statistics 4, 105-123 (1975).
6. Denison, D. G. T. Bayesian Methods for Nonlinear Classification and Regression. (John Wiley & Sons, 2002).
7. Hastie, T., Tibshirani, R. & Friedman, J. The Elements of Statistical Learning. (Springer Science & Business Media, 2013).
8. De Brabanter, K., De Brabanter, J., Suykens, J. A. K. & De Moor, B. Approximate confidence and prediction intervals for least squares support vector regression. IEEE Trans Neural Netw 22, 110-120 (2011).
9. Dickhaus, T. & Gierl, J. Simultaneous test procedures in terms of p-value copulae. Economic Risk (2012). Available at: sfb649.wiwi.hu-berlin.de/papers/pdf/SFB649DP2012-049.pdf. (Accessed: 11 Oct. 2012)
10. Stange, J., Bodnar, T. & Dickhaus, T. Uncertainty quantification for the family-wise error rate in multivariate copula models. Asta-Advances in Statistical Analysis 99, 281-310 (2015).
11. Cule, E., Vineis, P. & De Iorio, M. Significance testing in ridge regression for genetic data. BMC Bioinformatics 12, 372 (2011).
12. Halawa, A. M. & Bassiouni, El, M. Y. Tests of regression coefficients under ridge regression models. Journal of Statistical Computation and Simulation 65, 341-356 (2000).
13. Nelsen, R. B. An Introduction to Copulas. (Springer Science & Business Media, 2013).
14. Genz, A. & Bretz, F. Comparison of methods for the computation of multivariate t probabilities. J. Comput. Graph. Stat 950-971 (2002).
15. Conneely, K. N. & Boehnke, M. So many correlated tests, so little time! Rapid adjustment of P values for multiple correlated tests. American Journal of Human Genetics 81, 1158-1168 (2007).
16. Schwartzman, A. & Lin, X. The effect of correlation in false discovery rate estimation. Biometrika 98, 199-214 (2011).
17. Storey, J. D., Taylor, J. E. & Siegmund, D. Strong control, conservative point estimation and simultaneous conservative consistency of false discovery rates: a unified approach. Journal of the Royal Statistical Society Series B-Statistical Methodology 66, 187-205 (2004).
18. Han, B., Kang, H. M. & Eskin, E. Rapid and Accurate Multiple Testing Correction and Power Estimation for Millions of Correlated Markers. PLoS Genet 5, (2009).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features hereinbefore set forth.

What is claimed is:

1. A method of identifying genomic enhancer regulatory elements comprising:
   fragmenting genomic DNA at accessible chromatin in a population of cells thereby generating genomic DNA fragments, wherein said fragmenting comprises transposition;
   amplifying the genomic DNA fragments;
   enriching the amplified genomic DNA fragments by size;
   integrating the enriched fragments into a vector to obtain a vector library, wherein the vector encodes a reporter gene and the enriched fragments are integrated into an untranslated region (UTR) of the reporter gene, whereby transcription of the reporter gene results in a transcript comprising the integrated fragment sequence;
   transfecting or transducing a cell line with the vector library, wherein the transcript comprising the integrated fragment sequences is expressed in the cell line; and
   sequencing the transcript expressed in the cell line, whereby integrated fragments comprising enhancer activity are identified.

2. The method according to claim 1, wherein the amplified genomic DNA fragments are selected for a size between about 150 and about 500 nucleotides long.

3. The method according to claim 1, wherein the amplified genomic DNA fragments are selected for a size between about 230 and about 500 nucleotides long.

4. The method according to claim 1, wherein the enriched fragments are integrated in a UTR downstream of the reporter gene.

5. The method according to claim 1, further comprising removing mitochondrial DNA.

6. The method according to claim 5, wherein the mitochondrial DNA is removed using a CRISPR system comprising guide sequences targeting the mitochondrial DNA sequences, wherein the mitochondrial DNA is cleaved.

7. The method according to claim 5, wherein the mitochondrial DNA is removed after the enriching the amplified genomic DNA fragments and before the integrating the enriched fragments.

8. The method according to claim 1, wherein the vector is a plasmid.

9. The method according to claim 1, wherein the vector is a viral vector.

10. The method according to claim 9, wherein the viral vector is a lentiviral vector.

11. The method according to claim 1, wherein the integrated fragments comprising enhancer activity is identified by measuring a ratio of a number of RNA sequencing reads comprising a fragment to the representation of the fragment in a non-transfected vector library.

12. The method according to claim 1, wherein the integrated fragments comprising enhancer activity is identified by comparing a sequenced genomic fragment to the chromatin state of a genomic locus of the fragment in the cell line, wherein fragments present in an enhancer chromatin state are selected.

13. The method according to claim 12, wherein the enhancer chromatin state comprises H3K27ac (histone H3 lysine 27 acetylation) and H3K4me1 (histone H3 lysine 4 mono-methylation).

14. The method according to claim 1, wherein the integrated fragments comprising enhancer activity is identified by comparing a sequenced genomic fragment to Long-Terminal-Repeat (LTR) retrotransposon sequences, wherein LTR sequences are not selected.

15. The method according to claim 1, further comprising detecting expression of the reporter gene in the cell line and sorting cells in the cell line based on expression levels of the reporter gene.

16. The method according to claim 1, wherein the population of cells is obtained from a tissue sample.

17. The method according to claim 1, wherein the population of cells is a tissue-specific cell line.

18. The method according to claim 1, wherein the population of cells is obtained by pooling cells or tissues from more than one individual.

19. The method according to claim 1, wherein the population of cells comprise immune cells.

20. The method according to claim 1, wherein the population of cells comprise cancer cells.

* * * * *

UNITED STATES PATENT AND TRADEMARK OFFICE
CERTIFICATE OF CORRECTION

| | |
|---|---|
| PATENT NO. | : 11,987,790 B2 |
| APPLICATION NO. | : 16/757296 |
| DATED | : May 21, 2024 |
| INVENTOR(S) | : Claussnitzer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 882 days.

Signed and Sealed this
Third Day of December, 2024

Katherine Kelly Vidal
Director of the United States Patent and Trademark Office

SEQUENCE LISTING

```
<160> NUMBER OF SEQ ID NOS: 5

<210> SEQ ID NO 1
<211> LENGTH: 66
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(43)
<223> OTHER INFORMATION: n is a, c, g, or t

<400> SEQUENCE: 1
tagagcatgc accggcaagc agaagacggc atacgagatn nnnatgtctc gtgggctcgg      60
agatgt                                                                66

<210> SEQ ID NO 2
<211> LENGTH: 36
<212> TYPE: DNA
```

```
<213> ORGANISM: Artificial Sequence
<220> FEATURE:
<223> OTHER INFORMATION: Synthetic

<400> SEQUENCE: 2
ggccgaattc gtcgatcgtc ggcagcgtca gatgtg                              36

<210> SEQ ID NO 3
<211> LENGTH: 26
<212> TYPE: DNA
<213> ORGANISM: Artificial Sequence
<220> FEATURE:
<223> OTHER INFORMATION: Synthetic

<400> SEQUENCE: 3
caaactcatc aatgtatctt atcatg                                         26

<210> SEQ ID NO 4
<211> LENGTH: 24
<212> TYPE: DNA
<213> ORGANISM: Artificial Sequence
<220> FEATURE:
<223> OTHER INFORMATION: Synthetic

<400> SEQUENCE: 4
caagcagaag acggcatacg agat                                           24

<210> SEQ ID NO 5
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (30)..(37)
<223> OTHER INFORMATION: n is a, c, g, or t

<400> SEQUENCE: 5
aatgatacgg cgaccaccga gatctacacn nnnnnnntcg tcggcagcgt c              51
```